(12) United States Patent  (10) Patent No.: US 8,673,190 B2
Sowden et al.  (45) Date of Patent: Mar. 18, 2014

(54) METHOD FOR MANUFACTURING DOSAGE FORMS

(75) Inventors: Harry S. Sowden, Glenside, PA (US); Bernard F. Plantz, Holland, PA (US); Shun Por Li, Lansdale, PA (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 13/313,504

(22) Filed: Dec. 7, 2011

(65) Prior Publication Data

US 2012/0074614 A1 Mar. 29, 2012

Related U.S. Application Data

(60) Division of application No. 10/911,263, filed on Aug. 4, 2004, now Pat. No. 8,114,328, which is a continuation of application No. 09/966,497, filed on Sep. 28, 2001, now Pat. No. 7,122,143.

(51) Int. Cl.
*B29C 41/02* (2006.01)
*B29C 43/34* (2006.01)

(52) U.S. Cl.
USPC ........ 264/109; 264/320; 264/571; 264/297.3; 264/297.8

(58) Field of Classification Search
None
See application file for complete search history.

(56) References Cited

U.S. PATENT DOCUMENTS

| | | |
|---|---|---|
| 545,832 A | 9/1895 | Turnbull |
| 582,438 A | 5/1897 | Scheidler |
| 599,865 A | 3/1898 | Richards |
| 1,036,647 A | 8/1912 | Komarek |
| 1,437,816 A | 12/1922 | Paine et al. |
| 1,505,827 A * | 8/1924 | Villasenor et al. ............... 425/89 |
| 1,900,012 A | 3/1933 | Ernst |
| 2,026,940 A * | 1/1936 | Hendryx ....................... 264/102 |
| 2,307,371 A | 1/1943 | Hileman |
| 2,415,997 A | 2/1947 | Eldred |
| 2,823,789 A | 2/1958 | Henning |
| 2,849,965 A | 9/1958 | Stott |
| 2,931,276 A | 4/1960 | Zerlin |
| 2,946,298 A | 7/1960 | Doepel et al. |
| 2,963,993 A | 12/1960 | Stott |
| 2,966,431 A | 12/1960 | Barry |
| 3,029,752 A | 4/1962 | Frank |
| 3,085,942 A | 4/1963 | Magid et al. |
| 3,096,248 A | 7/1963 | Rudzki |

(Continued)

FOREIGN PATENT DOCUMENTS

| | | |
|---|---|---|
| CN | 1092641 A | 9/1994 |
| CN | 1137926 A | 12/1996 |

(Continued)

OTHER PUBLICATIONS

D'Arcy et al. International Journal of Pharmaceutics vol. 88(1992) 285-291.

(Continued)

*Primary Examiner* — Edmund H. Lee
(74) *Attorney, Agent, or Firm* — Laura A. Donnelly

(57) ABSTRACT

Systems, methods and apparatuses for manufacturing dosage forms, and to dosage forms made using such systems, methods and apparatuses are provided. Novel compression, thermal cycle molding, and thermal setting molding modules are disclosed. One or more of such modules may be linked, preferably via novel transfer device, into an overall system for making dosage forms.

6 Claims, 80 Drawing Sheets

(56) References Cited

U.S. PATENT DOCUMENTS

| | | | |
|---|---|---|---|
| 3,108,046 A | 10/1963 | Harbit | |
| 3,146,169 A | 8/1964 | Stephenson et al. | |
| 3,177,280 A | 4/1965 | Ford et al. | |
| 3,185,626 A | 5/1965 | Baker | |
| 3,279,360 A | 10/1966 | Smith et al. | |
| 3,300,063 A | 1/1967 | Jensen et al. | |
| 3,328,840 A * | 7/1967 | Vinson | 425/78 |
| 3,330,400 A | 7/1967 | Alexander | |
| 3,371,136 A | 2/1968 | Johannsen | |
| 3,430,535 A | 3/1969 | Campbell | |
| 3,432,592 A | 3/1969 | Speiser | |
| 3,458,968 A | 8/1969 | Gregory Jr. | |
| 3,555,608 A | 1/1971 | Maekawa et al. | |
| 3,563,170 A | 2/1971 | Cvacho et al. | |
| 3,567,043 A | 3/1971 | Sirvet et al. | |
| 3,584,114 A | 6/1971 | Cavalli et al. | |
| 3,605,479 A | 9/1971 | Bradlee | |
| 3,627,583 A | 12/1971 | Troy et al. | |
| 3,640,654 A * | 2/1972 | Smith | 425/78 |
| 3,656,518 A | 4/1972 | Aronson | |
| 3,726,622 A | 4/1973 | De Troyer et al. | |
| 3,804,570 A | 4/1974 | Hoschele et al. | |
| 3,811,552 A | 5/1974 | Wagers et al. | |
| 3,832,252 A | 8/1974 | Higuchi et al. | |
| 3,851,751 A | 12/1974 | Jones | |
| 3,884,143 A | 5/1975 | Ackley | |
| 3,891,375 A | 6/1975 | Pilewski et al. | |
| 3,912,441 A | 10/1975 | Shimada et al. | |
| 3,975,888 A | 8/1976 | Jones | |
| 3,988,403 A | 10/1976 | Angell, Jr. et al. | |
| 3,999,922 A * | 12/1976 | Shimada | 425/210 |
| 4,061,452 A * | 12/1977 | DeSantis | 425/78 |
| 4,061,453 A * | 12/1977 | DeSantis | 425/78 |
| 4,076,819 A | 2/1978 | Maffrand | |
| 4,097,606 A | 6/1978 | Chavkin et al. | |
| 4,139,589 A | 2/1979 | Beringer et al. | |
| 4,173,626 A | 11/1979 | Dempski et al. | |
| 4,230,693 A | 10/1980 | Izzo et al. | |
| 4,268,243 A | 5/1981 | Koshkin et al. | |
| 4,271,142 A | 6/1981 | Puglia et al. | |
| 4,271,206 A | 6/1981 | Fariel et al. | |
| 4,273,793 A | 6/1981 | Fariel et al. | |
| 4,279,926 A | 7/1981 | Bruzzese et al. | |
| 4,292,017 A | 9/1981 | Doepel | |
| 4,327,076 A | 4/1982 | Puglia et al. | |
| 4,362,757 A | 12/1982 | Chen et al. | |
| 4,371,516 A | 2/1983 | Gregory et al. | |
| 4,372,942 A | 2/1983 | Cimiluca | |
| 4,392,493 A | 7/1983 | Niemeijer | |
| 4,413,709 A | 11/1983 | Kazumi | |
| 4,425,332 A | 1/1984 | James | |
| 4,449,983 A | 5/1984 | Cortese et al. | |
| 4,473,526 A | 9/1984 | Buhler et al. | |
| 4,518,335 A | 5/1985 | Pujari | |
| 4,528,335 A | 7/1985 | Selby et al. | |
| 4,533,345 A | 8/1985 | Louw | |
| 4,543,370 A | 9/1985 | Porter et al. | |
| 4,544,345 A | 10/1985 | Buhler et al. | |
| 4,569,650 A | 2/1986 | Kramer | |
| 4,576,604 A | 3/1986 | Guittard et al. | |
| 4,643,894 A | 2/1987 | Porter et al. | |
| 4,661,521 A | 4/1987 | Salpekar et al. | |
| 4,665,116 A | 5/1987 | Kornhaber et al. | |
| 4,683,256 A | 7/1987 | Porter et al. | |
| 4,684,534 A | 8/1987 | Valentine | |
| 4,686,212 A | 8/1987 | Ducatman et al. | |
| 4,724,150 A | 2/1988 | Knebl et al. | |
| 4,725,441 A | 2/1988 | Porter et al. | |
| 4,744,741 A | 5/1988 | Glover et al. | |
| 4,749,575 A | 6/1988 | Rotman | |
| 4,757,090 A | 7/1988 | Salpekar et al. | |
| 4,762,719 A | 8/1988 | Forester | |
| 4,781,714 A | 11/1988 | Eckenhoff et al. | |
| 4,801,461 A | 1/1989 | Hamel et al. | |
| 4,802,924 A | 2/1989 | Woznicki et al. | |
| 4,808,413 A | 2/1989 | Joshi et al. | |
| 4,813,818 A | 3/1989 | Sanzone | |
| 4,820,524 A | 4/1989 | Berta | |
| 4,828,841 A | 5/1989 | Porter et al. | |
| 4,828,845 A | 5/1989 | Zamudio-Tena et al. | |
| 4,851,226 A | 7/1989 | Julian et al. | |
| 4,853,249 A | 8/1989 | Takashima et al. | |
| 4,857,330 A | 8/1989 | Stephens et al. | |
| 4,863,742 A | 9/1989 | Panoz et al. | |
| 4,865,849 A | 9/1989 | Conte et al. | |
| 4,873,231 A | 10/1989 | Smith | |
| 4,882,167 A | 11/1989 | Jang | |
| 4,894,234 A | 1/1990 | Sharma et al. | |
| 4,894,236 A | 1/1990 | Jang et al. | |
| 4,898,733 A | 2/1990 | DePrince et al. | |
| 4,906,478 A | 3/1990 | Valentine et al. | |
| 4,929,446 A | 5/1990 | Bartolucci | |
| 4,936,440 A | 6/1990 | Focke et al. | |
| 4,943,227 A | 7/1990 | Facchini | |
| 4,965,027 A | 10/1990 | Takahashi | |
| 4,980,169 A | 12/1990 | Oppenheimer et al. | |
| 4,980,170 A | 12/1990 | Schneider et al. | |
| 4,984,240 A | 1/1991 | Keren-Zvi et al. | |
| 4,992,277 A | 2/1991 | Sangekar et al. | |
| 4,996,061 A | 2/1991 | Webb et al. | |
| 5,002,970 A | 3/1991 | Eby, III | |
| 5,006,297 A | 4/1991 | Brown et al. | |
| 5,030,447 A | 7/1991 | Joshi et al. | |
| 5,059,112 A | 10/1991 | Wieser | |
| 5,073,379 A | 12/1991 | Klimesch et al. | |
| 5,075,114 A | 12/1991 | Roche | |
| 5,088,915 A | 2/1992 | Korsch et al. | |
| 5,089,270 A | 2/1992 | Hampton et al. | |
| 5,098,715 A | 3/1992 | McCabe et al. | |
| 5,100,675 A | 3/1992 | Cho et al. | |
| 5,145,868 A | 9/1992 | von Sprecher et al. | |
| 5,146,730 A | 9/1992 | Sadek et al. | |
| 5,154,278 A | 10/1992 | Deutsch | |
| 5,158,728 A | 10/1992 | Sanderson et al. | |
| 5,169,645 A | 12/1992 | Shukla et al. | |
| 5,178,878 A | 1/1993 | Wehling et al. | |
| 5,188,840 A | 2/1993 | Iida et al. | |
| 5,190,927 A | 3/1993 | Chang et al. | |
| 5,200,191 A | 4/1993 | Steele et al. | |
| 5,213,738 A | 5/1993 | Hampton et al. | |
| 5,213,808 A | 5/1993 | Bar-Shalom et al. | |
| 5,223,264 A | 6/1993 | Wehling et al. | |
| 5,228,916 A | 7/1993 | Berta | |
| 5,229,164 A | 7/1993 | Pins et al. | |
| 5,234,099 A | 8/1993 | Berta | |
| 5,267,577 A | 12/1993 | Rizzoli et al. | |
| 5,274,162 A | 12/1993 | Glazier | |
| 5,275,822 A | 1/1994 | Valentine et al. | |
| 5,286,497 A | 2/1994 | Hendrickson et al. | |
| 5,342,626 A | 8/1994 | Winston, Jr. et al. | |
| 5,350,548 A | 9/1994 | Hinzpeter et al. | |
| 5,362,508 A | 11/1994 | Wheeler et al. | |
| 5,368,863 A | 11/1994 | Eckenhoff et al. | |
| 5,391,378 A | 2/1995 | Sanderson | |
| 5,405,642 A | 4/1995 | Gilis et al. | |
| 5,415,868 A | 5/1995 | Smith et al. | |
| 5,421,447 A | 6/1995 | Ruth et al. | |
| 5,424,075 A | 6/1995 | Daher et al. | |
| 5,427,614 A | 6/1995 | Wittwer et al. | |
| 5,429,226 A | 7/1995 | Ensch et al. | |
| 5,429,484 A | 7/1995 | Honda et al. | |
| 5,436,026 A | 7/1995 | Berta | |
| 5,456,563 A | 10/1995 | Halbo | |
| 5,456,920 A | 10/1995 | Matoba et al. | |
| 5,459,983 A | 10/1995 | Sadek et al. | |
| 5,464,631 A | 11/1995 | Hoover et al. | |
| 5,464,632 A | 11/1995 | Cousin et al. | |
| 5,464,633 A | 11/1995 | Conte et al. | |
| 5,489,436 A | 2/1996 | Hoy et al. | |
| 5,494,681 A | 2/1996 | Cuca et al. | |
| 5,500,227 A | 3/1996 | Oshlack et al. | |
| 5,510,385 A | 4/1996 | Stroppolo et al. | |
| 5,511,361 A | 4/1996 | Sauter | |
| 5,525,179 A | 6/1996 | Stickling | |

(56) References Cited

U.S. PATENT DOCUMENTS

| | | | |
|---|---|---|---|
| 5,538,125 A | 7/1996 | Berta | |
| 5,550,002 A | 8/1996 | Kojima et al. | |
| 5,558,879 A | 9/1996 | Chen et al. | |
| 5,578,316 A | 11/1996 | Bhardwaj et al. | |
| 5,578,336 A | 11/1996 | Monte | |
| 5,607,045 A | 3/1997 | Hermann Kronseder | |
| 5,609,010 A | 3/1997 | Sauter | |
| 5,614,207 A | 3/1997 | Shah et al. | |
| 5,626,896 A | 5/1997 | Moore et al. | |
| 5,630,871 A | 5/1997 | Jordan | |
| 5,643,984 A | 7/1997 | Mueller et al. | |
| 5,648,033 A * | 7/1997 | Bogue et al. | 264/109 |
| 5,656,296 A | 8/1997 | Khan et al. | |
| 5,658,589 A | 8/1997 | Parekh et al. | |
| 5,672,364 A * | 9/1997 | Kato et al. | 425/89 |
| 5,679,406 A | 10/1997 | Berta | |
| 5,681,583 A | 10/1997 | Conte et al. | |
| 5,681,584 A | 10/1997 | Savastano et al. | |
| 5,705,189 A | 1/1998 | Lehmann et al. | |
| 5,711,961 A | 1/1998 | Reiner et al. | |
| 5,738,874 A | 4/1998 | Conte et al. | |
| 5,743,377 A | 4/1998 | Kronseder | |
| 5,756,123 A | 5/1998 | Yamamoto et al. | |
| 5,782,337 A | 7/1998 | Langland | |
| 5,788,979 A | 8/1998 | Alt et al. | |
| 5,795,588 A | 8/1998 | Sauter | |
| 5,807,579 A | 9/1998 | Vilkov et al. | |
| 5,813,513 A | 9/1998 | Taube | |
| 5,824,338 A | 10/1998 | Jacobs et al. | |
| 5,827,548 A | 10/1998 | Lavallee et al. | |
| 5,827,563 A | 10/1998 | Battist et al. | |
| 5,827,874 A | 10/1998 | Meyer et al. | |
| 5,830,501 A | 11/1998 | Dong et al. | |
| 5,830,502 A | 11/1998 | Dong et al. | |
| 5,834,035 A | 11/1998 | Osada et al. | |
| 5,837,301 A | 11/1998 | Arnott et al. | |
| 5,840,334 A | 11/1998 | Raiden et al. | |
| 5,853,760 A | 12/1998 | Cremer | |
| 5,871,079 A | 2/1999 | Nannini et al. | |
| 5,871,781 A | 2/1999 | Myers et al. | |
| 5,879,728 A | 3/1999 | Graff et al. | |
| 5,897,910 A | 4/1999 | Rosenberg et al. | |
| 5,912,013 A | 6/1999 | Rudnic et al. | |
| 5,922,352 A | 7/1999 | Chen et al. | |
| 5,942,034 A | 8/1999 | Brehant et al. | |
| 5,962,053 A | 10/1999 | Merritt, II | |
| 5,996,768 A | 12/1999 | Boyce et al. | |
| 5,997,905 A | 12/1999 | McTeigue et al. | |
| 6,001,391 A | 12/1999 | Zeidler et al. | |
| 6,020,002 A | 2/2000 | Myers et al. | |
| 6,099,859 A | 8/2000 | Cheng et al. | |
| 6,103,257 A | 8/2000 | Nisonoff | |
| 6,103,260 A | 8/2000 | Luber et al. | |
| 6,106,267 A * | 8/2000 | Aylward | 425/352 |
| 6,117,479 A | 9/2000 | Hogan et al. | |
| 6,120,802 A | 9/2000 | Breitenbach et al. | |
| 6,126,877 A | 10/2000 | Gille et al. | |
| 6,149,939 A | 11/2000 | Strumor et al. | |
| 6,149,943 A | 11/2000 | McTeigue et al. | |
| 6,177,125 B1 | 1/2001 | Voss | |
| 6,183,681 B1 | 2/2001 | Sullivan et al. | |
| 6,194,000 B1 | 2/2001 | Smith et al. | |
| 6,200,590 B1 | 3/2001 | Eley | |
| 6,210,710 B1 | 4/2001 | Skinner | |
| 6,213,283 B1 | 4/2001 | Bailey et al. | |
| 6,217,903 B1 | 4/2001 | Skinner | |
| 6,217,907 B1 | 4/2001 | Hunter et al. | |
| 6,227,836 B1 | 5/2001 | Kato et al. | |
| 6,234,300 B1 | 5/2001 | De Vos et al. | |
| 6,245,356 B1 | 6/2001 | Baichwal | |
| 6,248,760 B1 | 6/2001 | Wilhelmsen | |
| 6,264,985 B1 | 7/2001 | Cremer | |
| 6,270,790 B1 | 8/2001 | Robinson et al. | |
| 6,270,805 B1 | 8/2001 | Chen et al. | |
| 6,272,446 B1 | 8/2001 | Baekke et al. | |
| 6,274,162 B1 | 8/2001 | Steffenino et al. | |
| 6,276,917 B1 | 8/2001 | Gutierrez et al. | |
| 6,322,819 B1 | 11/2001 | Burnside et al. | |
| 6,326,028 B1 | 12/2001 | Nivaggiolo et al. | |
| 6,350,398 B1 | 2/2002 | Breitenbach et al. | |
| 6,358,525 B1 | 3/2002 | Guo et al. | |
| 6,365,185 B1 | 4/2002 | Ritschel et al. | |
| 6,372,254 B1 | 4/2002 | Ting et al. | |
| 6,394,094 B1 | 5/2002 | McKenna et al. | |
| 6,395,298 B1 | 5/2002 | Flanagan et al. | |
| 6,405,853 B1 | 6/2002 | Cook et al. | |
| 6,423,256 B1 | 7/2002 | Kothrade et al. | |
| 6,433,015 B1 | 8/2002 | Meyer | |
| 6,482,349 B1 * | 11/2002 | Kohara et al. | 264/517 |
| 6,499,984 B1 | 12/2002 | Ghebre-Sellassie et al. | |
| 6,558,722 B2 | 5/2003 | Corriveau et al. | |
| 6,669,883 B1 | 12/2003 | Rosenberg et al. | |
| 6,727,213 B2 | 4/2004 | Waschenbach et al. | |
| 6,730,646 B1 | 5/2004 | Waschenbach et al. | |
| 6,737,005 B1 | 5/2004 | Rosenberg et al. | |
| 6,742,646 B2 | 6/2004 | Sowden et al. | |
| 6,767,200 B2 | 7/2004 | Sowden et al. | |
| 6,837,696 B2 | 1/2005 | Sowden et al. | |
| 6,880,694 B2 | 4/2005 | Sowden | |
| 6,913,766 B1 | 7/2005 | Krumme et al. | |
| 6,982,094 B2 | 1/2006 | Sowden | |
| 6,991,808 B2 | 1/2006 | Brubaker et al. | |
| 7,182,199 B2 | 2/2007 | Sowden et al. | |
| 7,217,381 B2 | 5/2007 | Sowden | |
| 7,297,345 B2 | 11/2007 | Sowden | |
| 7,323,192 B2 | 1/2008 | Luber et al. | |
| 2001/0001280 A1 | 5/2001 | Dong et al. | |
| 2001/0024678 A1 | 9/2001 | Scott et al. | |
| 2002/0028240 A1 | 3/2002 | Sawada et al. | |
| 2002/0082299 A1 | 6/2002 | Meyer | |
| 2002/0187190 A1 | 12/2002 | Cade et al. | |
| 2003/0015814 A1 | 1/2003 | Krull et al. | |
| 2003/0072799 A1 | 4/2003 | Sowden et al. | |
| 2003/0086973 A1 | 5/2003 | Sowden et al. | |
| 2003/0124183 A1 | 7/2003 | Sowden et al. | |
| 2003/0203016 A1 | 10/2003 | Suwelack | |
| 2003/0224043 A1 | 12/2003 | Appel et al. | |
| 2004/0129174 A1 | 7/2004 | Li et al. | |
| 2004/0166080 A1 | 8/2004 | Assmus et al. | |
| 2005/0008696 A1 | 1/2005 | Sowden et al. | |
| 2005/0147677 A1 | 7/2005 | Sowden | |

FOREIGN PATENT DOCUMENTS

| | | |
|---|---|---|
| DE | 2710307 | 9/1977 |
| DE | 2752971 A | 6/1979 |
| DE | 4025487 A | 2/1992 |
| DE | 19834180 A1 | 2/2000 |
| DE | 19954420 A1 | 5/2001 |
| DE | 19963569 A1 | 7/2001 |
| EP | 0234670 A | 9/1987 |
| EP | 0239983 B1 | 10/1987 |
| EP | 0279682 A | 8/1988 |
| EP | 0320320 A | 6/1989 |
| EP | 0088556 B1 | 9/1989 |
| EP | 0387885 B1 | 9/1990 |
| EP | 0455599 A1 | 11/1991 |
| EP | 0294993 B1 | 12/1991 |
| EP | 0861659 A1 | 2/1992 |
| EP | 0481547 A1 | 4/1992 |
| EP | 0531524 B1 | 3/1993 |
| EP | 0572731 A1 | 12/1993 |
| EP | 0610854 A | 8/1994 |
| EP | 0611032 A1 | 9/1994 |
| EP | 0622408 A | 11/1994 |
| EP | 0646650 A | 4/1995 |
| EP | 0788790 A2 | 2/1996 |
| EP | 0740938 B1 | 11/1996 |
| EP | 0864324 A | 3/1997 |
| EP | 0771533 B1 | 7/1997 |
| EP | 0619854 B1 | 3/1998 |
| EP | 0834516 B1 | 4/1998 |
| EP | 0875245 A | 11/1998 |
| EP | 0950402 B1 | 2/1999 |

(56) References Cited

FOREIGN PATENT DOCUMENTS

| | | |
|---|---|---|
| EP | 0963836 A1 | 12/1999 |
| EP | 1029892 | 8/2000 |
| EP | 1077065 A1 | 2/2001 |
| FR | 1603314 A | 4/1971 |
| FR | 2604904 | 4/1988 |
| GB | 759081 A | 10/1956 |
| GB | 866681 A | 4/1961 |
| GB | 994742 | 5/1961 |
| GB | 888038 | 1/1962 |
| GB | 936386 | 9/1963 |
| GB | 1144915 | 3/1969 |
| GB | 1227837 A | 4/1971 |
| GB | 1235926 A | 6/1971 |
| GB | 1372040 | 10/1974 |
| GB | 1464388 | 2/1977 |
| GB | 1510772 | 5/1978 |
| GB | 2182559 A | 5/1987 |
| GB | 2197778 A | 6/1988 |
| GB | 2284760 A | 6/1995 |
| JP | 37-2644 | 1/1960 |
| JP | 52119474 * | 10/1977 |
| JP | 03261719 A | 11/1991 |
| JP | 04008288 | 1/1992 |
| JP | 07-116228 | 5/1995 |
| JP | 08245372 A | 9/1996 |
| JP | 2001-072579 | 6/1999 |
| JP | 2000197997 * | 7/2000 |
| NL | 8602556 | 5/1988 |
| WO | WO93/13758 | 7/1993 |
| WO | WO94/06416 A1 | 3/1994 |
| WO | WO9407470 A1 | 4/1994 |
| WO | WO95/02396 A1 | 1/1995 |
| WO | WO95/15156 A1 | 6/1995 |
| WO | WO96/07401 A | 3/1996 |
| WO | WO97/06695 A1 | 2/1997 |
| WO | WO97/15293 A2 | 5/1997 |
| WO | WO98/20870 A1 | 5/1998 |
| WO | WO99/00122 A1 | 1/1999 |
| WO | WO99/02136 A1 | 1/1999 |
| WO | WO99/20745 | 4/1999 |
| WO | WO99/22769 A1 | 5/1999 |
| WO | WO99/32092 A1 | 7/1999 |
| WO | WO99/51209 A1 | 10/1999 |
| WO | WO99/56730 A1 | 11/1999 |
| WO | WO99/62496 A1 | 12/1999 |
| WO | WO00/18447 A | 4/2000 |
| WO | WO0025755 A1 | 5/2000 |
| WO | WO00/40223 | 7/2000 |
| WO | WO00/61110 | 10/2000 |
| WO | WO2001000179 | 1/2001 |
| WO | WO01/15889 A1 | 3/2001 |
| WO | WO01/21155 A1 | 3/2001 |
| WO | WO01/26633 A1 | 4/2001 |
| WO | WO01/26634 A1 | 4/2001 |
| WO | WO01/32150 | 5/2001 |
| WO | WO01/43943 A | 6/2001 |
| WO | WO01/56550 A1 | 8/2001 |
| WO | WO02/19833 A | 3/2002 |
| WO | WO03/000293 A | 1/2003 |
| WO | WO03/020246 A1 | 3/2003 |
| WO | WO03/028619 A2 | 4/2003 |

OTHER PUBLICATIONS

Daoudal, J.; "Appetising tablet for domestic animals . . . "; "Tablet for domestic animal" EP0320320A2; Jun. 14, 1999; Derwent World Patents Index, Dialog File No. 351 Accession No. 7909478; Derwent Information Ltd. Abstract.

Eith, L., et al., "Injection-Moulded Drug-Delivery Systems", Manufacturing Chemist (Jan. 1987), pp. 21-25.

C. De Brabander et al., "Matrix mini-tablets based on starch/microcrystalline wax mixtures" International Journal of Pharmaceutics, Netherlands Apr. 20, 2000, vol. 199, No. 2, pp. 195-203 XP002233674.

Catellani et al. Internation Journal of Pharmaceutics vol. 88(1992) 285-291 "Centrifugal die filling system in a new rotary tablet machine."

Cuff & Rauf Pharm Tech Jun. 1998 96-106 "A Preliminary Evaluation of Injection Molding as a Technology to Produce Tablets."

Grove, R. "Tips for Chocolate Liqueur Cherries", Candy Industry, Nov. 1994, p. 23.

Hawleys Condensed Chemical Dictionary, 12th Edition, 1993, pp. 960-921.

http://www.espi-metals.com/tech/mesh.htm. accessed May 14, 2009.

Lachman, Leon et al., "Chapter II-Tablets", The Theory and Practice of Industrial Pharmacy, (1996), pp. 293-345.

Leiberman et al. Pharmaceutical Dosage Forms-Tablets, vol. 2, 2nd ed., Marcel Dekker Inc., 1990, pp. 213-217, 327-329.

Patent Abstracts of Japan vol. 012, No. 091 (M-679) Mar. 24, 1988 & JP62230600A (Kyowa Hakko Kogyo Co Ltd.) Oct. 9, 1987 abstract.

Patent Abstracts of Japan vol. 007, No. 050(M-197) Feb. 26, 1983 & JP 0617096A (Yoshitsuka Seikl:KK) Dec. 8, 1982 abstract.

Patent Abstracts of Japan vol. 018, No. 514 (M-1680) Sep. 28, 1994 & JP 0617096A (Kao Corp) Jun. 28, 1994 abstract.

Repin J.A. et al; "Injection moulding machine for mass production . . . " "Jet moulding machine for products from thermoplastic polymer materials" DE2752971A1; Jun. 7, 1979; Drewent World Patents Index; Dialog File No. 351 Accession No. 2236199; Derwent Information Ltd. Abstract.

Rosato, Domminick & Donald, "Injection Molding Handbook", The Complete Molding Operation Technology, Performance, Economics (1986), pp. 189-191 & 794-795.

Websters II, New College Dictionary p. 691, Sep. 2004.

Translation of Japanese Examiners Notification of Reasons for Refusal, Mar. 14, 2006.

The Elizabeth Companies Tablet Design Training Manual (Elizabeth Carbide Die Co., Inc., p. 7 (McKeesport, PA), Jul. 2003.

Uhlherr, PHT, et al., "Static Measurement of Yield Stress Using a Cylindrical Penetrometer," Korea-Australia Rheology, Journal, vol. 14, No. 1, Mar. 2002, pp. 17-23.

* cited by examiner

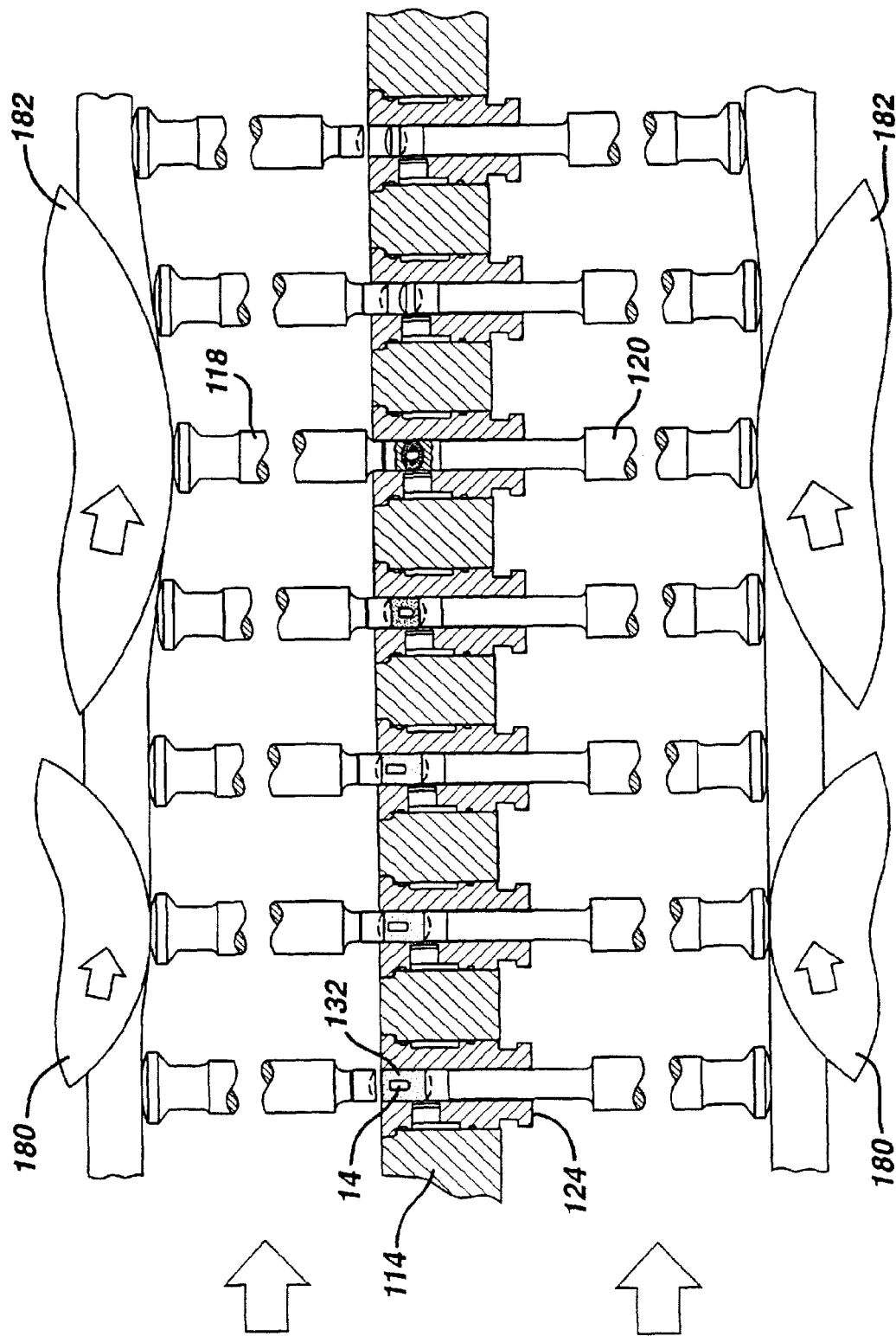

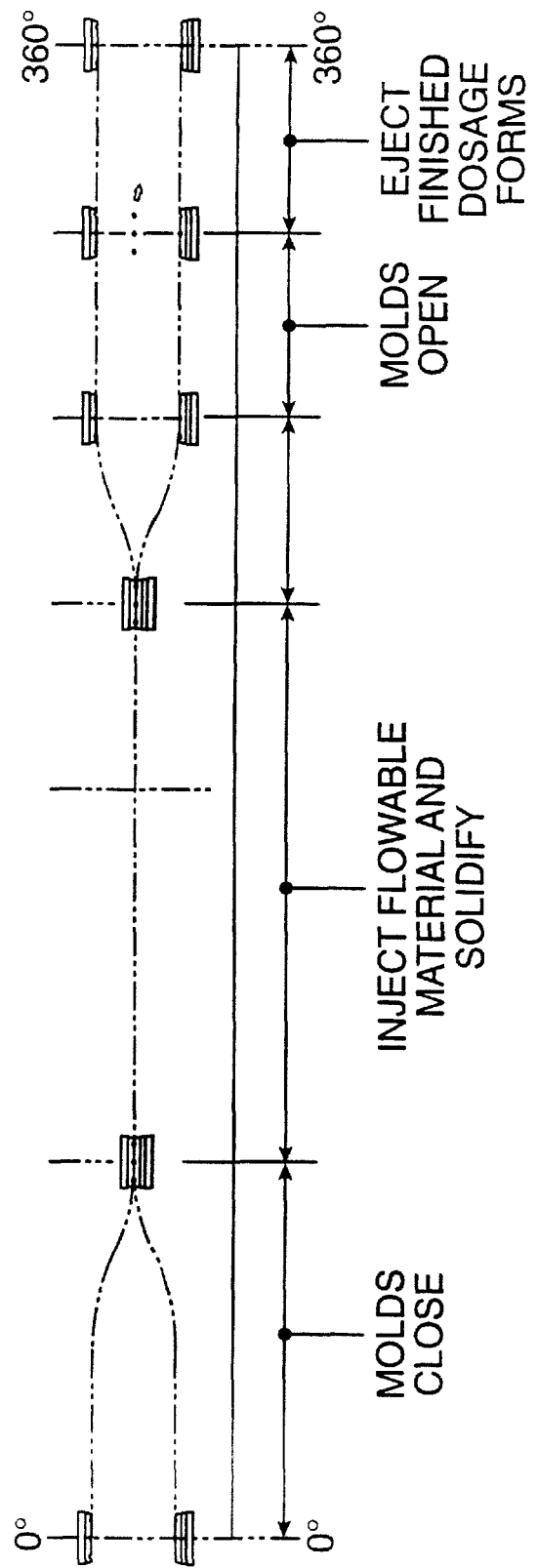

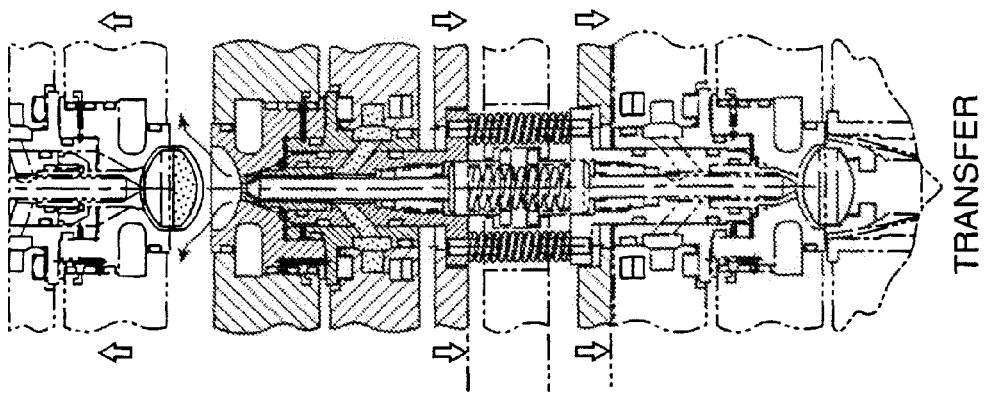
FIG. 50 TRANSFER
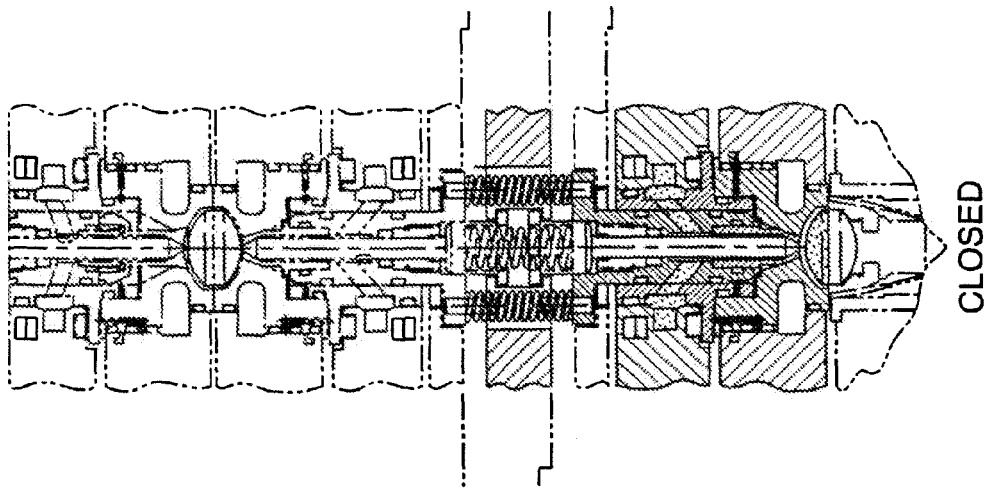
FIG. 49 CLOSED
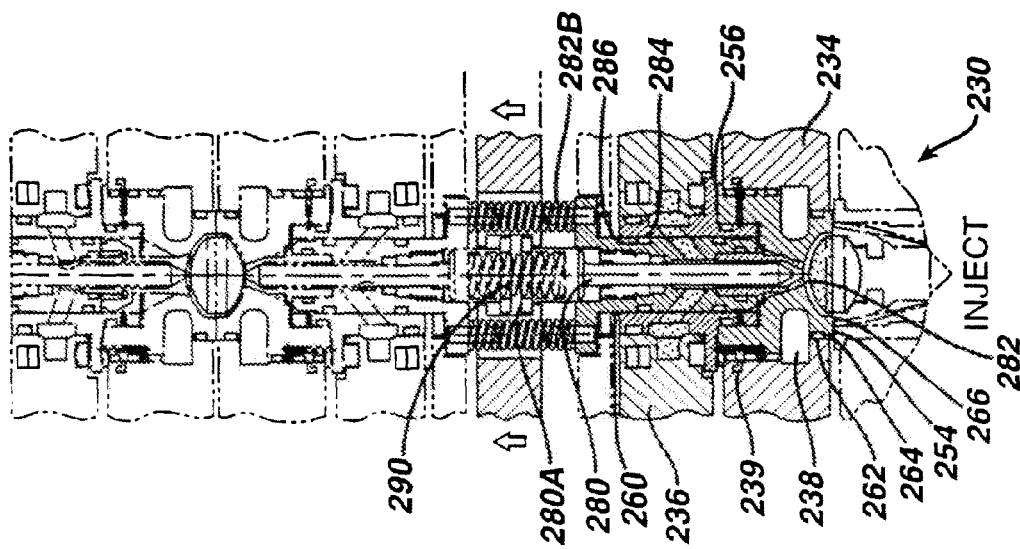
FIG. 48 INJECT

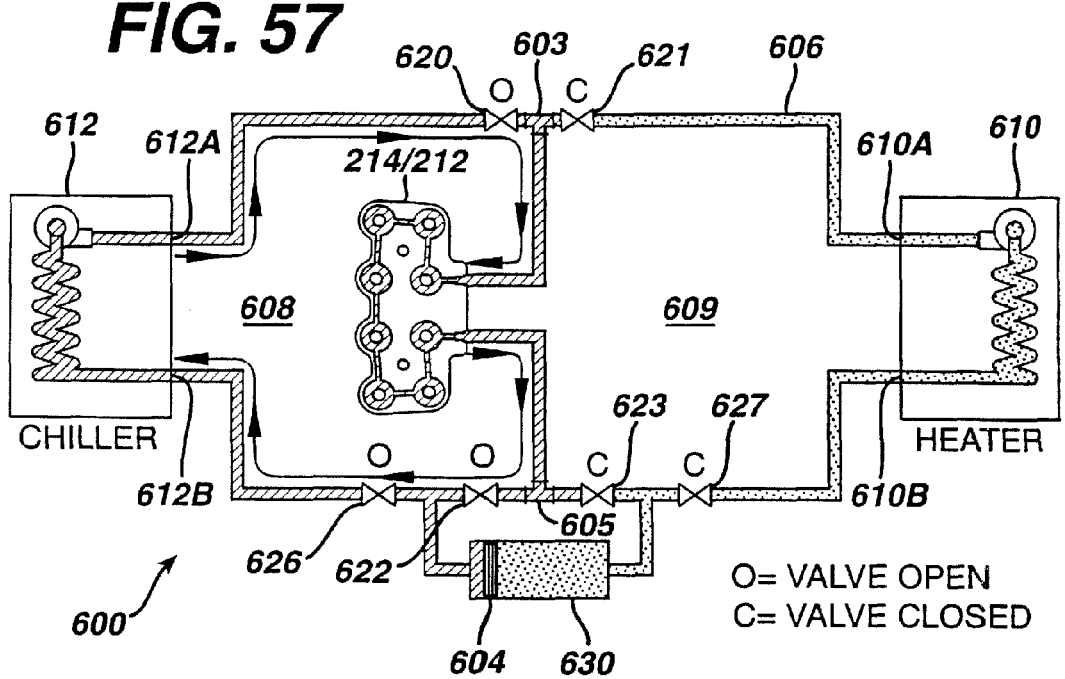
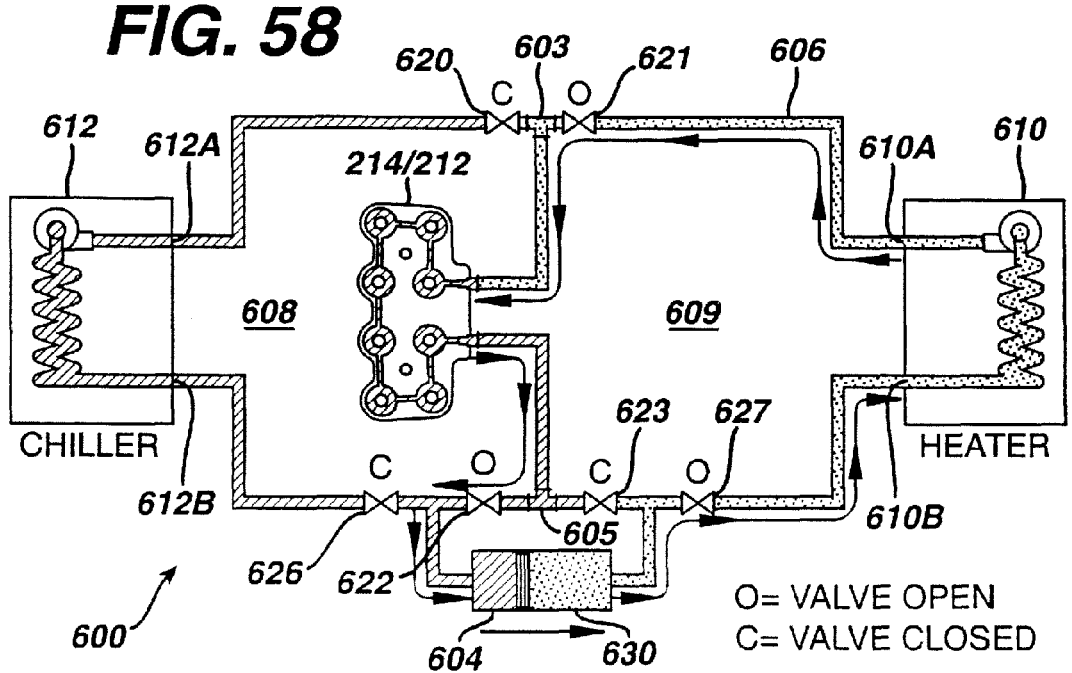

O = VALVE OPEN
C = VALVE CLOSED

O = VALVE OPEN
C = VALVE CLOSED

O = VALVE OPEN
C = VALVE CLOSED

O = VALVE OPEN
C = VALVE CLOSED

O = VALVE OPEN
C = VALVE CLOSED

O = VALVE OPEN
C = VALVE CLOSED

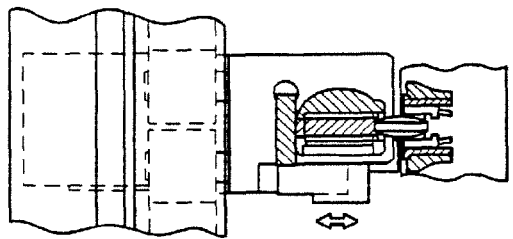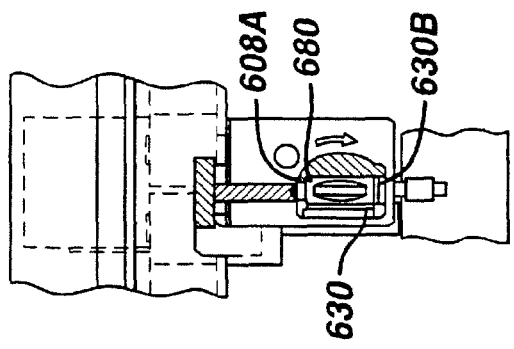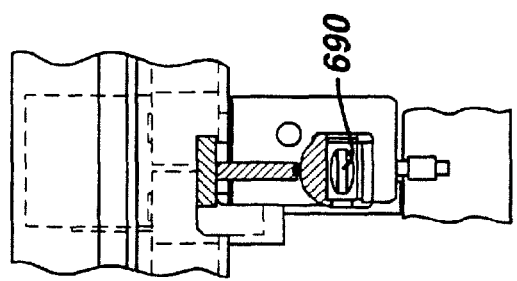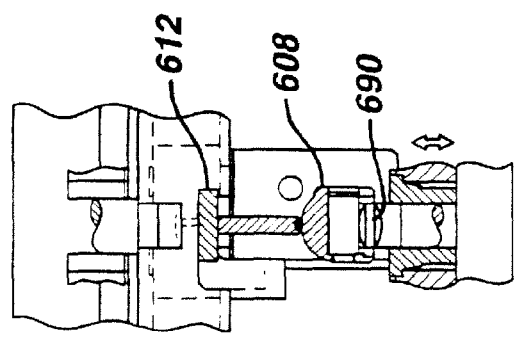

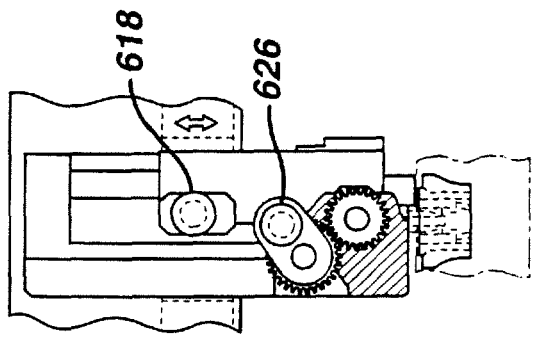
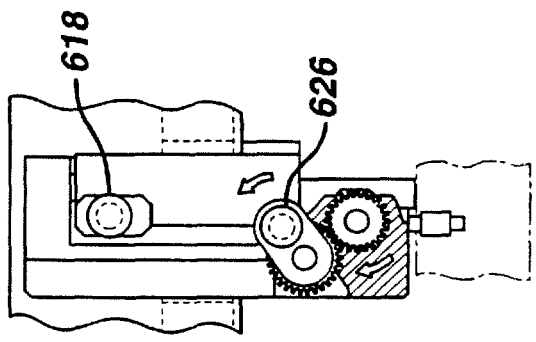
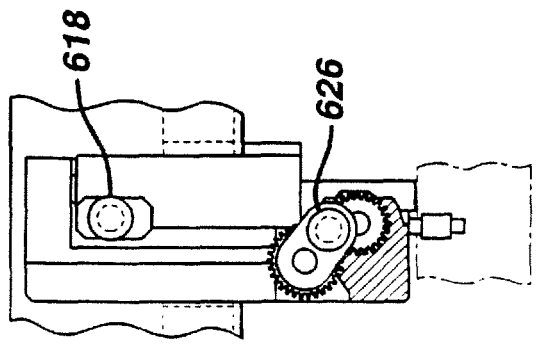

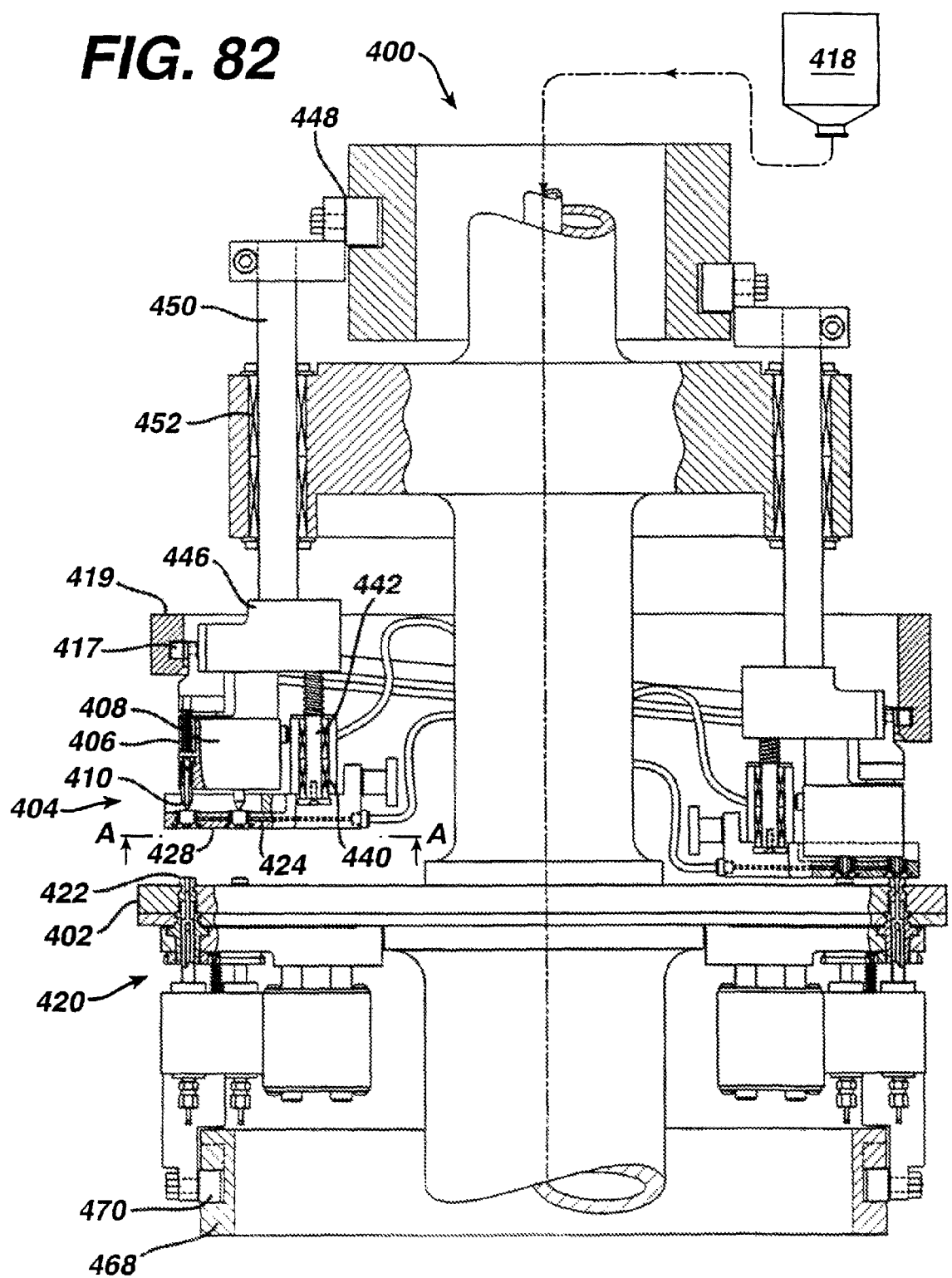

US 8,673,190 B2

METHOD FOR MANUFACTURING DOSAGE FORMS

This application is a divisional of U.S. Ser. No. 10/911,263 filed Aug. 4, 2004, U.S. Pat. No. 8,114,328, which is a continuation of U.S. Ser. No. 09/966,497 filed Sep. 28, 2001, now U.S. Pat. No. 7,122,143, the complete disclosures of which are hereby incorporated by reference herein for all purposes.

FIELD OF THE INVENTION

This invention relates generally to systems, methods and apparatuses for manufacturing dosage forms, and to dosage forms made using such systems, methods and apparatuses.

BACKGROUND OF THE INVENTION

A variety of dosage forms, such as tablets, capsules and gelcaps are known in the pharmaceutical arts. Tablets generally refer to relatively compressed powders in various shapes. One type of elongated, capsule-shaped tablet is commonly referred to as a "caplet." Capsules are typically manufactured using a two piece gelatin shell formed by dipping a steel rod into gelatin so that the gelatin coats the end of the rod. The gelatin is hardened into two half-shells and the rod extracted. The hardened half-shells are then filled with a powder and the two halves joined together to form the capsule. (See generally, HOWARD C. ANSEL ET AL., *Pharmaceutical Dosage Forms and Drug Delivery Systems* (7th Ed. 1999).)

Gelatin-coated tablets, commonly known as geltabs and gelcaps, are an improvement on gelatin capsules and typically comprise a tablet coated with a gelatin shell. Several well known examples of gelcaps are McNeil Consumer Healthcare's acetaminophen based products sold under the trade name Tylenol®. U.S. Pat. Nos. 4,820,524; 5,538,125; 5,228,916; 5,436,026; 5,679,406; 5,415,868; 5,824,338; 5,089,270; 5,213,738; 5,464,631; 5,795,588; 5,511,361; 5,609,010; 5,200,191; 5,459,983; 5,146,730; 5,942,034 describe geltabs and gelcaps and methods and apparatuses for making them. Conventional methods for forming gelcaps are generally performed in a batchwise manner using a number of stand alone machines operating independently. Such batch processes typically include the unit operations of granulating, drying, blending, compacting (e.g., in a tablet press), gelatin dipping or enrobing, drying, and printing.

Unfortunately, these processes have certain drawbacks. For example, because these systems are batch processes, each of the various apparatuses employed is housed in a separate clean room that must meet FDA standards. This requires a relatively large amount of capital in terms of both space and machinery. A process that would increase and streamline production rates would therefore provide many economic benefits including a reduction in the size of facilities needed to mass produce pharmaceutical products. Generally, it would be desirable to create a continuous operation process, as opposed to a batch process, for formation of gelcaps and other dosage forms.

Furthermore, gel dipping and drying operations are in general relatively time consuming. Thus, a process that simplifies the gelatin coating operation in particular and reduces drying time would also be advantageous.

Current equipment for making gelcaps and geltabs is designed to produce these forms only according to precise specifications of size and shape. A more versatile method and apparatus, which could be used to produce a variety of dosage forms to deliver pharmaceuticals, nutritionals, and/or confections, would therefore also be advantageous.

Accordingly, applicants have now discovered that a wide variety of dosage forms, including compressed tablets, gelcaps, chewable tablets, liquid fill tablets, high potency dosage forms, and the like, some of which in and of themselves are novel, can be made using unique operating modules. Each operating module performs distinct functions, and therefore may be used as a stand alone unit to make certain dosage forms. Alternatively, two or more of the same or different operating modules may be linked together to form a continuous process for producing other dosage forms. In essence, a "mix and match" system for the production of dosage forms is provided by the present invention. Preferably, the operating modules may be linked together as desired to operate as a single continuous process.

SUMMARY OF THE INVENTION

In a first embodiment, the invention provides a method of making dosage forms, comprising the steps of: a) compressing a powder into a compressed dosage form in a compression module; b) transferring said compressed dosage form to a thermal cycle molding module; c) molding a flowable material around said compressed dosage form in said thermal cycle molding module; and d) hardening said flowable material so as to form a coating over said compressed dosage form; wherein steps (a) through (d) are linked together such that essentially no interruption occurs between said steps.

The invention also provides a method of making dosage forms, comprising the steps of: a) compressing a first powder into a compressed dosage form in a first compression module; b) transferring said compressed dosage form to a thermal cycle molding module; c) molding a flowable material around said compressed dosage form in said thermal cycle molding module; d) hardening said flowable material so as to form a coating over said compressed dosage form; e) transferring said coated compressed dosage form to a second compression module; and f) compressing a second powder around said coated compressed dosage form in said second compression module to form a compressed, coated, compressed dosage form; wherein steps (a) through (f) are linked together such that essentially no interruption occurs between said steps.

The invention further provides a method of making a dosage form, comprising the steps of: a) forming an insert; b) transferring said insert to a thermal cycle molding module; c) molding a flowable material around said insert in said thermal cycle molding module; and d) hardening said flowable material so as to form a coating over said insert; wherein steps (a) through (d) are linked together such that essentially no interruption occurs between said steps.

The invention further provides a method of making a dosage form, comprising the steps of: a) forming at least two inserts; b) transferring said inserts to a thermal cycle molding module; c) molding a flowable material around said inserts in said thermal cycle molding module; and d) hardening said flowable material so as to form a coating over said inserts to form a dosage form comprising at least two inserts surrounded by a coating; wherein steps (a) through (d) are linked together such that essentially no interruption occurs between said steps.

The invention also provides a method of making dosage forms, comprising the steps of: a) forming an insert; b) transferring said insert to a compression module; c) compressing a powder around said insert into a compressed dosage form in a compression module; wherein steps (a) through (c) are linked together such that essentially no interruption occurs between said steps.

The invention also provides a linked apparatus for making dosage forms containing a medicant, comprising: a) a compression module having means for forming compressed dosage forms by compressing a powder containing said medicant; b) a transfer device having means for continuously transferring said compressed dosage forms from said compression module to a thermal cycle molding module; and c) a thermal cycle molding module having means for continuously molding a coating of flowable material over said compressed dosage forms.

The invention further provides an apparatus for making dosage forms containing a medicant, comprising: a) a first rotor comprising a plurality of die cavities disposed around the circumference thereof so as to be carried around a first circular path by said rotor, each of said die cavities having an opening for receiving powder and at least one punch mounted for displacement into said die cavity, whereby displacement of said punch into said die cavity compresses powder contained in said die cavity into a compressed dosage form; b) a second rotor comprising a plurality of mold cavities disposed around the circumference thereof so as to be carried around a second circular path by said second rotor, each of said mold cavities capable of enclosing at least a portion of a compressed dosage form and capable of receiving flowable material so as to coat said portion of said compressed dosage form enclosed by said mold cavity; and c) a transfer device for transferring compressed dosage forms from said first rotor to said second rotor, said transfer device comprising a plurality of transfer units guided around a third path, a first portion of said third path being coincident with said first circular path and a second portion of said third path being coincident with said second circular path.

The invention also provides a method of forming compressed dosage forms, comprising: a) placing a supply of powder in flow communication with a die, said die comprising a die cavity therein in flow communication with a filter; b) applying suction to said die cavity so as to cause powder to flow into said die cavity, said suction being applied to said die cavity through said filter; c) isolating said filter from said powder in said die cavity; and d) compressing said powder in said die cavity so as to form a compressed dosage form while said filter is isolated therefrom.

The invention also provides an apparatus for forming compressed dosage forms, comprising: a) a suction source; b) a die cavity having (i) a first port for placing said die cavity in flow communication with said suction source, whereby said suction source applies suction to said die cavity, and (ii) a second port for placing said die cavity in flow communication with a supply of powder, whereby said suction source assists said powder in flowing into said die cavity; (c) a filter disposed between said suction source and said second port, whereby suction is applied to said die cavity through said filter; and (d) a punch for compressing said powder in said die cavity so as to form said compressed dosage forms.

The invention also provides an apparatus for forming compressed dosage forms from a powder, comprising a) a die table having a plurality of die cavities therein, said die cavities being arranged in multiple, concentric rows around the perimeter of said die table; b) punches aligned with and insertable into said die cavities for compressing said powder into compressed dosage forms in each of said die cavities; and c) rollers aligned with each of said concentric rows of die cavities for pressing said punches into said die cavities, each roller being sized such that the dwell time under compression of all of said punches is equal.

The invention also provides a rotary compression module for forming compressed dosage forms from a powder, comprising a) a single fill zone; b) a single compression zone; c) a single ejection zone; d) a circular die table having a plurality of die cavities therein; and e) punches aligned with and insertable into said die cavities for compressing said powder into compressed dosage forms in each of said die cavities; wherein the number of die cavities in said module is greater than the maximum number of die cavities that can be arranged in a single circle around the circumference of a similar die table having the same diameter as the circular die table, and wherein the dwell time under compression of all of said punches is equal.

The invention further provides compressed dosage forms made from a powder having a minimum orifice diameter of flowablility greater than about 10 mm as measured by the Flowdex test, the relative standard deviation in weight of said compressed dosage forms being less than about 2%, and made using a linear velocity at the die of at least about 230 cm/sec.

The invention also provides compressed dosage forms made from a powder having a minimum orifice diameter of flowablility greater than about 15 mm as measured by the Flowdex test, the relative standard deviation in weight of said compressed dosage forms being less than about 2%, and made using a linear velocity at the die of at least about 230 cm/sec.

The invention also provides compressed dosage forms made from a powder having a minimum orifice diameter of flowablility greater than about 25 mm as measured by the Flowdex test, the relative standard deviation in weight of said compressed dosage forms being less than about 2%, and made using a linear at the die velocity of at least about 230 cm/sec.

The invention also provides compressed dosage forms made from a powder having a minimum orifice diameter of flowablility greater than about 10 mm as measured by the Flowdex test, the relative standard deviation in weight of said compressed dosage forms being less than about 1%, and made using a linear velocity at the die of at least about 230 cm/sec.

The invention also provides compressed dosage forms made from a powder having a minimum orifice diameter of flowablility greater than about 10 mm as measured by the Flowdex test, the relative standard deviation in weight of said compressed dosage forms being less than about 2%, and made using a linear velocity at the die of at least about 115 cm/sec.

The invention also provides compressed dosage forms made from a powder having an average particle size of about 50 to about 150 microns and containing at least about 85 percent by weight of a medicant, the relative standard deviation in weight of said compressed dosage forms being less than about 1%.

The invention also provides compressed dosage forms containing at least about 85 percent by weight of a medicant and being substantially free of water soluble polymeric binders, the relative standard deviation in weight of said compressed dosage forms being less than about 2%.

The invention also provides compressed dosage forms containing at least about 85 percent by weight of a medicant and being substantially free of water soluble polymeric binders, the relative standard deviation in weight of said compressed dosage forms being less than about 1%.

The invention also provides compressed dosage forms containing at least about 85 percent by weight of a medicant selected from the group consisting of acetaminophen, ibuprofen, flurbiprofen, ketoprofen, naproxen, diclofenac, aspirin, pseudoephedrine, phenylpropanolamine, chlorpheniramine maleate, dextromethorphan, diphenhydramine, famotidine, loperamide, ranitidine, cimetidine, astemizole, terfenadine, fexofenadine, loratadine, cetirizine, antacids, mixtures thereof and pharmaceutically acceptable salts thereof, and being substantially free of water soluble polymeric binders, the relative standard deviation in weight of said compressed dosage forms being less than about 2%.

The invention also provides compressed dosage forms containing at least about 85 percent by weight of a medicant and being substantially free of hydrated polymers, the relative standard deviation in weight of said compressed dosage forms being less than about 2%.

The invention also provides compressed dosage forms containing at least about 85 percent by weight of a medicant and being substantially free of hydrated polymers, the relative standard deviation in weight of said compressed dosage forms being less than about 1%.

The invention also provides compressed dosage forms containing at least about 85 percent by weight of a medicant selected from the group consisting of acetaminophen, ibuprofen, flurbiprofen, ketoprofen, naproxen, diclofenac, aspirin, pseudoephedrine, phenylpropanolamine, chlorpheniramine maleate, dextromethorphan, diphenhydramine, famotidine, loperamide, ranitidine, cimetidine, astemizole, terfenadine, fexofenadine, loratadine, cetirizine, antacids, mixtures thereof and pharmaceutically acceptable salts thereof, and being substantially free of hydrated polymers, the relative standard deviation in weight of said compressed dosage forms being less than about 2%.

The invention also provides a method of making a dosage form containing a first medicant, which comprises a) injecting through a nozzle a flowable material containing said first medicant into a mold cavity; and b) hardening said flowable material into a molded dosage form having a shape substantially the same as the mold cavity.

The invention provides a method of making a molded dosage form which comprises a) heating a flowable material; b) injecting said flowable material through an orifice into a mold cavity; and c) hardening said flowable material into a molded dosage form having a shape substantially the same as the mold cavity; wherein said hardening step (c) comprises cooling said flowable material and wherein said mold cavity is heated prior to said injecting step (b) and cooled during said hardening step (c).

The invention also provides a method of coating a substrate, comprising the steps of: a) enclosing at least a portion of said substrate in a mold cavity; b) injecting a flowable material into said mold cavity so as to coat at least a portion of said substrate with said flowable material; and c) hardening said flowable material to form a coating over at least a portion of said substrate.

The invention also provides a method of applying at least one flowable material to a substrate having first and second portions comprising: masking said first portion of said substrate; exposing said second portion to a mold cavity; injecting said flowable material onto said second portion; and hardening said flowable material on said second portion of said substrate.

The invention also provides a method of applying at least one flowable material to a substrate having first and second portions comprising: exposing said first portion to a first mold cavity; injecting said flowable material onto said first portion; hardening said flowable material on said first portion of said substrate; retaining said first portion in said first mold cavity.

The invention provides a method of coating a substrate with first and second flowable materials, comprising the steps of: a) enclosing a first portion of said substrate in a first mold cavity; b) injecting a first flowable material into said first mold cavity so as to coat said first portion with said first flowable material; c) hardening said first flowable material to form a coating over said first portion; d) enclosing a second portion of said substrate in a second mold cavity; e) injecting a second flowable material into said second mold cavity so as to coat said second portion with said second flowable material; and f) hardening said second flowable material to form a coating over said second portion.

The invention provides an apparatus for molding substrates comprising a plurality of mold cavities, each mold cavity having an internal surface and comprising an orifice for delivering flowable material to said mold cavity, said orifice being matable with a valve tip that in its closed position forms part of said internal surface.

The invention also provides an apparatus for molding substrates comprising a plurality of mold cavities, a heat source, a heat sink, and a temperature control system, said temperature control system comprising a tubing system disposed proximal to said mold cavities and connected to said heat source and said heat sink for circulating heat transfer fluid through said heat source, through said heat sink, and proximal to said mold cavities, such that said mold cavities may be heated and cooled by said heat transfer fluid.

The invention also provides a nozzle system for a molding apparatus, comprising a nozzle and an ejector means, said nozzle surrounding and being concentric with said ejector means.

The invention provides an apparatus for coating compressed dosage forms, comprising: a) a mold cavity for enclosing at least a first portion of said compressed dosage form; b) means for injecting a flowable material into said mold cavity to coat at least said first portion of said compressed dosage form with said flowable material; and c) means for hardening said flowable material so as to form a coating over at least said first portion said compressed dosage form.

The invention also provides an apparatus for coating a compressed dosage form having a first portion and a second portion, comprising: a) a mold cavity for enclosing said first portion of said compressed dosage form; b) a nozzle for injecting a flowable material into said mold cavity to coat said first portion of said compressed dosage form with said flowable material; c) a temperature control system capable of heating and cooling said mold cavity; and d) an elastomeric collet for sealing said second portion of said compressed dosage form while said first portion of said compressed dosage form is being coated.

The invention also provides a molding module for molding coatings onto compressed dosage forms, comprising a rotor capable of rotating about a central axis and a plurality of mold units mounted thereon, each mold unit comprising: a) a mold cavity for enclosing at least a first portion of said compressed dosage form; b) means for injecting a flowable material into said mold cavity to coat at least said first portion of said compressed dosage form with said flowable material; and c) means for hardening said flowable material so as to form a coating over at least said first portion said compressed dosage form.

The invention also provides a molding module for coating a compressed dosage form having a first portion and a second portion, comprising a rotor capable of rotating about a central axis and a plurality of mold units mounted thereon, each mold unit comprising: a) a mold cavity for enclosing said first portion of said compressed dosage form; b) a nozzle for injecting a flowable material into said mold cavity to coat said first portion of said compressed dosage form with said flowable material; c) a temperature control system capable of heating and cooling said mold cavity; and d) an elastomeric collet for sealing said second portion of said compressed dosage form while said first portion of said compressed dosage form is being coated.

The invention also provides an apparatus for coating compressed dosage forms, comprising: a) a lower retainer comprising a plurality of collets mounted therein; b) a center mold assembly comprising first and second groups of insert assemblies mounted on opposing sides thereof, each of said insert assemblies of said first group aligned with and facing one of said collets, said lower retainer and said center mold assembly mounted for relative movement so as to bring said first group of insert assemblies into engagement with said collets; c) an upper mold assembly comprising upper insert assemblies mounted therein, each of said upper insert assemblies aligned with and facing one of said insert assemblies of said second group, said upper mold assembly and said center mold assembly mounted for relative movement so as to bring said upper insert assemblies into engagement with said second group of insert assemblies; d) a supply of flowable material; and e) a first passage placing said supply of flowable material in flow communication with said first and second group of insert assemblies, and a valve actuator assembly for controlling the flow of said flowable material to said first and second groups of insert assemblies.

The invention also provides a dosage form comprising a substrate having an injection molded coating surrounding at least a portion of the substrate.

The invention also provides a dosage form comprising a substrate having a thermal cycle molded material disposed on at least a portion of the substrate.

The invention also provides a dosage form comprising a substrate having a coating thereon, said coating having a thickness of about 100 to about 400 microns; the relative standard deviation in thickness of said coating being less than 30%; wherein said coating is substantially free of humectants.

The invention also provides a dosage form comprising a tablet having a coating thereon, said coating having a thickness of about 100 to about 400 microns, wherein the relative standard deviation in thickness of said dosage form is not more than about 0.35%; and wherein said coating is substantially free of humectants.

The invention also provides an apparatus for transferring substrates from a first location to a second location, comprising: a) a flexible conveying means; b) a plurality of transfer units mounted to said conveying means, said transfer units being capable of holding said substrates; c) a cam track defining a path between said first and second locations; and d) means for driving said conveying means along said cam track.

The invention also provides an apparatus for transferring substrates from a first operating module comprising a first rotor adapted to carry said substrates around a first circular path to a second operating module comprising a second rotor adapted to carry said substrates around a second circular path, said apparatus comprising a flexible conveying means traversing a third path, a first portion of said third path being coincident with a portion of said first circular path and a second portion of said third path being coincident with a portion of said second circular path.

The invention also provides a method for making an insert, comprising the steps of: a) injecting a starting material in flowable form comprising a medicant and a thermal setting material into a molding chamber having a shape; b) solidifying said starting material so as to form a solid insert having the shape of said molding chamber; and c) ejecting said solid insert from said molding chamber, wherein said steps occur during rotation of said molding chambers about a central axis.

The invention provides an apparatus for molding substrates from a starting material in flowable form, comprising a plurality of molding chambers and a plurality of nozzles aligned with said molding chambers, said molding chambers and said nozzles mounted on a rotor capable of rotation about a central axis, said nozzles being displaceable in a direction parallel to said central axis, such that as said rotor rotates, said nozzles engage and disengage said molding chambers.

The invention also provides a dosage form comprising a medicant, said dosage form prepared by molding a flowable material, said dosage form having no more than one axis symmetry and being substantially free visible defects.

BRIEF DESCRIPTION OF THE DRAWINGS

FIG. 16 is a view taken along an arc of the compression module during compression.

FIGS. 26A-C illustrate one embodiment of a thermal cycle molding module according to the invention in which dosage forms per se are made.

FIGS. 48-50 are cross-sectional views of a preferred nozzle system of a center mold assembly.

FIGS. 57-59 depict another embodiment of a temperature control system for the thermal cycle molding module.

FIGS. 81A-G illustrate operation of a rotational transfer device according to the invention, FIGS. 81E, 81F, and 81G being rear views of FIGS. 81B, 81C, and 81D, respectively.

FIG. 82 is a side view of a thermal setting molding module according to the invention.

DESCRIPTION OF PREFERRED EMBODIMENTS

Overview

The methods, systems, and apparatuses of this invention can be used to manufacture conventional dosage forms, having a variety of shapes and sizes, as well as novel dosage forms that could not have been manufactured heretofore using conventional systems and methods. In its most general sense, the invention provides: 1) a compression module for making compressed dosage forms from compressible powders, 2) a thermal cycle molding module for making molded dosage forms, or for applying a coating to a substrate, 3) a thermal setting molding module for making molded dosage forms, which may take the form of inserts for dosage forms, 4) a transfer device for transferring dosage forms from one module to another, and 5) a process for making dosage forms comprising at least two of the above modules linked together, preferably via the transfer device. Such process may be run on a continuous or indexing basis.

Figure 1A:
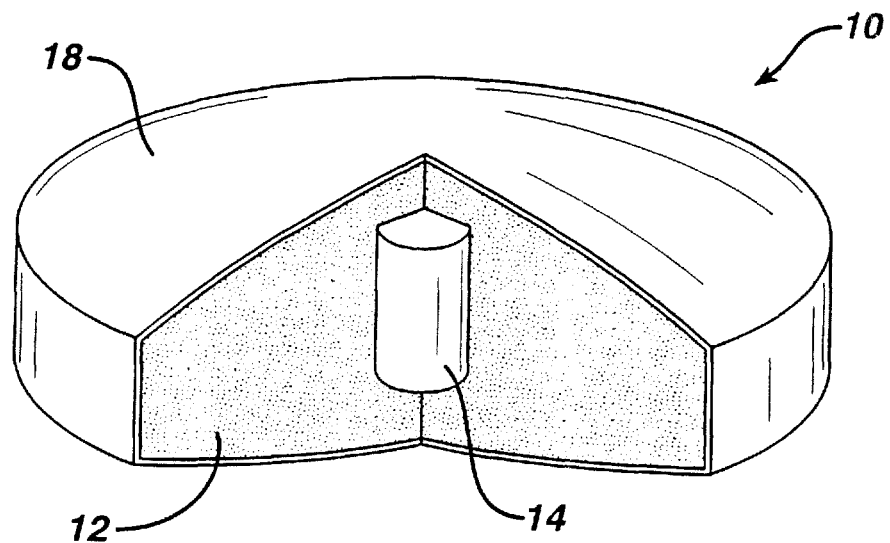
FIGS. 1A and 1B are examples of dosage forms made according to the invention.
Figure 1B:
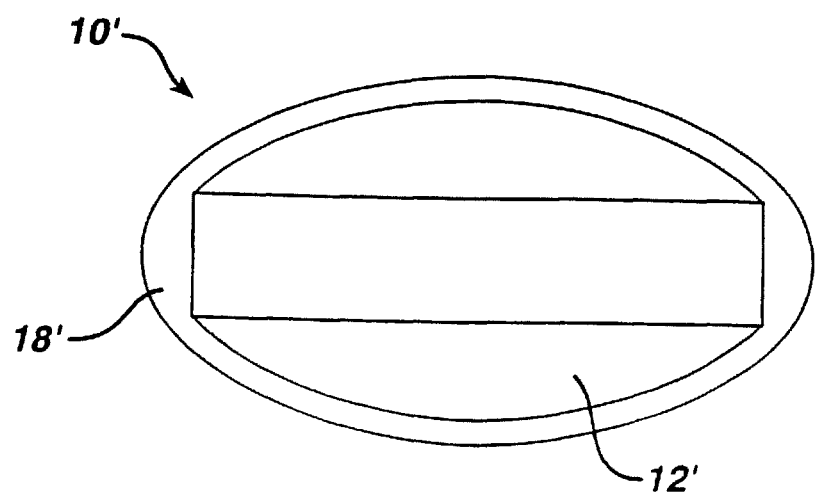
Figure 2:
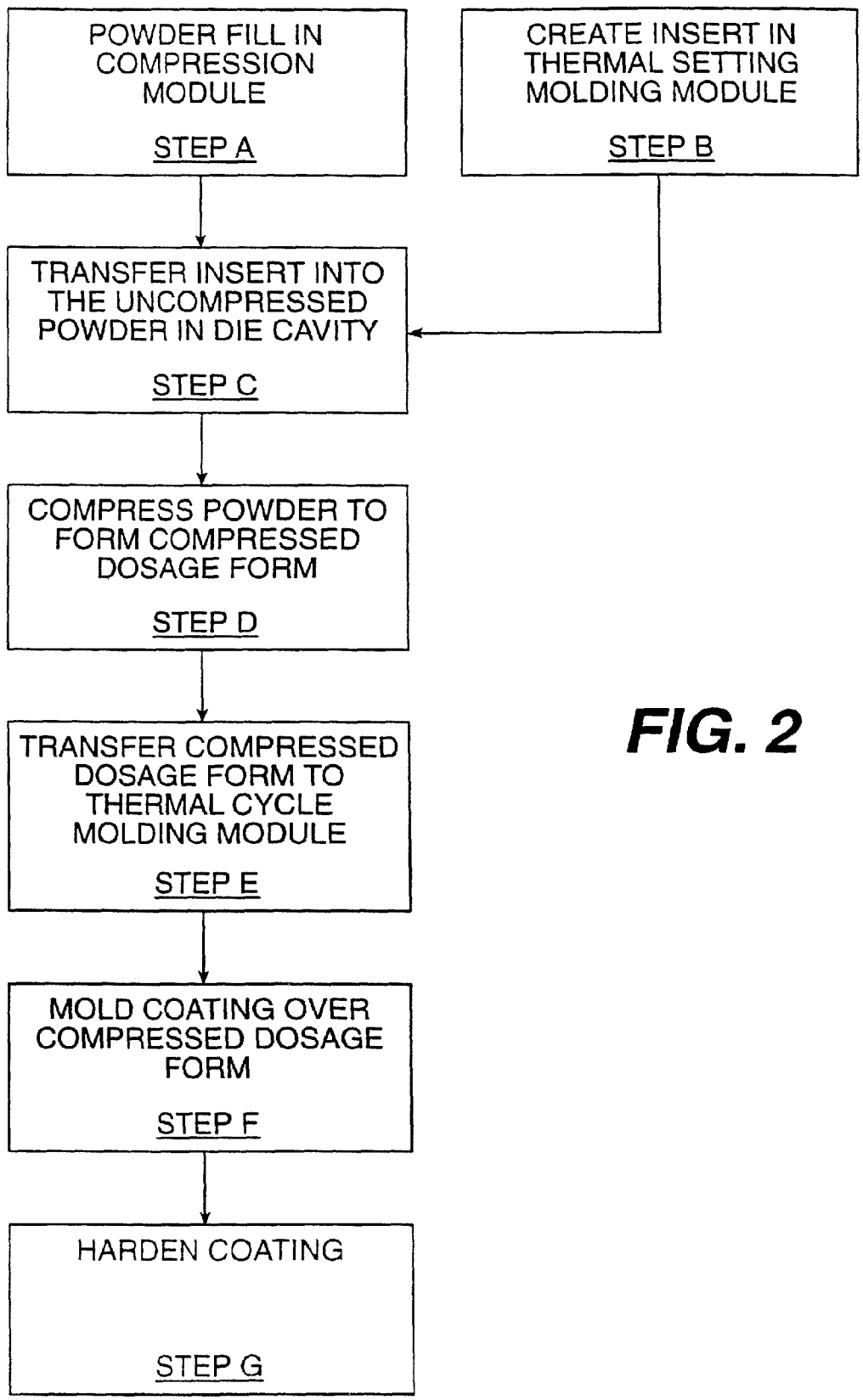
FIG. 2 is a flow chart of an embodiment of the method of the invention.
Figure 3:
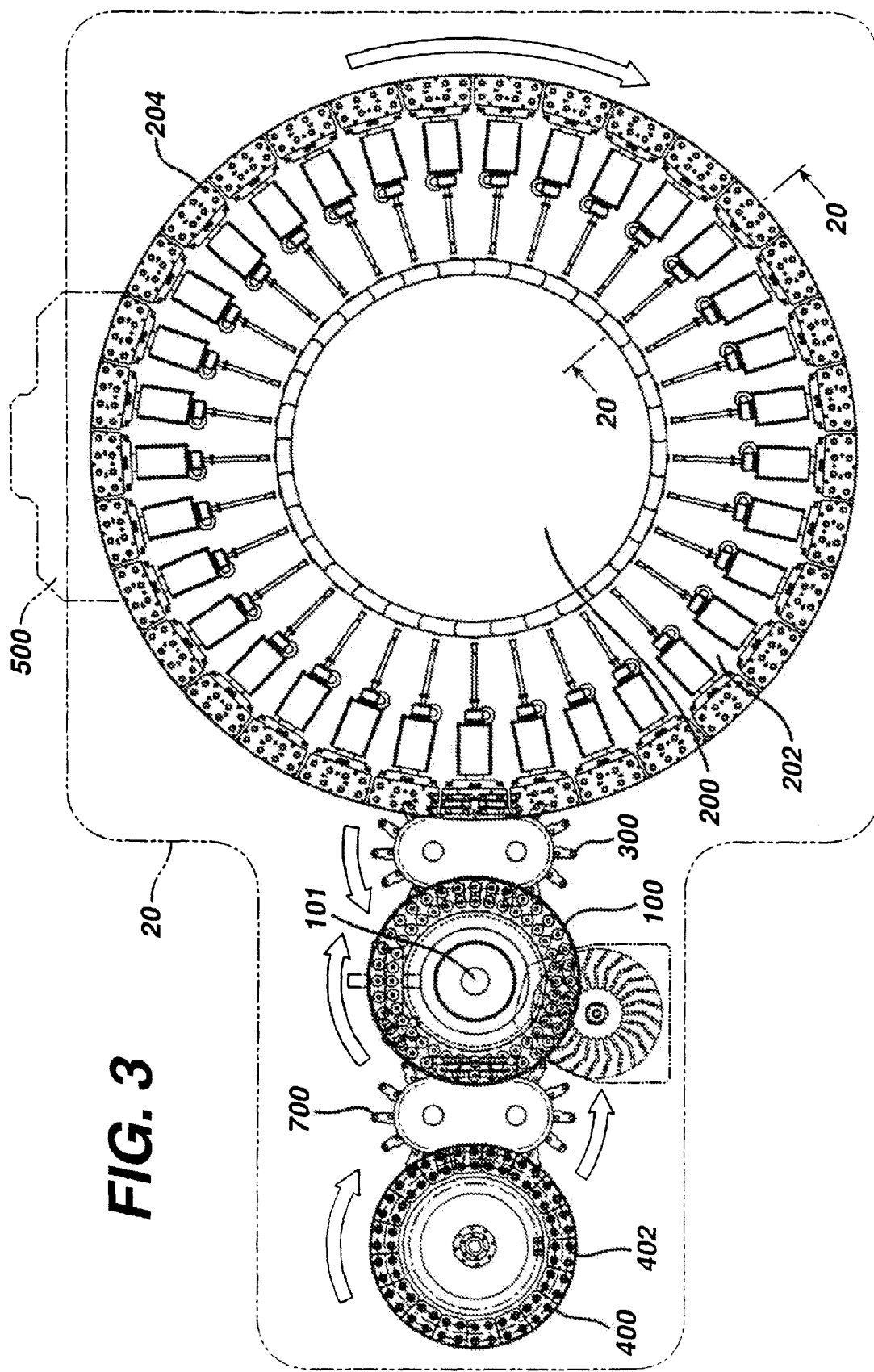
FIG. 3 is a plan view, partially schematic, of a system for manufacturing dosage forms according to the invention.
Figure 4:
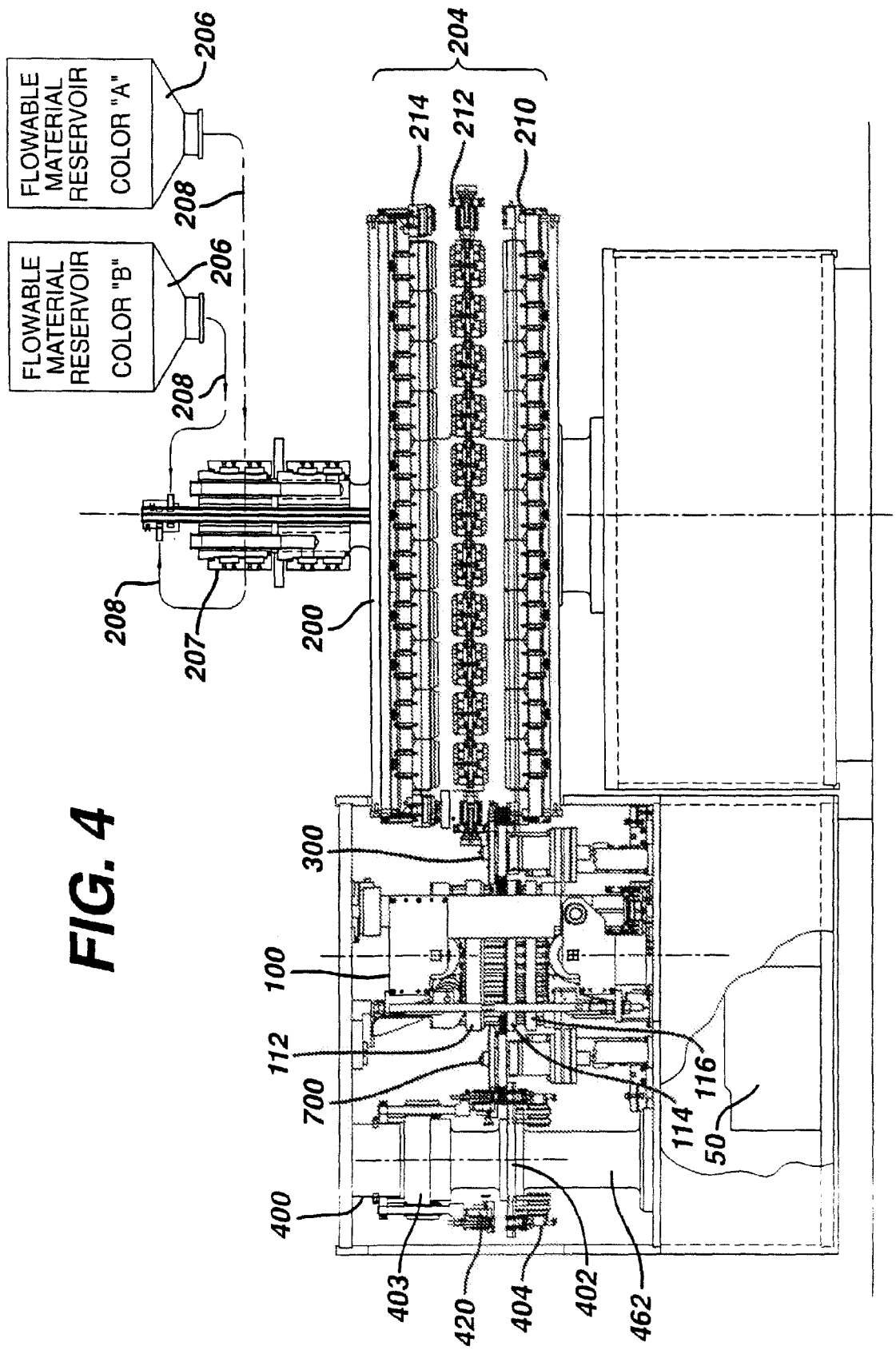
FIG. 4 is an elevational view of the system shown in FIG. 3.

FIG. 2 is a flow chart illustrating a preferred method for producing certain dosage forms according to the invention, which employs all of the operating modules linked into a continuous process. In particular, the method reflected in FIG. 2 produces a dosage form 10 comprising a molded coating 18 on the outside surface of a compressed dosage form 12 also containing an insert 14 as shown in FIG. 1A. FIGS. 3 and 4 depict a preferred system for practicing the method illustrated in FIG. 2. FIG. 1B illustrates an alternative dosage form 10' that may be made according to the invention comprising a molded coating 18' over a compressed dosage form 12'. It may be appreciated from FIG. 1B that the coating and the compressed dosage form need not have the same shape.

By way of overview, this preferred system 20 comprises a compression module 100, a thermal cycle molding module 200 and a transfer device 300 for transferring a compressed dosage form made in the compression module 100 to the thermal cycle molding module 200 as shown in FIGS. 3 and 4. Linkage of the compression module, transfer device, and the thermal cycle molding module in this manner results in a continuous, multi-station system. Compression is accomplished in the first module, molding of a coating around the resulting compressed dosage form is performed in the second module, and transfer of the dosage form from one module to the other is accomplished by the transfer device.

In other preferred embodiments, the system 20 also includes a thermal setting molding module 400 for forming a molded dosage form, which may comprise the final dosage form or be an insert for incorporation into another dosage form. In a preferred embodiment, the insert comprises a high potency additive. The invention is not limited to the type or nature of insert. Rather, the term insert is used simply to denote a pellet-type component embedded in another dosage form. Such an insert may itself contain a medicant, and retains its shape while being placed within the powder.

When used in the preferred, linked system comprising a compression module, the insert is formed in Step B of FIG. 2. Following this, the insert is inserted into uncompressed powder within compression module 100. After insertion the powder and insert are compressed (Step C of FIG. 2). The thermal setting molding module 400 can be separate from or part of the compression module 100. If the thermal setting molding module is separate from the compression module 100, a transfer device 700 can be used to transfer the insert from the thermal setting molding module 400 to the compression module 100.

The linked system for creating dosage forms, as well as each individual operating module, provide many processing advantages. The operating modules may be used separately or together, in different sequences, depending on the nature of the dosage form desired. Two or more of the same operating modules may be used in a single process. And although the apparatuses, methods and systems of this invention are described with respect to making dosage forms, it will be appreciated that they can be used to produce non-medicinal products as well. For example, they may be used to make confections or placebos. The molding module can be used with numerous natural and synthetic materials with or without the presence of a medicant. Similarly, the compression module can be used with various powders with or without drug. These examples are provided by way of illustration and not by limitation, and it will be appreciated that the inventions described herein have numerous other applications.

When linked in a continuous process, the operating modules can each be powered individually or jointly. In the preferred embodiment shown in FIGS. 3 and 4, a single motor 50 powers the compression module 100, the thermal cycle molding module 200, and the transfer device 300. The motor 50 can be coupled to the compression module 100, the thermal cycle molding module 200 and the transfer device 300 by any conventional drive train, such as one comprising gears, gear boxes, line shafts, pulleys, and/or belts. Of course, such a motor or motors can be used to power other equipment in the process, such as the dryer 500 and the like.

Compression Module

Figure 5:
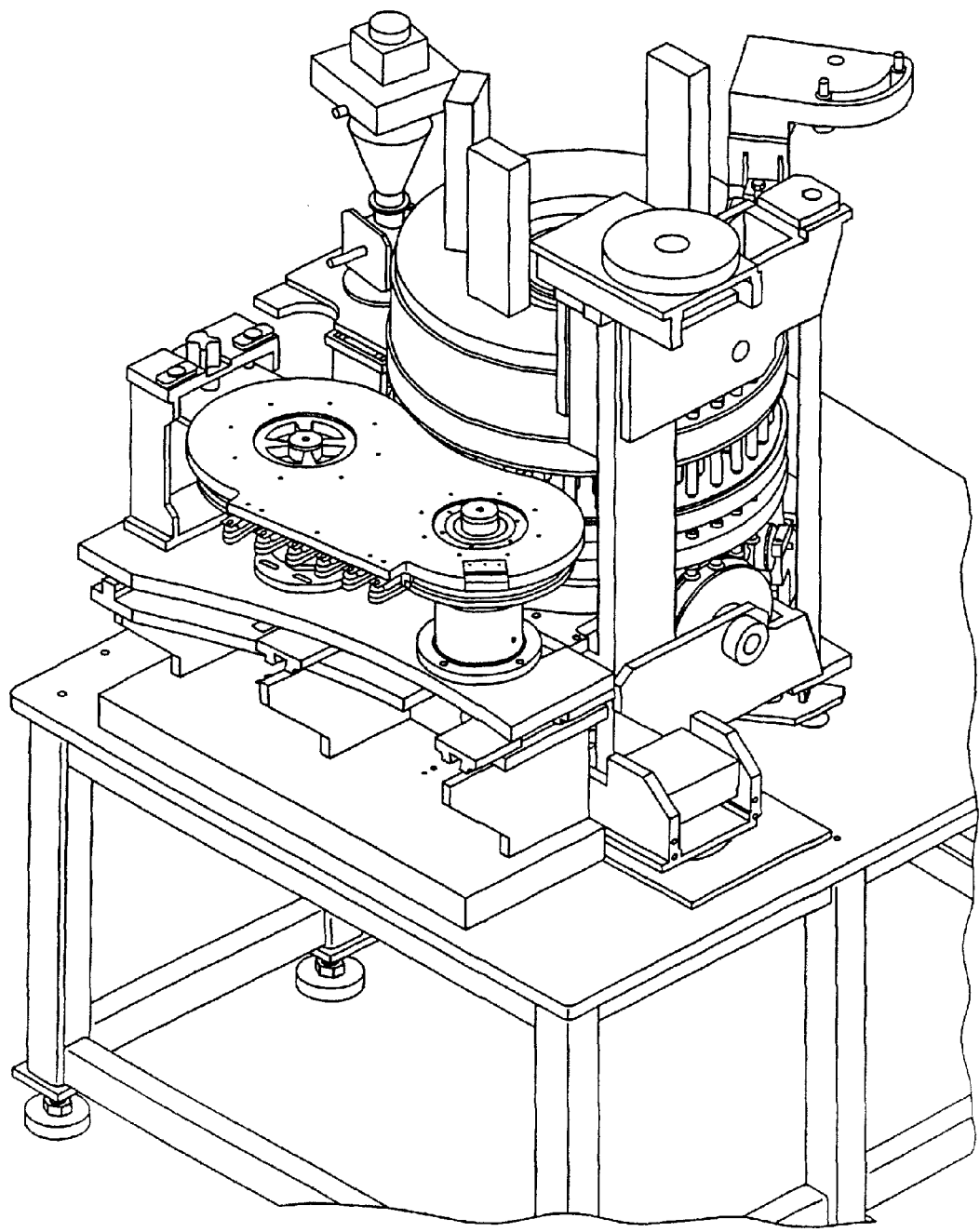
FIG. 5 is a three dimensional view of a compression module and transfer device according to the invention.

FIGS. 5-25 generally depict the compression module 100. FIG. 5 depicts a three dimensional view of the compression module 100 and the transfer device 300. The compression module 100 is a rotary device that performs the following functions: feeding powder to a cavity, compacting the powder into a compressed dosage form and then ejecting the compressed dosage form. When the compression module is used in conjunction with the thermal cycle molding module 200, upon ejection from the compression module the compressed dosage form may be transferred to the molding module either directly or through the use of a transfer device, such as transfer device 300 described below. Optionally, an insert formed by another apparatus, such as the thermal setting molding module 400 described below, can be inserted into the powder in the compression module before the powder is compressed into the compressed dosage form.

Figure 6:
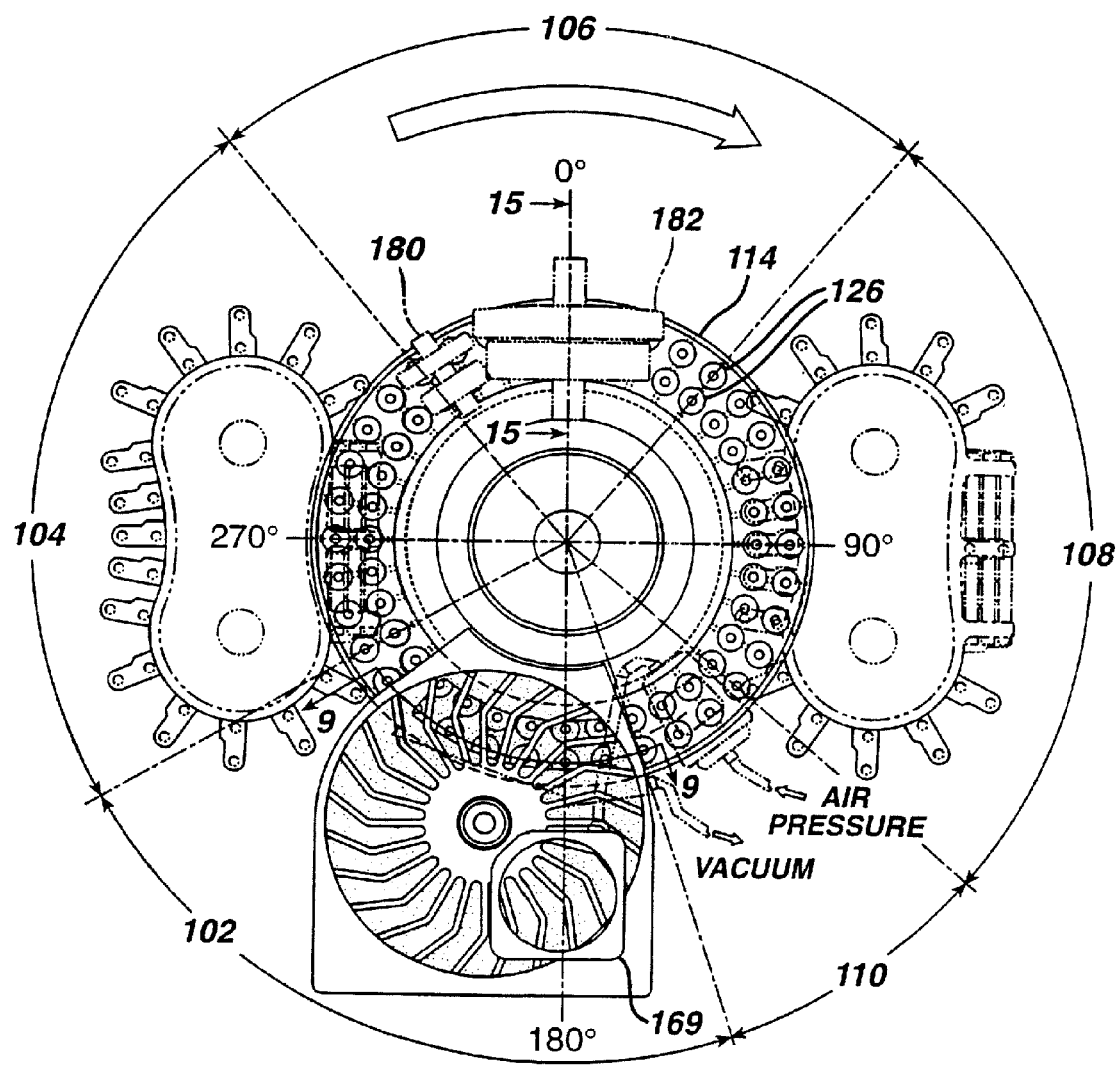
FIG. 6 is top view of a portion of the compression module shown in FIG. 5.

In order to accomplish these functions the compression module 100 preferably has a plurality of zones or stations, as shown schematically in FIG. 6, including a fill zone 102, an insertion zone 104, a compression zone 106, an ejection zone 108 and a purge zone 110. Thus, within a single rotation of the compression module 100 each of these functions are accomplished and further rotation of the compression module 100 repeats the cycle.

Figure 7:
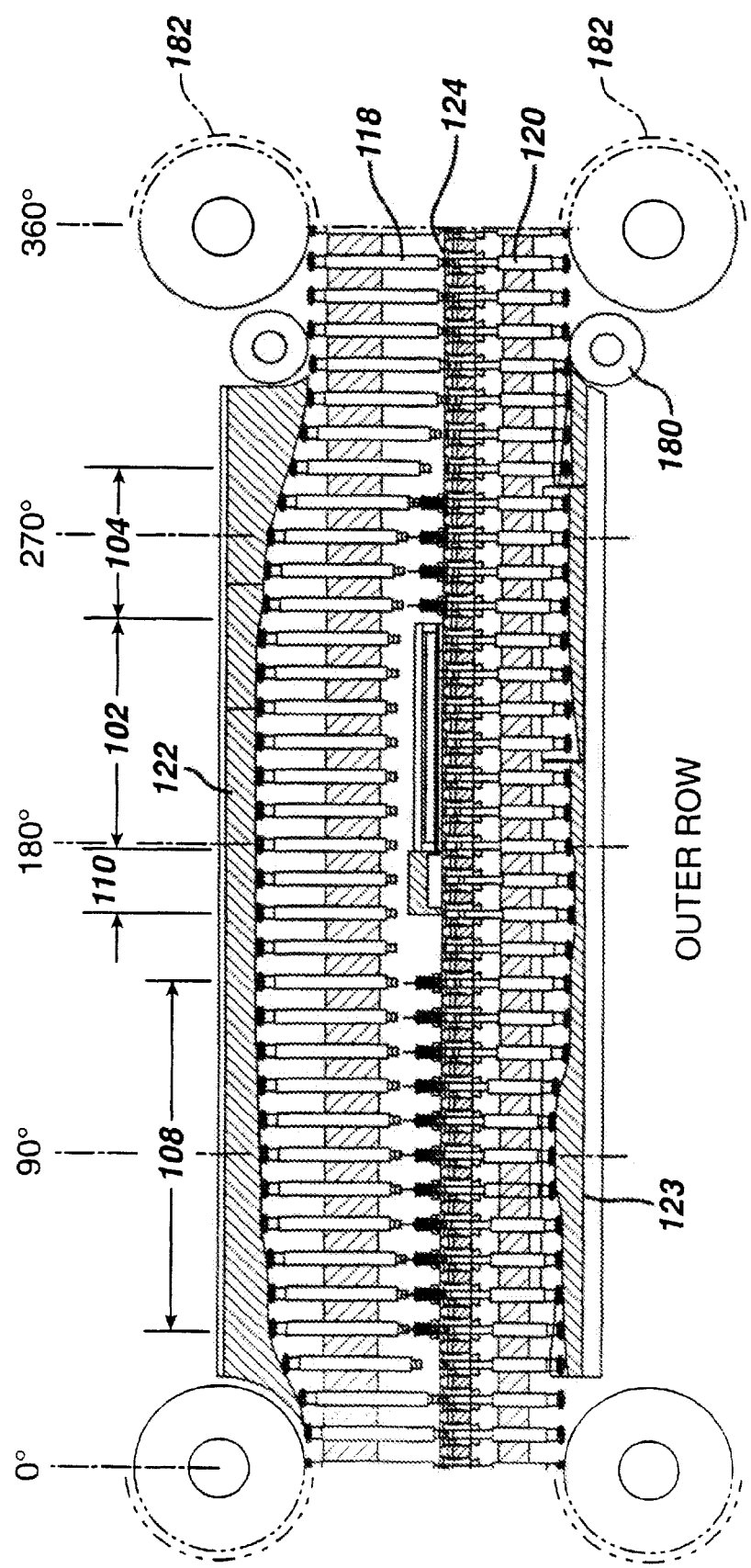
FIG. 7 depicts the path of one row of punches of a compression module during a revolution of the compression module.
Figure 8:
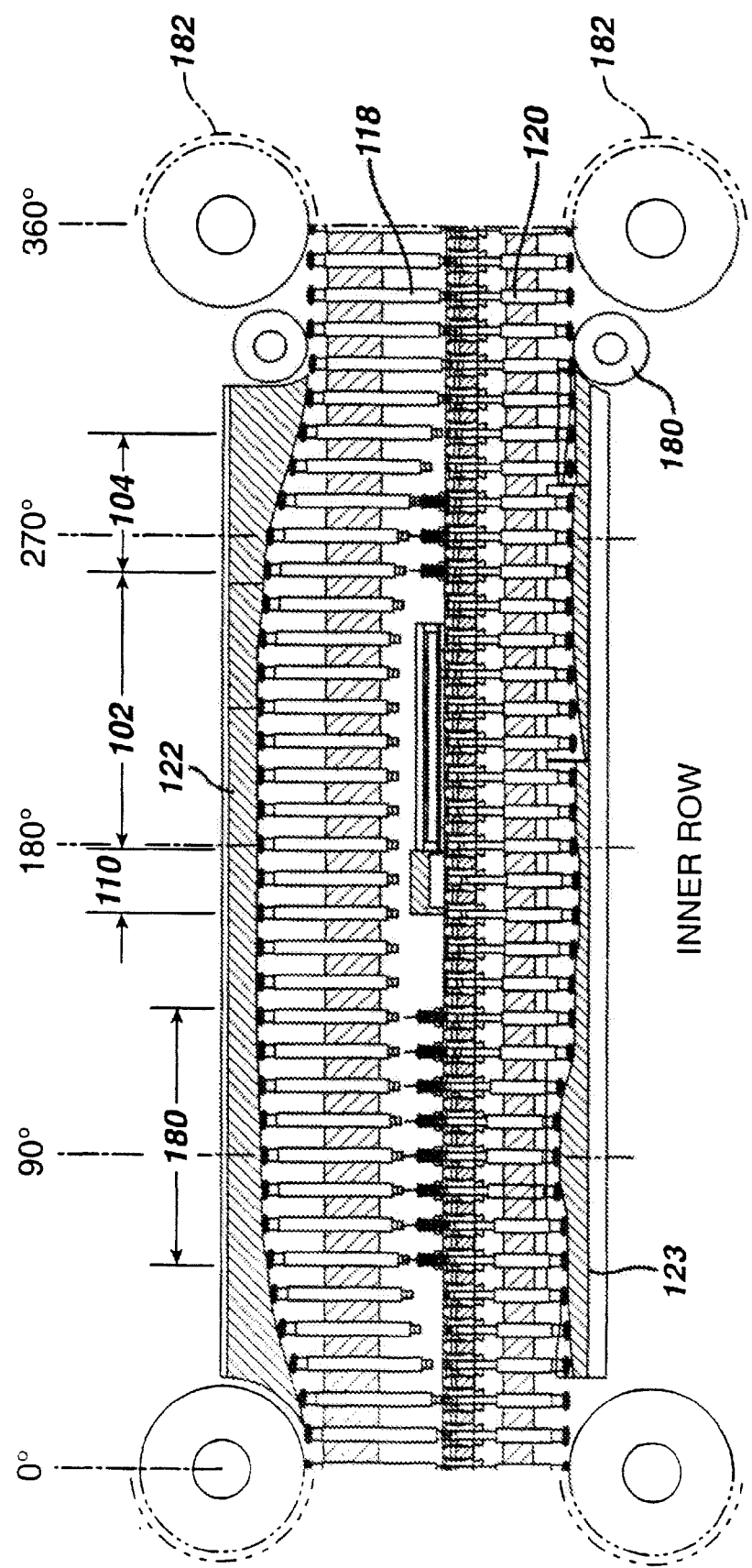
FIG. 8 depicts the path of another row of punches of the compression module during a revolution of the compression module.
Figure 9:
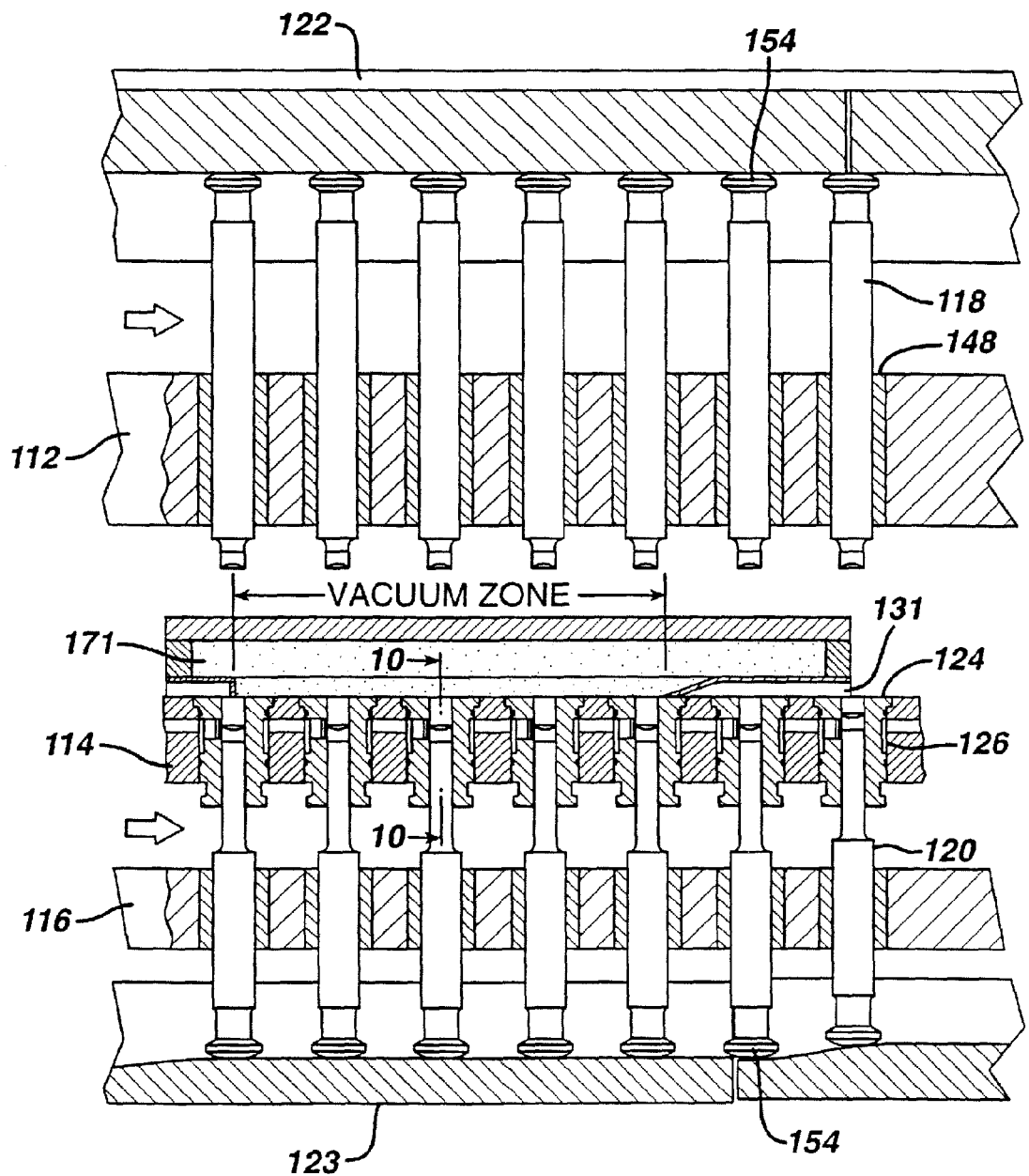
FIG. 9 is a partial cross-section of a compression module during compression.
Figure 14:
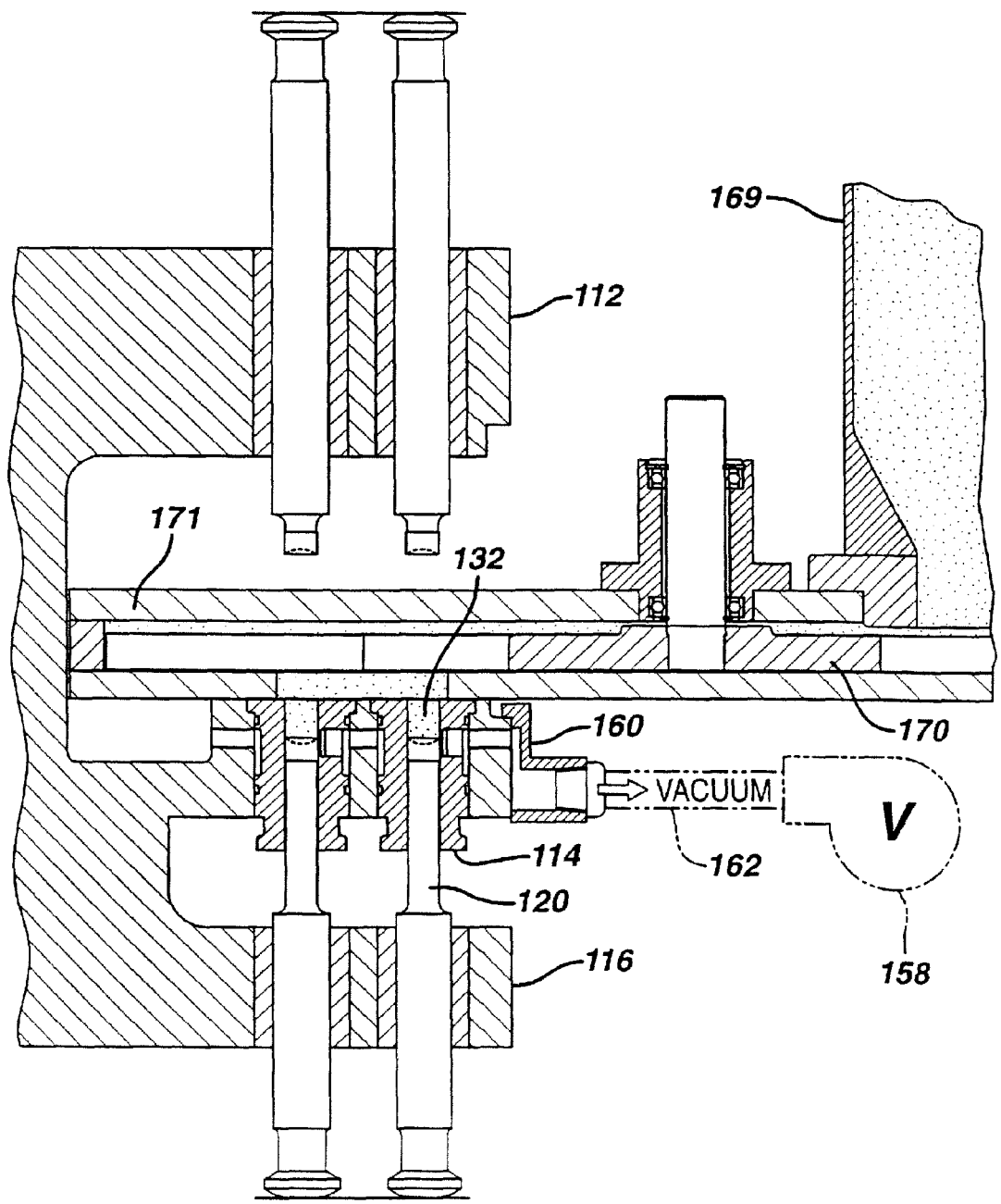
FIG. 14 is a cross-sectional view of a portion of the fill zone of the compression module.

As shown generally in FIGS. 4, 5, 9 and 14, the rotary portion of the compression module generally includes an upper rotor 112, a circular die table 114, a lower rotor 116, a plurality of upper 118 and lower 120 punches, an upper cam 122, a lower cam 123 and a plurality of dies 124. FIG. 9 depicts a portion of the rotors 112, 116, and die table 114 from a side view, while FIG. 14 depicts a vertical cross-section through the rotors 112, 116 and die table 114. FIG. 16 depicts an annular cross-section through rotors 112, 116 and die table 114. FIGS. 7 and 8 are two dimensional representations of the circular path the punches 118, 120 follow as they rotate with respect to the cams 122, 123 with the rotors removed from the drawing for purposes of illustration. The upper rotor 112, die table 114 and lower rotor 116 are rotatably mounted about a common shaft 101 shown in FIG. 3.

Each of the rotors 112, 116 and the die table 114 include a plurality of cavities 126 which are disposed along the circumferences of the rotors and die table. Preferably, there are two circular rows of cavities 126 on each rotor, as shown in FIG. 6. Although FIG. 6 only shows the die table 114, it will be appreciated that the upper 112 and lower rotors 116 each have the same number of cavities 126. The cavities 126 of each rotor are aligned with a cavity 126 in each of the other rotors and the die table. There are likewise preferably two circular rows of upper punches 118 and two circular rows of lower punches 120, as best understood with reference to FIGS. 4, 5, 9 and 14. FIG. 7 depicts the outer row of punches, and FIG. 8 illustrates the inner row of punches.

Conventional rotary tablet presses are of a single row design and contain one powder feed zone, one compression zone and one ejection zone. This is generally referred to as a single sided press since tablets are ejected from one side thereof. Presses offering a higher output version of the single row tablet press employing two powder feed zones, two tablet compression zones and two tablet ejection zones are commercially available. These presses are typically twice the diameter of the single sided version, have more punches and dies, and eject tablets from two sides thereof. They are referred to as double sided presses.

In a preferred embodiment of the invention the compression module described herein is constructed with two concentric rows of punches and dies. This double row construction provides for an output equivalent to two single side presses, yet fits into a small, compact space roughly equal to the space occupied by one conventional single sided press. This also provides a simplified construction by using a single fill zone 102, a single compression zone 106, and a single ejection zone 108. A single ejection zone 108 is particularly advantageous in the linked process of the invention, because the complexity of multiple transfer devices 300, 700 having double sided construction is avoided. Of course, a compression module with one row or more than two rows can also be constructed.

The upper punches 118 illustrated in FIGS. 7-9 extend from above the cavities 126 in the upper rotor 112 through the cavities 126 in the upper rotor and, depending on their position, either proximal to or within the cavities 126 of the die table 114. Similarly, the lower punches extend from beneath the cavities 126 in the lower rotor 116 and into the cavities 126 in the die table 114, as is also best understood with reference to FIGS. 7-9. The cavities 148 in the upper and lower rotors serve as guides for the upper 118 and lower 120 punches respectively.

Disposed within each of the cavities 126 of the die table is a die 124. FIGS. 9-14 depict the dies 124 and cross sections through the die table 114. FIG. 9 is a partial cross section of the die table 114 taken along an arc through a portion of the die table 114. FIG. 14 is a cross section taken vertically along a radius though the die table 114. Because there are preferably two circular rows of dies, the two rows of dies lie along two concentric radii, as best understood with reference to FIGS. 6 and 14.

Figure 10:
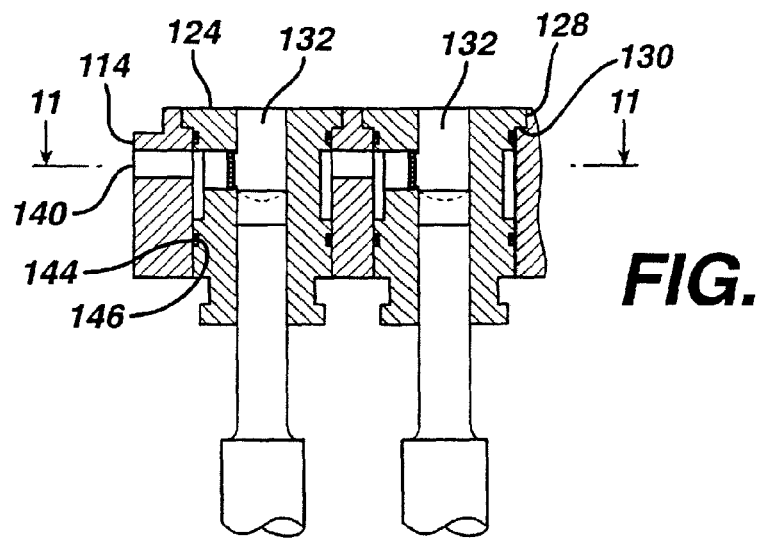
FIG. 10 is a cross-section taken through line 10-10 of FIG. 9.

Preferably, the dies 124 are metallic, but any suitable material will suffice. Each die 124 may be retained by any of a variety of fastening techniques within the respective cavity 126 of the die table 114. For example, the dies 124 may be shaped so as to have a flange 128 that rests on a seating surface 130 formed in the die table 114 and a pair of o-rings 144 and grooves 146, as best understood with reference to FIG. 10. FIG. 10 is an enlarged view of the dies shown in FIG. 9 without the upper punches inserted into the dies. It will be appreciated that all the dies 124 are similar in construction.

Each die 124 comprises a die cavity 132 for receiving the upper and lower punches 118, 120. The die cavities 132 and the lower punches 118 that extend a distance into the die cavities 132 define the volume of powder to be formed into the compressed dosage form and hence the dosage amount. Thus, the size of die cavity 132 and the degree of insertion of the punches into the die cavities 132 can be appropriately selected or adjusted to obtain the proper dosage.

Figure 11:
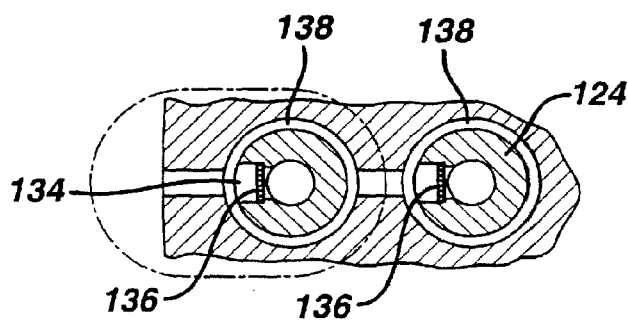
FIG. 11 is a cross-section taken through line 11-11 of FIG. 10.
Figure 12:
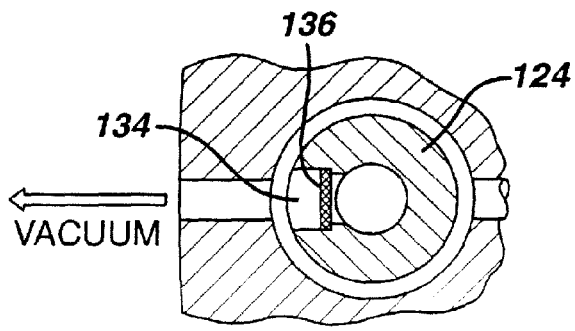
FIG. 12 is an enlarged view of the die cavity area circled in FIG. 11.
Figure 12A:
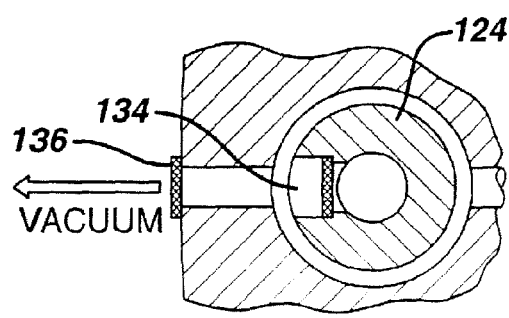
FIG. 12A shows another embodiment of a die cavity of the compression module.
Figure 13:
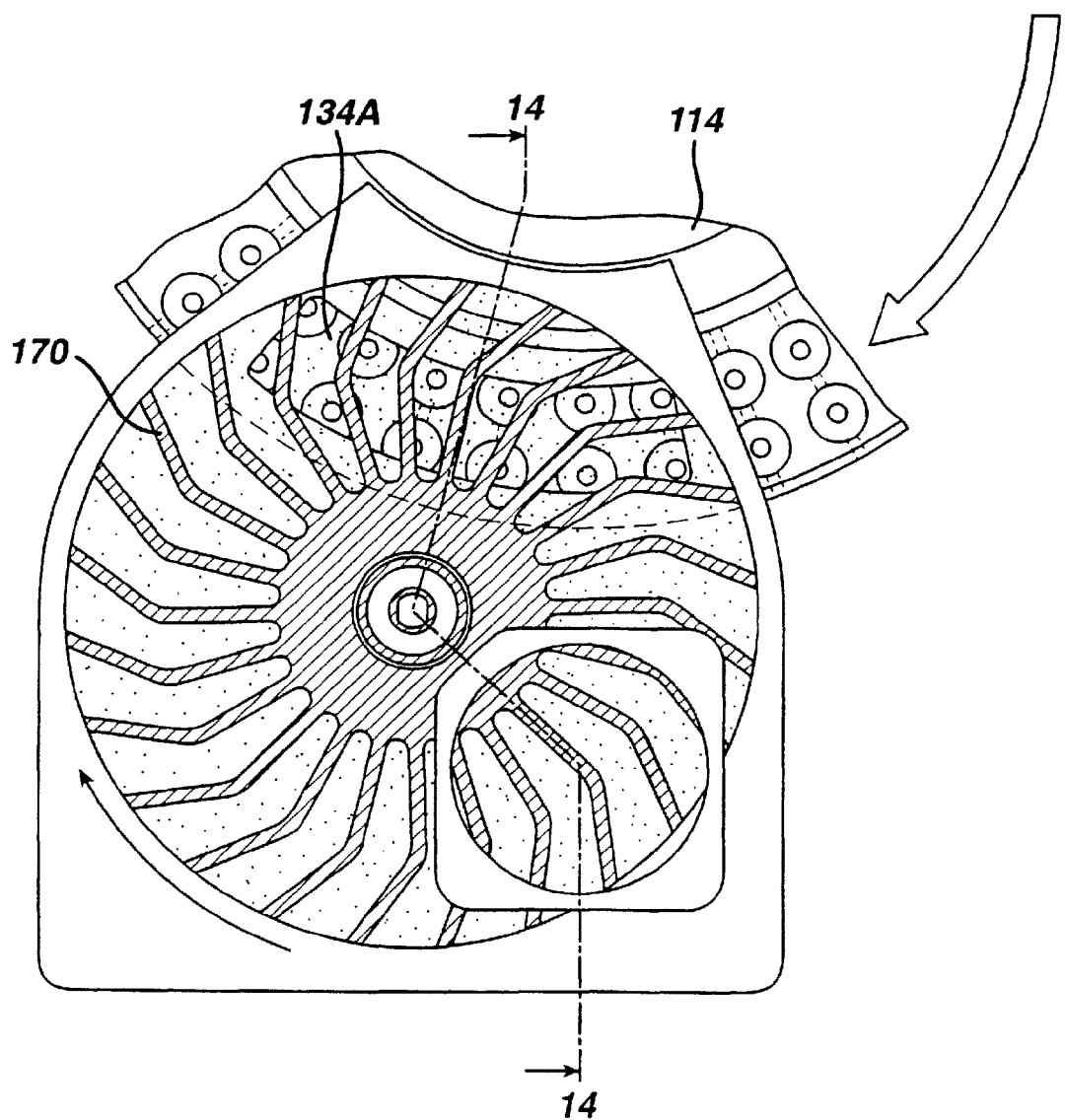
FIG. 13 is a top view of the fill zone of the compression module.

In a preferred embodiment, the die cavities are filled using the assistance of a vacuum. Specifically, each die 124 has at least one port 134 disposed within it, as shown in FIGS. 10, 11, and 12. Disposed within or proximal to each port 134 is a filter 136. The filters 136 are generally a metallic mesh or screen appropriately sized for the particles that will be flowing through the die cavities 134. One surprising feature of the present compression module is that the filters may comprise screens having a mesh size larger than the average particle size of the powder, which is typically about 50 to about 300 microns. While the filters 136 are preferably metallic, other suitable materials may be employed, such as fabrics, porous metals or porous polymer constructions. The filter 136 may be a single stage or multi-stage filter, but in the preferred embodiment the filter 136 is a single stage filter. The filter may also be located anywhere in the vacuum passages. Alternatively, it can be located externally to the die table as shown in FIG. 12A. In a preferred embodiment the filters are located in the die wall ports 134 as close as possible to the punches. See FIG. 12. This creates the least amount of residue requiring purging and subsequent recycling in the purge zone 110 and powder recovery system. The top of the die cavity 132 is preferably open and defines a second port.

The die table 114 preferably comprises channels 138 within it that circle each pair of dies 124 and extend to the ports 134, as best shown in FIG. 11. In addition the die table 114 preferably has a plurality of relatively small openings 140 on its outer periphery that connect each of the respective channels 138, so that the die cavities can be connected to a vacuum source (or suction source). Disposed along a portion of the periphery of the die table 114 are a stationary vacuum pump 158 and a vacuum manifold 160, which make up a portion of the fill zone 102, as shown in FIG. 14. The vacuum pump 158 provides a source of vacuum for pulling powder into the die cavities 132. The vacuum pump 158 is connected to the vacuum manifold 160 with suitable tubing 162. The vacuum manifold 160 is aligned with the openings 140. As the die table 114 rotates during operation of the vacuum pump 158, the openings 140 in the die table 114 become aligned with the vacuum manifold 160 and a vacuum is formed through the respective channel 138 and die cavity 132.

Vacuum is accordingly applied through the respective ports 134 and channels 138 to pull powder into the die cavity 132. See FIGS. 20 and 21. A seal can be created around the ports 134 and the channel 138 proximal to the port 134 with any of a variety of techniques. In the preferred embodiment shown a seal is created using o-rings 144 and grooves 146.

Conventional tablet presses rely on highly flowable powders and the effects of gravity to fill the die cavity. The performance of these machines in terms of fill accuracy and press speed are therefore entirely dependent on the quality and flowabilty of the powder. Since non-flowing and poorly flowing powders cannot be effectively run on these machines these materials must be wet granulated in a separate batch process which is costly, time consuming, and energy inefficient.

The preferred vacuum fill system described is advantageous over conventional systems in that poorly flowing and non-flowing powders can be run at high speed and high accuracy without the need for wet granulation. In particular, powders having a minimum orifice diameter of flowability greater than about 10, preferably 15, more preferably 25 mm, as measured by the Flowdex test, may be successfully compressed into dosage forms in the present compression module. The Flowdex test is performed as follows. The minimum orifice diameter is determined using a Flodex Apparatus Model 21-101-050 (Hanson Research Corp., Chatsworth, Calif.), which consists of a cylindrical cup for holding the powder sample (diameter 5.7 cm, height 7.2 cm), and a set of interchangeable disks, each with a different diameter round opening at the center. The disks are attached to the cylindrical cup to form the bottom of the "cup." For filling, the orifice is covered with a clamp. Minimum orifice diameter measurements are performed using 100 g samples of powder. A 100 g sample is placed into the cup. After 30 seconds the clamp is removed, and the powder allowed to flow out of the cup through the orifice. This procedure is repeated with increasingly smaller orifice diameters until the powder no longer flows freely through the orifice. The minimum orifice diameter is defined as the smallest opening through which the powder flows freely.

Moreover, compression of such relatively poorly flowing powders may be done while operating the compression module at high speeds, i.e., the linear velocity of the dies is typically at least about 115 cm/sec, preferably at least about 230 cm/sec. In addition, weight variations in the final compressed dosage forms are significantly less, since vacuum filling of the die cavity causes a densifying effect on the powder in the die cavity. This minimizes the density variations powders typically exhibit due to compaction, static head pressure variation, or lack of blend homogeneity. The relative standard deviation in weight of compressed dosage forms made according to the invention is typically less than about 2%, preferably less than about 1%.

In addition, better content uniformity can also be achieved with the present vacuum fill system, since little mechanical agitation is required to cause the powder to flow into the die cavity. In conventional tablet presses, the mechanical agitation required to assure die filling has the adverse effect of segregating small from large particles.

Known powder filling equipment employ vacuum to fill uncompressed powders into capsules or other containers. See. For example, Aronson, U.S. Pat. No. 3,656,518 assigned to Perry Industries, Inc. However, these systems have filters that are always in contact with the powder and therefore unsuitable for adaptation to compression machines. Forces on the order of 100 kN can be experienced during compression of powders into dosage forms. Such high forces would damage the filters. U.S. Pat. No. 4,292,017 and U.S. Pat. No. 4,392,493 to Doepel describe a high speed rotary tablet compression machine which uses vacuum die filling. However separate turntables are used for filling and compression. Dies are filled on the first turntable and thereafter transferred to a separate turntable for compression. Advantageously, according to the invention, the filters are protected during compression, since the lower punches move above the filter port prior to the die cavities entering the compression zone.

Powder is fed into the die cavities 132 in the fill zone 102. The powder may preferably consist of a medicant optionally containing various excipients, such as binders, disintegrants, lubricants, fillers and the like, as is conventional, or other particulate material of a medicinal or non-medicinal nature, such as inactive placebo blends for tableting, confectionery blends, and the like. One particularly preferred formulation comprises medicant, powdered wax (such as shellac wax, microcrystalline wax, polyethylene glycol, and the like), and optionally disintegrants and lubricants and is described in more detail in commonly assigned co-pending U.S. patent application Ser. No. 09/966,493 (US 200310068373A1), entitled "Immediate Release Tablet" which is hereby incorporated by reference.

Suitable medicants include for example pharmaceuticals, minerals, vitamins and other nutraceuticals. Suitable pharmaceuticals include analgesics, decongestants, expectorants, antitussives, antihistamines, gastrointestinal agents, diuretics, bronchodilators, sleep-inducing agents and mixtures thereof. Preferred pharmaceuticals include acetaminophen, ibuprofen, flurbiprofen, ketoprofen, naproxen, diclofenac, aspirin, pseudoephedrine, phenylpropanolamine, chlorpheniramine maleate, dextromethorphan, diphenhydramine, famotidine, loperamide, ranitidine, cimetidine, astemizole, terfenadine, fexofenadine, loratadine, cetirizine, antacids, mixtures thereof and pharmaceutically acceptable salts thereof. More preferably, the medicant is selected from the group consisting of acetaminophen, ibuprofen, pseudoephedrine, dextromethorphan, diphenhydramine, chlorpheniramine, calcium carbonate, magnesium hydroxide, magnesium carbonate, magnesium oxide, aluminum hydroxide, mixtures thereof, and pharmaceutically acceptable salts thereof.

The medicant(s) is present in the dosage form in a therapeutically effective amount, which is an amount that produces the desired therapeutic response upon oral administration and can be readily determined by one skilled in the art. In determining such amounts, the particular medicant being administered, the bioavailability characteristics of the medicant, the dose regime, the age and weight of the patient, and other factors must be considered, as known in the art. Preferably, the compressed dosage form comprises at least about 85 weight percent of medicant.

If the medicant has an objectionable taste, and the dosage form is intended to be chewed or disintegrated in the mouth prior to swallowing, the medicant may be coated with a taste masking coating, as known in the art. Examples of suitable taste masking coatings are described in U.S. Pat. No. 4,851,226, U.S. Pat. No. 5,075,114, and U.S. Pat. No. 5,489,436. Commercially available taste masked medicants may also be employed. For example, acetaminophen particles which are encapsulated with ethylcellulose or other polymers by a coacervation process may be used in the present invention. Coacervation-encapsulated acetaminophen may be purchased commercially from Eurand America, Inc. Vandalia, Ohio, or from Circa Inc., Dayton, Ohio.

Suitable excipients include fillers, which include water-soluble compressible carbohydrates such as dextrose, sucrose, mannitol, sorbitol, maltitol, xylitol, lactose, and mixtures thereof, water insoluble plasticly deforming materials such as microcrystalline cellulose or other cellulosic derivatives, water-insoluble brittle fracture materials such as dicalcium phosphate, tricalcium phosphate, and the like; other conventional dry binders such as polyvinyl pyrrolidone, hydroxypropylmethylcellulose, and the like; sweeteners such as aspartame, acesulfame potassium, sucralose, and saccharin; lubricants, such as magnesium stearate, stearic acid, talc, and waxes; and glidants, such as colloidal silicon dioxide. The mixture may also incorporate pharmaceutically acceptable adjuvants, including, for example, preservatives, flavors, antioxidants, surfactants, and coloring agents. Preferably however, the powder is substantially free of water soluble polymeric binders and hydrated polymers.

Included within the fill zone 102 may be a doctor blade 131 as shown in FIG. 9 that "doctors" or levels the powder along the die table 114 as the die table 114 rotates through the fill zone 102. In particular, as a filled die cavity 132 rotates past the powder bed, the die table 114 passes against the doctor blade 131 (as shown in FIG. 9) which scrapes the surface of the die table 114 to assure the precise leveling and measurement of powder filling the die cavity 132.

After the punches leave the fill zone 102 they enter the insertion zone 104. In this zone the lower punches 120 may retract slightly to allow for an optional insert to be embedded into the soft uncompressed powder in the die cavity 132 via a transfer device 700. This mechanism is described in greater detail below.

After continued rotation and before entering the compression zone 106, the upper punch 118 is pushed into the die cavity 132 by the cam track 122 as shown in FIGS. 7, 8 and 16. Following this, the upper and lower punches 118, 120 engage the first stage rollers 180 as shown in FIG. 16 where force is applied to the powder via the first stage rollers. After this initial compression event, the punches enter the second stage rollers 182 as shown in FIG. 16. The second stage rollers 182 drive the punches 118, 120 into the die cavity 132 to further compress the powder into the desired compressed dosage form. Once past the compression zone the upper punches retract from the die cavity 132 and the lower punches begin to move upward prior to entering the ejection zone 108.

Figure 15:
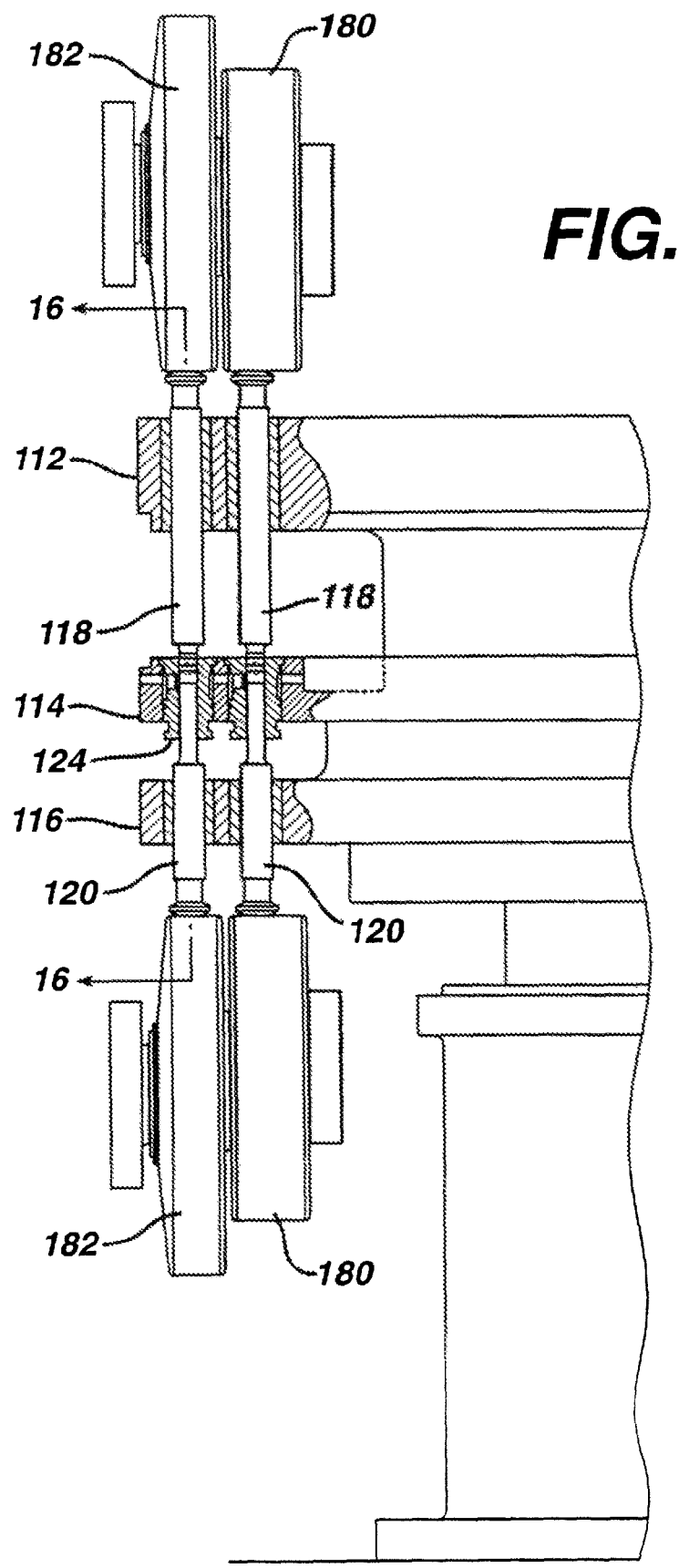
FIG. 15 is a cross section taken through line 15-15 of FIG. 6.

Because the distances traveled by the outer and inner rows of punches along their respective circular paths differ, the sizes of the rollers 180 and 182 that activate each row differ. This enables compression of the inner and outer rows to be simultaneous. In particular, the rollers that activate the inner row are smaller in diameter than the rollers that activate the outer row (as shown in FIG. 15), but the inner and outer rollers have their greatest diameter along the same radial line. Thus, the outer row punches and inner row punches will each begin to be compressed at the same time, thus entering the die cavities simultaneously. By assuring the same dwell time under compression, consistency of compressed dosage form thickness between inner and outer rows is assured. This thickness control is particularly important should the compressed dosage forms be subjected to subsequent operations, such as the application of coatings and the like.

Figure 17A:
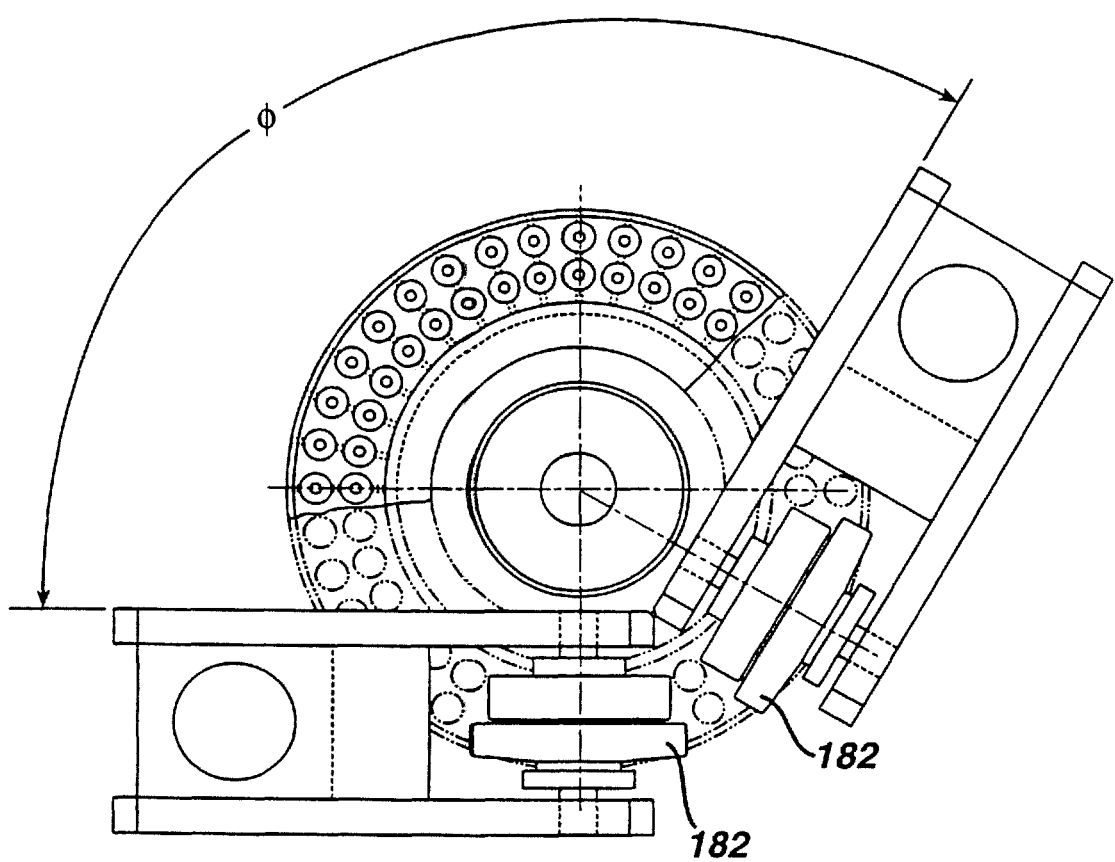
FIGS. 17A-C illustrate one embodiment of a "C" frame for the compression rollers.
Figure 17C:
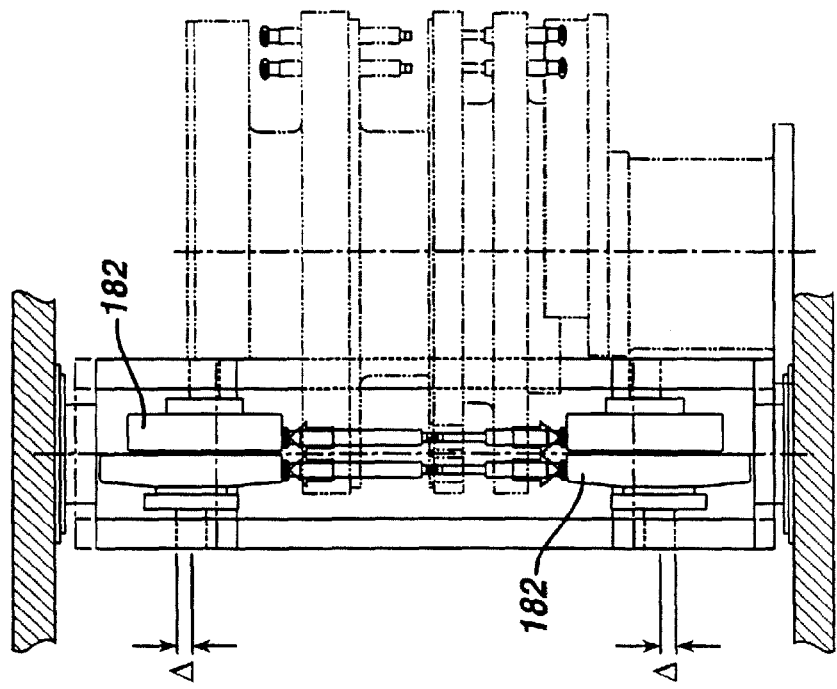
Figure 17B:
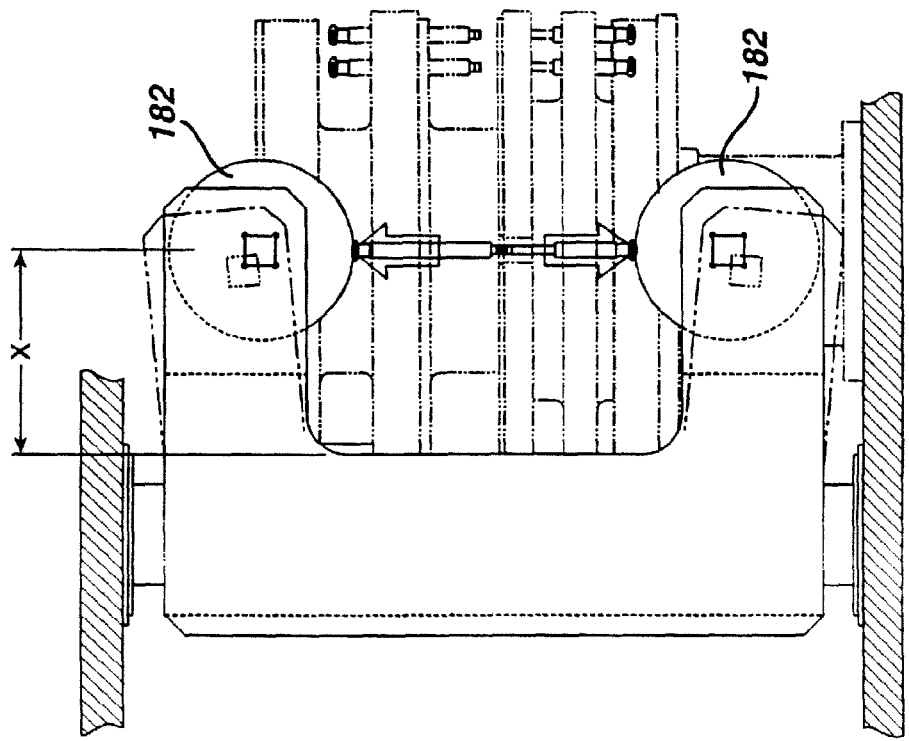

FIGS. 17, 18, and 19 are three possible geometries for the compression frame on which the compression rollers are mounted. FIG. 17 illustrates one possible "C" geometry for the compression frame. As shown in FIGS. 17B and 17C deflection of the compression frame displaces the rollers by the amount "Δ" under the significant forces of compression (The double row compression module illustrated here preferably has twice this rating or 200 kN.) An advantage of the frame geometry depicted in FIGS. 17A through 17C is that the displacement Δ is parallel to the radial axis of the compression rollers 182. This slight deflection can easily be compensated for by thickness controls on the machine. However, as shown in FIG. 17A, the frame occupies a significant amount of space. Accordingly there is less room for other equipment to be mounted on or near the compression module (this is represented by angle ϕ).

Figure 18A:
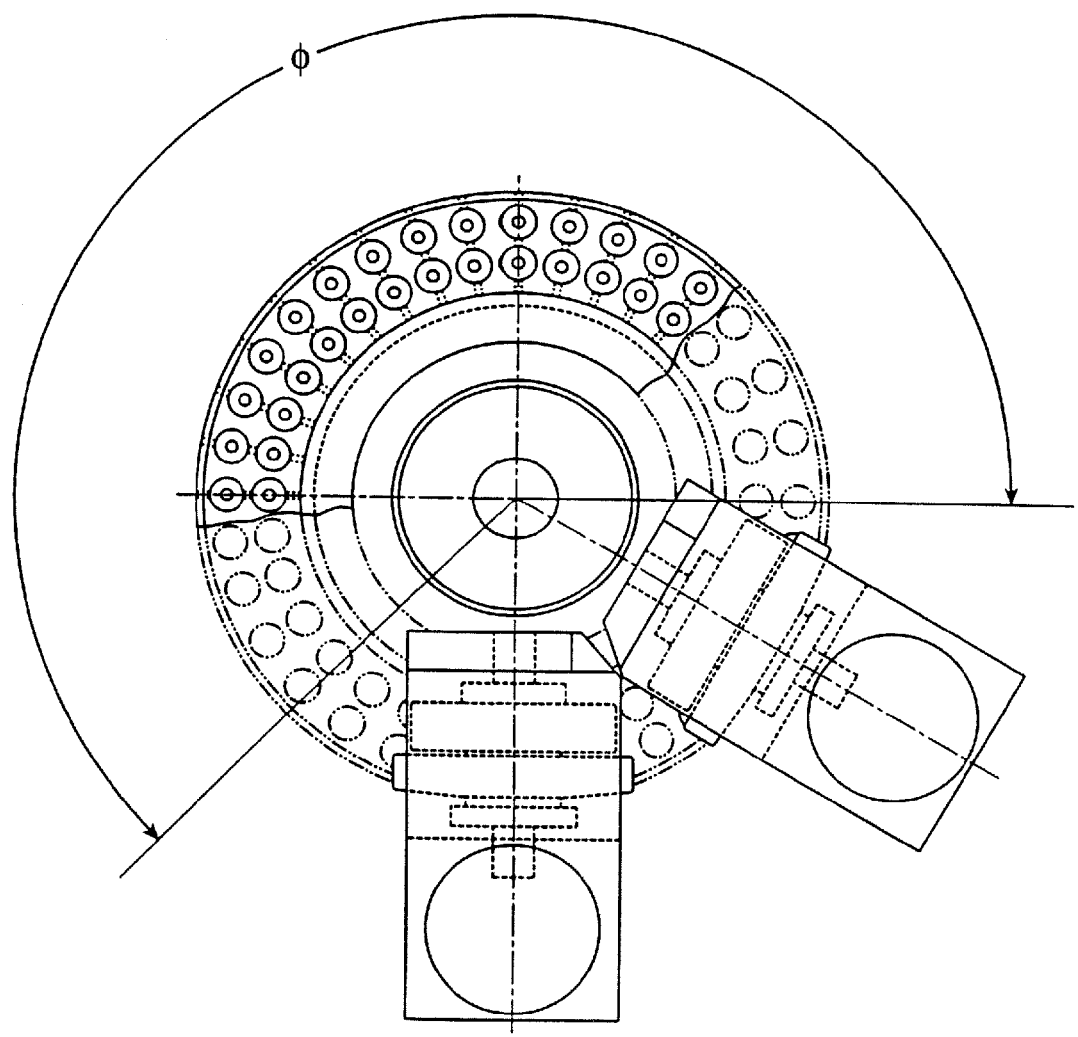
FIGS. 18A-C illustrate another embodiment of a "C" frame for the compression rollers.
Figure 18C:
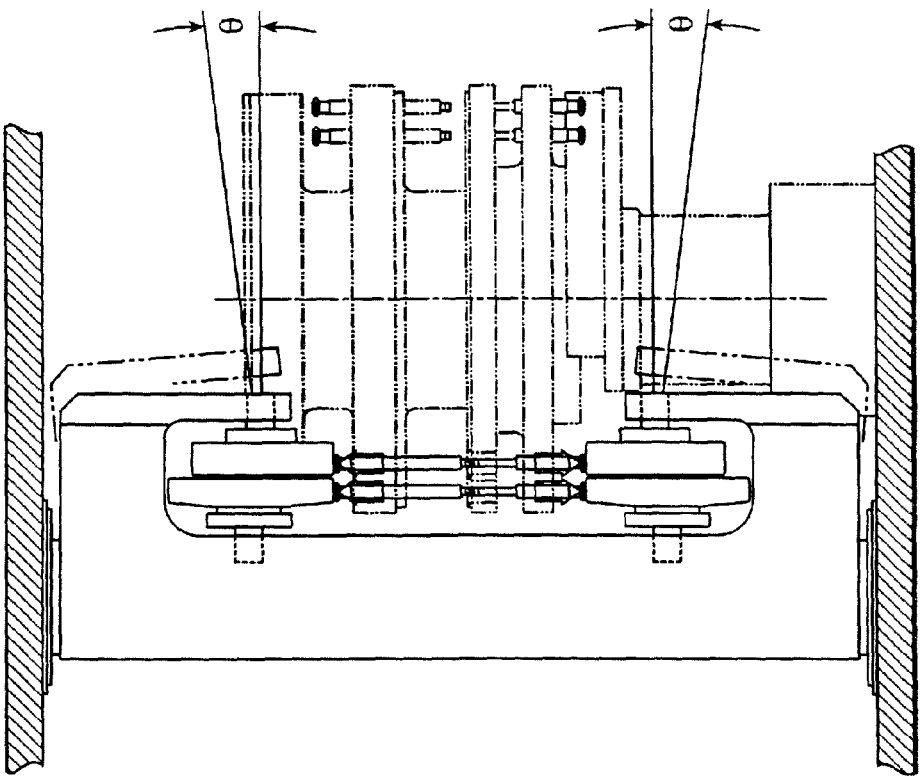
Figure 18B:
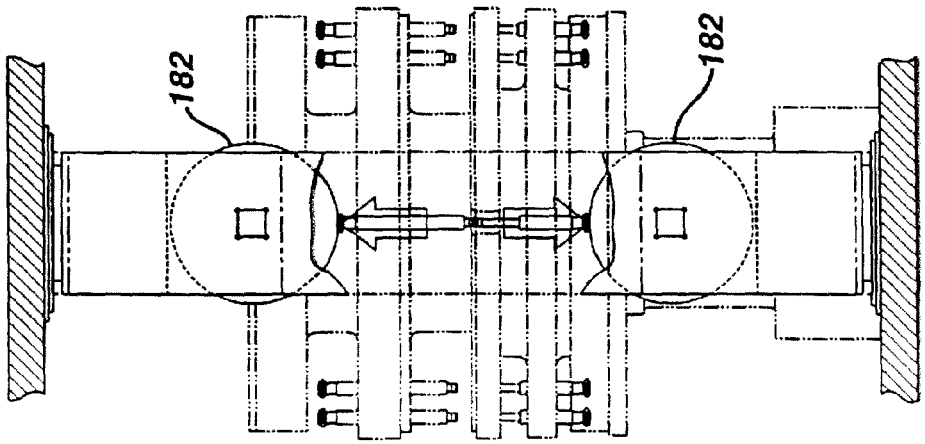

FIGS. 18A through 18C illustrate an alternate "C" frame geometry. This arrangement has the advantage of occupying significantly less space than the arrangement outlined in FIGS. 17A through 17C. However in this embodiment, deflection of the compression frame displaces the rollers out of the horizontal plane. This is represented by angle θ in FIG. 18C. θ increases as the load increases. The net effect is an inconsistency between inner and outer row compressed dosage form thickness that also varies with compression force.

Figure 19A:
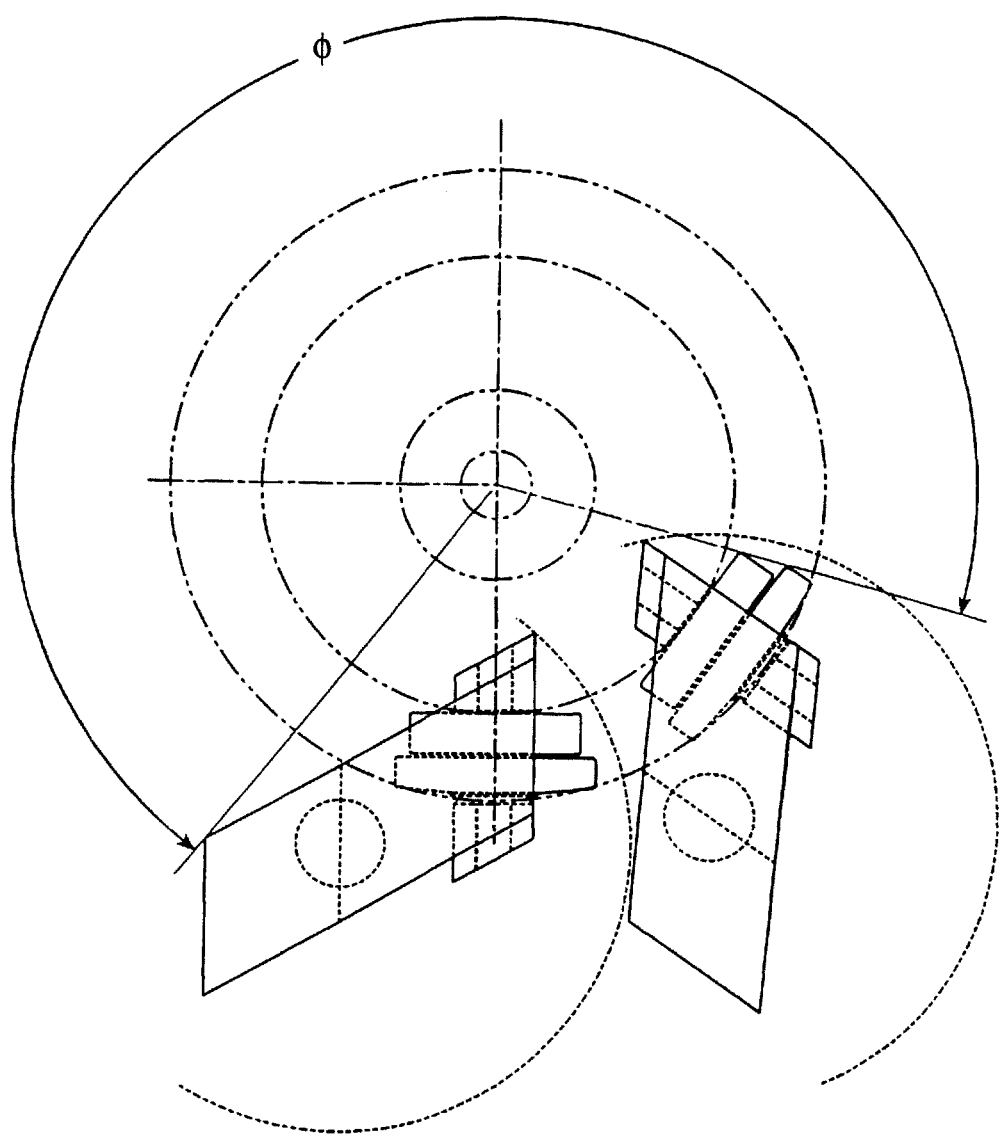
FIGS. 19A-C illustrate a preferred embodiment of a "C" frame for the compression rollers.
Figure 19C:
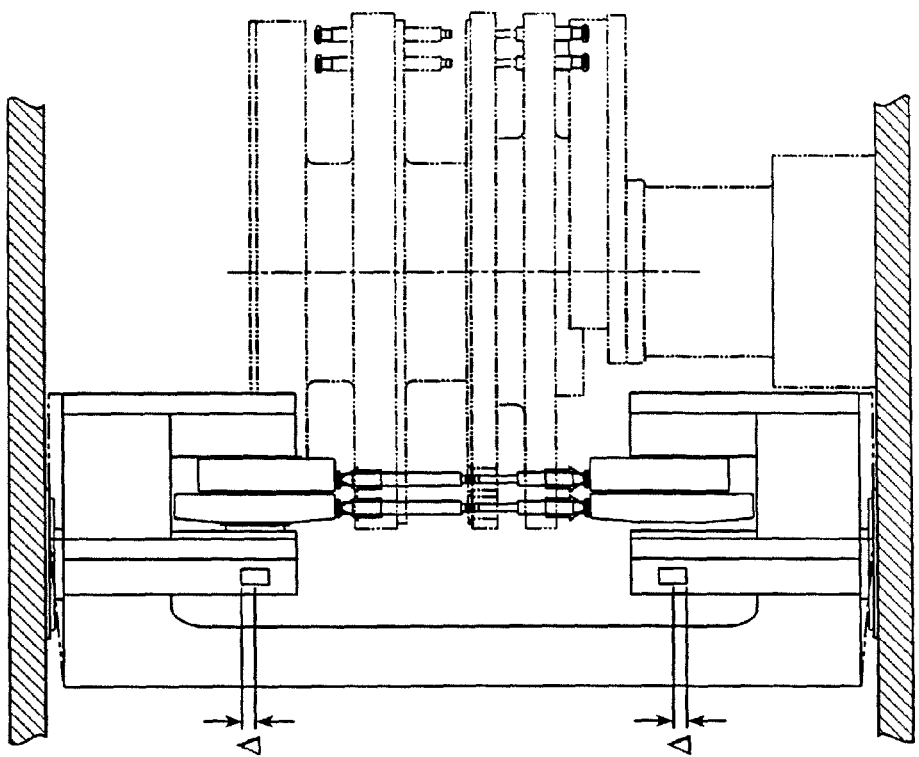
Figure 19B:
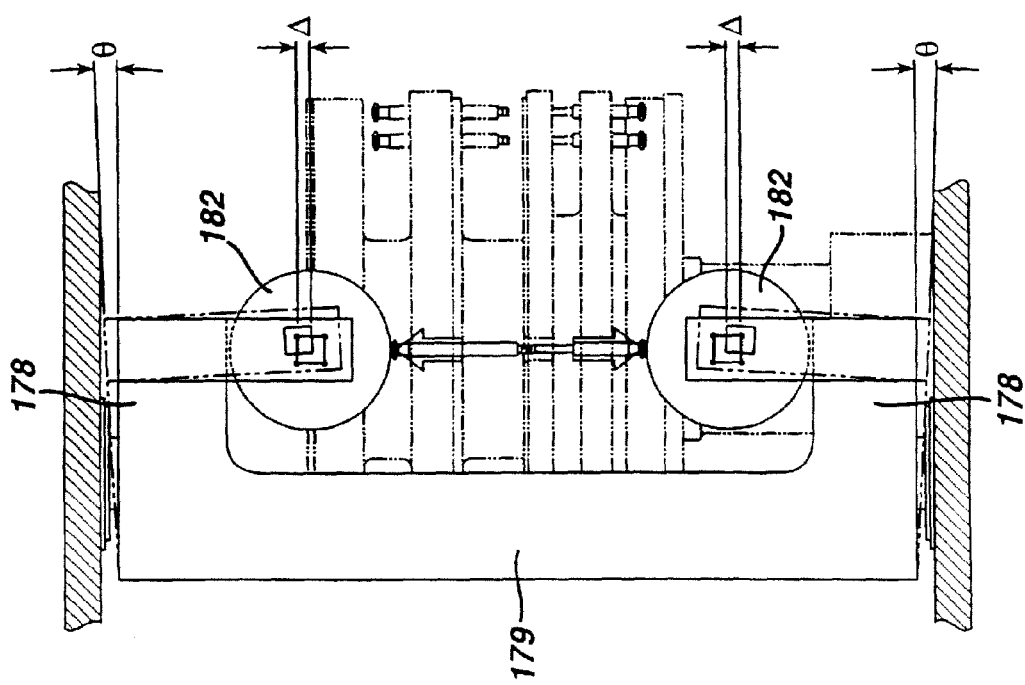
Figure 19D:
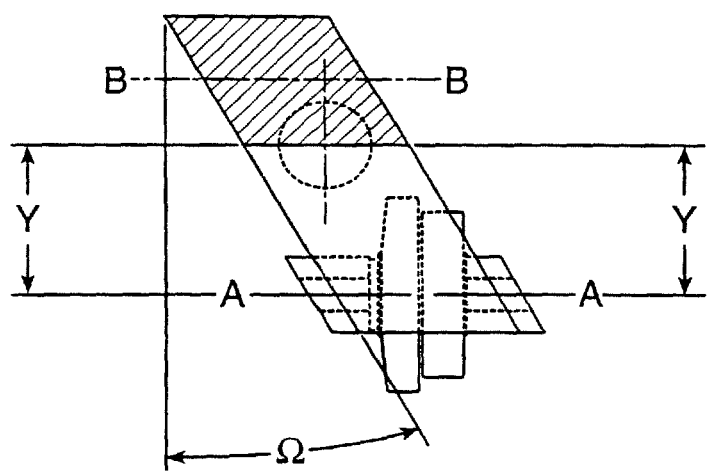

FIGS. 19A through 19D illustrate a preferred embodiment of the compression frame. As shown in FIG. 19D, the frame comprises a throat 179 and two arms 178. The arms 178 forms an oblique angle Ω with respect to the axial axis of the rollers A-A. As shown in FIGS. 19B and 19D despite deflection of the frame anhd displacement Δ of the rollers, the rollers remain horizontal. An additional advantage of this construction is a significantly greater free space angle ϕ, as shown in FIG. 19A. This compression frame configuration can also advantageously pivot about an axis away from the compression module to allow for access or removal of the die table.

Following the formation of the compressed dosage form in the compression zone 106, the respective die cavity 132 rotates to ejection zone 108 as shown in FIG. 6. The upper punches 118 move upward due to the slope of the cam tracks 122 as shown in FIGS. 7, 8, and 16 and out of the die cavities. The lower punches 120 move upward and into the die cavities 132 until eventually the lower punches 120 eject the compressed dosage form out of the die cavity 132, and optionally into a transfer device 300 as shown in FIG. 6.

In the purge zone 110, excess powder is removed from the filters 136 after the compressed dosage form has been ejected from the die cavities 132. This cleans the filters before the next filling operation. The purge zone 110 accomplishes this by blowing air through or placing suction pressure on the filters 136 and channels 138.

Figure 20:
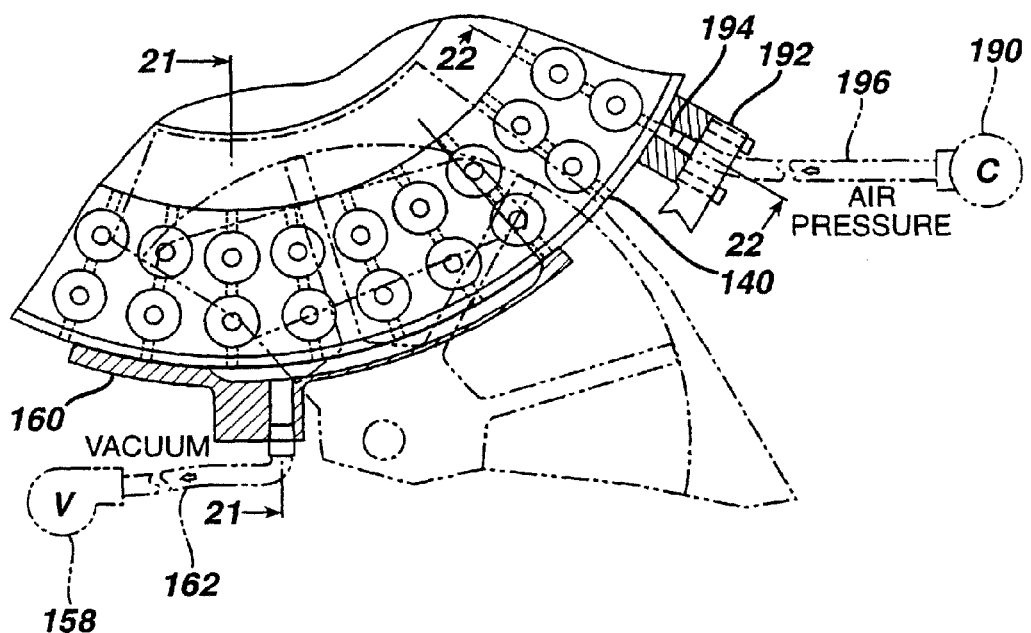
FIG. 20 is a top view of the purge zone and the fill zone of the compression module.
Figure 21:
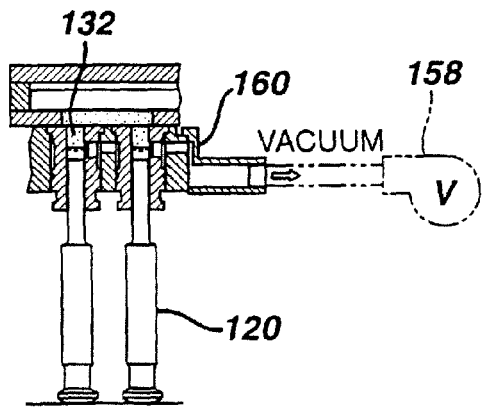
FIG. 21 is a cross-section taken through line 21-21 of FIG. 20.
Figure 22:
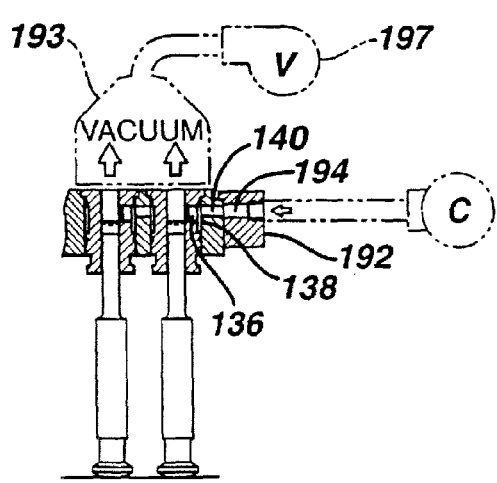
FIG. 22 is a cross-section taken through line 22-22 of FIG. 20.

In a preferred embodiment the purge zone 110 includes a stationary positive pressure source 190, such as an air pump or pressurized air bank, and a pressure manifold 192, as shown schematically in FIG. 12. The pressure manifold 192 may be disposed proximal to the periphery of the die table 114 and between the compression zone 106 and the fill zone 102, as best understood with reference to FIGS. 20 and 22. The pressure manifold 192 preferably has at least one port 194 (although any number of ports can be used) that can be placed in fluid communication with the filters as the die table 114 rotates. Pressure source 190 applies pressure through tubing 196 and the pressure manifold 192 to each respective channel 138 and die cavity 132 as the die table 114 rotates and the openings 140 become aligned with the pressure manifold ports 194, as shown in FIGS. 20 and 22. It will be appreciated from FIGS. 7 and 8 that in the purge zone 110 the upper punches 118 are removed from the die cavities 132 and the lower punches 120 are disposed beneath the filters 136, so that pressure can be applied through the openings 140 as shown in FIG. 22. When the lower punch 120 is inserted into the die cavity 132 above the filters 136 and die ports 134, die cavity 132 is disconnected from the vacuum source 142, and vacuum is no longer exerted on the powder.

The positive pressure cleans out the filters to remove any buildup of powder by transmitting pressurized air from the pressure manifold through the channels and through the die cavities. The pressurized air blows the powder up through the top of the die cavities to a collection manifold 193, shown in FIGS. 22, 24 and 25. From the collection manifold, the powder can be sent to a collection chamber or the like and if desired reused.

In order to increase the efficiency of the purge zone 110, the purge zone 110 may further include a suction source 197 that applies suction to the collection manifold 193 as shown in FIG. 22 and a collection chamber 193 that receives the powder from the suction source 197.

Figure 23:
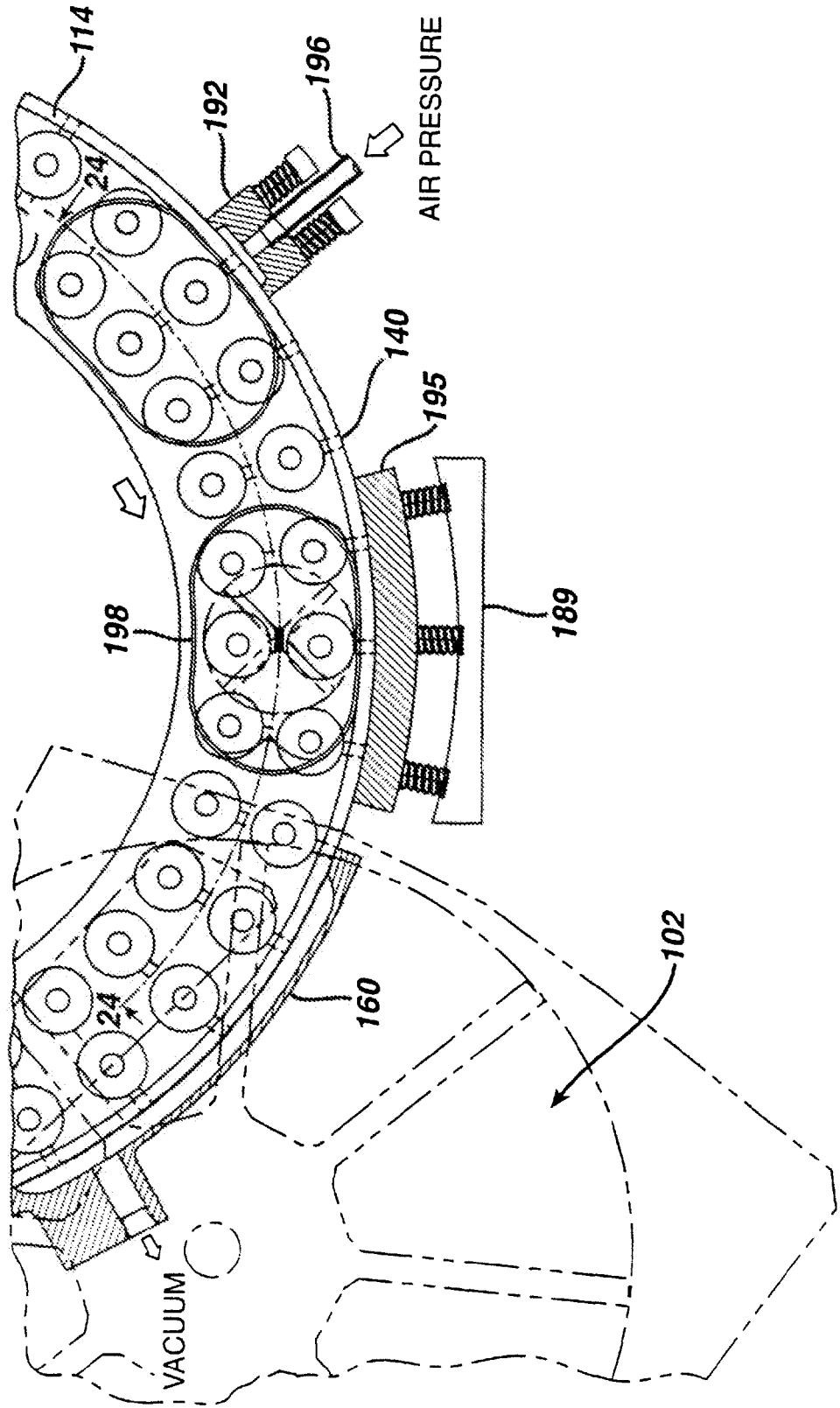
FIG. 23 illustrates an embodiment of a powder recovery system for the compression module.
Figure 24:
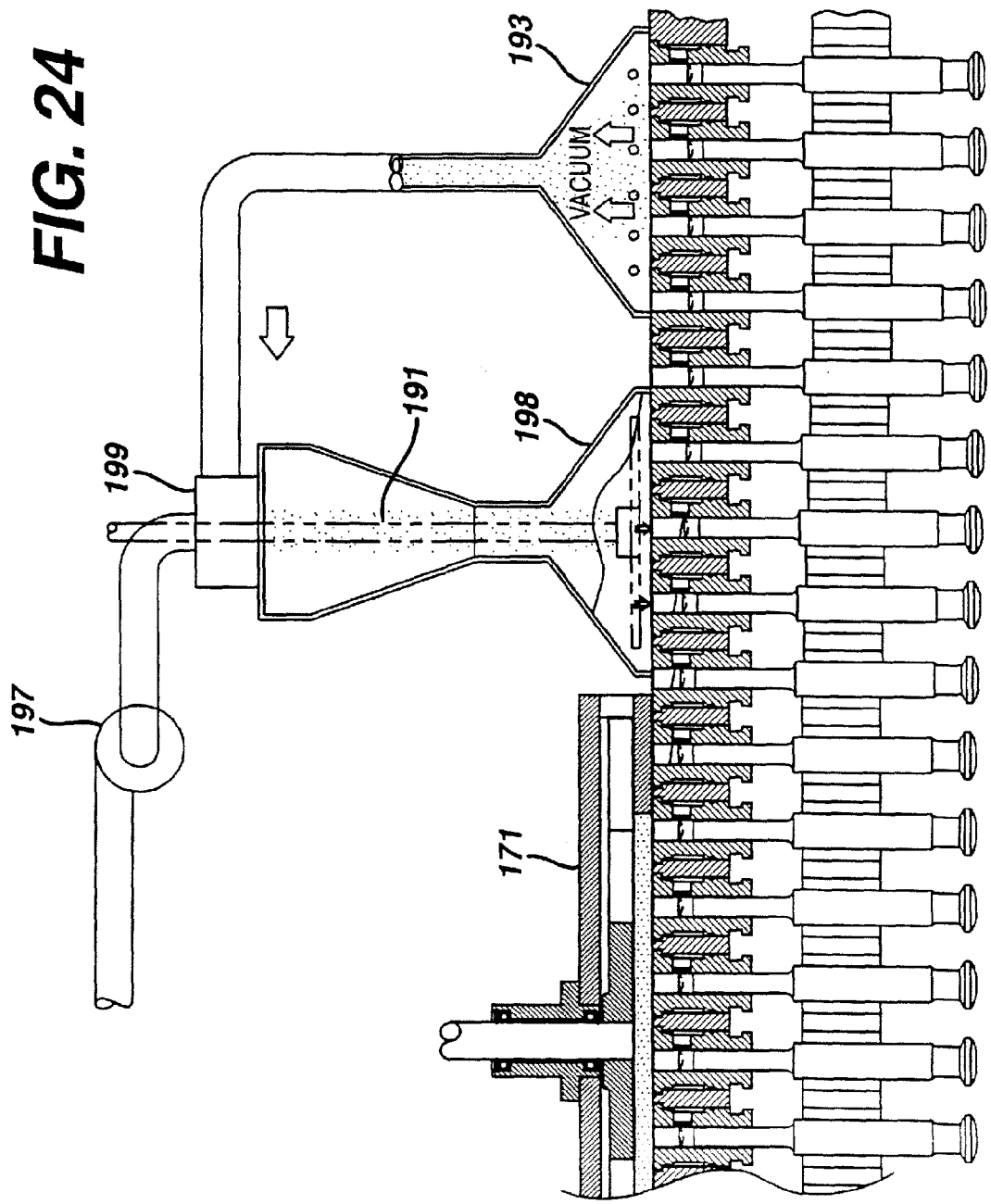
FIG. 24 is a cross-section taken along line 24-24 of FIG. 23.

If desired the purge zone 110 can include a recovery system to recover the removed powder and send it back to hopper 169 or the powder bed 171. This is advantageous because it minimizes waste. One embodiment of the recovery system is depicted in FIGS. 23 and 24. The recovery system feeds the purged powder into the die cavities 132 prior to their arrival at the fill zone 102. In this embodiment, the recovery system includes shoe block 195, a blower 197, a cyclone receiver 199, a delivery manifold 198, and an agitator 191. The shoe block 195 is disposed about and contacts a portion of the periphery of the die table 114 between the pressure manifold 192 and the fill zone 102 as shown in FIG. 23. The shoe block 195 may be spring loaded by springs 189 so that it fits tightly against the die table 114 as the die table 114 rotates past it. The shoe block 195 is aligned with the openings 140 in the die table 114 to create a pressure seal between the openings 140 and the shoe block 189. This pressure seal prevents purged powder in the die cavities 132 from being blown back out of the die cavities. Alternately, shoe block 195 can be dispensed with if the lower punches 120 are moved upward to cover the die ports 134 and then moved down again prior to entering the fill zone 102.

The blower 197 shown in FIG. 24 is coupled to the collection manifold 193 to pull powder from the die cavities 132. The blower 197 sends purged powder from the collection manifold 193 to the cyclone dust separator 199, which operates at a partial vacuum. The cyclone dust separator 199 collects the purged powder and sends it to the delivery manifold 198 as shown in FIG. 24. A filter bag dust separator can be substituted for the cyclone dust separator. Once the dust is separated from the air stream 199 it falls into the delivery manifold 198, as shown in FIG. 24

The delivery manifold 198 is disposed just above the die table 114 so that as the die table 114 rotates, the top of the die table 114 comes into contact with the delivery manifold 198, creating a pressure seal between the delivery manifold 198 and the die table 114. The die cavities are open to the delivery manifold 198 as shown in FIG. 24 so that purged powder can flow into the die cavities by gravity or other means such as an optional vacuum source (not shown). The agitator 191 rotates within the delivery manifold 198 to direct the purged powder to the die cavities 132.

In operation, the die table 114 rotates proximal to the pressure manifold 192 and beneath the collection manifold 193. As described above, pressurized air is sent through the openings 140 in the periphery of the die table and vacuum is applied to the collection manifold 193 and the two together cause powder to flow from the channels 138 and the die cavities 132 as shown in FIG. 24 to the collection manifold 193.

From the collection manifold 193, the purged powder flows to the cyclone dust separator 199 where the purged powder is directed to the agitator 191 and the delivery manifold 198. The die table 114 continues to rotate so that the purged die cavities 132 pass to the shoe block 195 as shown in FIG. 23. The openings 140 of the die cavities are sealed by the shoe block 195 so that powder can flow into the die cavities 132, but will not flow out of the openings 140. The delivery manifold 198 directs the purged powder from the cyclone dust separator 199 back into the die cavities 132. Following this, the die table 114 continues to rotate to the fill zone 102.

Figure 25:
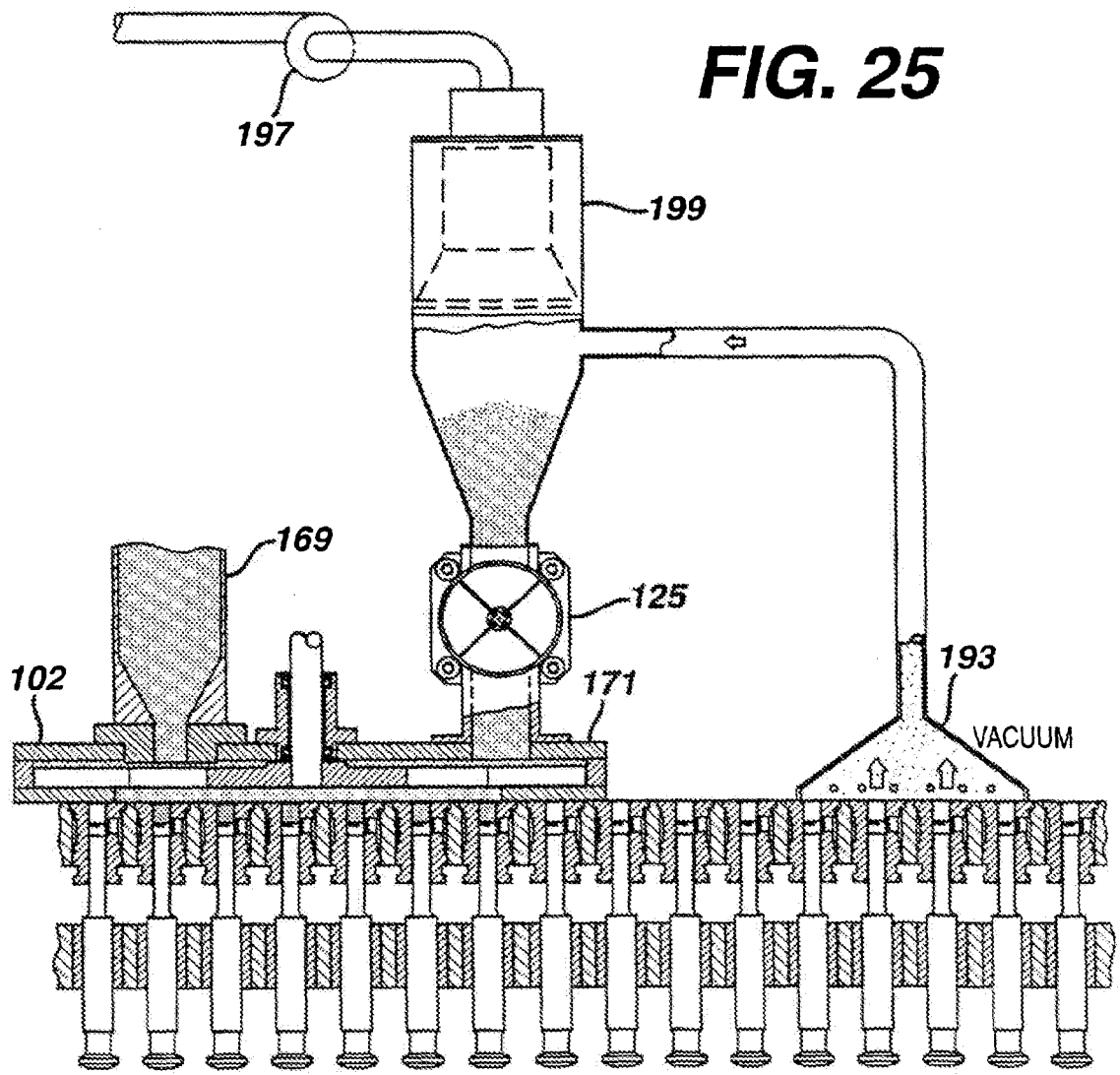
FIG. 25 shows an alternative embodiment of a powder recovery system for the compression module.

An alternate embodiment of the powder recovery system is shown in FIG. 25. This embodiment dispenses with the delivery manifold 198 and shoe block 195. Purged powder is delivered back into the fill zone 102 rather than into the die cavity 134. A rotary valve 125 is employed to prevent powder from powder bed 171 from entering the cyclone dust separator 199. A series of two gate or flap valves (not shown) may also be used in place of the rotary valve 125.

The above systems for purging the powder from the die cavities 132 and channels 138 prevents powder build-up and minimizes waste. Of course, this invention in its broadest sense can be practiced without such a purge zone 110 or a recovery system.

Thermal Cycle Molding Module

The thermal cycle molding module 200 may function in one of several different ways. It may for example be used to form a shell or coating over at least part of a dosage form such as a compressed dosage form such as a tablet. It may also be used as stand alone equipment to produce a molded dosage form per se. Such a coating or dosage form is made from a flowable material. Preferably, the molding module is used to apply a coating of flowable material to a dosage form. More preferably, the molding module is used to apply a coating of a flowable material to a compressed dosage form made in a compression module of the invention and transferred via a transfer device also according to the invention. The coating is formed within the molding module by injecting the flowable material, preferably comprising a natural or synthetic polymer, into a mold assembly around the dosage form. The flowable material may or may not comprise a medicant and appropriate excipients, as desired. Alternately, the molding module may be used to apply a coating of flowable material to a molded dosage form, or other substrate.

Advantageously, the thermal cycle molding module may be used to apply smooth coatings to substrates that are irregular in topography. The coating thickness achieved with the thermal cycle molding module typically ranges from about 100 to about 400 microns. However, the relative standard deviation in the thickness of the coating can be as high as about 30%. This means the outside of the coated dosage form can be made to be highly regular and smooth, even if the substrate below it is not. Once coated, the relative standard deviations in thickness and diameter of the coated dosage form are typically not greater than about 0.35%. Typical coated dosage form thicknesses (shown in FIG. 89 as t) are on the order of about 4 to 10 mm, while typical coated dosage form diameters (d in FIG. 89) range from about 5 to about 15 mm. It should be noted that subcoats, which are often present in conventional dosage forms, are not necessary on dosage forms coated using the thermal cycle molding module.

The thermal cycle molding module 200 preferably cycles between hot and cold temperatures during operation. Preferably, the actual mold cavity is held at a temperature generally above the melting point or gel point of the flowable material during injection and filling thereof. After the mold cavity is filled its is quickly decreased to below the melting point or gel point of the flowable material thus causing it to solidify or set. The mold itself is thin like an "egg shell," and constructed of a material with a high thermal conductivity, such that the mass and geometry of the mold have a negligible effect on the speed at which this thermal cycle is accomplished.

A significant advantage, then, of the thermal cycle molding module is the dramatically reduced cycle times it affords due to the fact that it can cycle between temperatures that are relatively far apart. The temperature differential between the actual mold cavity and the flowable material is the major driving force in the solidification rate of the flowable material. By substantially increasing this rate higher equipment output can be achieved and subsequent savings in equipment, labor, and plant infrastructure can be realized.

Moreover, molding of gelatin or similar materials, for example non-polymers such as the basic elements, metals, water, and alcohol, have not previously been possible using conventional molding techniques such as injection molding. Precise control over the temperature and pressure of such materials, as well as the mold cavity temperature are required to assure these materials are sufficiently flowable to fill the mold cavity completely. On the other hand, the mold cavity must subsequently be cooled enough to assure that the material will eventually solidify. In particular, gelatin, once hydrated, has a very abrupt transition temperature between the liquid phase and the solid or gel phase. It therefore cannot be characterized as a thermoplastic material. Accordingly, in order to mold gelatin and materials like it the temperature of the mold must cycle from a first temperature above its melting or gel point (to assure that the material will flow and completely fill the mold cavity) to a second temperature below its melting or gel point (to solidify it).

In a preferred embodiment of the invention, the flowable material comprises gelatin. Gelatin is a natural, thermogelling polymer. It is a tasteless and colorless mixture of derived proteins of the albuminous class which is ordinarily soluble in warm water. Two types of gelatin—Type A and Type B—are commonly used. Type A gelatin is a derivative of acid-treated raw materials. Type B gelatin is a derivative of alkali-treated raw materials. The moisture content of gelatin, as well as its Bloom strength, composition and original gelatin processing conditions, determine its transition temperature between liquid and solid. Bloom is a standard measure of the strength of a gelatin gel, and is roughly correlated with molecular weight. Bloom is defined as the weight in grams required to move a half-inch diameter plastic plunger 4 mm into a 6.67% gelatin gel that has been held at 10° C. for 17 hours.

In a preferred embodiment wherein the flowable material is an aqueous solution comprising 20% 275 Bloom pork skin gelatin, 20% 250 Bloom Bone Gelatin, and approximately 60% water, the mold cavities are cycled between about 35° C., and about 20° C. in about 2 seconds (a total of 4 seconds per cycle).

Other preferred flowable materials comprise polymeric substances such as polysaccharides, cellulosics, proteins, low and high molecular weight polyethylene glycol (including polyethylene oxide), and methacrylic acid and methacrylate ester copolymers. Alternative flowable materials include sucrose-fatty acid esters; fats such as cocoa butter, hydrogenated vegetable oil such as palm kernel oil, cottonseed oil, sunflower oil, and soybean oil; mono- di- and triglycerides, phospholipids, waxes such as Carnauba wax, spermaceti wax, beeswax, candelilla wax, shellac wax, microcrystalline wax, and paraffin wax; fat-containing mixtures such as chocolate; sugar in the form on an amorphous glass such as that used to make hard candy forms, sugar in a supersaturated solution such as that used to make fondant forms; carbohydrates such as sugar-alcohols (for example, sorbitol, maltitol, mannitol, xylitol), or thermoplastic starch; and low-moisture polymer solutions such as mixtures of gelatin and other hydrocolloids at water contents up to about 30%, such as for example those used to make "gummi" confection forms.

The flowable material may optionally comprise adjuvants or excipients, in which may comprise up to about 20% by weight of the flowable material. Examples of suitable adjuvants or excipients include plasticizers, detackifiers, humectants, surfactants, anti-foaming agents, colorants, flavorants, sweeteners, opacifiers, and the like. In one preferred embodiment, the flowable material comprises less than 5% humectants, or alternately is substantially free of humectants, such as glycerin, sorbitol, maltitol, xylitol, or propylene glycol. Humectants have traditionally been included in pre-formed films employed in enrobing processes, such as that disclosed in U.S. Pat. No. 5,146,730 and U.S. Pat. No. 5,459,983, assigned to Banner Gelatin Products Corp., in order to ensure adequate flexibility or plasticity and bondability of the film during processing. Humectants function by binding water and retaining it in the film. Pre-formed films used in enrobing processes can typically comprise up to 45% water. Disadvantageously, the presence of humectant prolongs the drying process, and can adversely affect the stability of the finished dosage form.

Advantageously, drying of the dosage form after it has left the thermal cycle molding module not is required when the moisture content of the flowable material is less than about 5%.

Whether coating a dosage form or preparing a dosage form per se, use of the thermal cycling molding module advantageously avoids visible defects in the surface of the product produced. Known injection molding processes utilize sprues and runners to feed moldable material into the mold cavity. This results in product defects such as injector marks, sprue defects, gate defects, and the like. In conventional molds, sprues and runners must be broken off after solidification, leaving a defect at the edge of the part, and generating scrap. In conventional hot runner molds, sprues are eliminated, however a defect is produced at the injection point since the hot runner nozzle must momentarily contact the chilled mold cavity during injection. As the tip of the nozzle retracts it pulls a "tail" with it, which must be broken off. This defect is particularly objectionable with stringy or sticky materials. Unwanted defects of this nature would be particularly disadvantageous for swallowable dosage forms, not only from a cosmetic standpoint but functionally as well. The sharp and jagged edges would irritate or scratch the mouth, tongue and throat.

The thermal cycle molding module avoids these problems. It employs nozzle systems (referred to herein as valve assemblies) each comprising a valve body, valve stem and valve body tip. After injection of flowable material into the mold cavity, the valve body tip closes the mold cavity while comforming seemlessly to the shape of the mold cavity. This technique eliminates visible defects in the molded product and also allows a wide range of heretofore unmoldable or difficult to mold materials to be used. Moreover, use of the thermal cycle molding module according to the invention avoids the production of scrap flowable material, in that substantially all of the flowable material becomes part of the finished product.

For convenience, the thermal cycle molding module is described generally herein as it is used to apply a coating to a compressed dosage form. However, FIG. 26A, which is explained further below, depicts an embodiment in which molded dosage forms per se are made using the thermal cycle molding module.

The thermal cycle molding module 200 generally includes a rotor 202, as shown in FIGS. 2 and 3 around which a plurality of mold units 204 are disposed. As the rotor 202 revolves, the mold units 204 receive compressed dosage forms, preferably from a transfer device such as transfer device 300. Next, flowable material is injected into the mold units to coat the compressed dosage forms. After the compressed dosage forms have been coated, the coating may be further hardened or dried if required. They may be hardened within the mold units or they may be transferred to another device such as a dryer. Continued revolution of the rotor 202 repeats the cycle for each mold unit.

Figure 29:
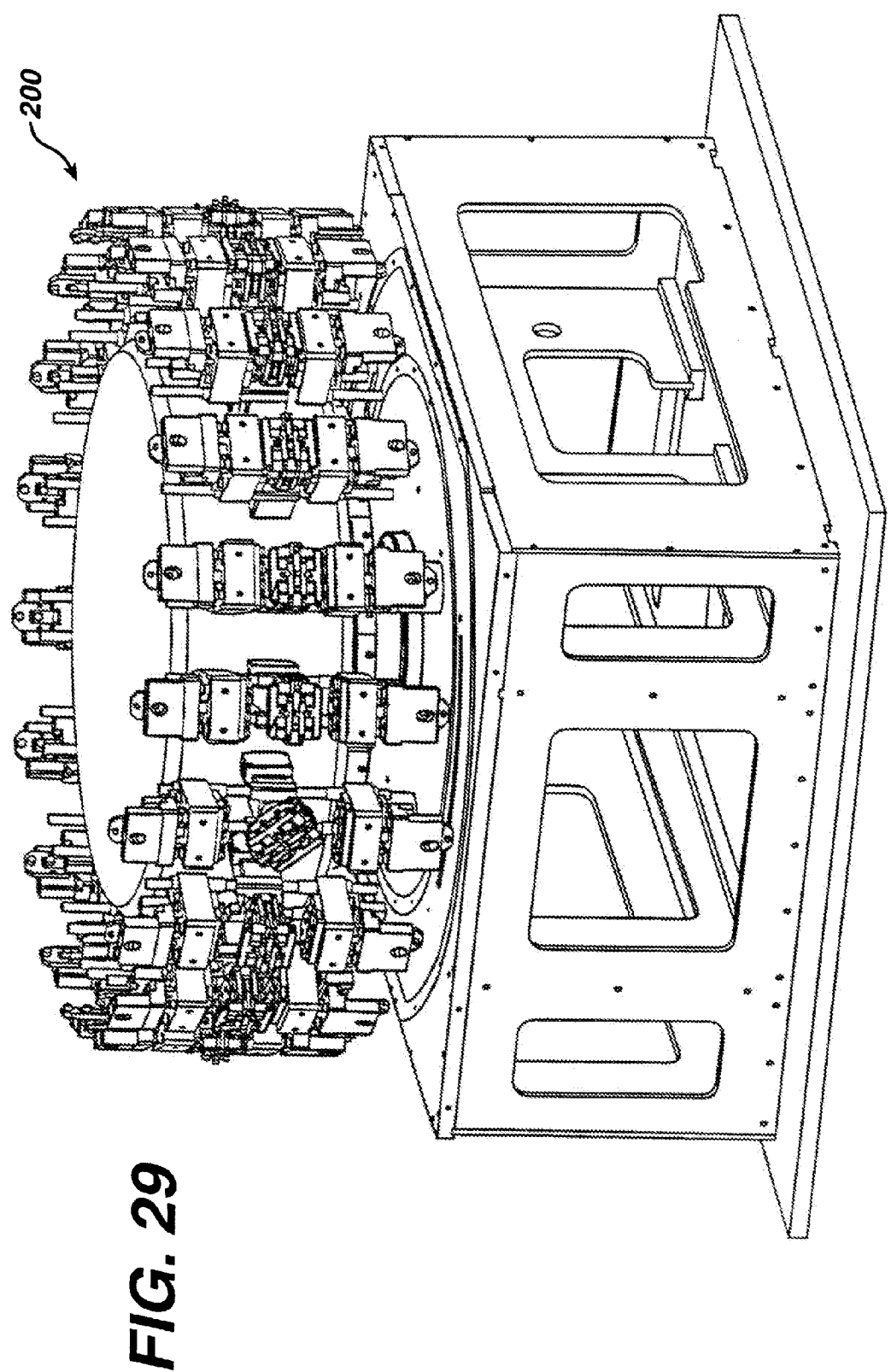
FIG. 29 is a three dimensional view of a thermal cycle molding module according to the invention.
Figure 30:
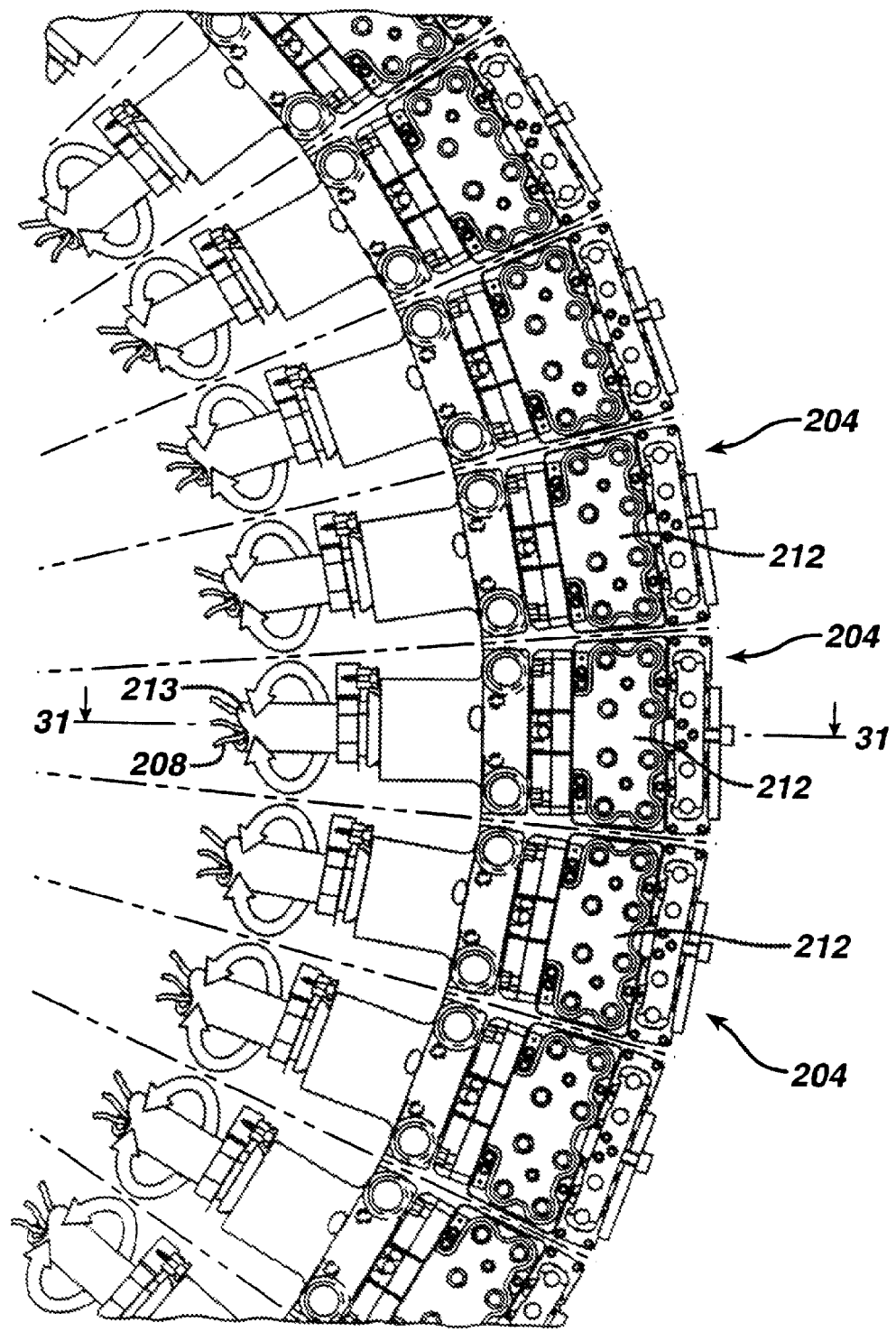
FIG. 30 depicts a series of center mold assemblies in a thermal cycle molding module.
Figure 31:
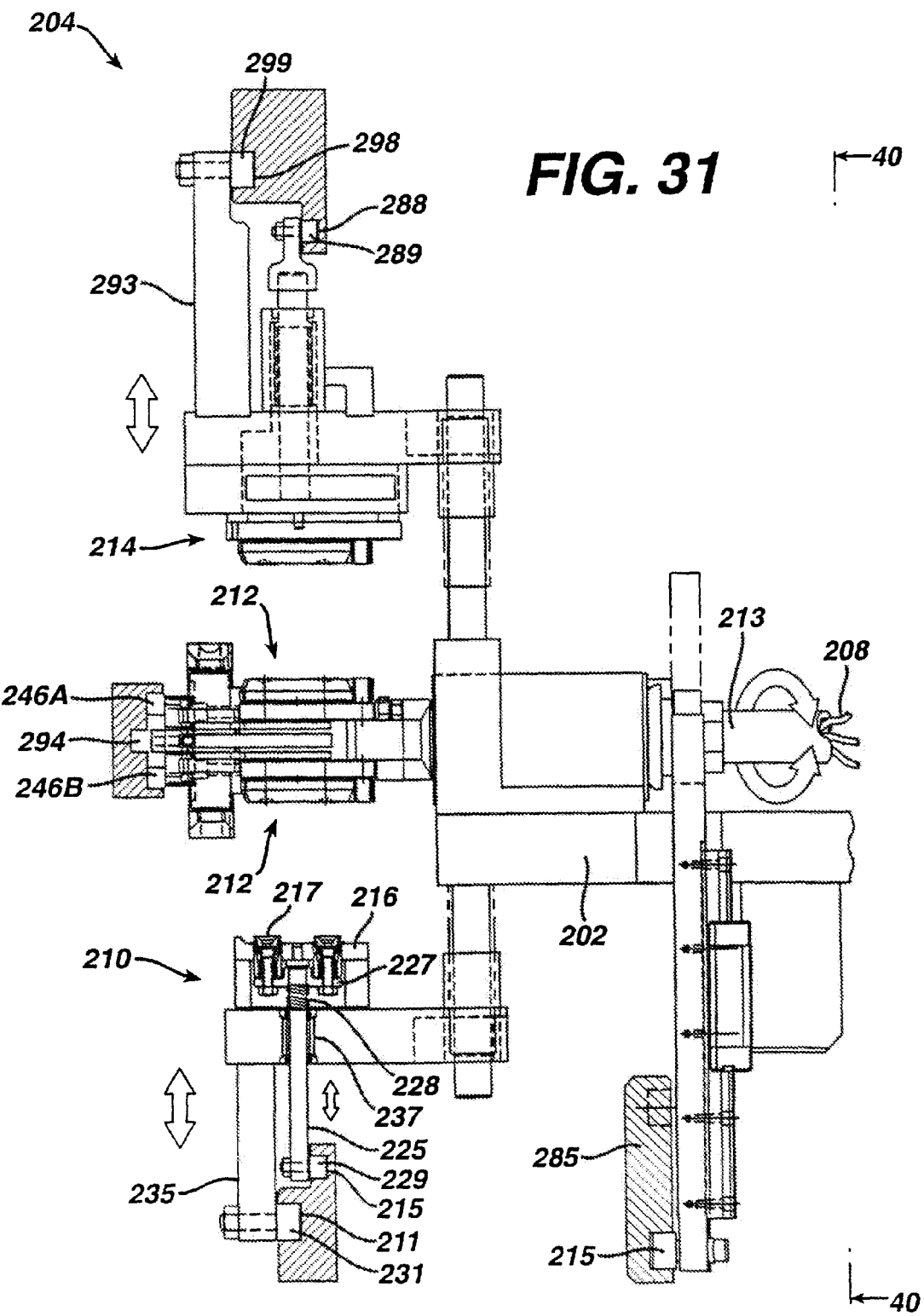
FIG. 31 is a cross-section taken along line 31-31 of FIG. 30.

FIG. 29 is a three dimensional view of the thermal cycle molding module 200 as described above. FIG. 30 is a partial view through a section of the thermal cycle molding module as viewed from above showing multiple mold units 204. FIG. 31 is a section through one of the mold units 204. The thermal cycle molding module 200 includes at least one reservoir 206 containing the flowable material, as shown in FIG. 4. There may be a single reservoir for each mold unit, one reservoir for all the mold units, or multiple reservoirs that serve multiple mold units. In a preferred embodiment, flowable material of two different colors are used to make the coating, and there are two reservoirs 206, one for each color. The reservoirs 206 may be mounted to the rotor 202 such that they rotate with the rotor 202, or be stationary and connected to the rotor via a rotary union 207 as shown in FIG. 4. The reservoirs 206 can be heated to assist the flowable material in flowing. The temperature to which the flowable material should be heated of course depends on the nature of the flowable material. Any suitable heating means may be used, such as an electric (induction or resistance) heater or fluid heat transfer media. Any suitable tubing 208 may be used to connect the reservoirs 206 to the mold unit 204. In a preferred embodiment, tubing 208 extends through each of the shafts 213 as shown in FIGS. 30 and 31 to each of the center mold assemblies 212.

A preferred embodiment of a mold unit 204 is shown in FIG. 31. The mold unit 204 includes a lower retainer 210, an upper mold assembly 214, and a center mold assembly 212. Each lower retainer 210, center mold assembly 212, and upper mold assembly 214 are mounted to the rotor 202 by any suitable means, including but not limited to mechanical fasteners. Although FIG. 31 depicts a single mold unit 204 all of the other mold units 204 are similar. The lower retainer 210 and the upper mold assembly 214 are mounted so that they can move vertically with respect to the center mold assembly 212. The center mold assembly 212 is preferably rotatably mounted to the rotor 202 such that it may rotate 180 degrees.

Figure 26A:
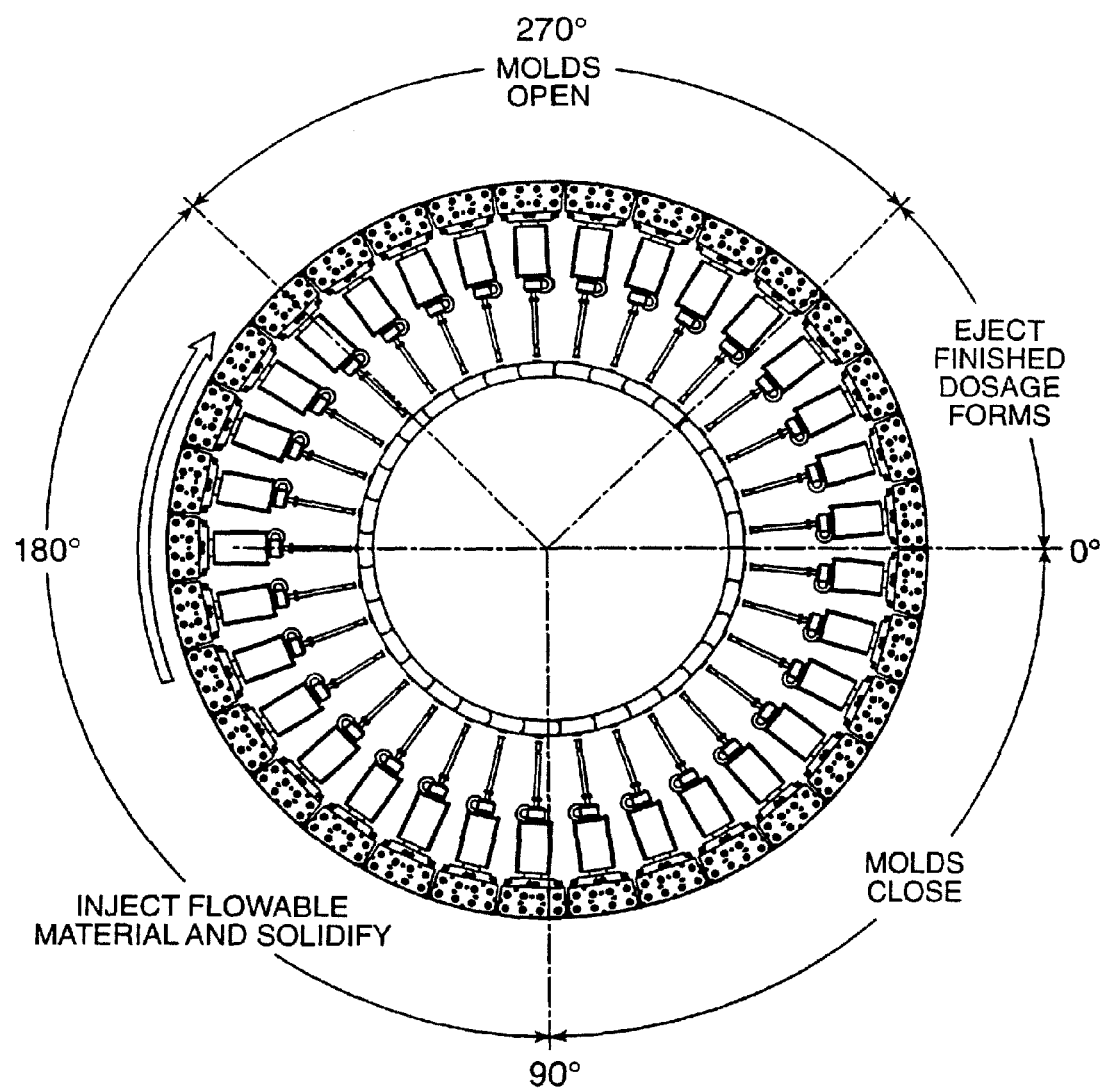
Figure 26C:
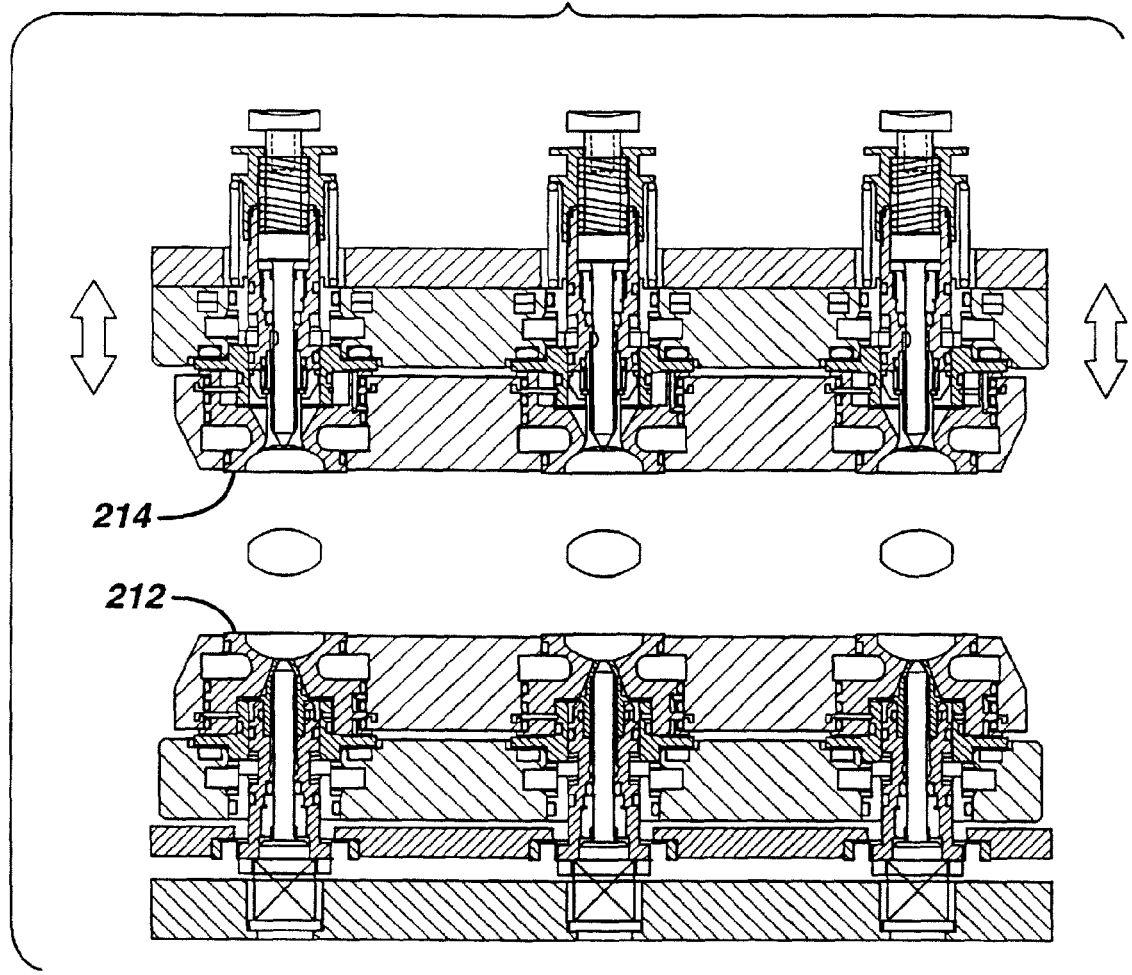

FIG. 26A depicts the sequence of steps for making a molded dosage form per se. This employs a simpler embodiment of the thermal cycle molding module is employed in that the center mold assembly 212 need not rotate. FIG. 26B is a timing diagram showing movement of the mold units 204 as the rotor 202 of the thermal molding module completes one revolution. FIG. 26C is a section through one of the mold units. At the beginning of the cycle (the rotor at the 0 degree position) the upper mold assembly 214 and the center mold assembly 212 are in the open position. As the rotor continues to revolve the mold assemblies close to form a mold cavity. After the mold assemblies close, hot flowable material is injected from either the upper mold assembly, the center mold assembly, or both into the mold cavity. The temperature of the mold cavity is decreased, and a thermal cycle is completed. After the flowable material hardens, the mold assemblies open. Upon further revolution of the rotor, the finished molded dosage forms are ejected thus completing one full revolution of the rotor.

Figure 27A:
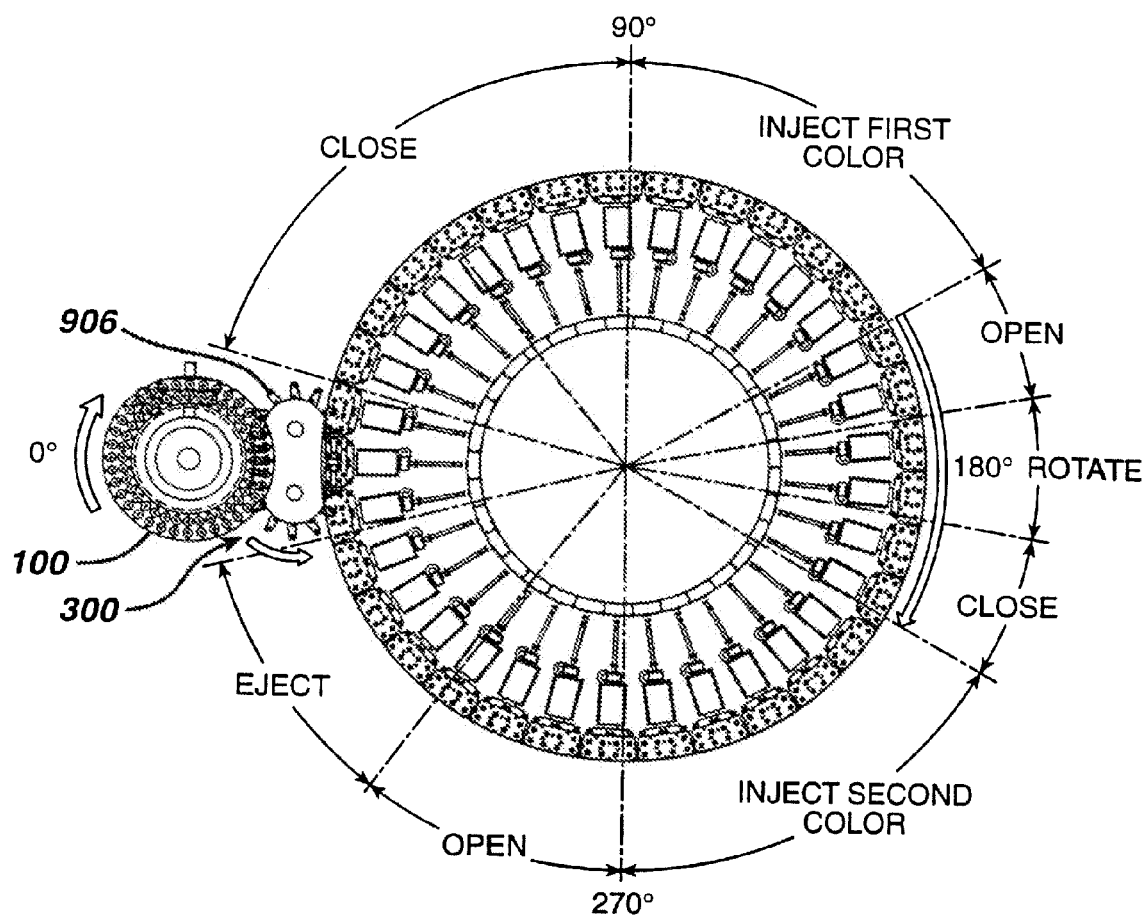
FIGS. 27A-C illustrate another embodiment of a thermal cycle molding module in which a coating is applied to a substrate.
Figure 27B:
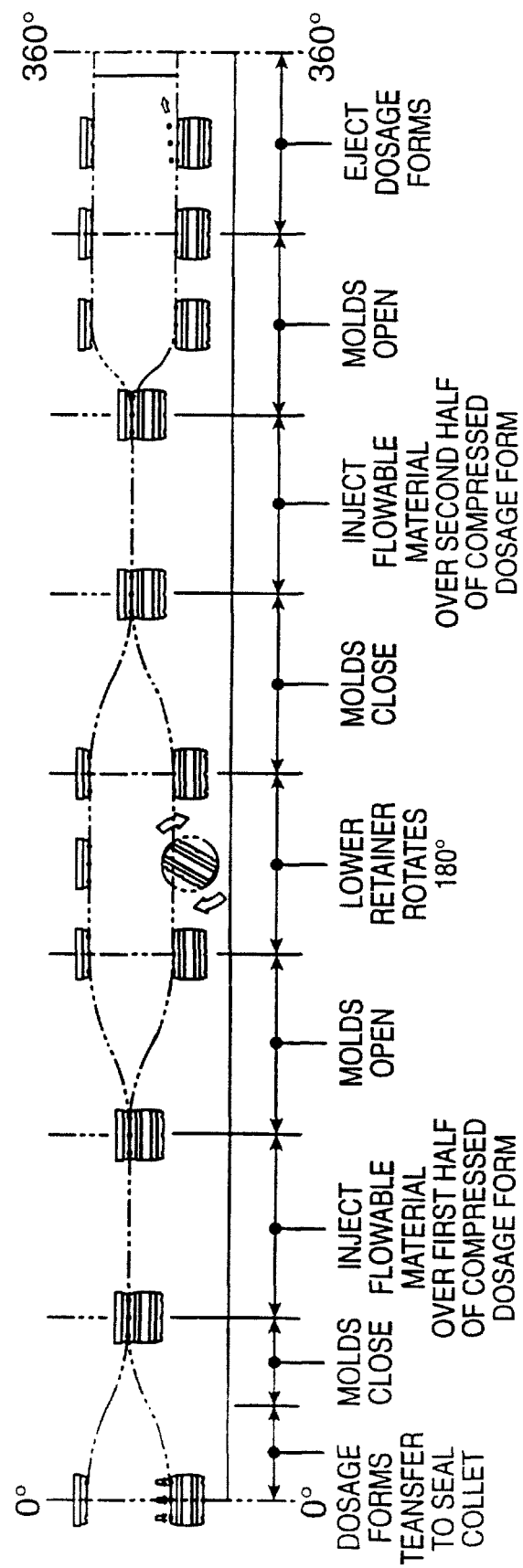
Figure 27C:
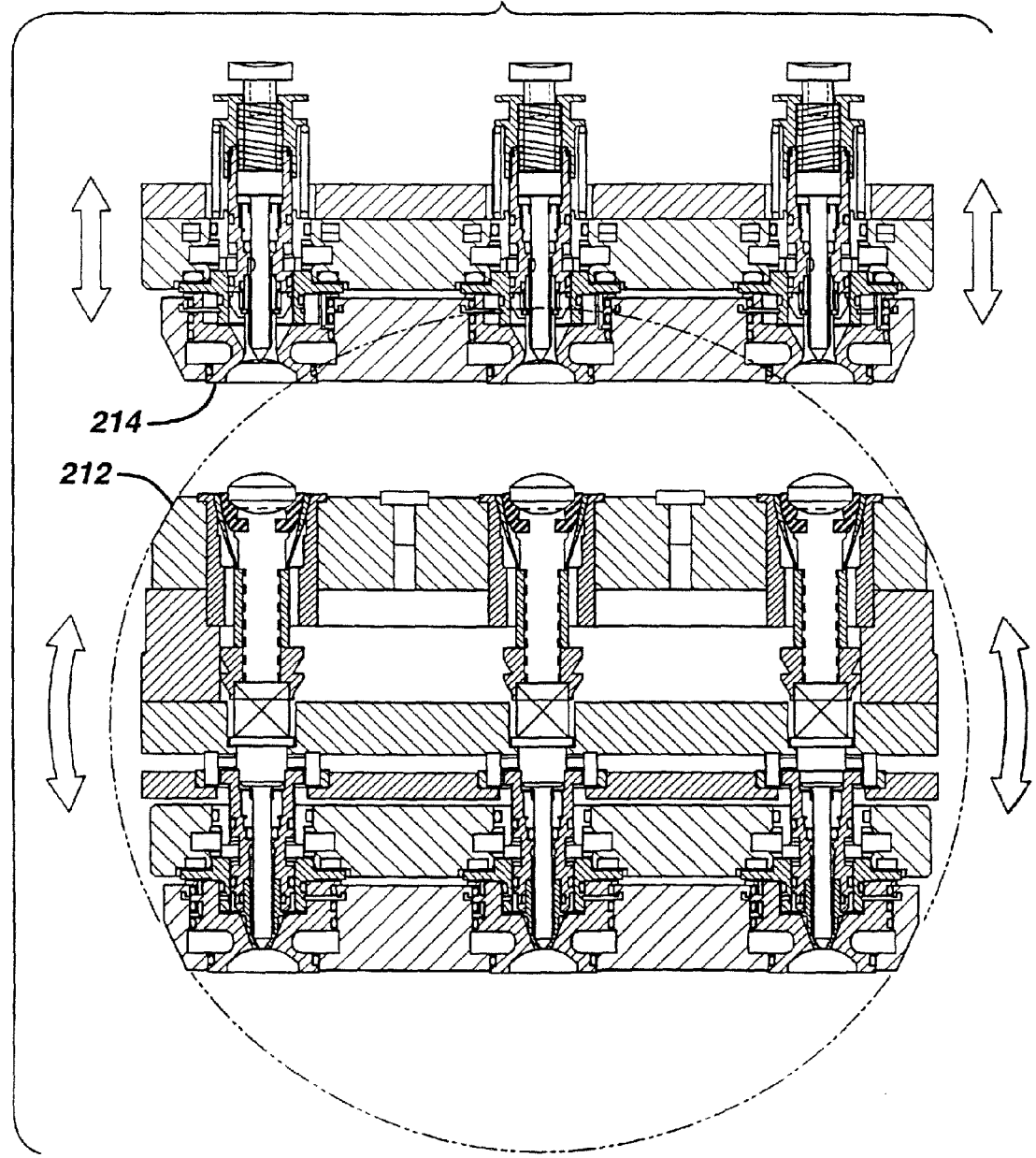

FIG. 27A depicts the sequence of steps for using a second embodiment of the thermal cycle molding module. Here a coating is formed over a compressed dosage form. In this embodiment, the thermal cycle molding module coats the first half of a dosage form during revolution of the rotor 202 between 0 and 180 degrees. The second half of the dosage form is coated during revolution of the rotor between 180 and 360 degrees. FIG. 27B is a timing diagram showing movement and rotation of the mold units as the rotor completes one revolution. FIG. 27C is a section through one of the mold units showing upper mold assembly 214 and center mold assembly 212. Note that the center mold assembly 212 in this embodiment is capable of rotation about its axis. At the beginning of the molding cycle (rotor at the 0 degree position) the mold assemblies are in the open position. Center mold assembly 212 has received a compressed dosage form, for example from a compression module according to the invention transferred via a transfer device also according to the invention. As the rotor continues to revolve, the upper mold assembly 214 closes against center mold assembly 212. Next, flowable material is injected into the mold cavity created by union of the mold assemblies to apply a shell to the first half of the compressed dosage form. The flowable material is cooled in the mold cavity. The mold assemblies open with the half coated compressed dosage forms remaining in the upper mold assembly 214. Upon further revolution of the rotor, the center mold assembly rotates 180 degrees. As the rotor moves past 180 degrees the mold assemblies again close and the uncoated half of the compressed dosage form is covered with flowable material. A thermal cycle is completed with setting or hardening of the coating on the second half of the compressed dosage form. The mold assemblies again open and the coated compressed dosage form is ejected from the thermal cycle molding module.

Figure 28A:
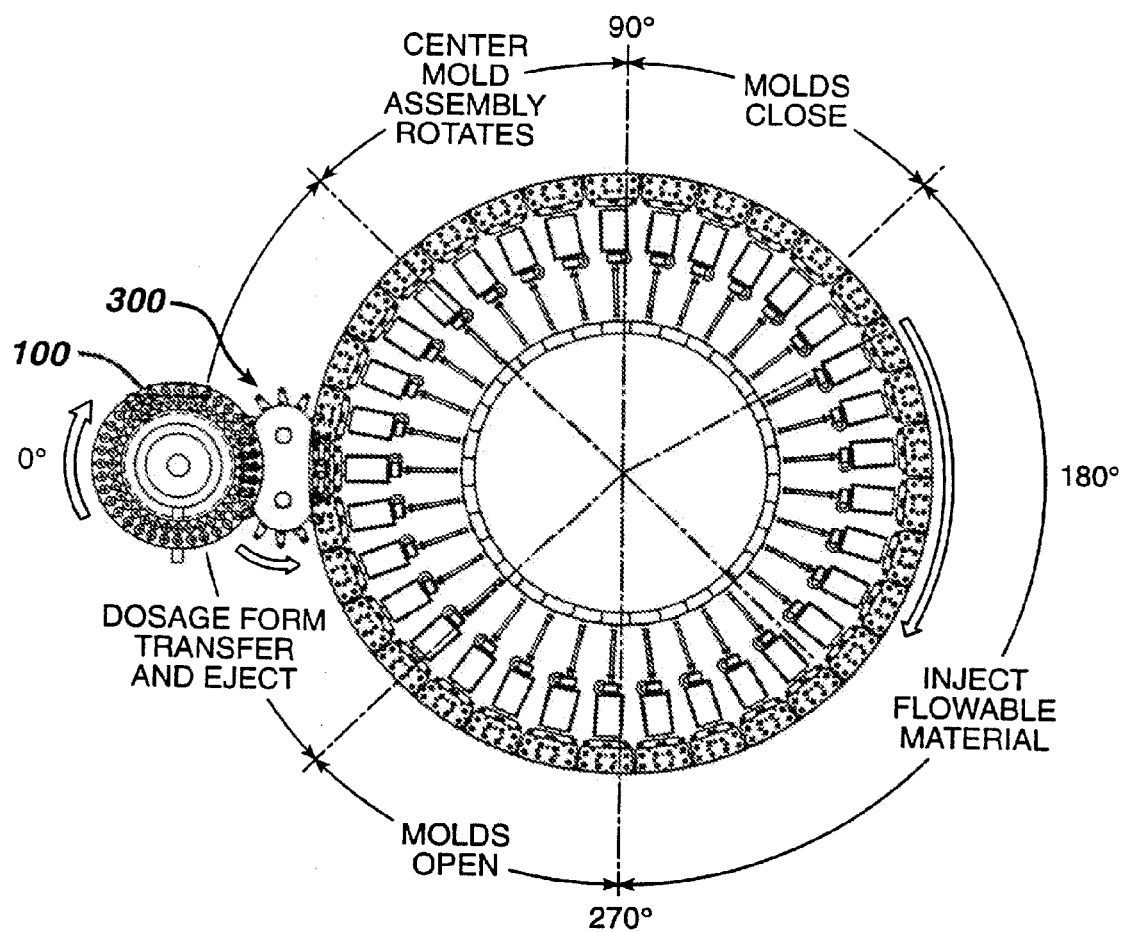
FIGS. 28A-C illustrate a preferred embodiment of a thermal cycle molding module in which a coating is applied to a substrate.

FIG. 28A depicts the sequence of steps for using a preferred embodiment of the thermal cycle molding module to form a coating over a compressed dosage form. In this embodiment, part of a compressed dosage form is coated in the mold cavity created by union of the lower retainer and the center mold assembly 212 during revolution of the rotor between 0 and 360 degrees. Simultaneously, the remainder of a second compressed dosage form, the first part of which has already been coated during a previous revolution of the rotor, is coated in the mold cavity created by the union of the center mold assembly and the upper mold assembly 214. Compressed dosage forms transit through the thermal cycle molding module in a helix, receiving partial coatings during a first full rotation of the rotor, and then the remainder of their coatings during a second full rotation of the rotor. Compressed dosage forms are therefore retained in the thermal cycle molding module for two revolutions of the rotor (720 degrees) prior to being ejected as finished products. This embodiment of the thermal cycle molding module is advantageous in that size of the molding module may be drastically reduced, i.e., to one half the diameter of the embodiment shown in FIG. 27A for a given dosage form output per rotation. This embodiment of the thermal cycle molding module is more economic to fabricate, operate, and house in a high output manufacturing plant.

Figure 28B:
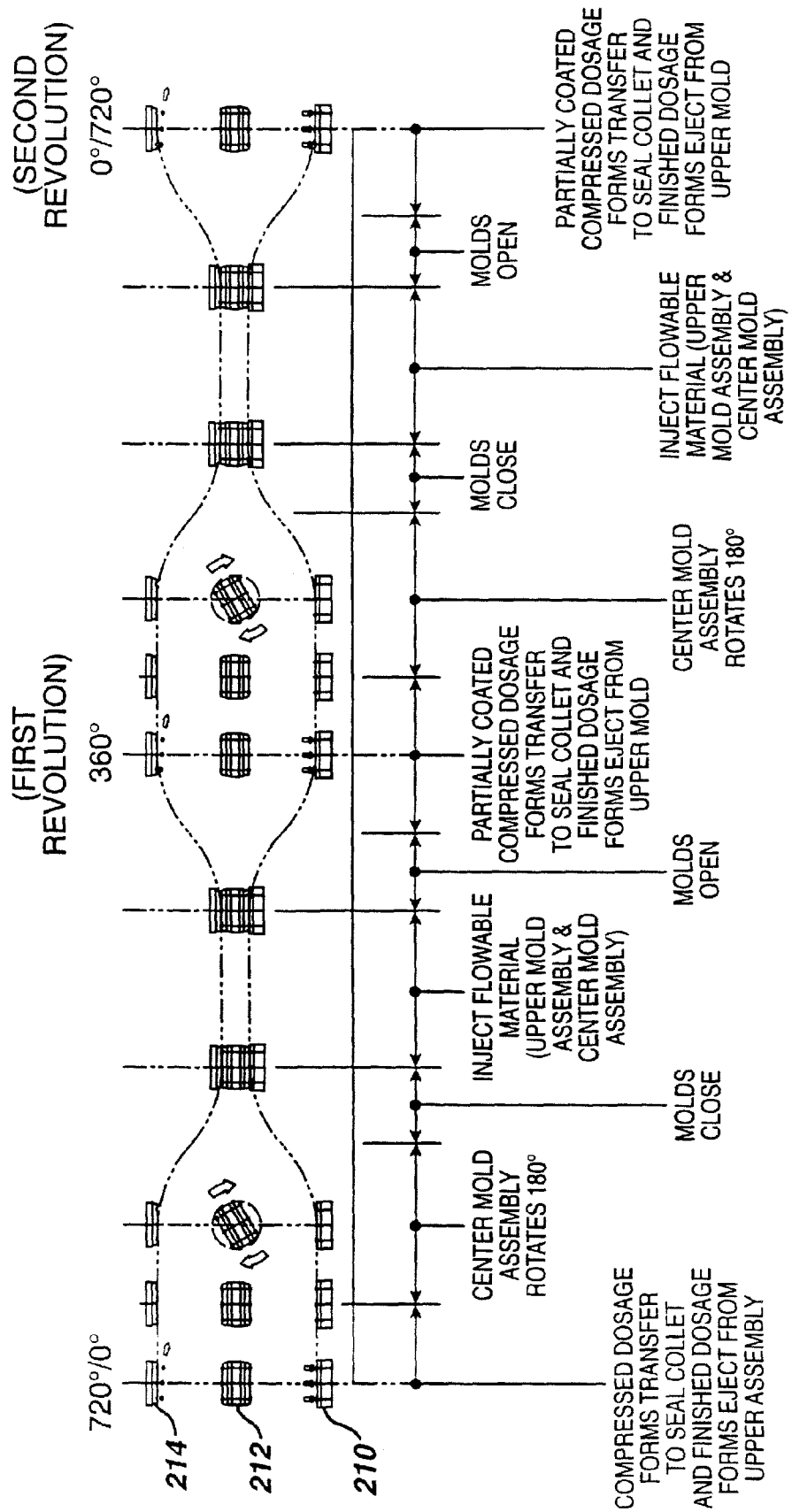
Figure 28C:
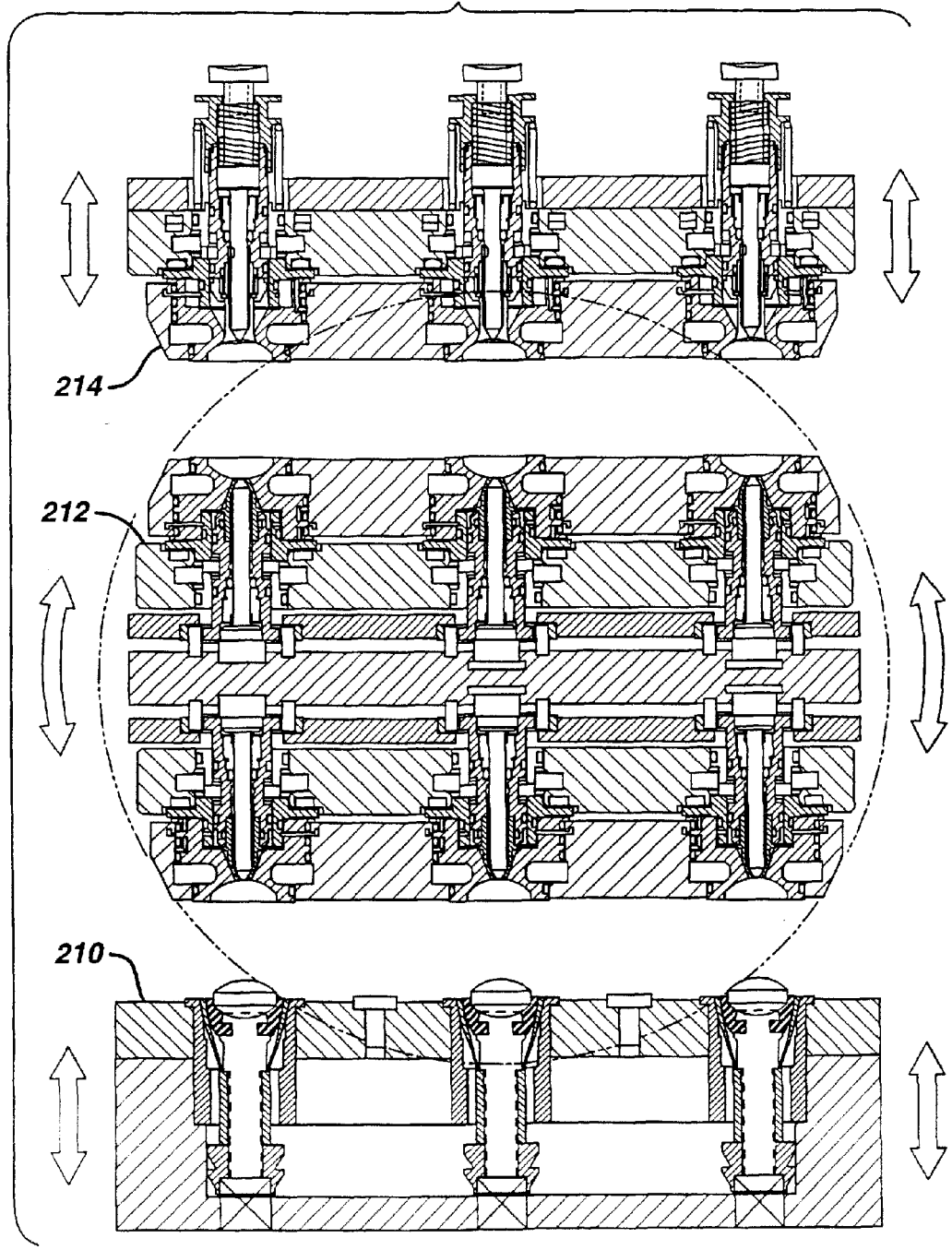
Figure 34:
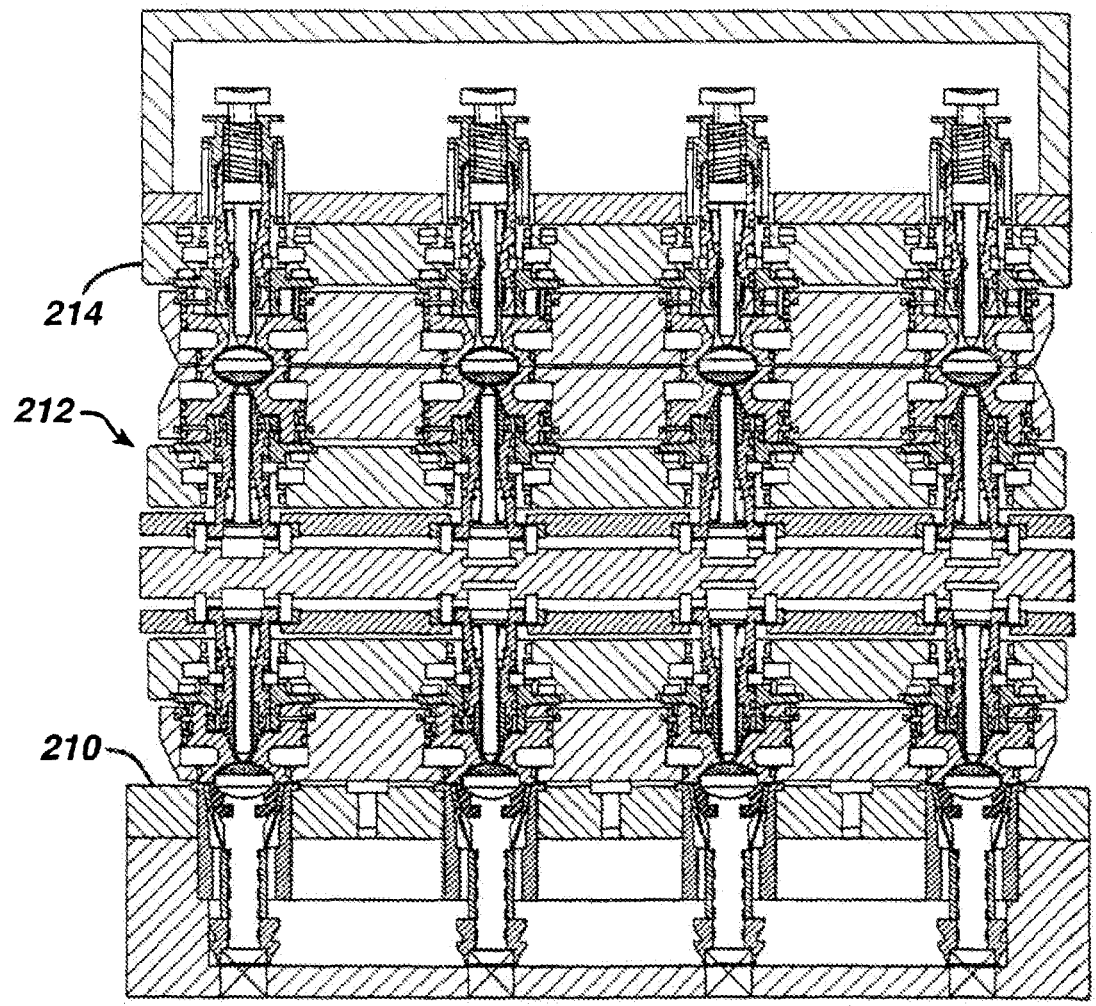

FIG. 28B is a timing diagram showing movement of the mold units and rotation of the center mold assembly as the rotor completes two revolutions (0 through 720 degrees). FIG. 28C is a section through one of the mold units. At the beginning of the cycle (0 degrees rotation of the rotor) the mold units are in the open position. The center mold assembly 212 contains a partially coated compressed dosage form. The lower mold assembly 210 receives an uncoated compressed dosage form, for example from a compression module 100 via a transfer device 300. Upon rotation of the rotor, the center mold assembly 212 rotates 180 degrees about its axis, which is radial to the rotor. This presents the partially coated compressed dosage form to the upper mold assembly 214, which is empty. The partially coated compressed dosage form is then disposed between the upper and center mold assemblies 212, 214. As the rotor continues to rotate, the mold units close. The lower retainer 210 and center mold assembly 212 create a seal around the uncoated compressed dosage form, as shown in FIG. 34.

Flowable material is injected into the mold cavity created between the lower retainer 210 and the center mold assembly 212 over the uncoated compressed dosage form to cover a part thereof. In a preferred embodiment, the flowable material coats about half of the uncoated compressed dosage form, the top half as shown in FIG. 34. Simultaneously with the mating of the lower retainer 210 and the center mold assembly 212, the center 212 and upper 214 mold assemblies mate to create seals around the partially coated compressed dosage form. Flowable material is injected through the upper mold assembly 214 into the mold cavity created by the center mold assembly and the upper mold assembly to coat the remaining portion of the partially coated compressed dosage form, the top portion as viewed in FIG. 34. The lower retainer 210 and upper mold assembly 214 are mated with the center mold assembly 212 simultaneously. Accordingly, when an uncoated compressed dosage form is being partially coated between the lower retainer 210 and the center mold assembly 212, the remainder of a partially coated compressed dosage form is being coated between the center 212 and upper mold assemblies 214.

Figure 32:
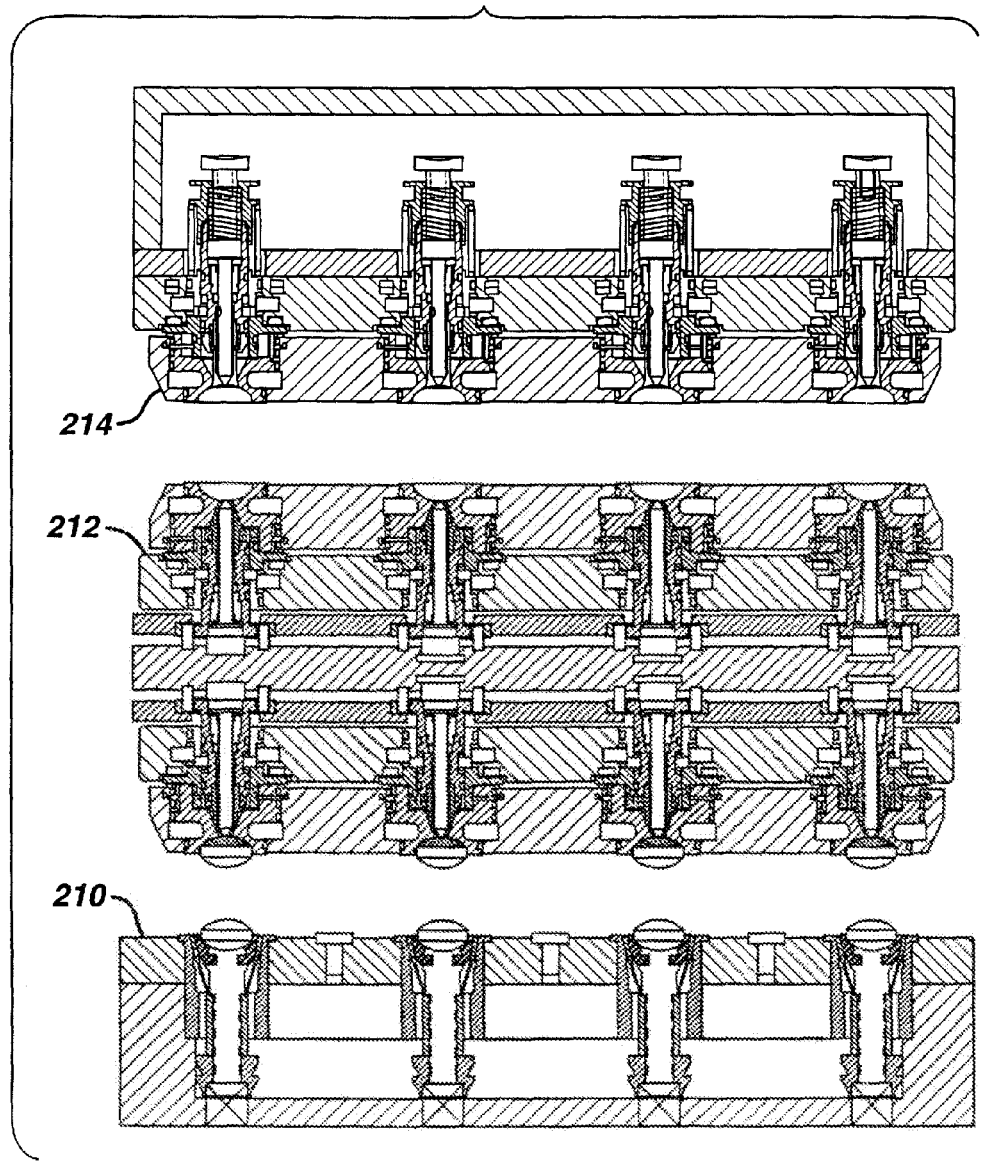
FIGS. 32-35 depict the opening, rotation and closing of the center mold assembly with the lower retainer and upper mold assembly.
Figure 33:
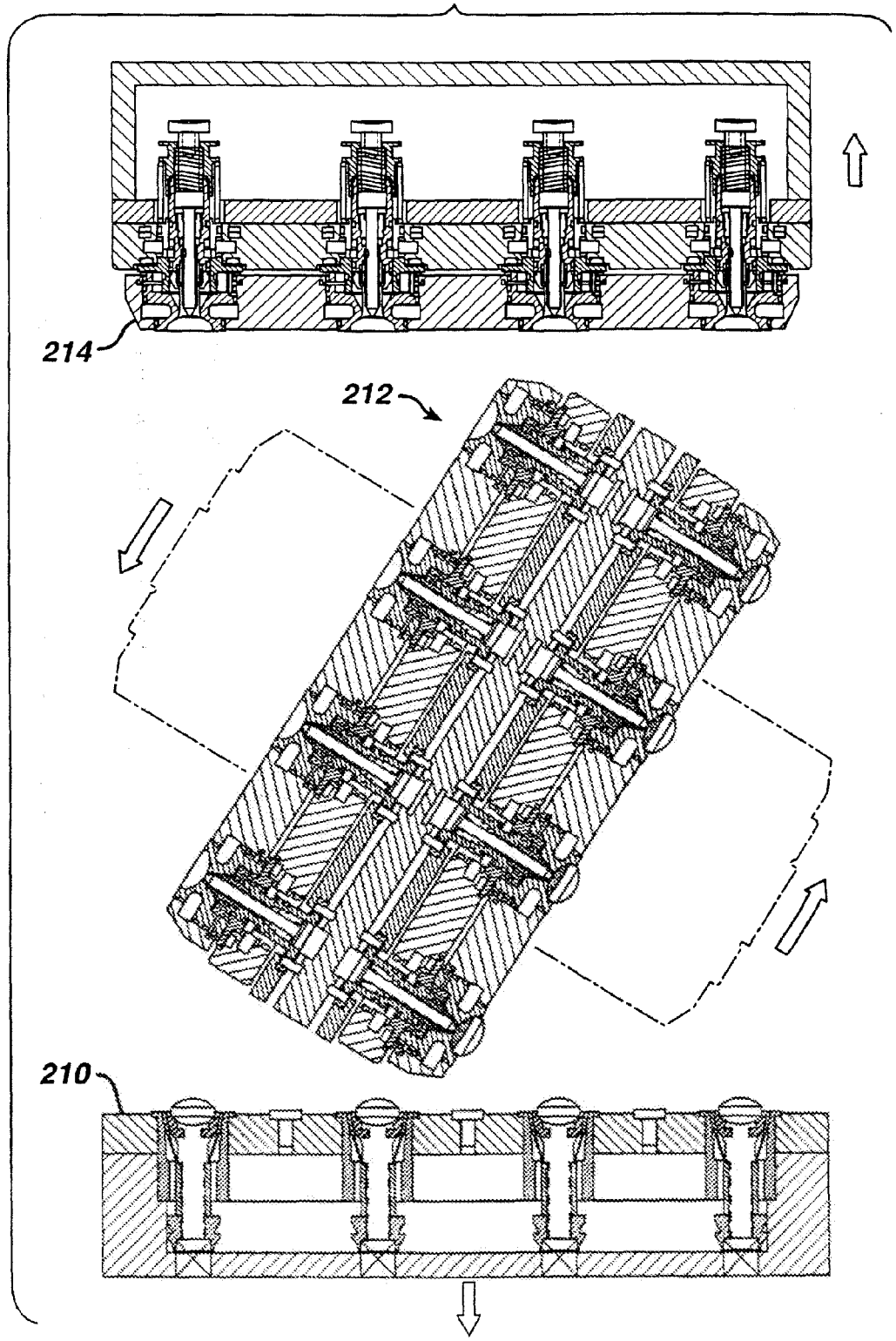
Figure 35:
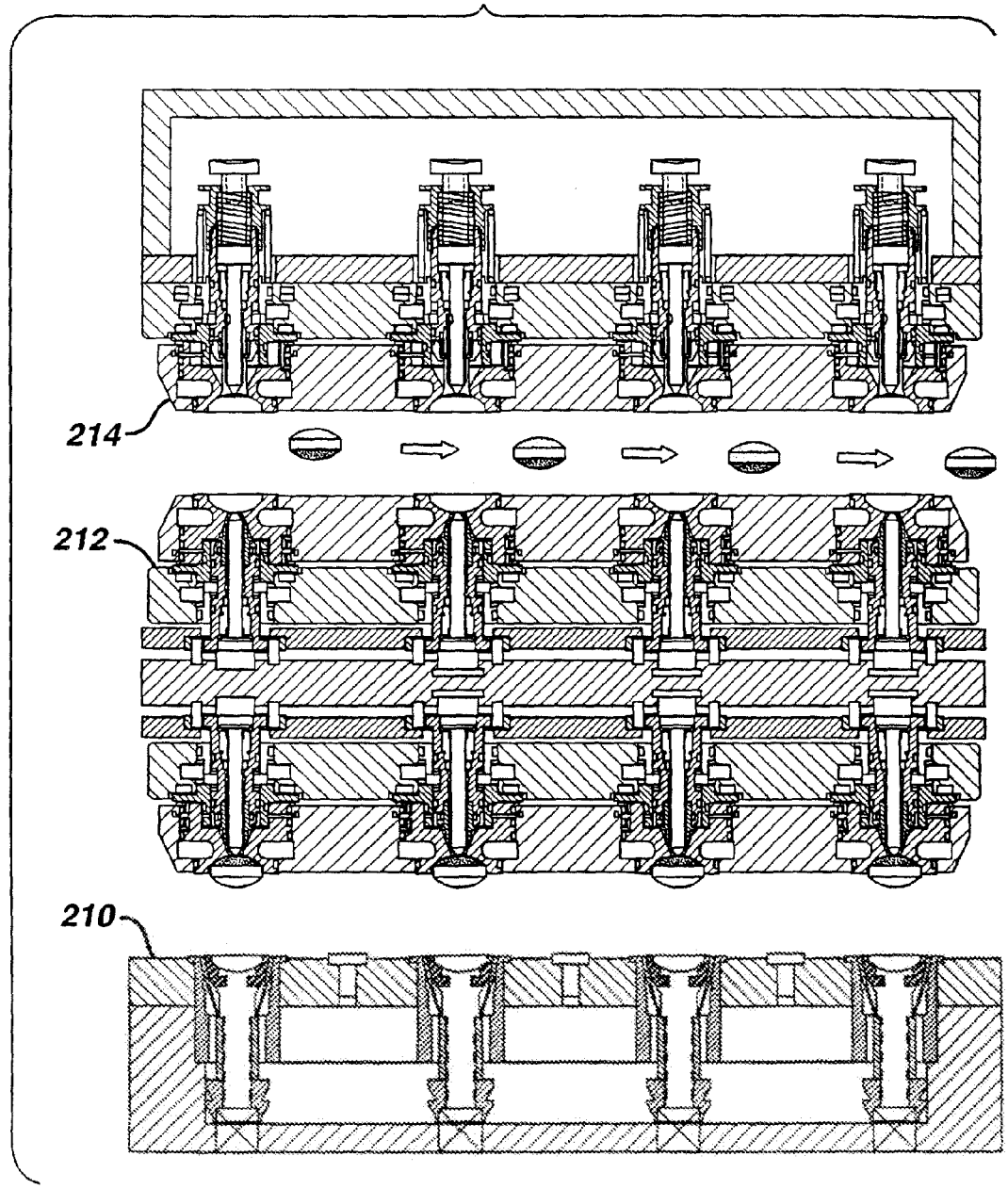

Following this, the lower retainer and the mold assemblies separate. The fully coated compressed dosage form is retained in the upper mold assembly 214. The partially coated compressed dosage form is retained in the center mold assembly 214, as shown in FIG. 35. The fully coated compressed dosage form is then ejected from the upper mold assembly 214 as shown schematically in FIG. 35. Following this, an uncoated compressed dosage form is transferred to the lower retainer 210, such that the lower retainer 210, center mold assembly 212, and upper mold assembly 214 return to the position of FIG. 32. The process then repeats itself.

In the preferred embodiment shown, each mold unit can coat eight compressed dosage forms. Of course, the mold units can be constructed to coat any number of compressed dosage forms. Additionally and preferably, the compressed dosage forms are coated with two different colored flowable materials. Any colors can be used. Alternatively, only a portion of the compressed dosage form may be coated while the remainder is uncoated.

The molds may also be constructed to impart regular or irregular, continuous or discontinuous, coatings, i.e., of various portions and patterns, to the dosage forms. For example, dimple patterned coatings, similar to the surface of a golf ball, can be formed using a molding module comprising mold insert having dimple patterns on their surfaces. Alternatively, a circumferential portion of a dosage form can be coated with one flowable material and the remaining portions of the dosage form with another flowable material. Still another example of an irregular coating is a discontinuous coating comprising holes of uncoated portions around the dosage form. For example, the mold insert may have elements covering portions of the dosage form so that such covered portions are not coated with the flowable material. Letters or other symbols can be molded onto the dosage form. Finally, the present molding module allows for precise control of coating thickness on a dosage form.

When used to form a coating on a dosage form, the molding module of this invention advantageously dispenses with the need for a subcoating on the dosage form. When conventional compressed dosage forms are coated by processes such as dipping, this generally requires placing a subcoating on the compressed dosage form prior to the dipping step.

Preferred embodiments of the lower retainer, center mold assembly and upper mold assembly are described below. These embodiments of the lower retainer, center mold assembly and upper mold assembly are part of a thermal cycle molding module for applying a coating to a compressed dosage form.

1. The Lower Retainer

The lower retainer 210 is mounted to the rotor 202 as shown in FIG. 31 in any suitable fashion and comprises a plate 216 and a dosage form holder 217. Each dosage form holder can be connected to the plate by any one of a variety of fastening techniques including without limitation snap rings and groves, nuts and bolts, adhesives and mechanical fasteners. Although the cross-section of the lower retainer shown in FIGS. 32 through 35 depicts only four dosage form holders 217, the lower retainer preferably has four additional dosage form holders for a total of eight. Each dosage form holder includes a flanged outer sleeve 218, an elastomeric collet 220, a center support stem 222 and a plurality of flexible fingers 223.

Figure 39A:
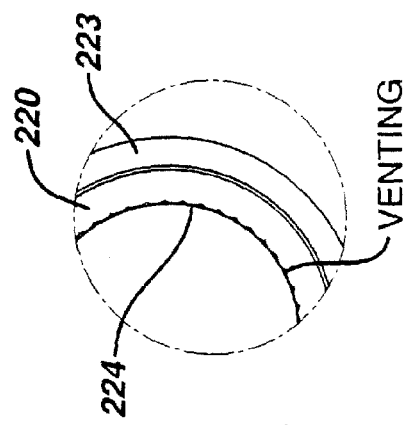
FIGS. 38 and 39 are top views of an elastomeric collet of a lower retainer.
Figure 39:
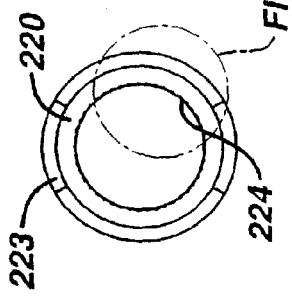
Figure 37:
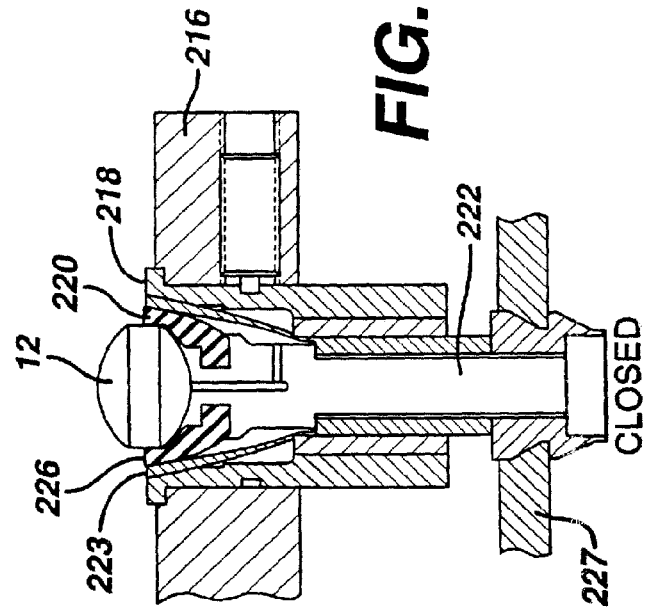
FIGS. 36 and 37 are cross-sectional views of a lower retainer of a thermal cycle molding module.
Figure 36:
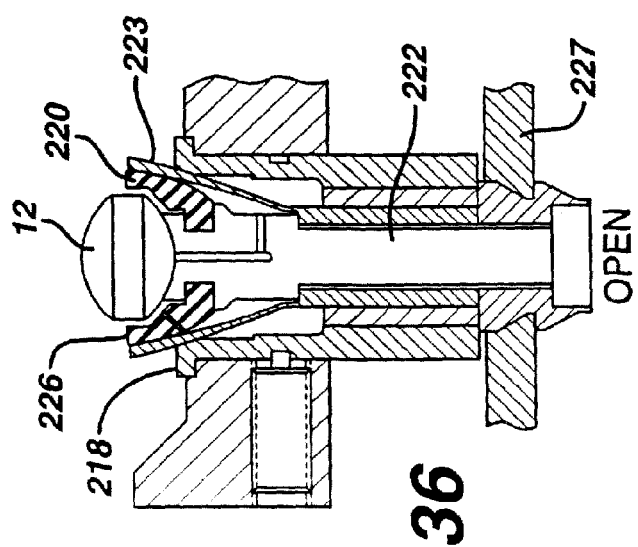

The configuration of the lower retainer is best understood with reference to FIGS. 36-39. The center support stem 222 establishes the vertical position of the dosage form. The elastomeric collet 220 masks and seals the periphery of the dosage form, as best illustrated in FIGS. 36 and 37. Each elastomeric collet 220 mates with a corresponding portion of the center mold assembly 212 in order to create a seal around the dosage form. Although the elastomeric collets can be formed in a variety of shapes and sizes, in a preferred embodiment the elastomeric collets are generally circular and have a corrugated inside surface 221 as shown in FIG. 39. The inside surface 221 comprises very small vent holes 224 for air to vent through when the lower retainer 210 is mated with the center mold assembly 212 and flowable material is injected over the top portion of the dosage form. The vent holes 224 are relatively small so that the flowable material injected over the dosage form from the center mold assembly 212 will generally not flow through the vent holes 224.

As shown in FIGS. 36-39 disposed about the elastomeric collet 220 are flexible fingers 223. The flexible fingers 223 are mounted within the lower retainer 210 by any suitable means and are attached to the support stem 222 to move up and down with the movement of the support stem 222, as best understood by comparing FIGS. 36 and 37. The flexible fingers can be coupled to the center support stem by any of a variety of fastening techniques.

Figure 38:
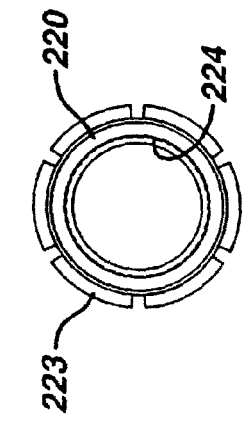

In the preferred embodiment shown, the flexible fingers 223 are metal and spring radially outward when pushed out as shown in FIGS. 37 and 38, so that a dosage form can be received by or released from an elastomeric collet 220. The flexible fingers 223 move radially inward when retracted by the center support stem 222 as shown in FIGS. 36 and 37 to hold the dosage form within the elastomeric collet 220 firmly. Since the fingers move radially inward they also provide a centering function. The flexible fingers 223 fit between the elastomeric collet 220 and the flanged outer sleeve 218 so that when the lower retainer 210 is mated with the center mold assembly 212, the dosage form is tightly held in place and a seal is created around the dosage form. When an uncoated dosage form is being transferred to the lower retainer 210 or a partially coated dosage form is being transferred from the lower retainer 210 to the center mold assembly 212, the center support stem 222 moves to an upward position as shown in FIG. 36 and the flexible fingers 223 expand radially outward. Expansion of the flexible fingers 223 allows the elastomeric collet 220 to expand as shown in FIG. 38. Radial expansion and contraction of the dosage form holder 217 can be accomplished by alternative means. For example the flexible fingers 223 can be replaced by rigid fingers that pivot on bearings and are actuated by cam followers. Alternatively linear bearings and plungers arranged in a radial fashion can move or collapse in the radial direction. Mechanisms similar to the shutter of a camera or inflatable bladders in the shape of an inner tube or torus can also provide similar actions and movements.

An actuator assembly 225 that includes in a preferred embodiment a spring 228, a plate 227, a linear bearing 237 and a small cam follower 229 as best shown in FIG. 31 can be used to accomplish the vertical movement required to close or open the dosage form holder 217. The plate 227 is mounted to the support stem 222 so that movement of the plate 227 in the vertical direction moves the support stem 222. In a preferred embodiment, there is one plate 227 for every eight support stems 222, as shown in FIG. 31. The spring 228 biases the plate 227 and therefore the support stems 222 to an upward position as shown in FIG. 36 in which the dosage form is not sealed within the dosage form holder 217. During rotation of the rotor 202, the small cam follower 229 rides in small cam track 215, which causes the plate 227 to move down to seal the dosage form in the dosage form holders 217 as shown in FIG. 37. After molding, the small cam follower 229 along with the spring 228 causes the plate 227 to move upward and release the dosage forms.

Because the flowable material is injected from above the dosage form, as viewed in FIGS. 34 and 37, the edge 226 of the elastomeric collet stops flow of the flowable material. Consequently, only the portion of the dosage form 12 shown in FIG. 36 that is above the elastomeric collet 220 will be coated when the lower retainer 210 and center mold assembly 210 are mated. This permits a first flowable material to be used to coat one part of the dosage form, and a second flowable material to coat the remainder of the dosage form—that portion which is beneath the elastomeric collet. Although the elastomeric collet is shaped so that about half of the dosage form will be coated at one time, the elastomeric collet can be of any desired shape to achieve a coating on only a certain portion of the dosage form.

When two halves of a dosage form are coated with different flowable materials, the two flowable materials may be made to overlap, or if desired, not to overlap. With the present invention, very precise control of the interface between the two flowable materials on the dosage form is possible. Accordingly, the two flowable materials may be made flush with each other with substantially no overlap. Or the two flowable materials may be made with a variety of edges, for example to allow the edges of the flowable materials to interlock.

Any suitable controls including without limitation mechanical, electronic, hydraulic or pneumatic can be used to move the lower retainer. In a preferred embodiment the controls are mechanical and include a large cam follower 231, large cam track 211 and actuator arm 235. The large cam follower 231 rides in large cam track 211 and moves up and down within the large cam track. The actuator arm connects the large cam follower to the lower retainer so that movement of the large cam follower up and down causes the lower retainer to move up and down. Thus, as rotor 202 rotates the lower retainer 210 rotates with the rotor 202 and the large cam follower 231 moves along the large cam track 211, which is stationary. When at a position to receive dosage forms, the lower retainer 210 is in a down position as shown in FIGS. 36 and 38. After dosage forms have been transferred to the lower retainer 210, the support stems 220 move down due to actuation of cam follower 229 and actuator assembly 225 to seal the dosage forms in the lower retainer 210 as shown in FIGS. 37 and 39.

Following this, the large cam follower 231 causes the lower retainer 210 to move up and mate with the center mold assembly as shown in FIG. 34. Once mated, the dosage form is partially coated in the center mold assembly 212. Continued rotation of the rotor 202 causes the large cam follower 231 to move down in the large cam track 211, which then causes the lower retainer 210 to lower and separate from the center mold assembly 212 back to the position in FIGS. 31 and 35. In addition, rotation of the rotor 202 also causes the actuator 225 to move the support stems 222 as described above. The support stem 222 moves to release the dosage forms just prior to or simultaneously with the lower retainer moving downward to separate from the center mold assembly 212. Thus, the lower retainer functions to receive dosage forms, hold dosage forms while being partially coated in the center mold assembly 212, and transfer dosage forms to the center mold assembly after they have been partially coated.

2. The Center Mold Assembly

The center mold assembly 212 is rotatably mounted to the rotor 202 on an axis that is radial to the rotor. That is, the axis of rotation of the center mold assembly is perpendicular to the axis of rotation of the rotor. The arrangement allows the center mold assembly to rotate 180 degrees (end for end) at a prescribed time while the thermal cycle molding module 200 is simultaneously revolving about its vertical axis. Preferably, the center mold assembly 212 is mounted so that it is capable of rotating 180 degrees in either direction. Alternatively, the center mold assembly can be mounted so that it rotates 180 degrees in a first direction and then rotates a further 180 degrees. FIG. 30 depicts several center mold assemblies 212 in a plan view. All of the center mold assemblies 212 are similarly mounted.

The center mold assembly comprises a series of back-to-back, identical insert assemblies 230. See FIGS. 32-35, 41 and 42. The center mold assembly 212 rotates partially coated dosage forms from their downwardly oriented positions to upwardly oriented positions. The upwardly pointing portions of the dosage forms, which have been coated with flowable material, can now receive the remainder of their coatings once the center mold assembly 212 mates with the upper mold assembly 214. Also, the insert assemblies previously pointing upward now point downward. Thus they are now in a position to mate with the lower retainer 210 to receive uncoated dosage forms.

Figure 40:
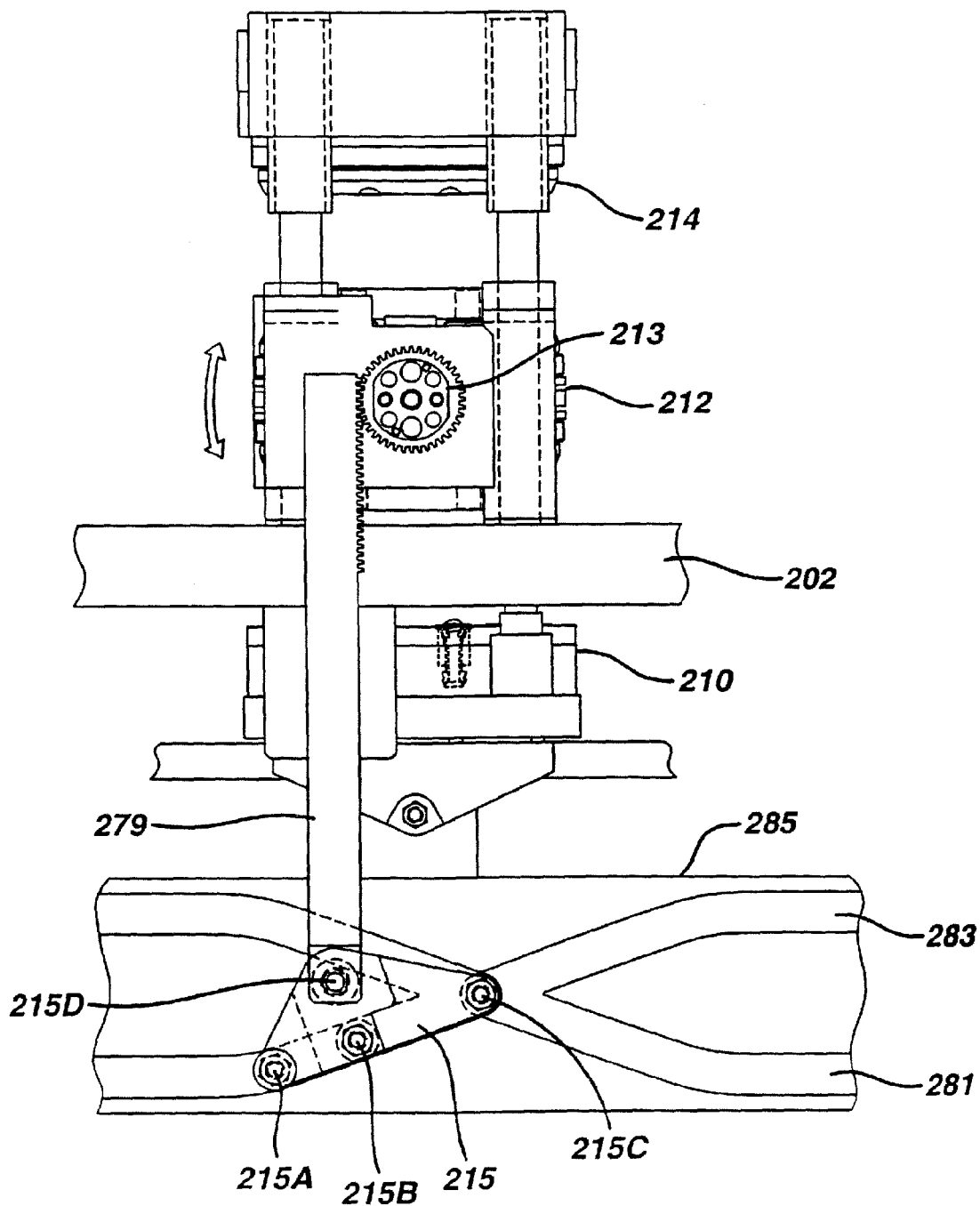
FIG. 40 shows a preferred cam system for the center mold assembly of the thermal molding module.

Rotation of the center mold assembly may be accomplished, for example, using the system shown in FIG. 40. Depicted in FIG. 40 are cam follower carriage 215, cam track ring 285 comprising an upper groove 283 and lower groove 281, linkage 279, shaft 213, and rotor 202. As shown, the linkage 279 is geared and shaft 213 has a geared portion, such that the shaft 213 will rotate as the linkage 279 moves up and down. The upper groove 283 and lower groove 281 of the cam track ring 285 are connected to each other by an "X" or crisscross pattern as shown in FIG. 40. This "X" pattern occurs at one location on the cam track ring. This allows the cam follower carriage 215 to follow the lower groove 281 during a first revolution (360 degrees) of the thermal cycle molding module 200. On a second revolution, the cam follower carriage 215 follows the upper groove 283. After 720 degrees of rotation the cam follower carriage 215 switches back to the lower groove 281 and the cycle repeats.

The groove pattern shown moves the linkage 279 up and down during rotation of the rotor to control the rotation of the shaft 213 and therefore the center mold assembly 212. Thus, as the cam follower carriage 215 moves down, the linkage 279 moves down and the shaft 213 and center mold assembly 212 rotate counter clockwise as shown in FIG. 40. Similarly, when the cam follower carriage 215 moves up, the linkage 279 moves up and drives the shaft 213 and center mold assembly 212 to rotate clockwise. Each center mold assembly 212 is similarly mounted to a cam follower carriage 215, so that each center mold 212 will similarly rotate first 180 degrees clockwise at the point where the upper and lower grooves cross, and then upon another revolution of the rotor 202 the center molds rotate 180 degrees counterclockwise.

The cam follower carriage 215 has a pivot point 215D upon which it is mounted to the linkage 279. Attached to the cam follower carriage 215 are three cam followers 215A, 215B, 215C which ride in the groove of the cam track ring 285. The use of three cam followers (215A, 215B, 215C,) assures that the cam follower carriage 215 follows the correct path across the "X" crossing point of the cam track ring 285, because the gap at the crossing point is shorter than the distance between any two cam followers. Upon crossing of the gap two of the three cam followers remain engaged in the cam track, while the third follower crosses the unsupported region at the crossing point. The path takes the form of a flattened or folded figure eight. The lower groove 281 is the bottom loop of the figure eight and the upper groove 283 forms the top loop.

Figure 46:
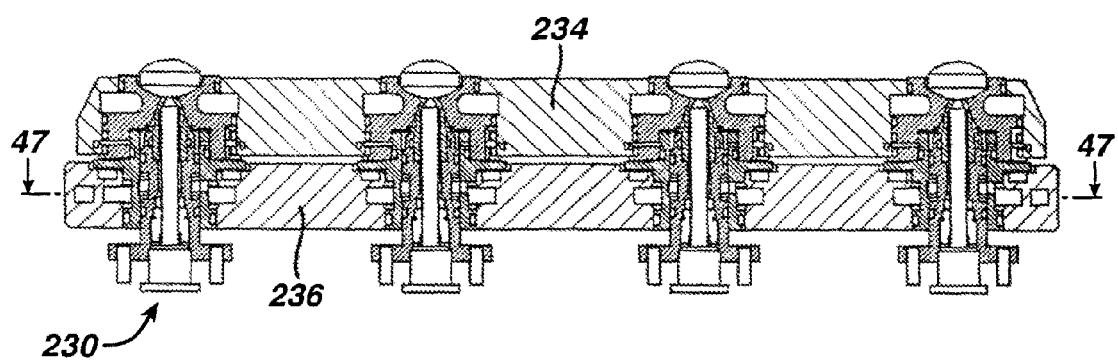

Flowable material is preferably heated and cooled in the center mold assembly as follows. Each center mold assembly 212 further includes a valve actuator assembly 232, a dosage form transfer actuator assembly 241, and a plurality of manifold plates 234, 236. See FIGS. 43-47. First manifold plates 234 and second manifold plates 236 house insert assembly 230, as shown in FIGS. 43 and 46.

Figure 43:
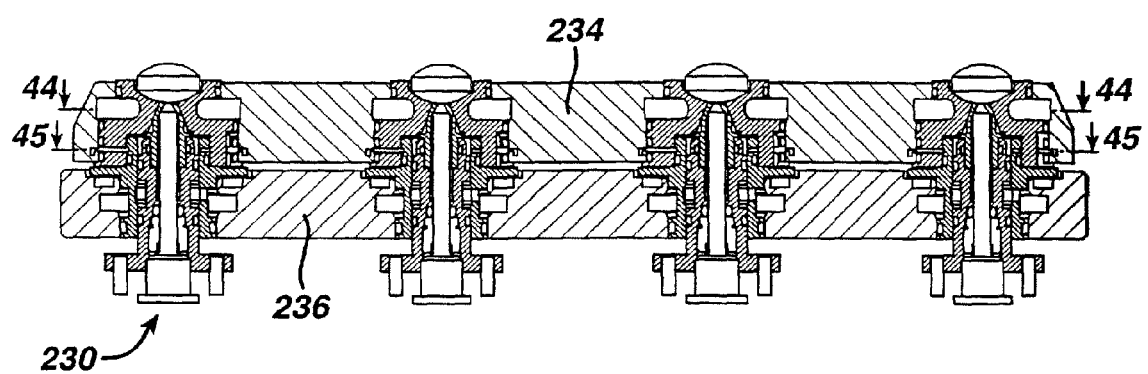
FIGS. 43 and 46 are cross-sectional views of a portion of the center mold assembly showing first and second manifold plates.
Figure 44:
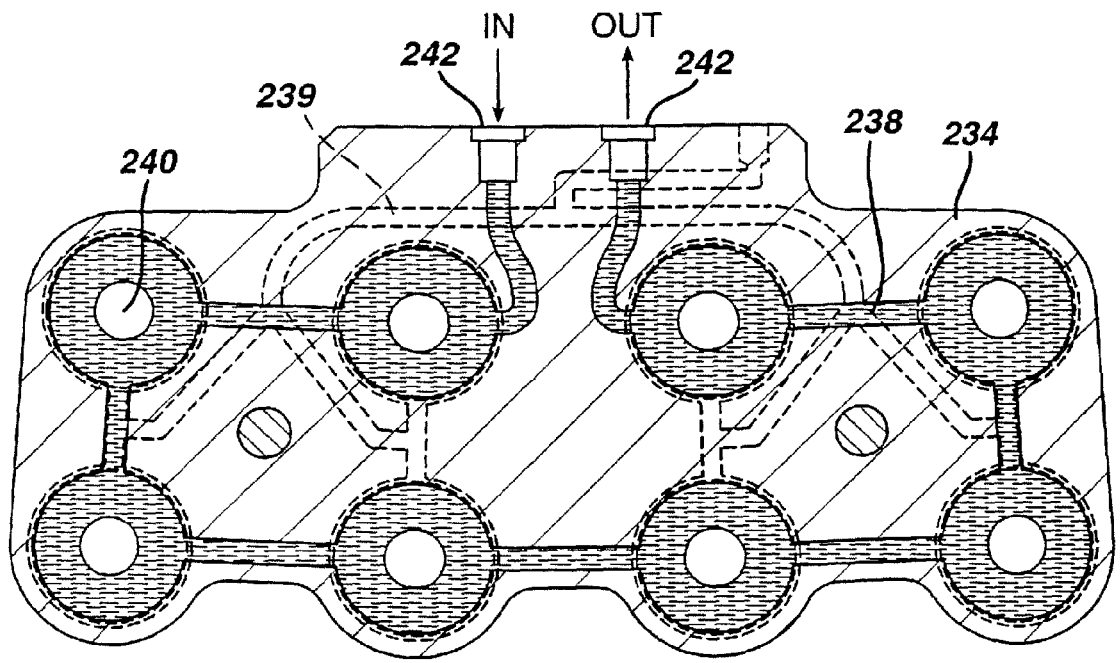
FIG. 44 is a cross-section taken along line 44-44 of FIG. 43.
Figure 45:
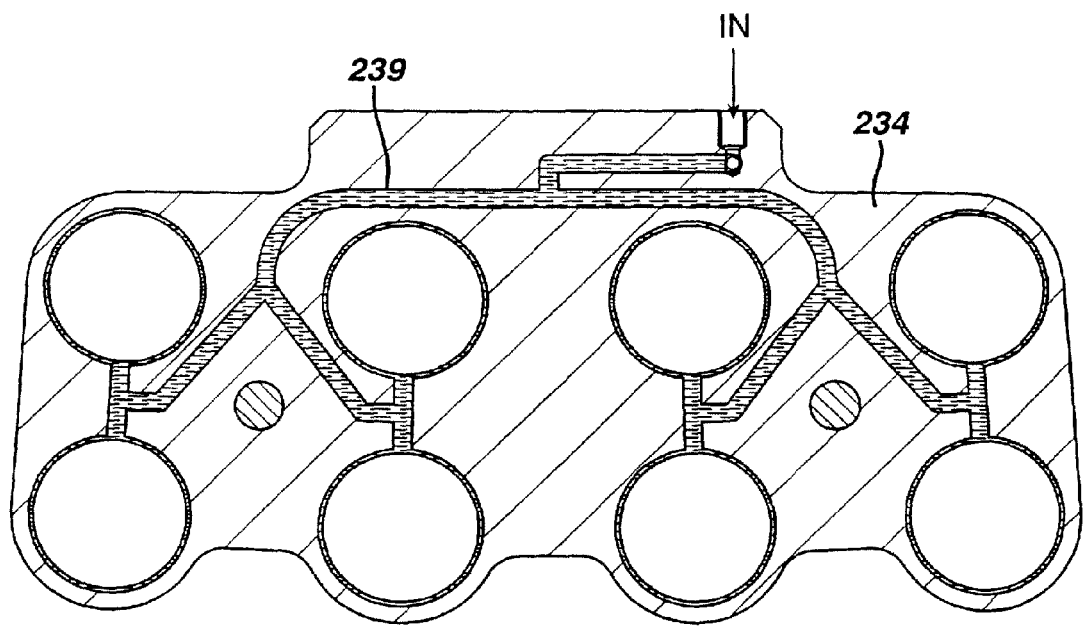
FIG. 45 is a cross-section taken along line 45-45 of FIG. 43.

Defined within the first manifold plate 234 is a continuous channel 238 that defines a coolant/heating flow path, as shown in FIGS. 43 and 44. Channel 238 traverses around the insert assembly 230. In a preferred embodiment the coolant/heating fluid is water but any suitable heat transfer fluid may be employed. First manifold plate 234 may also have inlet and outlet ports 242 through which the coolant can flow through to the channels 238. Ports 242 couple the coolant channels 238 to the heat transfer system described below. The first manifold plate 234 may be mounted by any suitable means in the center mold assembly 212, one of which is by mechanical fasteners.

Preferably, hot fluid flows through the channels 238 to heat the center mold assemblies 212 just prior to and during the injection of the flowable material. Heating can begin prior to or after enclosing the dosage forms within the mold assemblies. Then, simultaneously with or after injection of the flowable material into the mold assemblies, the heat transfer fluid is preferably switched from hot to cold to solidify the flowable material.

Figure 47:
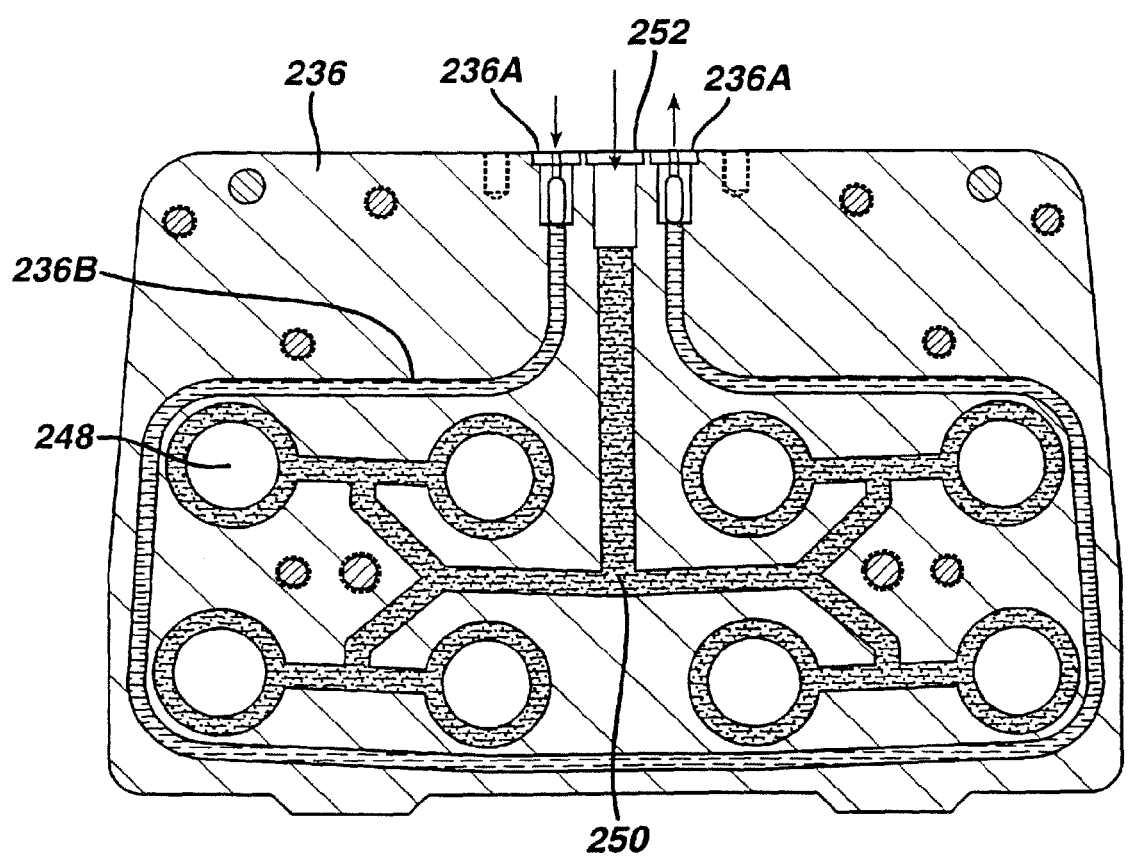
FIG. 47 is a cross-section taken along line 47-47 of FIG. 46.

The second manifold plate 236 comprises a plurality of holes 248 that are aligned with holes 240 in the respective first manifold plate 234, so that an insert assembly 230 can be fixed within the holes 240, 242. The second manifold plate 236 also comprises channels 250 as shown in FIG. 47. The flowable material flows through the channels 250 to the insert assembly 230, which directs the flowable material to the dosage forms. Flowable material connector ports 252 may also be included within the second manifold plate 236 that allow connection of tubing 208 to channels 250. Thus, flowable material can be injected from the reservoir 206 through the tubing 208, ports 252, channels 250 and to the insert assembly 230.

As shown in FIGS. 46 and 47, the second manifold plate 236 may optionally comprise a heating flow path 236B to warm the insert assembly 230 and maintain the flowable material temperature above its melting point. Depending on the type of flowable material used, this heating may or may not be needed. For example, some flowable materials need to be relatively warm to exhibit good flow properties. Heating flow path 236B circulates through the second manifold plate 236 and connects to ports 236A. From the ports, tubing (not shown) can be used to connect the heating flow path 236B to a heat exchanger that maintains the heating fluid warm. Preferably, the heating fluid is water.

Each insert assembly 230 preferably comprises a stationary part, which includes a center insert 254, and a moveable part, which is in essence a nozzle and comprises a valve body 260, a valve stem 280 and valve body tip 282, as shown best in FIGS. 41 and 48-50. Although FIGS. 48-50 illustrate one nozzle or valve assembly, in a preferred embodiment there are preferably sixteen such nozzles or valve assemblies per center mold assembly 212, eight facing the upper mold assembly and eight facing the lower retainer. FIG. 49 depicts the insert assembly 230 in its closed position. FIG. 48 shows the insert assembly 230 positioned for injection of flowable material. FIG. 50 illustrates the insert assembly 230 in the dosage form transfer position.

The center insert 254 may be mounted to the first manifold plate 234 by any suitable means, and is preferably sealed with o-rings 262 and grooves 264 to prevent leakage of flowable material, as shown in FIG. 48. The coolant channels 238 are defined between the first manifold plate 234 and the center insert 254. The center insert 254 is constructed from a material that has a relatively high thermal conductivity, such as stainless steel, aluminum, berylium-copper, copper, brass, or gold. This ensures that heat can be transferred from the heat transfer fluid through the center insert to the flowable material. Heating ensures that the flowable material will flow into the center mold insert upon injection, and cooling at least partially hardens the flowable material. Depending on the type of flowable material used, however, heating may not be needed.

Each center insert 254 comprises a center cavity 266 within it, the surface of which defines the final shape of the dosage form. In a preferred embodiment, center cavity 266 covers about half of a dosage form and is designed such that when mated with the lower retainer 210 or upper mold assembly 214 the dosage form will be covered and sealed. Center cavities 266 can be appropriately shaped and sized based on the parameters of the dosage form. Moreover, the surface of the center cavities may be designed to form coatings having a variety of features, i.e., dimple patterns (similar to a golf ball), holes, symbols including letters and numbers, or other shapes and figures. Use of the center cavities described herein also permits precise control over the thickness of the molded coating. In particular, with the present thermal cycle molding module 200 coatings having thicknesses of about 0.003 to about 0.030 inches may be consistently obtained.

In a preferred embodiment, an air passage 239 is also disposed through the first manifold plate 234. See FIG. 45. Compressed air is fed through the air passage 239 and used to assist in ejection of the coated dosage form from the center mold assembly 212 to the upper mold assembly 214. Although air is preferred for this purpose, the invention is not limited thereto. An alternative ejector means, such as an ejector pin, may be used. The air can be pressurized to a relatively small pressure and can be provided from air banks or the like that lead to a connection port in the first manifold plate 234.

The movable portion of the insert assembly 230 includes the valve body 260, the valve stem 280, and the valve body tip 282. See FIG. 48. The valve stem 280 is independently moveable. The valve stem 280 and valve body 260 are slidably mounted within the insert assembly 230. In the preferred embodiment shown, a plurality of o-rings 284 and grooves 286 seal the moveable portions of the insert assembly to the stationary portion of the insert assembly. Disposed around the valve stem 280 and the valve body tip 282 is a flowable material path through which flowable material traveling through the second manifold plate 236 flows when the insert assembly is in the open position (FIG. 48).

Although the center mold assembly 212 is constructed with identical insert assemblies 230 on both sides of its rotary axis, each insert assembly 230 performs a different function depending on whether it is oriented in the up or in the down position. When facing down, the insert assemblies 230 are actuated to inject flowable material to coat a first portion of a dosage form. The insert assemblies 230 that are facing up are presenting partially coated dosage forms to the upper mold assembly 214. During this time, the upward facing insert assemblies are in a neutral position. Prior to the molds opening however, the upward facing insert assemblies are actuated to allow compressed air to enter the center cavity 266. This ejects the now completely coated dosage forms from the upward facing insert assemblies. Thus the completed dosage forms remain seated or held in the upper mold assembly 230.

Figure 41:
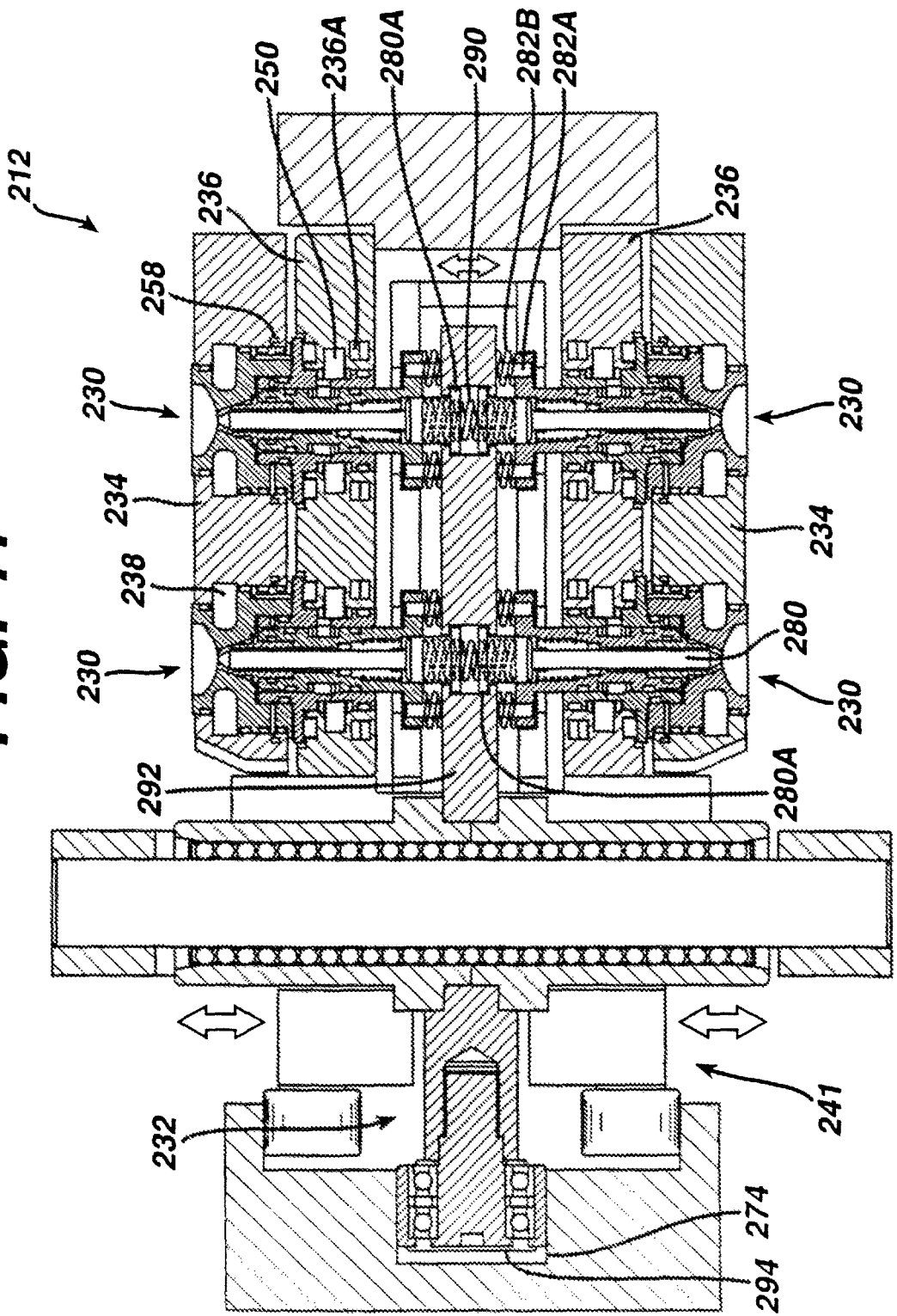
FIG. 41 is a cross-section of the center mold assembly showing one embodiment of a valve actuator assembly therefor.
Figure 42:
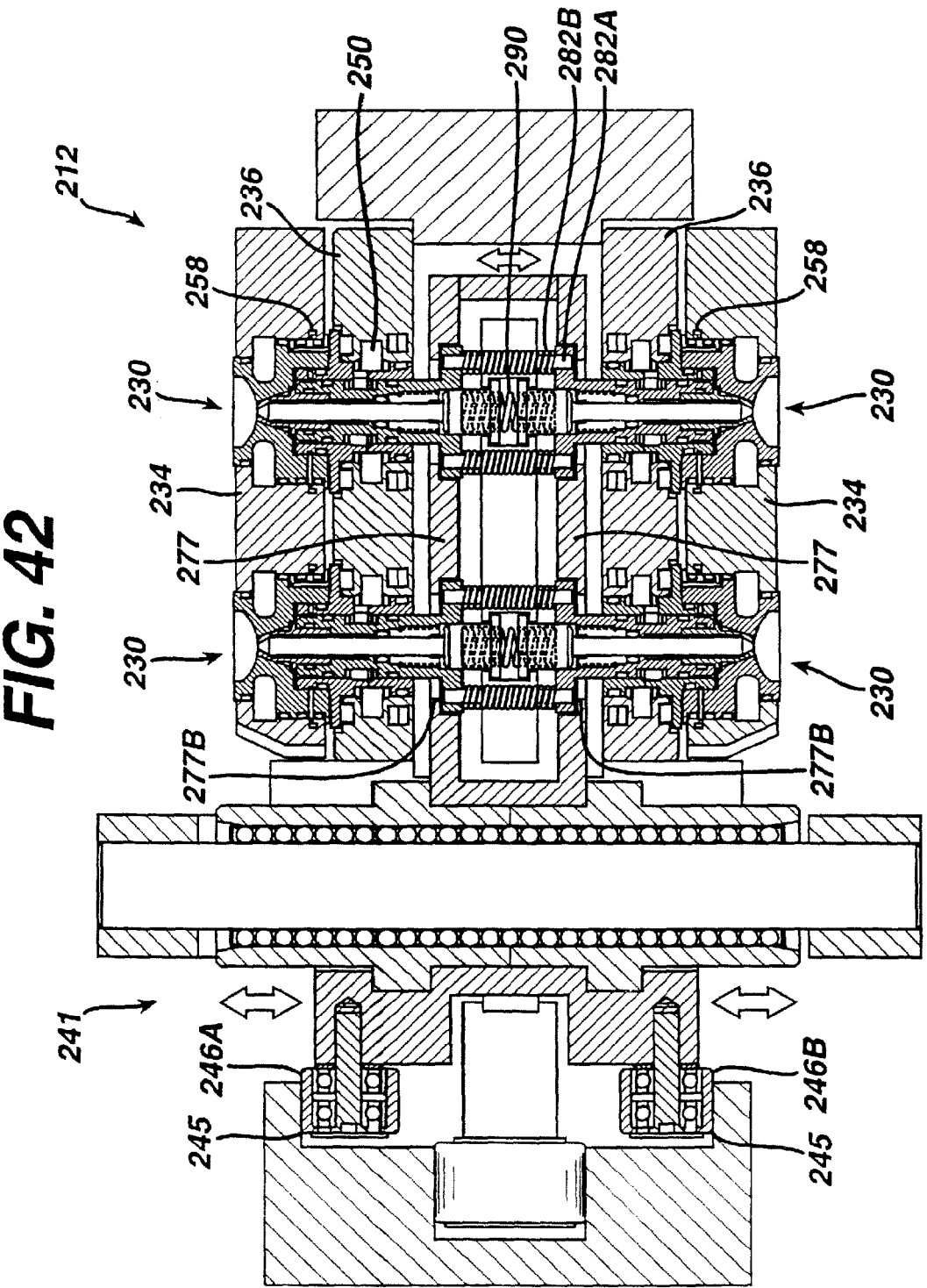
FIG. 42 is a cross-section of the center mold assembly showing one embodiment of an air actuator assembly therefor.

Advantageously, the center mold assembly is designed to be actuated with just one valve actuator assembly 232 and just one air actuator assembly 241 (FIGS. 41 and 42). The valve actuator assembly 232 only actuates the insert assemblies 230 that are facing down, while the air actuator assembly 241 actuates only those insert assemblies 230 facing up.

Downward facing valve stem 280 is spring loaded to the closed position of FIG. 49 by spring 290. Downward facing valve stem 280 is moveable between the closed position of FIG. 49 and the open position of FIG. 48 by valve actuator assembly 232 shown in FIG. 41. In the preferred embodiment shown, the valve actuator assembly 232 comprises an actuator plate 292 and cam follower 294 mounted thereto. Spring 290 is mounted within the valve stem 280 to spring load the valve stem 280 to the closed position. An end of the valve stem 280 is mounted within the actuator plate 292 as shown in FIG. 41, so that the valve stem will move with the actuator plate 292. Actuator plate 292 is mounted to move up and down as viewed in FIG. 41. Cam follower 294 is shown in FIGS. 31 and 41. It rides in the cam track 274 disposed around the rotor 202. Cam follower 294 moves up and down according to the profile of cam track 274 to move the actuator plate 292 and thereby control movement of the downward facing valve stem 280.

Actuator plate 292 moves upward and opens the downward facing insert assemblies as viewed in FIG. 48 by moving and pulling the downward facing valve stems 280 against the bias of spring 290 from the position of FIG. 49 to the position of FIG. 48. Opening of the downward facing valve stems ports flowable material to dosage forms disposed between the center mold assembly 212 and the lower retainer 210. Following this, cam follower 294 and actuator plate 292 move down to release the downward facing valve stems 280. Due to the bias of spring 290, the downward facing valve stems 280 move to the closed position of FIG. 49 to stop the flow of flowable material.

When actuator plate 292 moves up as viewed in FIG. 48, the upward facing insert assemblies 230 remain stationary and closed. The upward facing valve stems 280 are compressed against spring 290 and do not open. No flowable material is provided to the upward facing insert assemblies 230. Dosage forms in the upward facing insert assemblies are coated by the upper mold assembly 214, described below. Similarly, no air is provided to the downward facing insert assemblies because dosage forms are only released from the upward facing insert assemblies.

After the flowable material has been ported and the downward facing insert assemblies 230 return to the position of FIG. 49, cam followers 246A and 246B and air actuator plate 277 (FIG. 42) initiate movement of the valve body tip 282 and valve stem 280 of the upward facing insert assemblies 230. This provides a path for air through the center mold insert. In particular, the upward facing valve body tip 282 and valve stem 280 move from the position of FIG. 49 to the position of FIG. 50 due to movement of cam followers 246A and 246B downward as viewed in FIG. 42. After the application of air, cam followers 246A and 246B move downward with the air actuator plate 277, permitting the upward facing insert assemblies 230 to return to the position of FIG. 49, ready for another cycle. Air actuator plate 277 does not move the downward facing insert assemblies 230 during this cycle. They do not receive air.

Air actuator plate 277 shown in FIG. 42 controls movement of the upward facing valve body tip 282, valve body 260 and valve stem 280 as follows. As shown in FIG. 42, pins 282A extend inward with respect to the center mold assembly 212 and springs 282B are mounted around the pins 282A. The springs 282B press against the upward facing valve bodies 260 and are compressed so that the upward facing valve body tip 282 and valve body 260 are normally in the closed position (FIG. 49). Cam 246A and air actuator plate 277 move downward to compress the springs 282A and push the upward facing valve body 260 and valve body tip 282 against the bias of the springs 282B to the opened position (FIG. 50).

FIG. 50 depicts an upward facing insert assembly 230 in the transfer position. In this position, the upward facing valve stem 280 and valve body tip 282 are withdrawn. The upward facing valve stem 280 rests against the upward facing valve body tip 282 to stop the flow of flowable material. With the valve body tip 282 withdrawn, however, air from can flow to the mold.

After the dosage forms have been transferred from the center mold assembly, the air actuator plate 277 returns up to release the upward facing valve body 260, valve body tip 282 and valve stem 280 to the closed position of FIG. 49.

3. The Upper Mold Assembly

The upper mold assembly 214, which is shown in FIGS. 51-54, is similar in construction to half of the center mold assembly 212. Like the center mold assembly 212, the upper mold assembly 214 directs flowable material to at least partially coat a dosage form. In particular, the upper mold assembly 214 has a plurality of upper insert assemblies 296 (eight in the preferred embodiment) that mate with corresponding insert assemblies 230.

Although the upper mold assembly is similar to the center mold assembly, the upper mold assembly does not rotate. Rather, the upper mold assembly 214 moves vertically up and down to mate with the center mold assembly via suitable controls as best understood by comparing FIGS. 32-35. Preferably, cam follower 299, cam track 298, and connector arm 293 (FIG. 51) are used to control the movement of the upper mold assembly 214. Small cam follower 289 and small cam track 288 control upper actuator plate 291. Cam follower 299, cam track 298, small cam follower 289, and small cam track 288 are similar in construction to the corresponding elements of the lower retainer 210.

The upper mold assembly 214 moves during rotation of the rotor 202 via cam follower 299 to mate with the center mold assembly 212 as shown in FIGS. 32-35 and at least partially coat a dosage form. After this, the cam follower 299 separates the upper mold assembly 214 from the center mold assembly 212 so that the finished, fully coated dosage form can be ejected and transferred from the thermal cycle molding module as shown in FIG. 35.

The upper mold assembly 214 comprises an upper second manifold plate 251 that ports flowable material to upper insert assemblies 296 and is similar in construction to the second manifold plate 236 of the center mold assembly 212. An upper first manifold plate 253 provides cooling/heating to the upper insert assemblies 296 and is similar in construction to the first manifold plate 234 of the center mold assembly 212.

Figure 54:
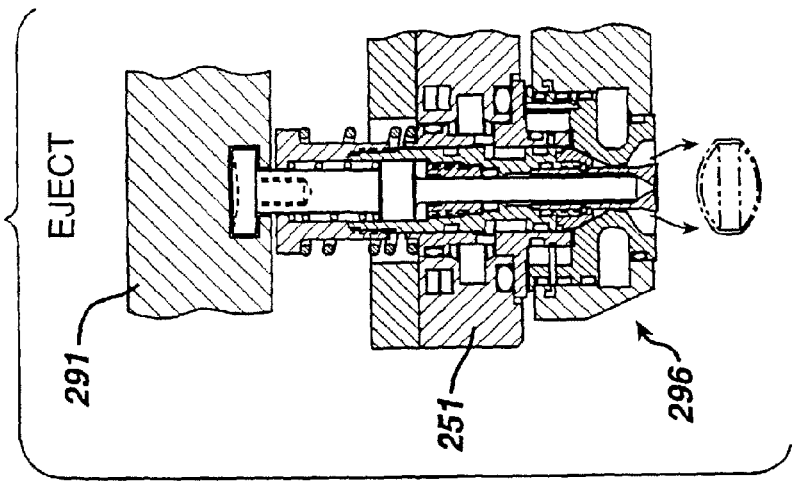
FIGS. 52-54 are cross-sectional view of the upper mold assembly and the center mold assembly of the thermal cycle molding module.
Figure 53:
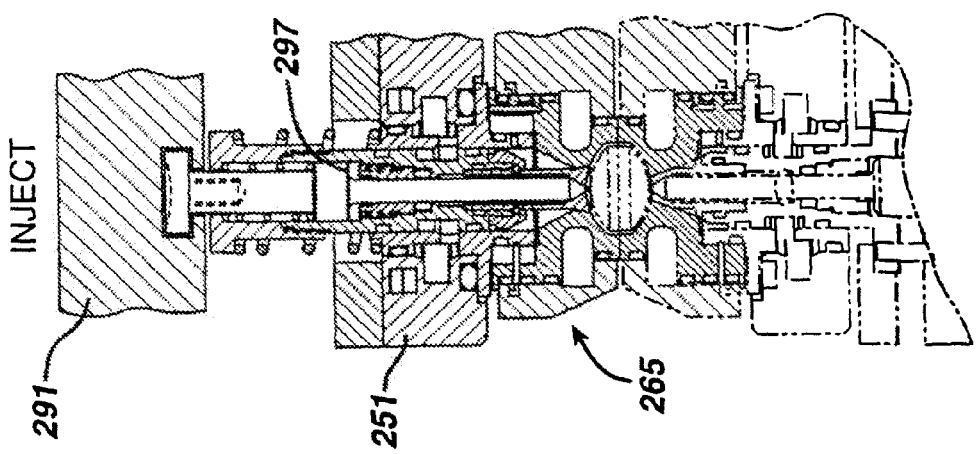
Figure 52:
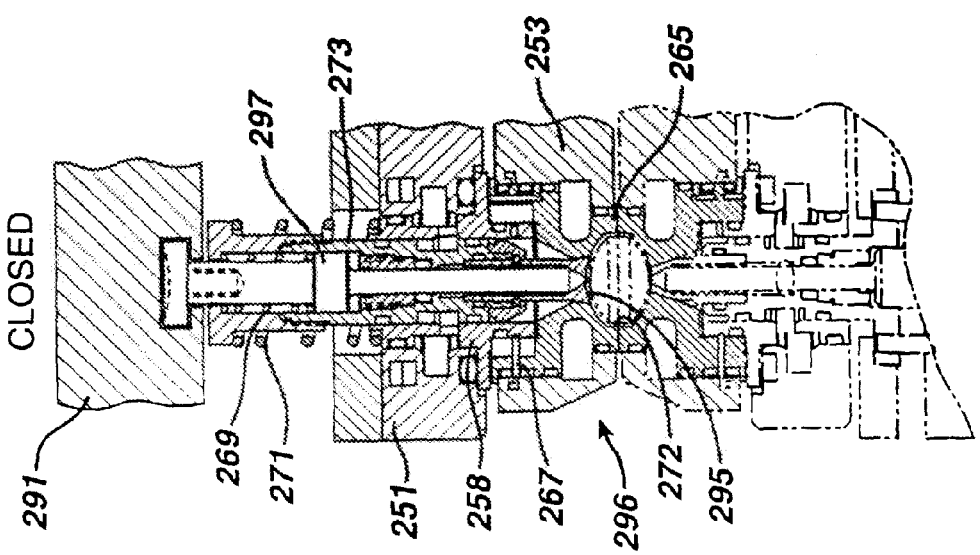

A seal around each dosage form is preferably created by contact between the upward facing insert assembly 230 of the center mold assembly 212 and the upper insert assembly 296 of the upper mold assembly 214, as best understood with reference to FIGS. 48-50. An upper insert assembly 296 is depicted in FIGS. 52-54 in the closed, open and eject positions, respectively. Similar to the insert assemblies 230, each upper insert assembly 296 includes a stationary portion that includes an upper insert 265 and a upper flanged insert 258 and a moveable portion that is basically a nozzle. The latter comprises an upper valve body 273, upper valve stem 297 and upper valve body tip 295. The upper valve stem 297 is moveable between open and closed positions to control flow of the flowable material to the dosage form. The upper valve body, upper valve stem and upper valve body tip define the flow path for the flowable material.

Each upper cavity 272 is appropriately sized so that the flowable material can flow over the dosage form and provide a coating of the desired thickness. Similar to the center cavity 266 of the center insert 254, the upper cavity 272 of the upper insert 265 can be of any desired shape and size or be provided with a surface pattern (such as dimples, letters, numbers, etc.).

One difference between the upper insert assembly 296 and the insert assembly 230 is that the upper valve body tip 295 forms part of the seal around the dosage form as shown in FIGS. 52-54 and moves outward rather than inward to eject a dosage form after it has been fully coated. FIG. 54 depicts the upper valve body tip 295 positioned to eject a dosage form. FIG. 52 depicts the upper valve body tip 295 positioned to receive a dosage form.

Figure 51:
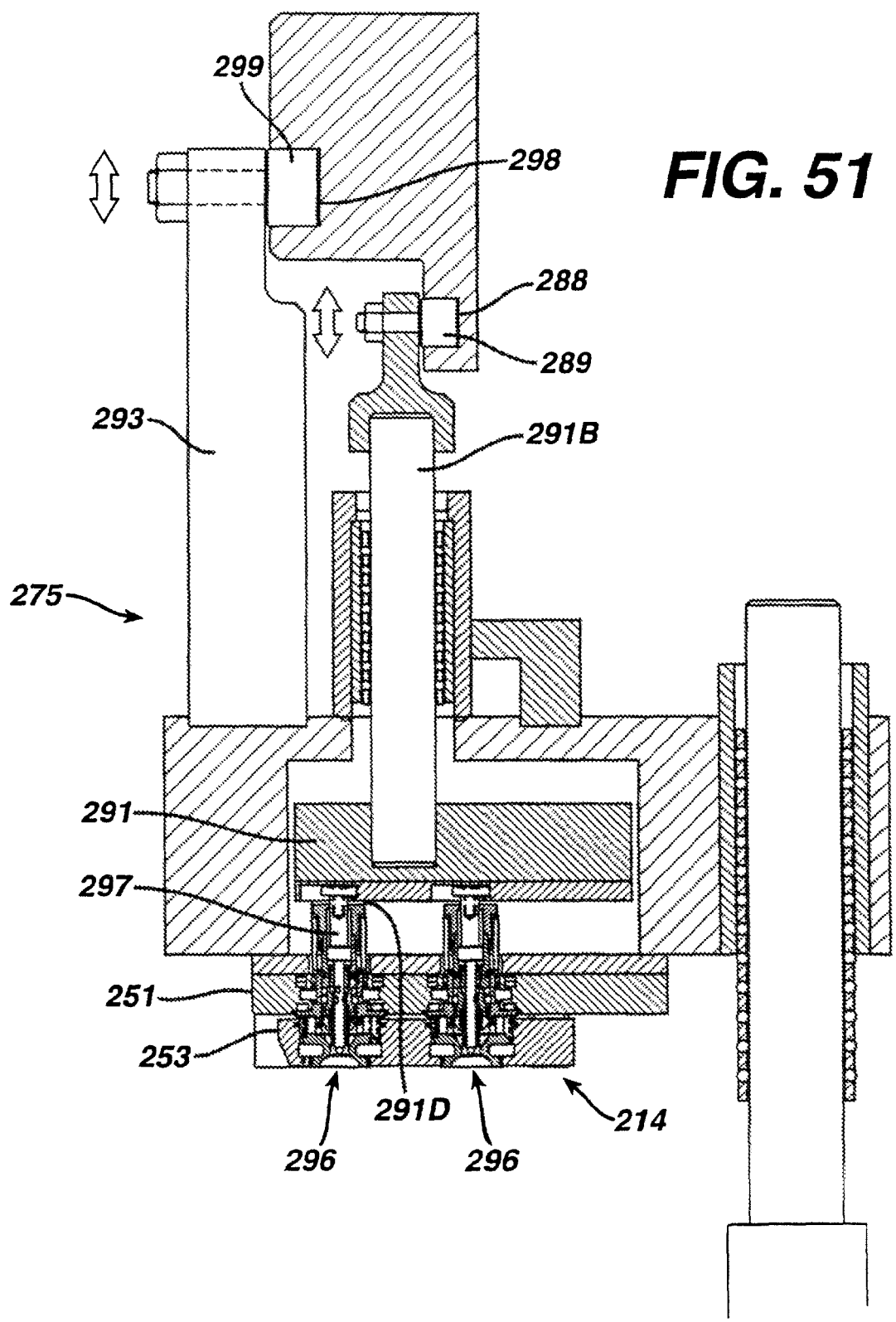
FIG. 51 is a cross-sectional view of an upper mold assembly of the thermal cycle molding module showing a cam system thereof.

An upper valve actuator 275 that includes an upper actuator plate 291, linkage 291B and cam follower 289 as shown in FIG. 51 actuate the upper insert assembly 296. In other embodiments, electronic or other mechanical controls can be used. The linkage 291B couples cam follower 289 to the upper actuator plate 291. The upper actuator plate 291 has a portion 291D that extends beneath a plunger so that when the upper actuator plate 291 moves up (FIG. 53) it pulls on valve stem 297. Upper actuator plate 291 also rests on top of upper valve stem 297 so that when the upper actuator plate 291 moves down, the plunger and the upper valve stem 297 are pushed down (FIG. 54).

As the rotor 202 rotates, cam follower 289, riding in cam track 298, moves up, causing the upper actuator plate 291 to rise and pull upper valve stem 297 against the bias of spring 269 and hence move it from the closed position of FIG. 52 to the open position of FIG. 53. After this, cam follower 289 moves down and causes upper actuator plate 291 to move upper valve stem 297 to the closed position of FIG. 52.

Next, cam follower 289 moves down and causes upper actuator plate 291 to move further down. When upper actuator plate 291 moves down, it depresses upper valve stem 297, which pushes upper valve body 273 and upper valve body tip 295 against the bias of spring 271. Upper valve body tip 295 thus assumes the position of FIG. 54 to eject a dosage form. In addition, as upper valve body tip 295 moves down air is ported around it from the compressed air path 267. As with the center mold assembly, compressed air in the upper mold assembly ensures that the coated dosage form does not stick to the upper insert 265 when it is ejected.

After the coated dosage form is ejected, it may be sent to a transfer device, dryer, or other mechanism. Following this, cam follower 289 and upper actuator plate 291 move back up. This in turn moves upper valve stem 297 and upper valve body tip 295 back to the position of FIG. 52 due to the bias of spring 271.

Similar to the center mold assembly, heated heat transfer fluid is directed through the upper first manifold plate 253 and upper insert assembly 296 to heat them during injection of the flowable material. Chilled heat transfer fluid is directed through the upper first manifold plate 253 and upper insert assembly 296 after the flowable material has been injected to harden it. In addition, warm heat transfer fluid can be sent through the upper second manifold plate 251 constantly to heat the flowable material above its melting point.

4. Temperature Control and Energy Recovery System

Preferably, the center and upper mold assemblies 212, 214 of the thermal cycle molding module are hot, i.e., above the melting point of the flowable material, when the flowable material is injected into them. This assists the flowable material in flowing. The mold assemblies are then preferably cooled, i.e., to below the melting or setting temperature of the flowable material, rather quickly to harden the flowable material.

In light of this cycle, a heat sink, a heat source and a temperature control system are preferably provided to change the temperature of the molds. Examples of heat sinks include but are not limited to chilled air, Ranque Effect cooling, and Peltier effect devices. Examples of heat sources include electric heaters, steam, forced hot air, Joule Thomson effect, ranque effect, ultrasonic, and microwave heating. In a preferred embodiment, a heat transfer fluid such as water or oil is used to transfer heat, while electric immersion heaters provide the heat source for the heat transfer fluid. Preferably, electrically powered freon chillers provide the heat sink for the heat transfer fluid.

Figure 55:
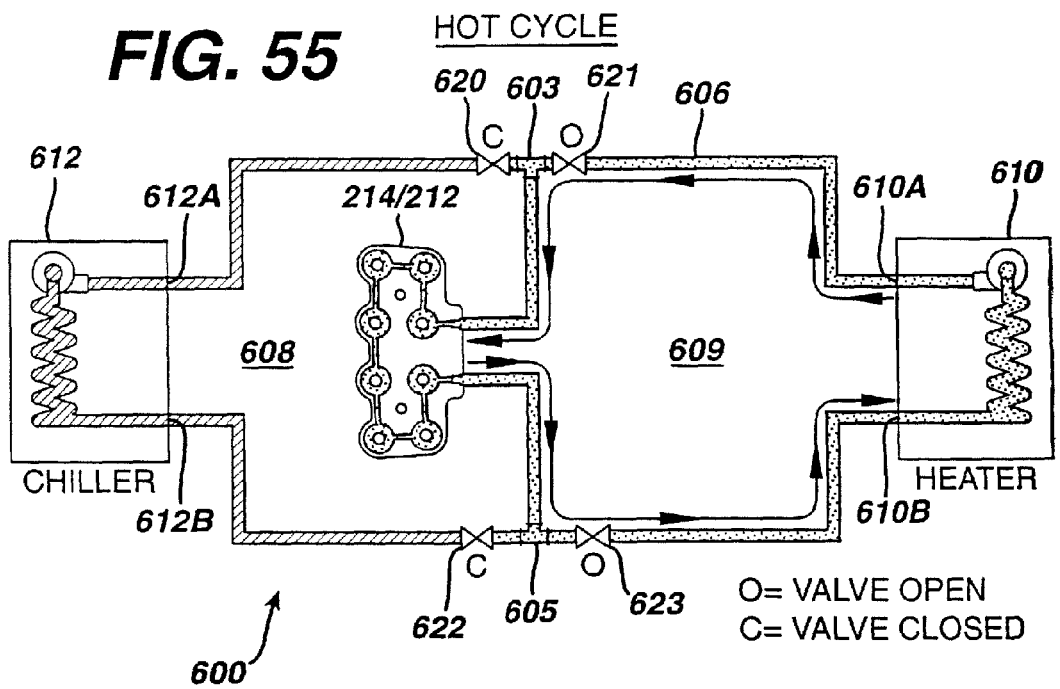
FIGS. 55 and 56 illustrate one embodiment of a temperature control system for the thermal cycle molding module.
Figure 56:
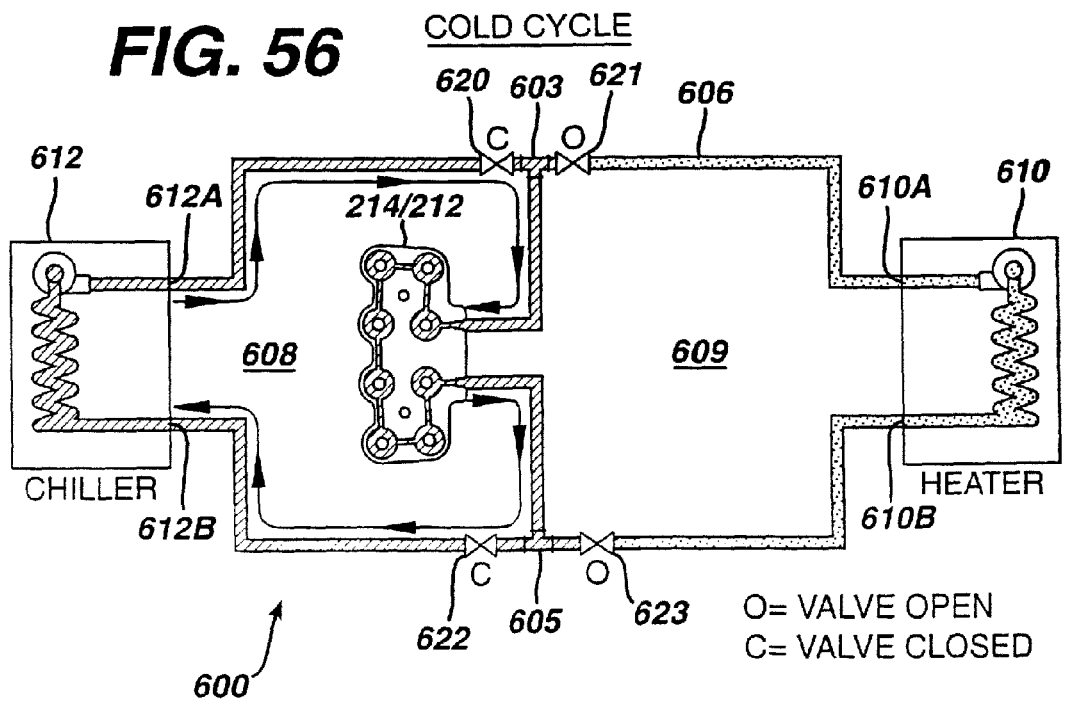

FIGS. 55 and 56 depict the preferred temperature control system 600 for the center mold assemblies and upper mold assemblies. Although only one mold assembly 214/212 is depicted, all mold assemblies are connected to the temperature control system in a similar fashion. Preferably, the temperature control system 600 includes a tubing system 606 and valves 620 to 623. Tubing system 606 includes a cold loop 608 for cooling mold assembly 214/212, and a hot loop 609 for heating them. Both loops share a common flow passageway between "T" fitting 603 and "T" fitting 605. Defined within the common flow passageway between "T" fitting 603 and "T" fitting 605 is a flow path in the mold assembly 214/212. Valves 620 to 623, which may be solenoid or mechanically operated, control the flow of cool or heated heat transfer fluid through the mold assembly 214/212. The system may also include a heater 610, which heats the hot loop, and a chiller 612, which provides a chilled fluid source for the cold loop. Outlet ports 612A and inlet ports 612B of the chiller and outlet ports 610A and inlet ports 610B of the heater can be connected to multiple molds, so that a single chiller and a single heater can support all of the upper molds 214 and center molds 212.

Valves 620 to 623 are initially in the position of FIG. 55. Valves 621 and 623 of the hot loop 609 are open so that hot heat transfer fluid can flow and circulate through the mold assembly 214/212. In contrast, the valves of the cold loop 620 and 622 are closed so that coolant cannot flow through that loop. After flowable material has been injected into the hot mold assembly 214/212, the cycle is switched to the cooling mode by closing solenoid valves 620 and 622 of the hot loop and opening valves 603 and 605 of the cold loop 608 (see FIG. 56). This blocks the flow of hot heat transfer fluid to the molds assembly 214/212, and starts the flow of chilled heat transfer fluid therethrough. Preferably, the center mold assembly 212 and the upper mold assembly 214 are capable of cycling in the temperature range of about 0 to about 100° C. in about 1 seconds to 30 seconds. In the preferred embodiment using gelatin at 60% moisture content, the center and upper mold assemblies 212, 214 cycle between about 35° C. and 20° C. in about 2 seconds.

The cold and hot heat transfer fluid thus flows in the common flow passageway between "T" fittings 603 and 605. When the valves switch from the heating mode to the cooling mode, the volume of hot heat transfer fluid enclosed within the common flow passageway is transferred to the cold side of the system. Conversely, hot heat transfer fluid trapped in the common flow passageway is transferred into the cold loop when the valves switch to the heating mode.

Figure 59:
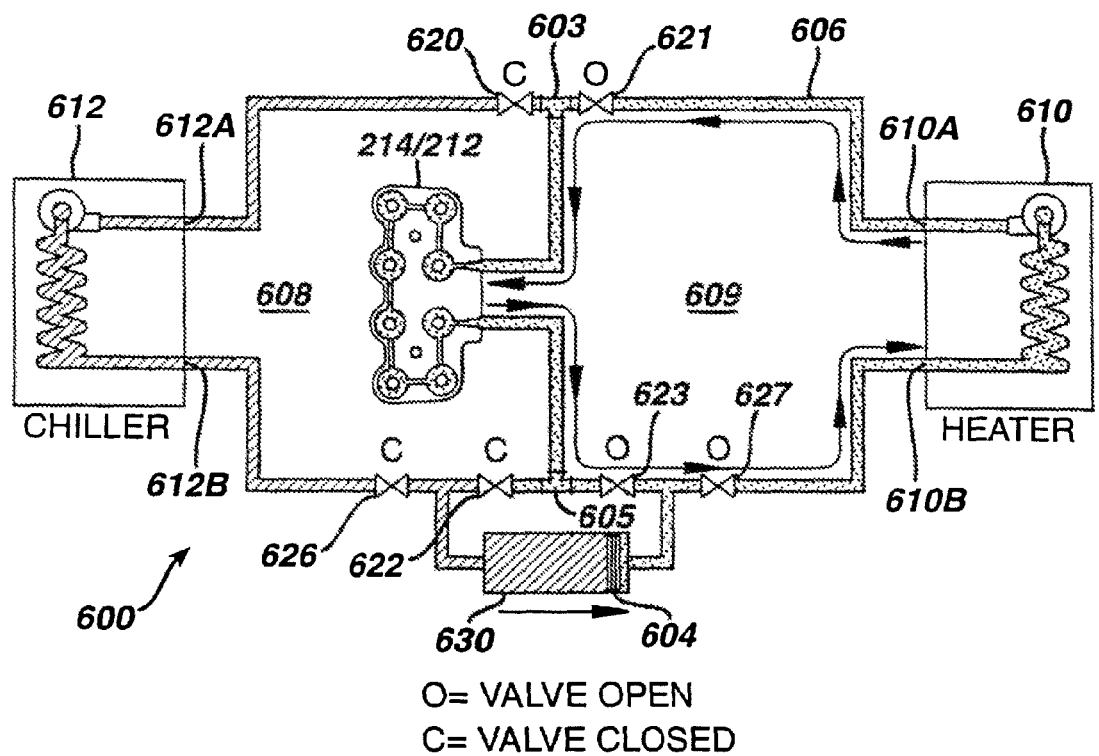

Although the volume of fluid in the common flow passageway is relatively small, and the cost of energy to heat and chill this volume of fluid is not unreasonable for a commercial process, a more preferred, energy efficient, and cost effective temperature control system is depicted in FIGS. 57-59. This preferred temperature control system 600 includes the following components additional to those described above: a fluid reservoir 630, a moveable piston 604 bisecting the fluid reservoir, and valves 626 and 627. The fluid reservoir can be replaced with two collapsible bladders (hot and cold), thus eliminating the need for the piston 604. For ease of description, however, the reservoir and piston embodiment is described herein. Valves 620, 621, 622, 623, 626 and 627, which may be solenoid or mechanically operated, control the flow of cool or hot heat transfer fluid through the system. Each mold assembly 214/212 has its own fluid reservoir 630, piston 604, and valves 620, 621, 622, 623, 626 and 627. Initially, the valves are in the position of FIG. 57. Valves 620, 622, and 626 of the cold loop are open so that cool heat transfer fluid can flow to the mold assembly 214/212. In contrast, the valves of the hot loop 621, 623, 627 are closed so that hot heat transfer fluid cannot flow through that loop. The piston 604 is forced to the cold loop side by the position of the valves 626, 622, 623, and 627.

When the system switches to heating mode the solenoid valves, which are controlled by an electronic signal or by mechanical (cam) actuation, close or open as shown in FIG. 58. Valves 620, 626, and 623 close and valves 621, 622, and 627 open. This blocks the flow of cool heat transfer fluid from the cold loop to the mold assembly 214/212 and starts the flow of hot heat transfer fluid through the mold assembly 214/212. This permits the hot heat transfer fluid to shift piston 604 to the position shown in FIG. 58. When piston 604 is in the far right position it is generally configured to contain a volume of liquid equal to fluid enclosed within the passageway between "T" fittings 603 and 605. This volume is tunable by adjusting when the valves open and close, or by adjusting the volume of the fluid reservoir 630. When piston 604 reaches its preselected rightmost position (FIG. 59) valves 622, 626, and 620 close and valves 621, 623, and 627 open. The fluid contained in the fluid reservoir to the left of piston 604 is cold. Fluid to the right of piston 604 is hot and most of this hot fluid has been evacuated from the cylinder. The heating mode of the system is now in progress in FIG. 59. When the system switches to cooling mode, piston 604 moves in the opposite direction (to the left) and fills with hot fluid thus reversing the process just described. By preventing or minimizing hot heat transfer fluid from entering the chilled side and by preventing cold heat transfer fluid from entering the hot side, energy losses are minimized and the system is maximally efficient.

Figure 60A:
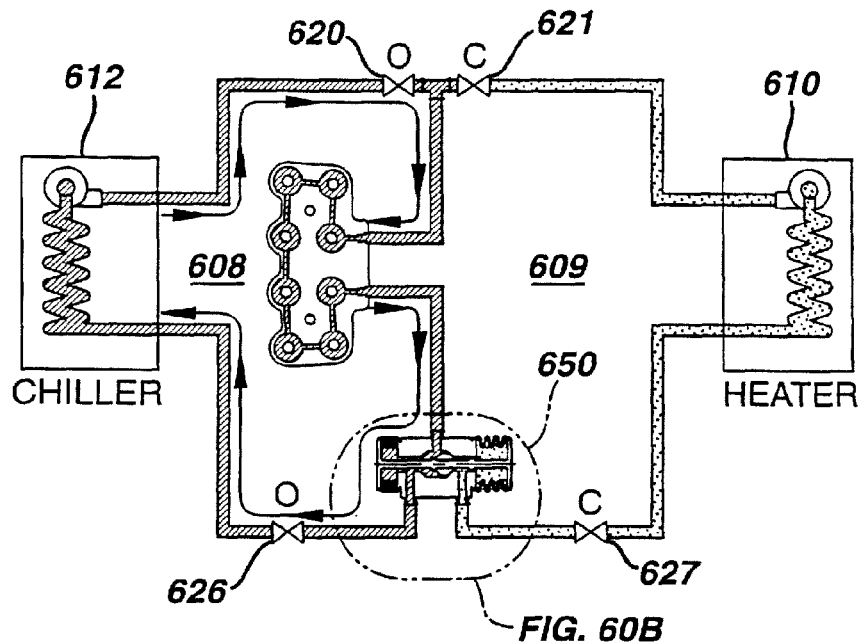
FIGS. 60-62 show a preferred embodiment of the temperature control system for the thermal cycle molding module.
Figure 60B:
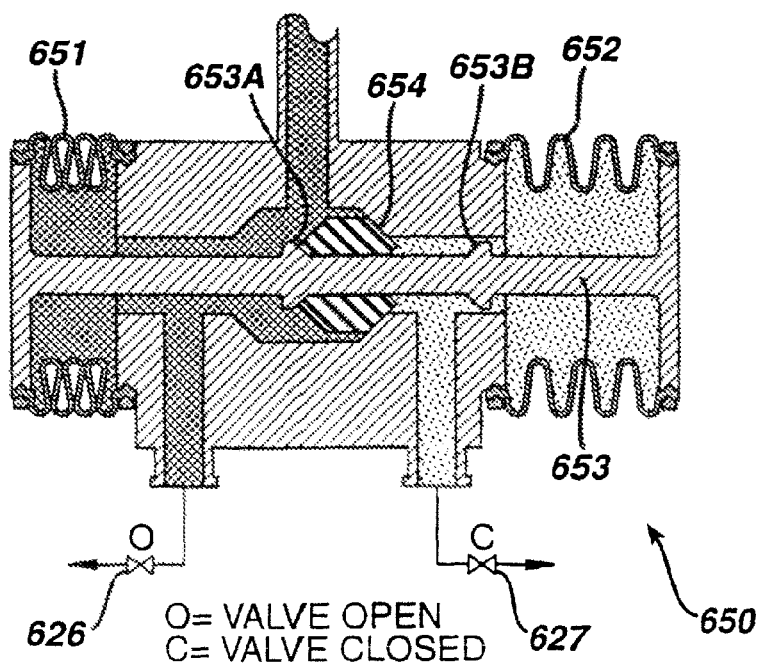
Figure 61:
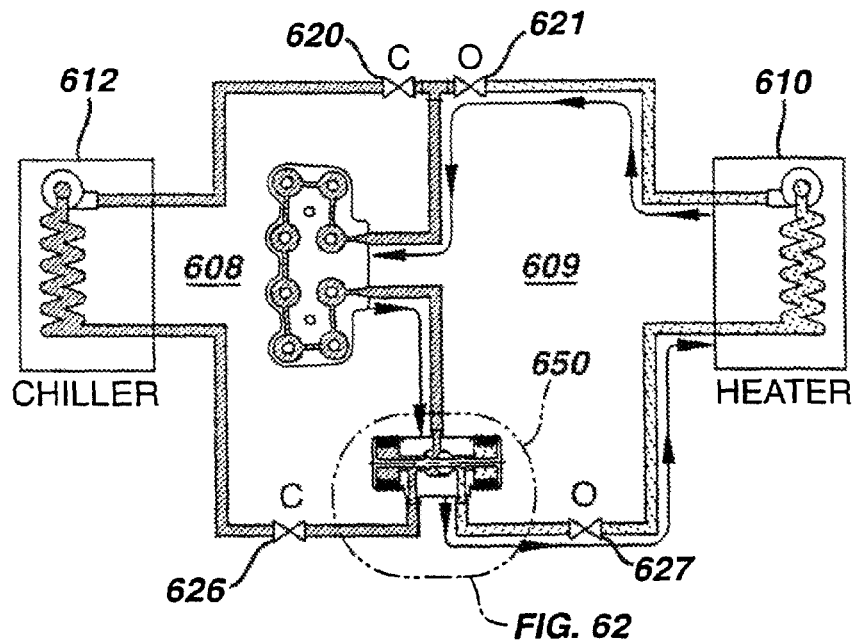
Figure 62:
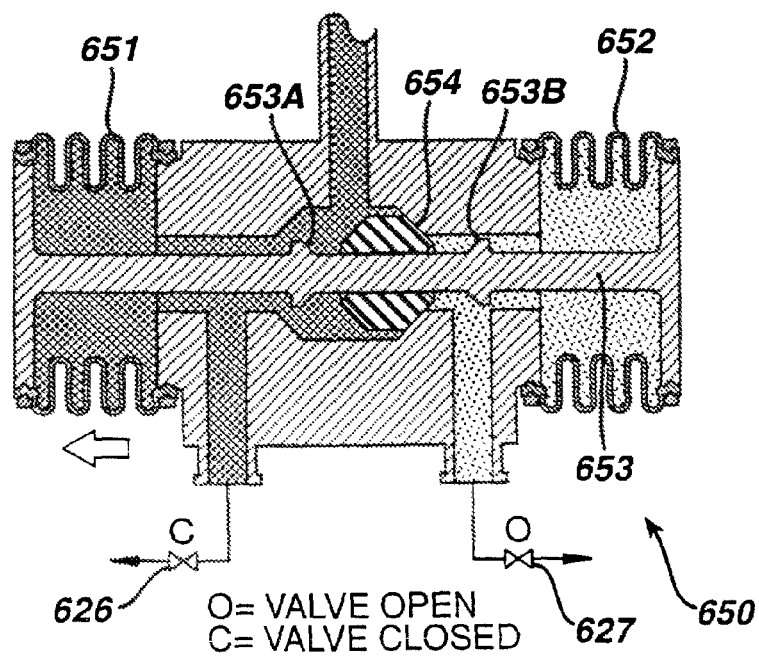

FIGS. 60-62 depict a particularly preferred embodiment of the temperature control system incorporating an automatic valve system 650. The automatic valve system 650 directs heat transfer fluid to energy recovery bladders 651 and 652. The automatic valve system 650 replaces valves 622 and 623 of the system described in FIGS. 57-59. Connecting energy recovery bladders together is connection rod 653. Slidably mounted to the connection rod 653 is valve slide 654.

Operation of the automatic valve system 650 is best understood by comparing FIGS. 60 through 62. In FIG. 60 cold heat transfer fluid is circulating and hot heat transfer fluid is not. The energy recovery bladders are shifted to the right most position with hot heat transfer fluid filling bladder 652. Valve slide 654 is seated in its right most position by a flanged portion 653A of connection rod 653 allowing fluid to pass to the left.

In FIG. 61, the temperature control system has just switched from cooling mode to heating mode by switching valves 620 and 626 from their open to closed positions. Valves 621 and 627 have switched from closed to open positions, allowing hot heat transfer fluid to begin flowing around loop 609. The pressure from the fluid in loop 609 forces energy recovery bladder 651 to fill and move to the left as shown in FIG. 61. Simultaneously, energy recovery bladder 652 empties and moves to left due to the linking of the bladders by connection rod 653. The valve slide 654 functions as a check valve and remains seated to the right due to pressure against its left face. As bladders 651 and 652 continue to move to the left, flanged portion 653B of connection rod 653 makes contact with the right face of valve slide 654, unseating it and shifting it to the left most position shown in FIG. 62. The temperature control system is now in the heating mode. When the temperature control system switches back from heating to cooling mode the cycle repeats and the bladders 651 and 652 move to the right.

As described above, valves 620 through 623 of the temperature control system can be of various designs known in art, such as spool, plug, ball, or pinch valves. These valves can be actuated by suitable means such as air, electrical solenoids, or by mechanical means such as cam tracks and cam followers. In a preferred embodiment, the valves are pinch valves and are actuated by mechanical cam tracks and cam followers as the thermal cycle molding module rotates. Known pinch valves are relatively simple devices comprising a flexible section of tubing and a mechanism that produces a pinching or squeezing action on the tubing. This tubing is compressed or "pinched" to block fluid flow therethrough. Release of the tubing allows fluid to flow. Accordingly, the pinch valve functions as a two-way valve.

Figure 63:
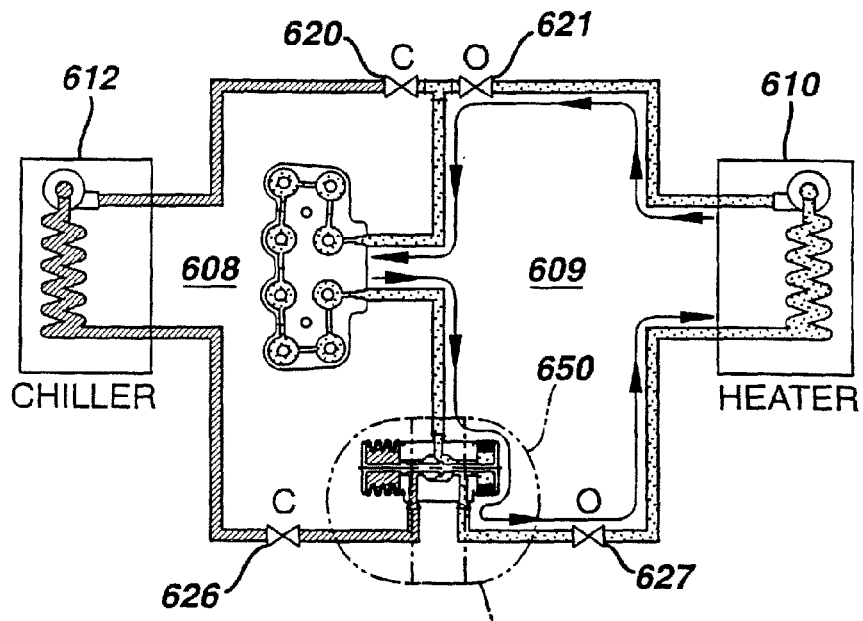
FIGS. 63-67 illustrate a rotary pinch valve system suitable for use in the temperature control system of the thermal cycle molding module.
Figure 64:
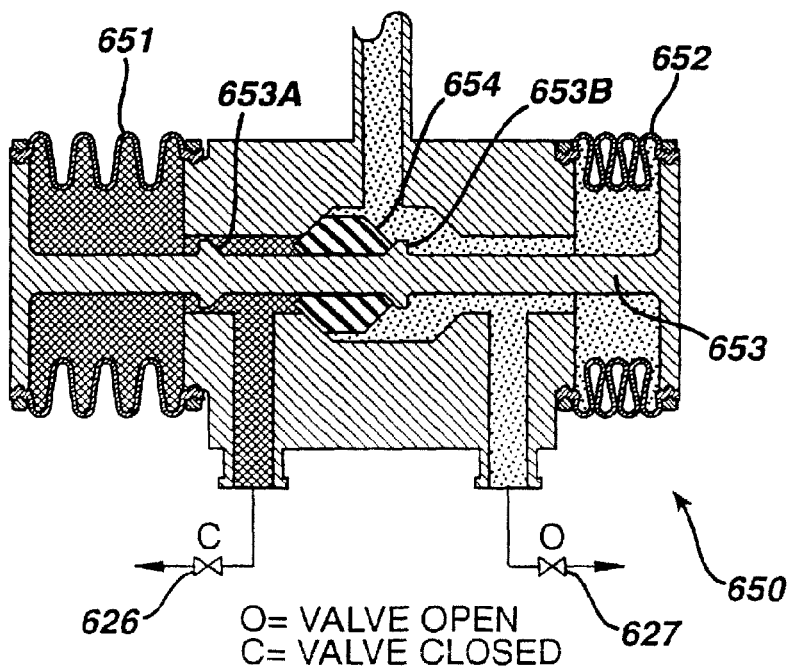
Figure 65:
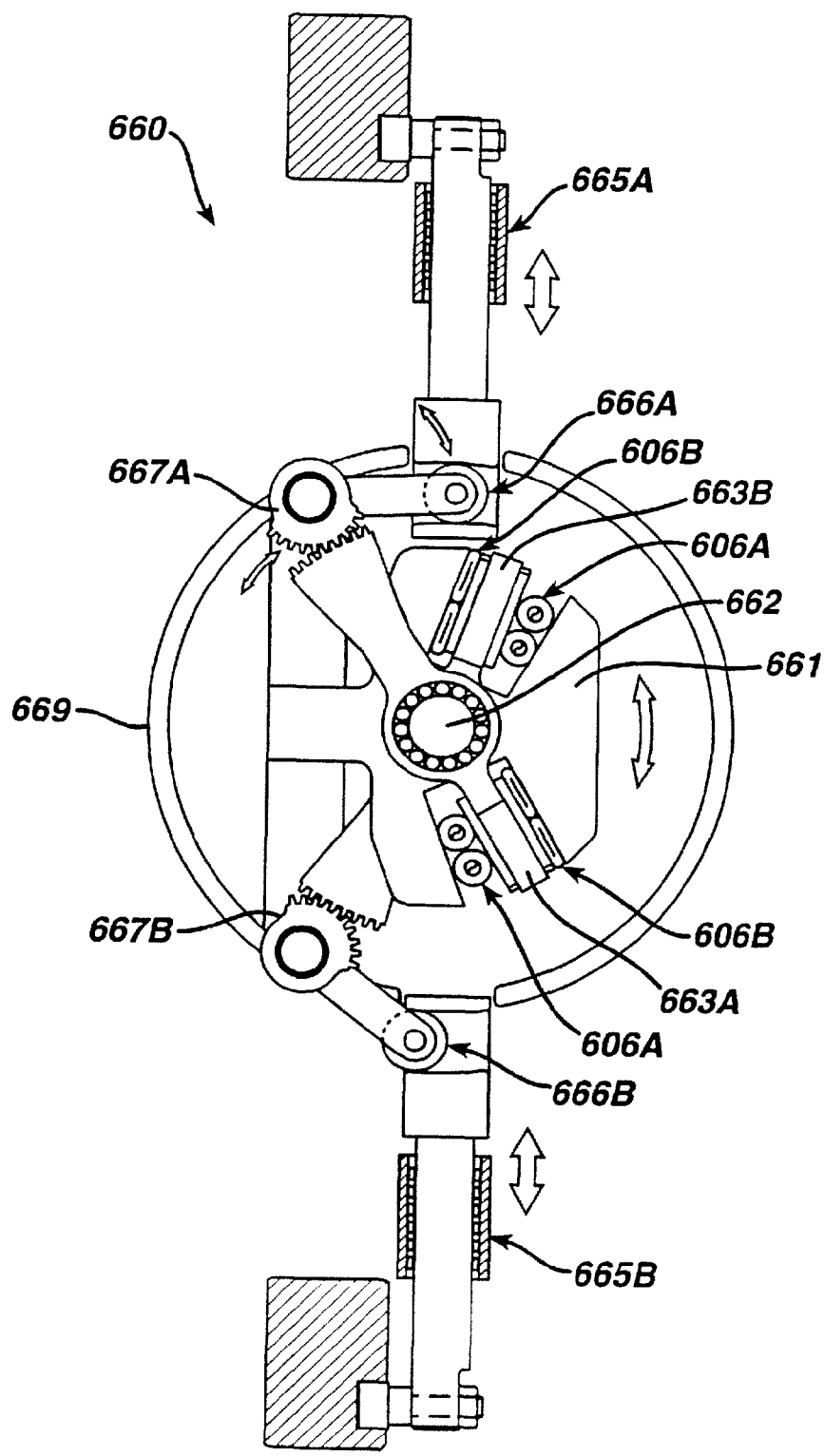
Figure 66:
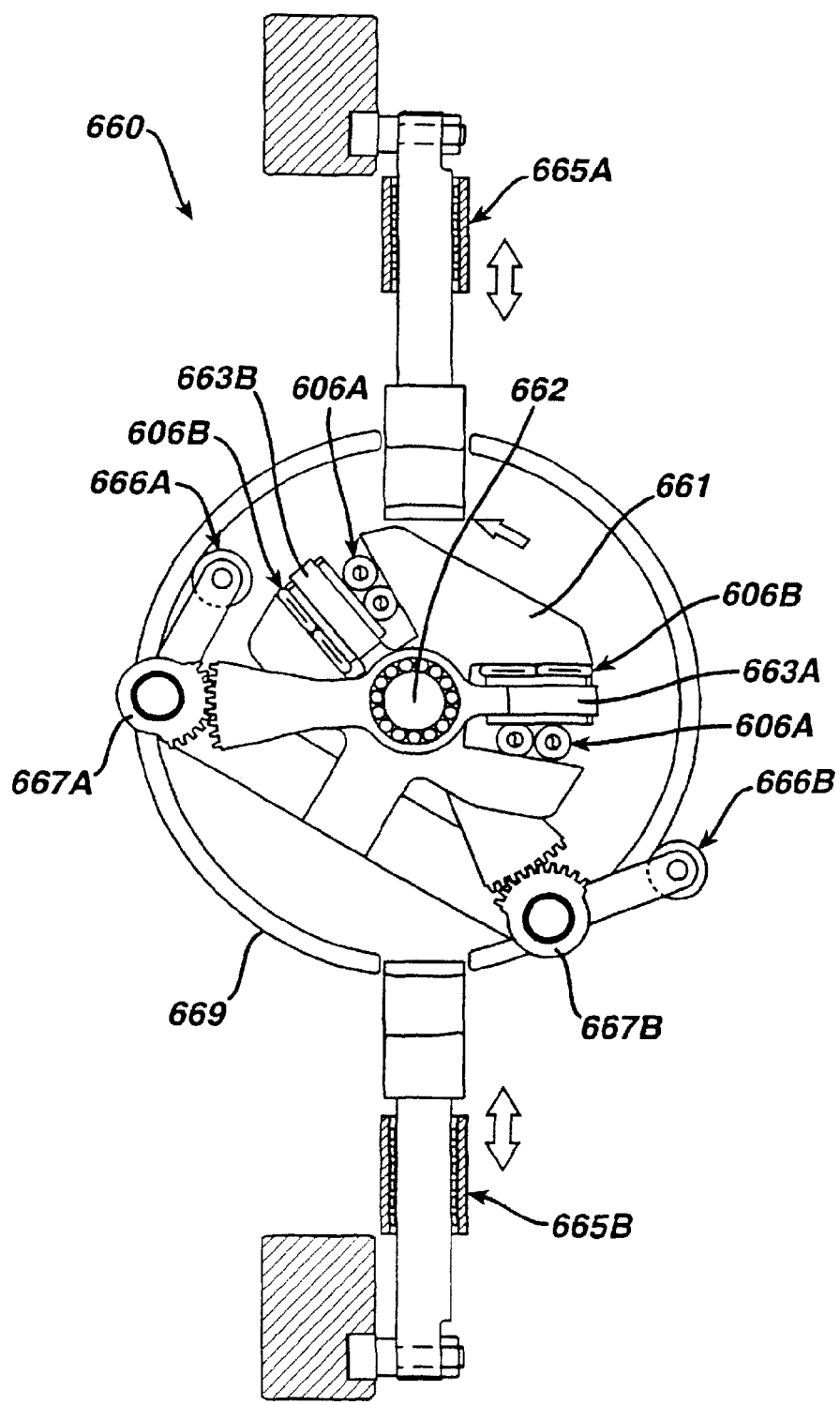
Figure 67:
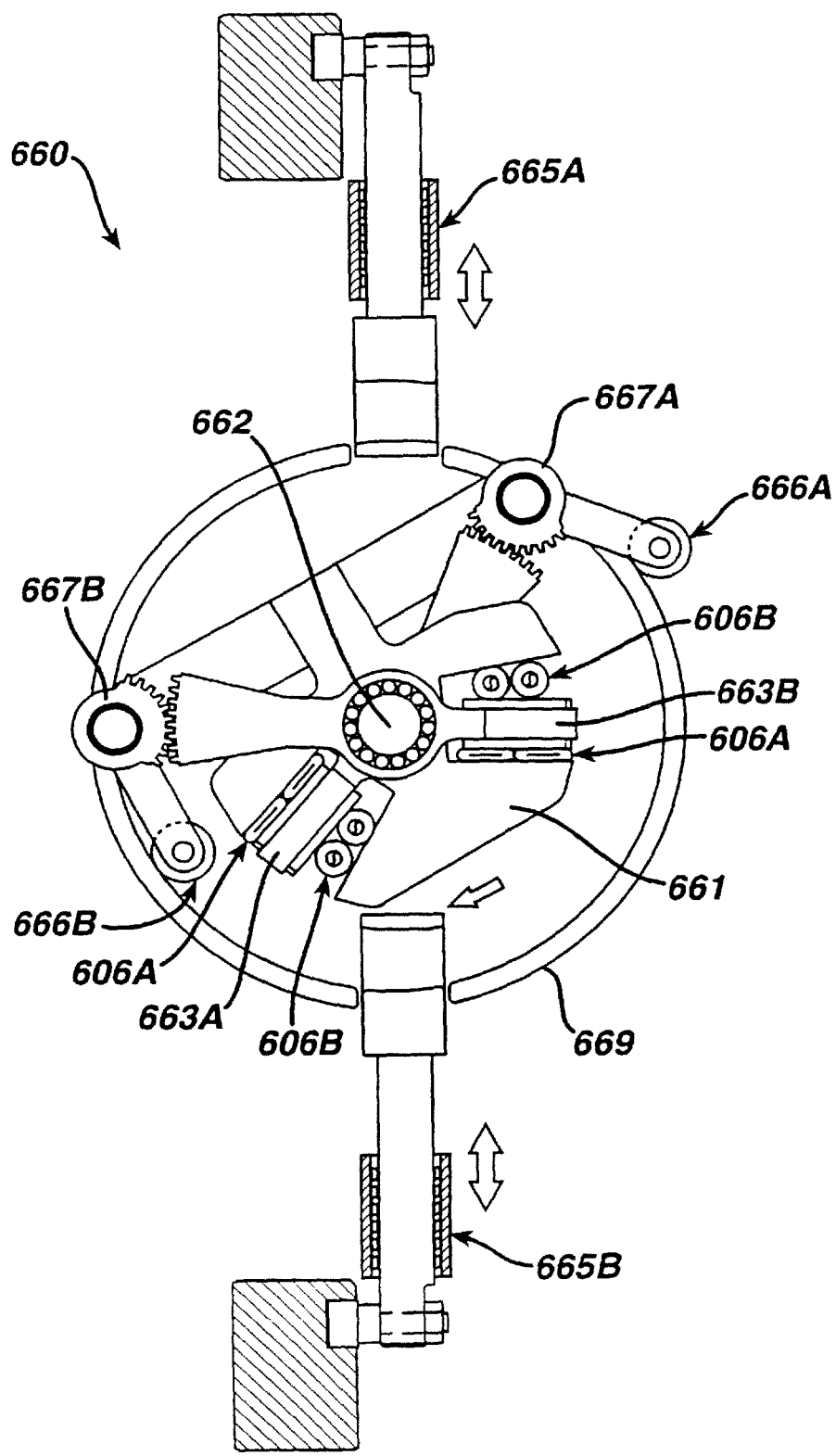

The pinch valves of the present temperature control system utilize a rotary design to "pinch" and "unpinch" flexible tubing. As described above, the center mold assembly rotates clockwise and then counterclockwise over an arc of 180 degrees. Feeding the center mold assembly are eight tubes 606 that supply heat transfer fluid (two supply and two return lines for each mold assembly). FIGS. 63-65 depict a rotary pinch valve assembly 660 of the invention. The rotary pinch valve assembly 660 comprises a valve anvil 661 fixed to shaft 662. Shaft 662 is attached to center mold assembly 212 (not shown) so that it can rotate about the same axis. Rotatably mounted to shaft 662 is valve pinch arm 663A. A similar valve pinch arm 663B is also rotatably mounted to shaft 662 and is free to move independently of valve pinch arm 663A. Actuating the valve pinch arms are valve actuators 665A and 665B, which move cam follows 666A and 666B in the vertical direction. The vertical rise and fall of actuators 665A and 665B causes corresponding movements of cam followers 666A and 666B, which imparts a rotational movement to valve pinch arms 663A and 663B via gears 667A and 667B, which are rotatably mounted to valve anvil 661. Gears 667A and 667B reduce or amplify the rotational movement of the valve pinch arms 663A and 663B by an amount proportional to the gear ratio. Although gears 667A and 667B are used in the preferred embodiment described here, in other embodiments they can be dispensed with. Rotational movement of the valve pinch arms can be imparted directly by cam followers and actuators.

The counter clockwise rotation of valve pinch arms 663A and 663B about shaft 661 causes tubes 606B to be squeezed closed and tubes 606A to remain open. Conversely, clockwise rotation of valve pinch arms 663A and 663B about shaft 661 causes tubes 606A to be squeezed closed and tubes 606B to remain open. The position of the valves (open or closed) depends on whether the orientation of center mold assembly 212 is up or down. It is also a requirement that the position of the valves remain unchanged (or controlled) as the center mold assembly makes its 180 degree rotation. As shown in FIG. 64, the circular cam track 669 allows cam followers 666A and 666B to remain in their fully actuated positions while the rotary pinch valve assembly 660 rotates clockwise and counter clockwise 180 degrees. Cam followers 666A and 666B can transit either the inner surface or outer surface of the circular cam track 669 as shown in FIG. 64.

Transfer Device

1. Structure of the Transfer Device

Known tablet presses use a simple stationary "take-off" bar to remove and eject tablets from the machine. Since the turrets of these machines rotate at fairly high speeds (up to 120 rpm), the impact forces on the tablets as they hit the stationary take-off bar are very significant. Dosage forms produced on these machines must therefore be formulated to posses very high mechanical strength and have very low friability just to survive the manufacturing process.

In contrast with prior art devices, the present transfer device is capable of handling dosage forms having a higher degree of friability, preferably containing little or no conventional binders. Thus, a preferred formulation for use with present invention comprises one or more medicants, disintegrants, and fillers, but is substantially free of binders. Dosage forms having a very high degree of softness and fragility may be transferred from any one of the operating modules of the invention as a finished product using the transfer device, or transferred from one operating module to another for further processing.

Figure 68:
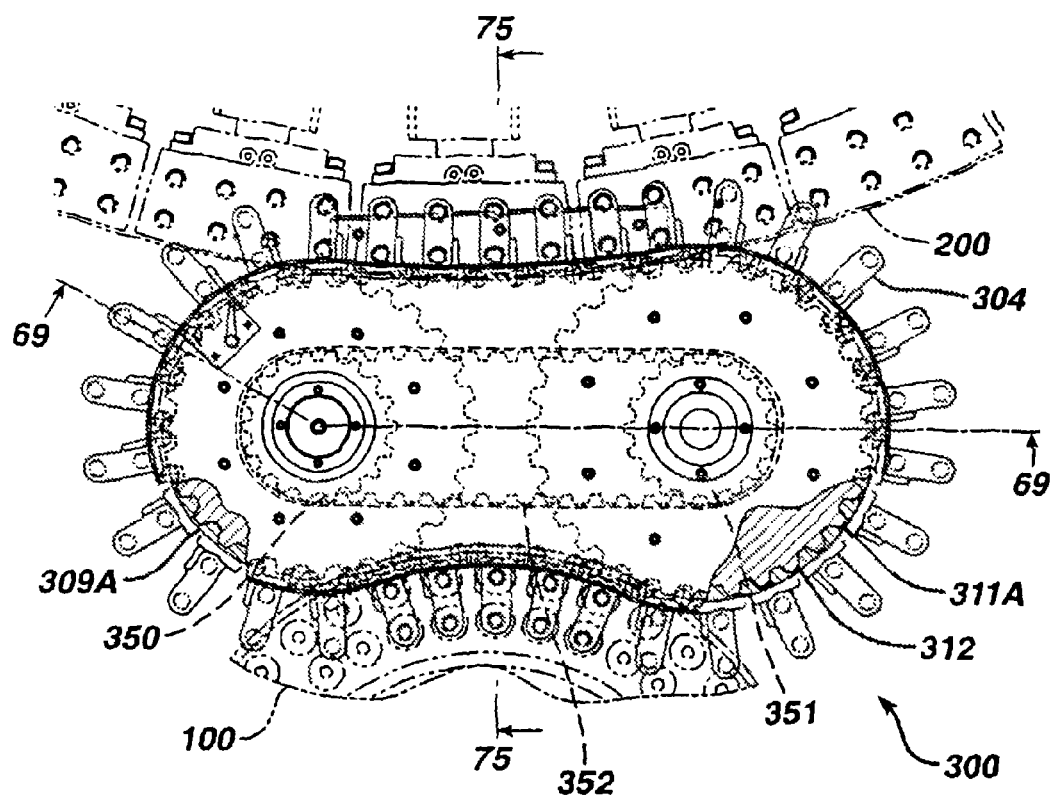
FIG. 68 is a top view of a transfer device according to the invention.

The present transfer device is a rotating device, as shown in FIGS. 3 and 68. It comprises a plurality of transfer units 304. It is preferably used for transferring dosage forms or inserts within a continuous process of the invention comprising one or more operating modules, i.e., from one operating module to another. For example, dosage forms may be transferred from a compression module 100 to a thermal cycle molding module 200, or from a thermal setting molding module 400 to a compression module 100. Alternatively, the transfer device can be used to transfer dosage forms or other medicinal or non-medicinal products between the devices used to make such products, or to discharge fragile products from such machines.

Transfer devices 300 and 700 are substantially identical in construction. For convenience, transfer device 300 will be described in detail below. Each of the transfer units 304 are coupled to a flexible conveying means, shown here as a belt 312 (FIGS. 68 and 69), which may be made of any suitable material, one example of which is a composite consisting of a polyurethane toothed belt with reinforcing cords of polyester or poly-paraphenylene terephthalamide (Kevlar®, E.I. duPont de Nemours and Company, Wilmington, Del.). The belt runs around the inner periphery of the device 300. The transfer units 304 are attached to the belt 312 as described below.

The transfer device can take any of a variety of suitable shapes. However, when used to transfer dosage forms or inserts between operating modules of the present invention, transfer device is preferably generally dog bone shaped so that it can accurately conform to the pitch radii of two circular modules, enabling a precision transfer.

The transfer device can be driven to rotate by any suitable power source such as an electric motor. In a preferred embodiment, the transfer device is linked to operating modules of the invention and is driven by mechanical means through a gearbox which is connected to the main drive motor 50. In this configuration the velocity and positions of the individual transfer units of the transfer device can be synchronized with the operating modules. In a preferred embodiment the drive train includes a drive pulley 309 and an idler pulley 311 which are in the preferred embodiment disposed inside of the transfer device 300. The drive shaft 307 connects the main drive train of the overall linked system to the drive pulley 309 of the transfer device. The drive shaft 307 drives the drive pulley 309 to rotate as shown in FIGS. 3 and 68. The drive pulley 309 has teeth 309A that engage teeth 308 disposed on the interior of belt 312, which in turn rotates the transfer device. The idler pulley 311 has teeth 311A that engage belt 312, which causes the idler to rotate with the belt 312. Other flexible drive systems, such as chains, linked belts, metal belts, and the like can be used to convey the transfer units 304 of the transfer device 300.

Figure 69:
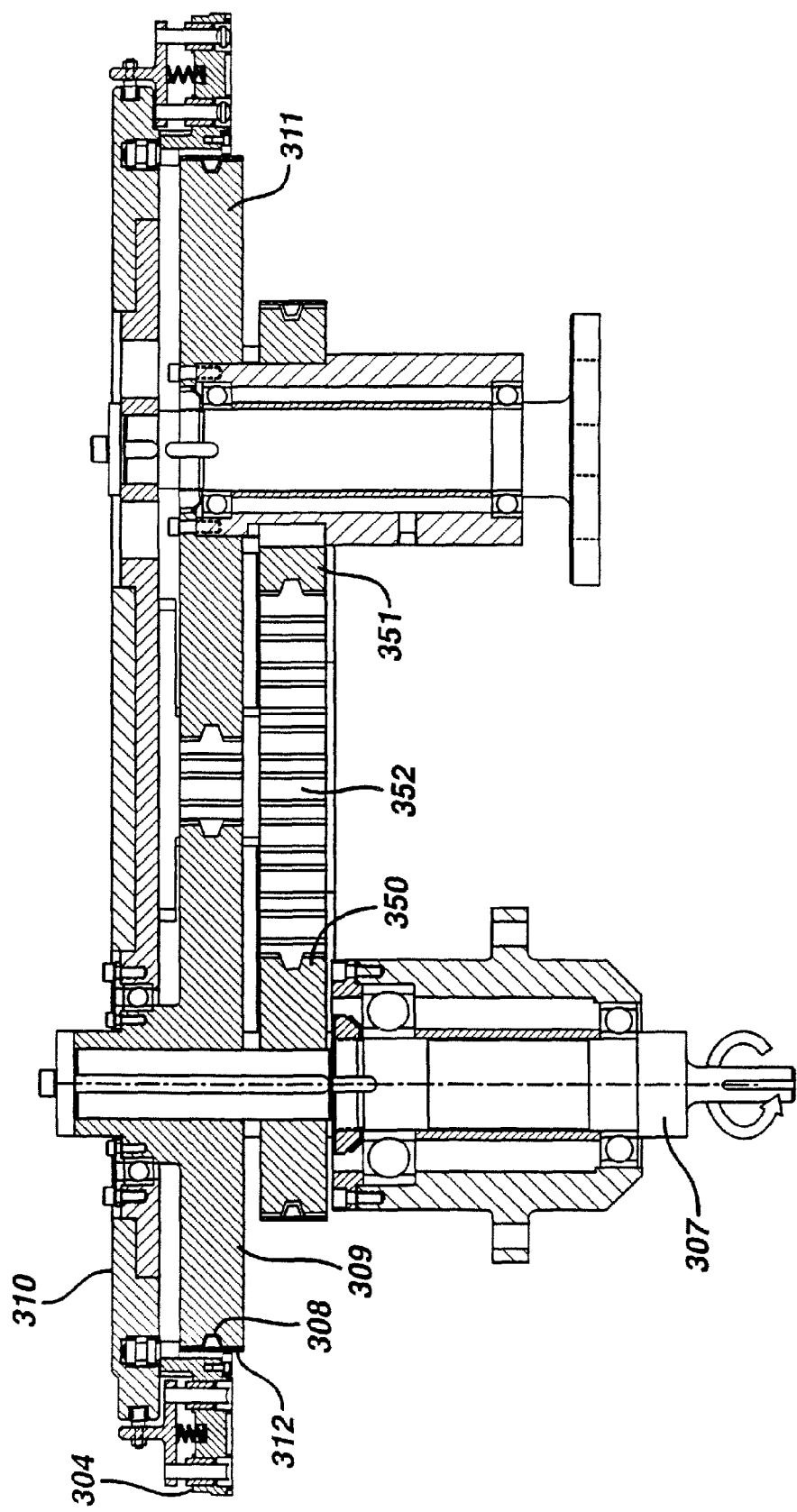
FIG. 69 is a cross-section taken along line 69-69 of FIG. 68.
Figure 70:
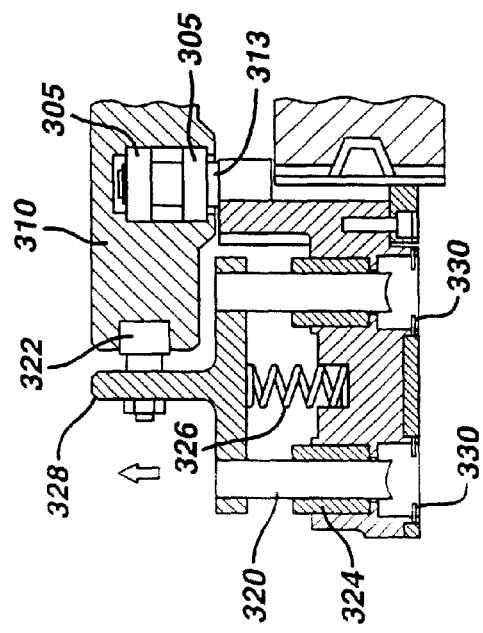

As shown in FIGS. 68 and 69, attached to the outer periphery of the transfer device 300 is a dog bone shaped cam track 310 which precisely determines the path for the belt and the transfer units. The radii of the cam track 310, the pitch distance between the transfer units 304, the pitch of the toothed belt 312, and the gear ratio between the drive pulley 309 and the main drive of the linked system are all selected such that the transfer device is precisely aligned with the operating modules linked to it. As each operating module rotates, the transfer device remains synchronized and phased with each, such that a precise and controlled transfer from one operating module to another is achieved. The velocity and position of the transfer unit 304 is matched to the velocity and position of the operating module along the concave portions of the cam track. Transfers are accomplished along this arc length. The longer the length of the arc, the greater the time available to complete a transfer. Riding in cam track 310 are cam followers 305 suitably mounted to the transfer units (FIG. 70).

In a preferred embodiment of this invention, both the drive pulley 309 and the idler pulley 311 are driven. FIGS. 68 and 69 depict a toothed pulley 350, a second toothed pulley 351 and a toothed belt 352. Pulleys 350, 351 and belt 352 connect the rotation of the drive pulley 309 with the rotation of the idler pulley 311. This advantageously eliminates any slack side condition in the belt. Linking of pulleys 309 and 311 could also be accomplished using gears, gear boxes, line shafts, chains and sprockets or by synchronized electric motors.

A preferred transfer unit 304 is depicted in FIGS. 70-75, and generally includes a pair of plunger shafts 320, one or preferably more than one cam follower 322, a plurality of bearings 324 to retain the plunger shafts 320, a spring 326, a plate 328 that secures the plunger shafts 320 to cam follower 322 thereby controlling their movement, and a retainer 330. Preferably, each transfer unit 304 is attached to flexible conveying means 312 in a cantilever configuration so that retainers 330 are cantilevered over the path of the dosage forms. This allows for multiple rows of retainers in the transfer unit and keeps contamination by dirty mechanical parts away from the dosage form and its sub components. Moreover, it allows the flexible conveying means to contact closely the operating modules to which it is connected, thereby allowing for a smooth transfer pathway.

Figure 72:
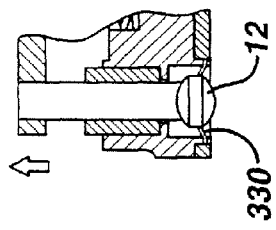
FIGS. 70-74 illustrate a preferred embodiment of a transfer unit of a transfer device according to the invention.
Figure 71:
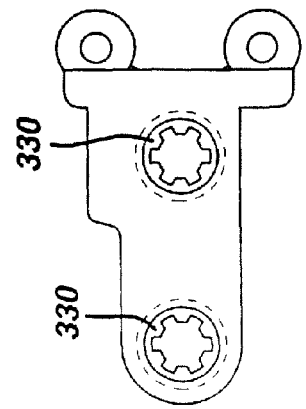

Retainers 330 are preferably flexible and constructed from an elastomeric material so that when no dosage form is inserted into the retainer 330, the retainer 330 generally points radially inward as shown in FIG. 71. When a dosage form is pushed into the retainer 330, the retainer 330 flexes upward as shown in FIG. 72. The dosage form passes the retainer 330 and releases it so that the retainer supports the dosage form in the transfer unit from below. A dosage form is ejected from a transfer unit by pushing down on the dosage form, thereby flexing the retainer and permitting the dosage form to be pushed out. Once released, the retainer 330 flexes back to its radially inward position so that it can receive another dosage form. In a preferred embodiment, the retainer 330 is circular and includes segmented fingers of elastomeric material as shown in FIG. 71, but it need not be so constructed. It need only be flexible enough to flex, hold the dosage form, and release the dosage form. Retainer 330 extends radially inward a distance such that when the dosage form is pushed past it, it holds the dosage form in place until it is ejected by the plunger shafts 320, as described below.

Cam follower 322 is disposed towards the top of the transfer unit 304. It is mounted so that it can move up and down as shown in FIGS. 70-74. Plate 328 is coupled to cam follower 322. Spring 326 is connected to transfer unit 304 and biases the plate 328 and cam follower 322 to an upper position. Plate 328 is also coupled to each plunger shaft 320, so that movement of the plate 328 will cause movement of the plunger shafts 320.

Figure 74:
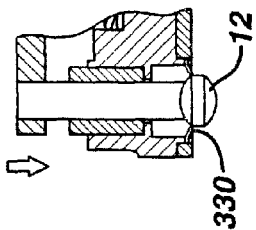

Each plunger shaft 320 is mounted within the transfer unit 304 by a plurality of bearings 324 that permit vertical movement of the plunger shafts 320. The plunger shafts 320 are mounted so that one end of each plunger shaft 320 can move into the respective space in which a dosage form is retained to eject it from the retainer 330, as shown in FIG. 74. As described below, the plunger shafts 320 move in response to movement of the plate 328 and the roller bearing 322 to eject dosage forms from the transfer unit 304. The plunger shafts 320 and bearings 324 may be made of any suitable material.

2. Operation of the Transfer Device

Figure 75:
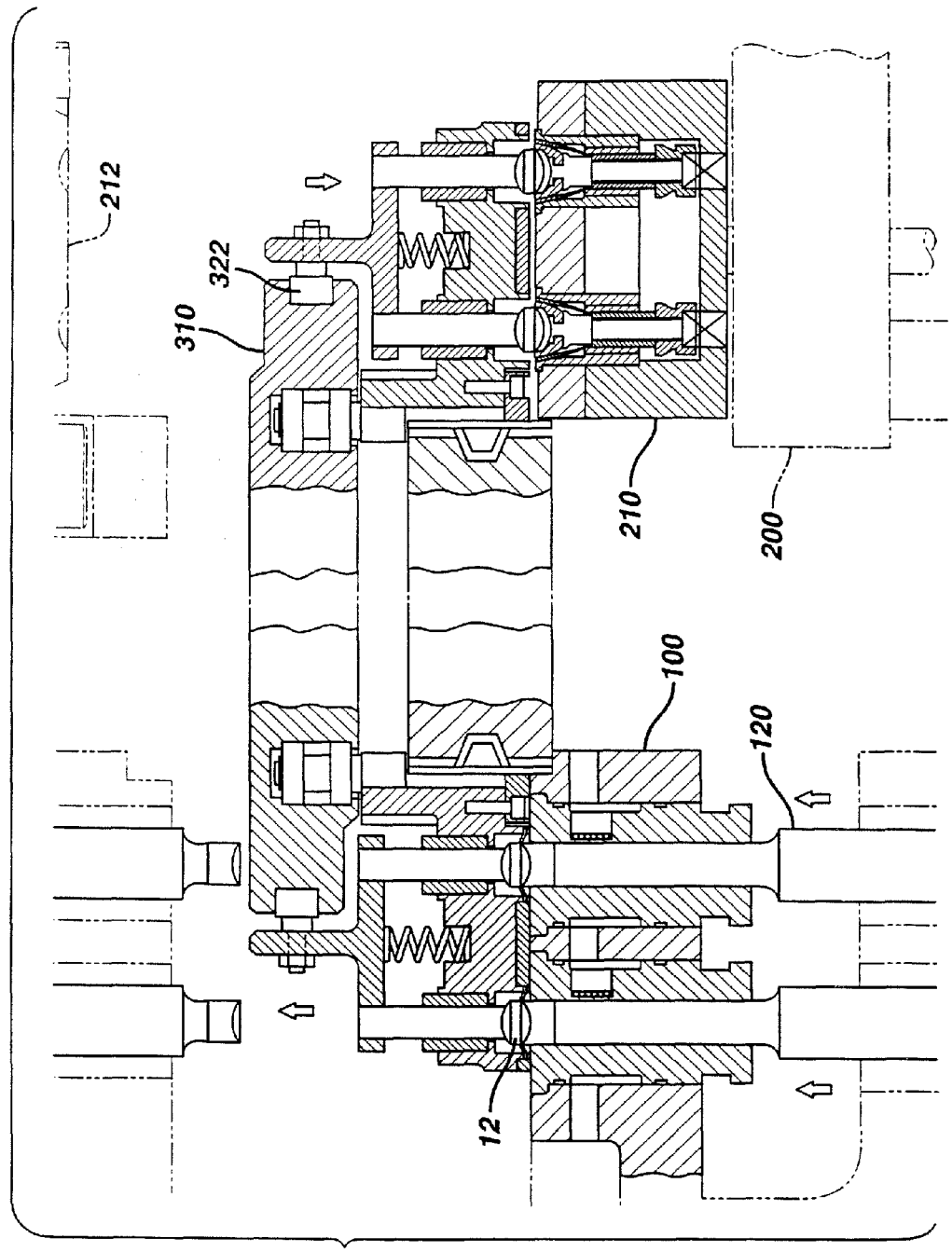
FIG. 75 is a cross-section taken along line 75-75 of FIG. 68.
Figure 76:
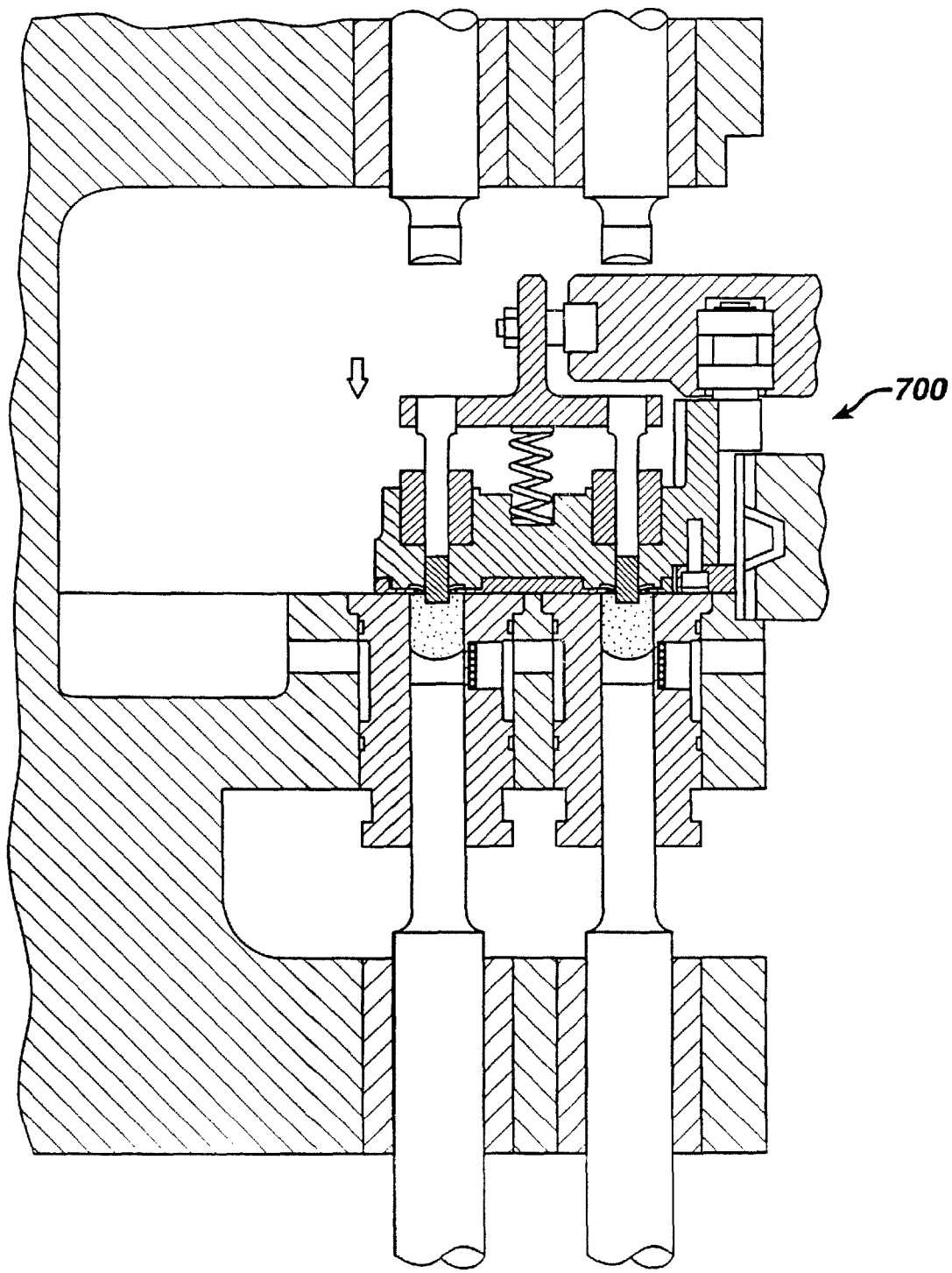
FIG. 76 shows a transfer device according to the invention transferring an insert from a thermal setting molding module to a compression module.

Operation of the transfer device is best understood with reference to FIGS. 3 and 70-75. A description of the operation of one transfer unit 304 is provided, but it will be understood that the other transfer units 304 operate in a similar fashion. Moreover, operation is described with respect to transfer of a dosage form from a compression module to a thermal cycle molding module, however, as stated above, transfer may be accomplished between any two operating modules or other devices. For example, FIG. 76 depicts a transfer device 700 transferring an insert from a thermal setting mold module to a compression module. The sole differences between transfer devices 300 and 700 are the geometry of the transferred object and the geometry of the transfer unit holders.

Figure 73:
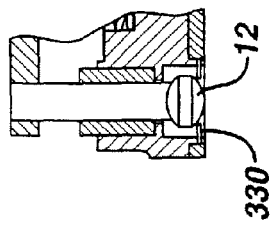

The transfer device operates as follows. The transfer unit 304 passes by the die table 114 of the compression module 100 and the two retainers 330 of the transfer unit 304 become aligned with die cavities 132 that are on a radial line, as shown on the left of FIG. 75. At the point of alignment, lower punch 120 moves upward in unison with plunger shafts 320 due to the cam tracks as described above. A dosage form 12 is ejected into the retainers 330 of the transfer unit 304 as shown in FIGS. 72, 73 and 75. The dosage form flexes the retainer 330 until it moves past the retainer 330 and is held in the transfer unit 304 by the retainer 330. Since the plunger shafts and lower punches capture the dosage form in a confined space with minimal clearance, the dosage form can not rotate or move randomly, which could jam this or subsequent apparatus. The dosage form is therefore fully controlled before, during, and after transfer. Rotation of the transfer device 300 and die table 114 of the compression module 100 are synchronized so that transfer units 304 will continually pass above the die cavities 132 and dosage forms will be continuously transferred to the transfer units 304.

Further rotation of the transfer device 300 by the drive pulley causes the belt 312 and its attached transfer units 304 to rotate. Eventually, the transfer units 304 containing the dosage forms reach the lower retainer 210 of the thermal cycle molding module 200, as shown in FIGS. 3 and 75. Cam 310 is disposed between the center mold assembly 212 and the lower retainer 210. The lower retainer 210 passes just beneath the transfer units 304. Thus, the transfer units 304 become aligned with two of the elastomeric collets 220 in the lower retainer. As the transfer unit 304 moves along cam track 310, cam track 310 pushes on the cam follower 322, which pushes on plate 328. Plate 328 moves the plunger shafts 320, which in turn move down and contact the dosage forms. This contact pushes the dosage forms past the elastomeric collets, and the dosage forms move out and into the elastomeric collets 220. Lower retainer 210 and the transfer device 300 are rotating at speeds that permit the dosage forms to be continuously transferred from the transfer units 304 to the lower retainers 210.

As the retainers 330 move past the thermal cycle molding module, plunger shafts 320 return to their original upward position.

3. Rotational Transfer Device

In a preferred alternate embodiment of this invention, a rotational transfer device is employed. Such a device is useful for handling dosage forms that must be both transferred from one piece of equipment and reoriented, for instance from a horizontal position to a vertical position, or vice versa. For example, two color gelcaps, elongated dosage forms in which the boundary between colors lies along the short axis of the dosage form (see FIG. 81), must be compressed horizontally along their long axis, but coated in a vertical position. Accordingly, gelcaps compressed in the present compression module 100 and coated the thermal molding module 200 must be both transferred from the compression module and reoriented into a vertical position.

Figure 77:
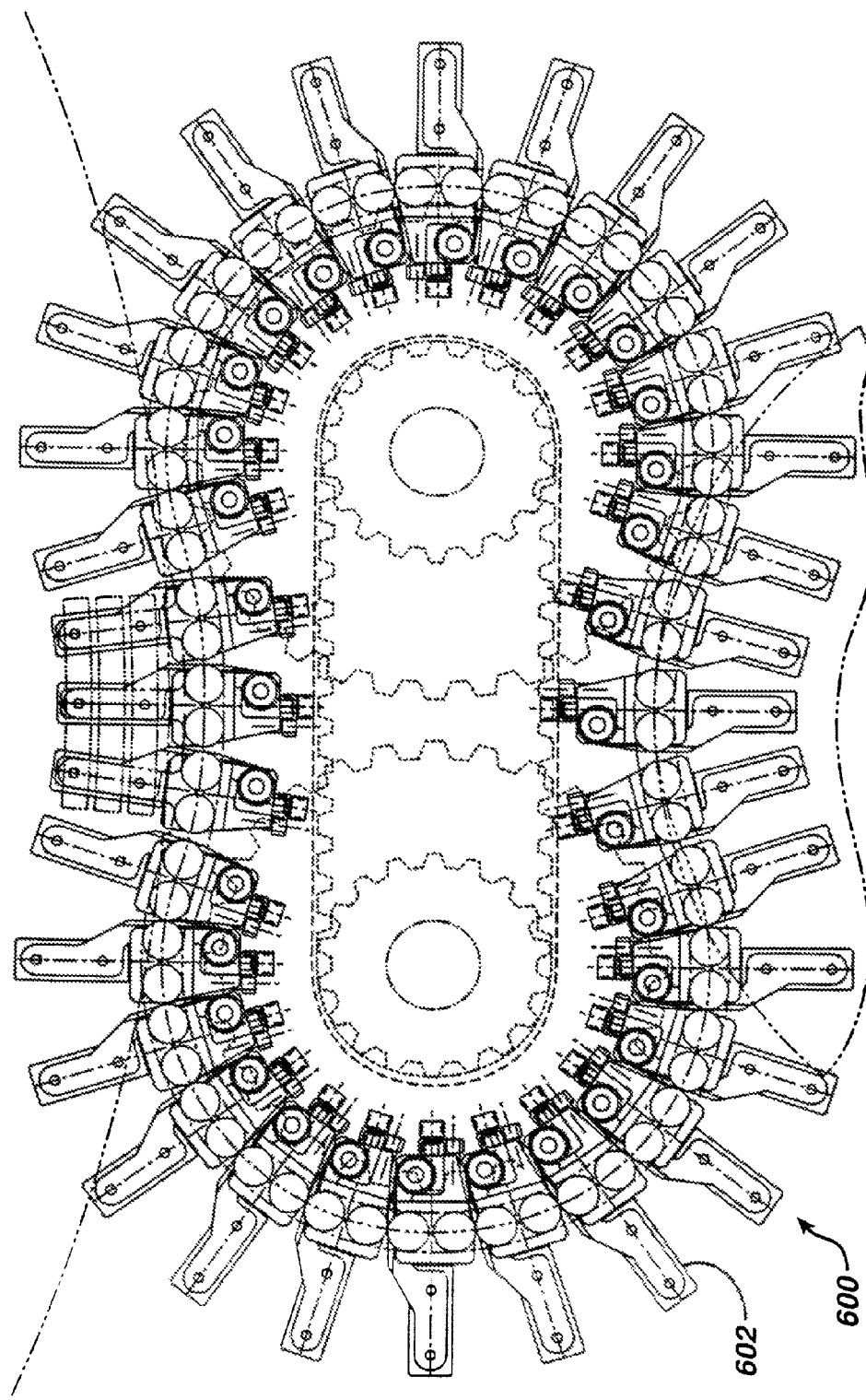
FIG. 77 is a top view of a rotational transfer device according to the invention.
Figure 78:
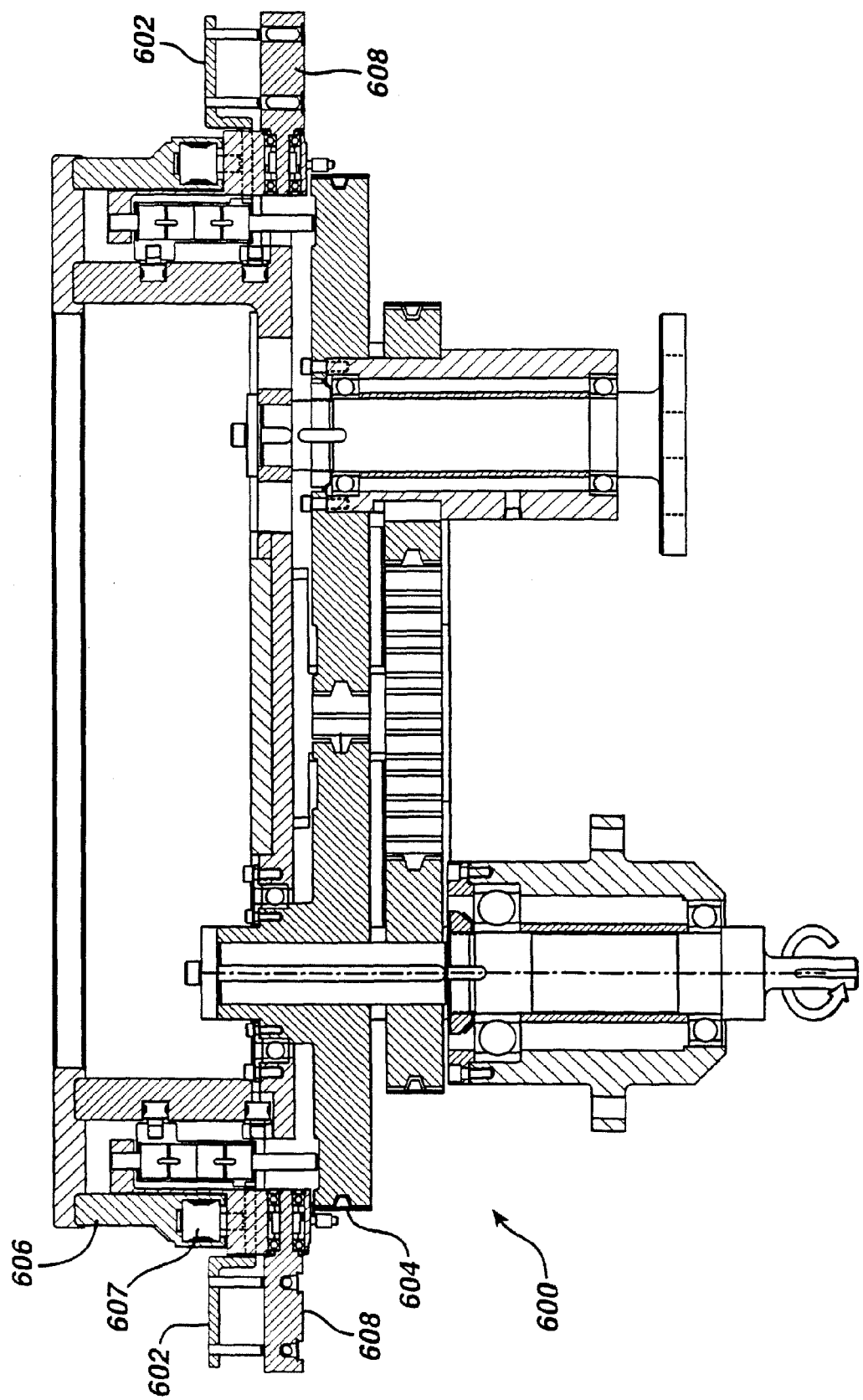
FIG. 78 is cross-sectional view of a rotational transfer device according to the invention.
Figure 79:
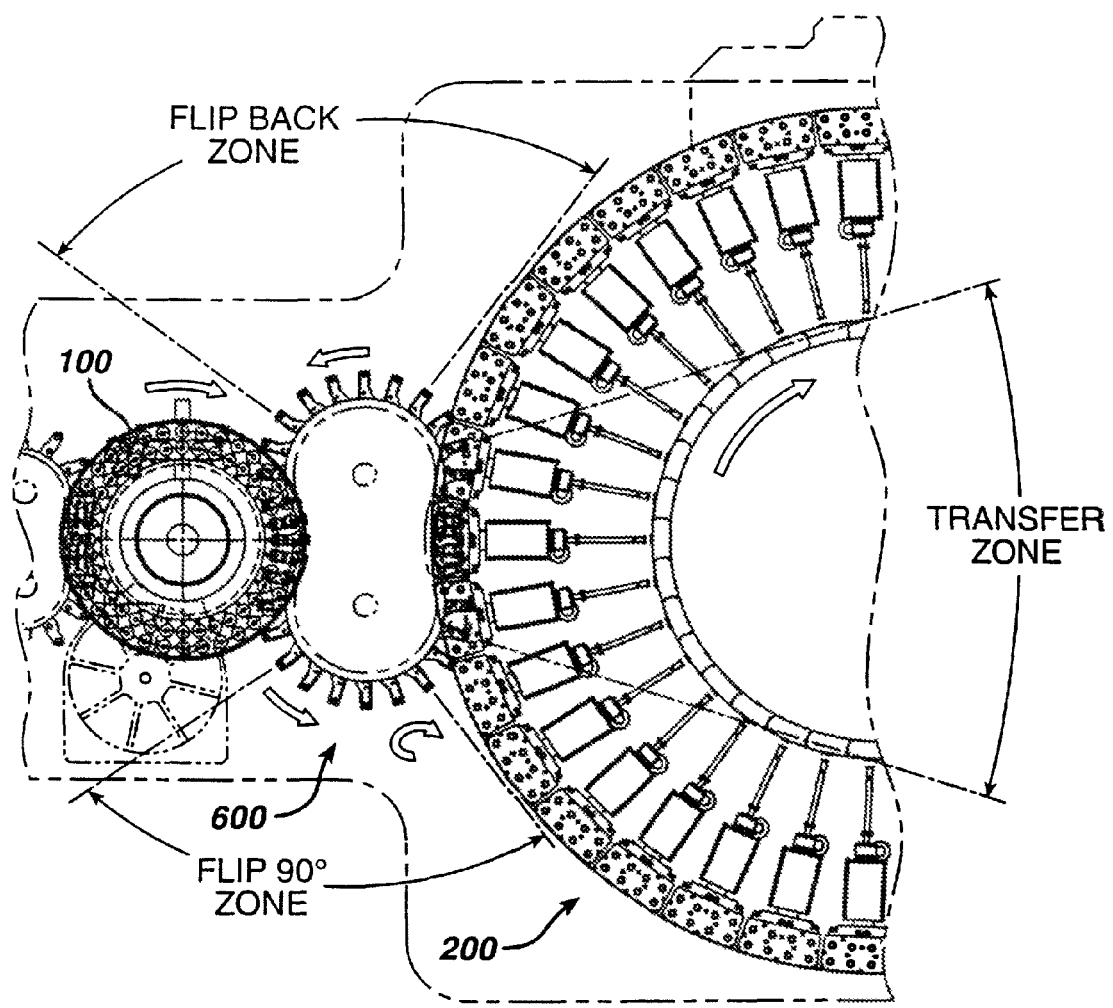
FIG. 79 depicts transfer of compressed dosage forms from a compression module to a thermal cycle molding module via a rotational transfer device according to the invention.

FIGS. 77-81 depict a preferred rotational transfer device 600, which is similar in construction to the transfer devices 300 and 700. Like transfer devices 300 and 700 the rotational transfer device 600 is a rotating device as shown in FIGS. 77 and 79. It comprises a plurality of rotatable transfer units 602 coupled to a toothed belt 604. Riding in the shaped cam track 606 are cam followers 607 suitably mounted to the transfer units 602.

Figure 80:
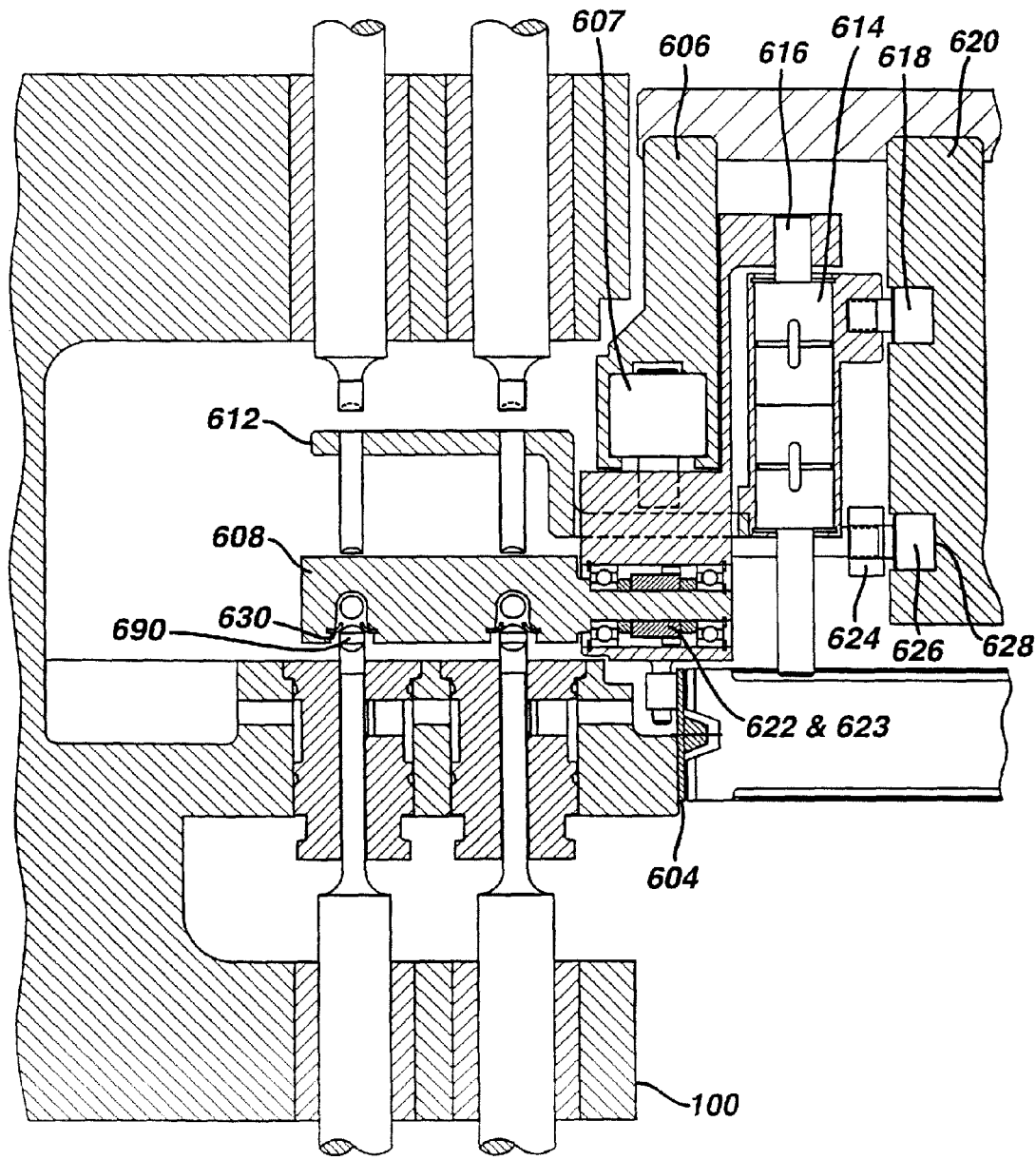
FIG. 80 is a further cross-sectional view of a rotational transfer device according to the invention.

Each transfer unit 602 consists of a dosage form holder 608 rotatably mounted in a housing. Connected to the housing is a shaft 616 (FIG. 80). Ejector pin assembly 612 slides on bearings 614 along shaft 616 and its vertical movement is controlled by cam follower 618 and cam track 620. Within the housing is gear 622, which is attached to the shaft of the dosage form holder 608 and gear 623 which is attached to the shaft of the actuator arm 624. Attached to actuator arm 624 is cam follower 626 which rides in cam track 628. The vertical rise and fall of cam track 628 causes a corresponding movement of cam follower 626 which imparts a rotational movement to actuator arm 624. As the actuator arm rotates, gears 622 and 623 amplify this rotation causing dosage form holder 608 to rotate by an amount proportional to the gear ratio. The gear arrangement and offset design of the actuator arm keep the transfer units symmetrical about the vertical axis between cam followers 607. This symmetry of construction is required to assure proper tracking of cam followers 618 and 626 and dosage form holder 608 as they transit through the various concave and convex radii of the rotational transfer device 600.

One sequence of operations of the rotational transfer device 600 is depicted in FIGS. 79-81. Elongated dosage forms (caplet 690) are compressed horizontally in the compression module 100 and are transferred through flexible retainers 630 into the dosage form holder 608, which is also in a horizontal orientation (FIG. 80, FIGS. 81A, 81B, and 81E). Upon further transit through shaped cam track 606 the dosage form holder 608 rotates 90 degrees to a vertical orientation due to motion of cam follower 626 within cam track 628 (FIGS. 81C and 81F). Upon reaching lower retainer 210 of thermal cycle molding module 200, caplet 690 is transferred through a second flexible retainer 630B via the vertical movement of ejector pin assembly 612. Ejector pin assembly 612 enters through holes 608A in dosage form holder 608 to evacuate the chamber 680 that holds caplet 690 (FIGS. 81C and F and FIGS. 81D and G). Caplet 690 is now transferred to the lower retainer 210 and upon further transit through the shaped cam track 606, the dosage form holder 608 rotates 90 degrees, returning to its horizontal position to begin the cycle over again (FIG. 79).

Hardening Apparatus

Dosage forms that have been coated with flowable material in the thermal cycle molding module are relatively hard compared with dosage forms that have coated using conventional dipping processes. Thus, the amount of drying needed after molding a coating onto a dosage form using the thermal cycle molding module is substantially less than that required with known dipping processes. Nevertheless, they may still require hardening, depending upon the nature of the flowable material.

Preferably, dosage forms coated in the thermal cycle molding module are relatively hard so that they can be tumble hardened relatively quickly. Alternatively, an air dryer may be used. Any suitable dryers may be used. A variety are generally understood in the art.

Thermal Setting Molding Module

The thermal setting molding module may be used to make dosage forms per se, coatings, inserts for dosage forms, and the like from a starting material in flowable form. The thermal setting molding module may be used as part of the overall system 20 of the invention (i.e., linked to other modules) or as a stand alone unit.

The thermal setting molding module 400 is a rotary apparatus comprising multiple hot injection nozzles and cold molding chambers. Each molding chamber has its own nozzle. Advantageously, the volume of the molding chambers is adjustable.

In a preferred embodiment of the invention, the thermal setting molding module is used to make inserts for dosage forms. The inserts can be made in any shape or size. For instance, irregularly shaped inserts (or dosage forms per se) can be made, that is shapes having no more than one axis of symmetry. Generally however, cylindrically shaped inserts are desired.

The inserts are formed by injecting a starting material in flowable form into the molding chamber. The starting material preferably comprises an medicant and a thermal setting material at a temperature above the melting point of the thermal setting material but below the decomposition temperature of the medicant. The starting material is cooled and solidifies in the molding chamber into a shaped pellet (i.e., having the shape of the mold). Injection and molding of the inserts preferably occurs as the thermal setting molding module 400 rotates. In a particularly preferred embodiment of the invention, a transfer device 700 (as described above) transfers shaped pellets from the thermal setting molding module to a compression module 100 (also described above) as generally shown in FIG. 2, to embed the shaped pellets into a volume of powder before such powder is compressed into a dosage form in the compression module.

The starting material must be in flowable form. For example, it may comprise solid particles suspended in a molten matrix, for example a polymer matrix. The starting material may be completely molten or in the form of a paste. The starting material may comprise a medicant dissolved in a molten material. Alternatively, the starting material may be made by dissolving a solid in a solvent, which solvent is then evaporated from the starting material after it has been molded.

The starting material may comprise any edible material which is desirable to incorporate into a shaped form, including medicants, nutritionals, vitamins, minerals, flavors, sweeteners, and the like. Preferably, the starting material comprises a medicant and a thermal setting material. The thermal setting material may be any edible material that is flowable at a temperature between about 37 and about 120° C., and that is a solid at a temperature between about 0 and about 35° C. Preferred thermal setting materials include water-soluble polymers such as polyalkylene glycols, polyethylene oxides and derivatives, and sucrose esters; fats such as cocoa butter, hydrogenated vegetable oil such as palm kernel oil, cottonseed oil, sunflower oil, and soybean oil; mono- di- and triglycerides, phospholipids, waxes such as Carnauba wax, spermaceti wax, beeswax, candelilla wax, shellac wax, microcrystalline wax, and paraffin wax; fat-containing mixtures such as chocolate; sugar in the form on an amorphous glass such as that used to make hard candy forms, sugar in a supersaturated solution such as that used to make fondant forms; low-moisture polymer solutions such as mixtures of gelatin and other hydrocolloids at water contents up to about 30% such as those used to make "gummi" confection forms. In a particularly preferred embodiment, the thermal setting material is a water-soluble polymer such as polyethylene glycol.

Figure 82A:
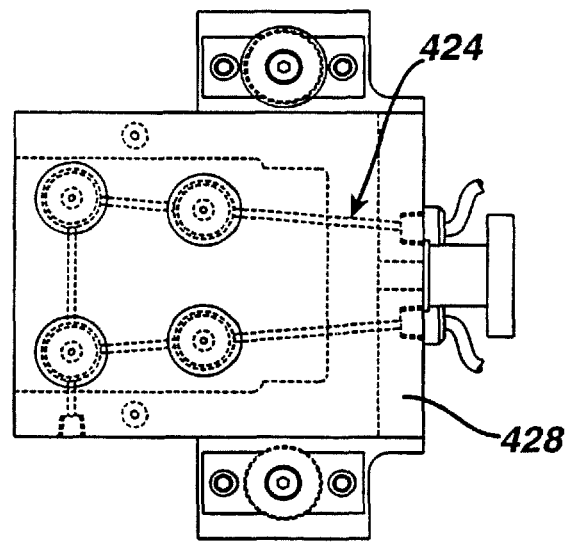
FIG. 82A is a cross-section taken along line A-A of FIG. 82.
Figure 84:
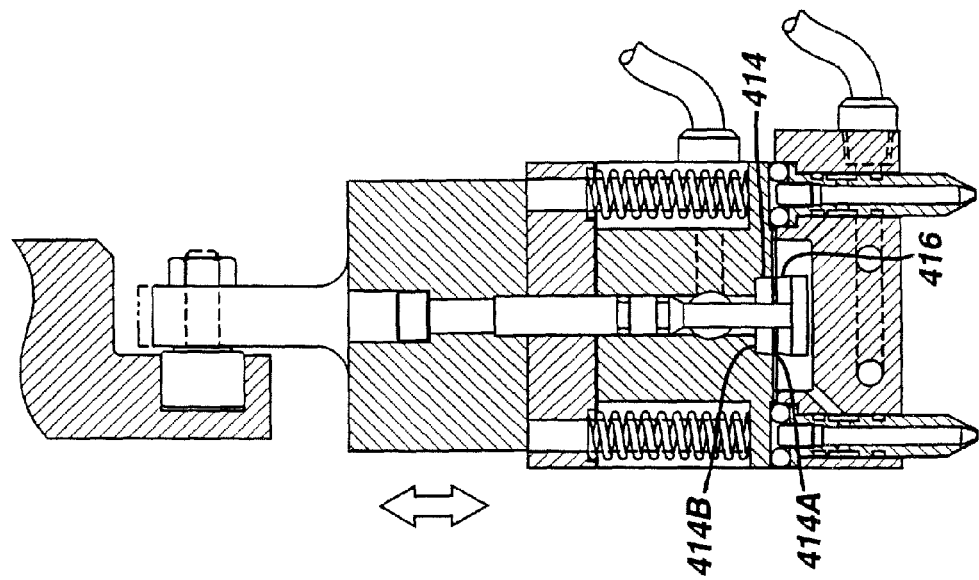
FIG. 84 is another front view of a thermal setting molding module according to the invention.
Figure 83:
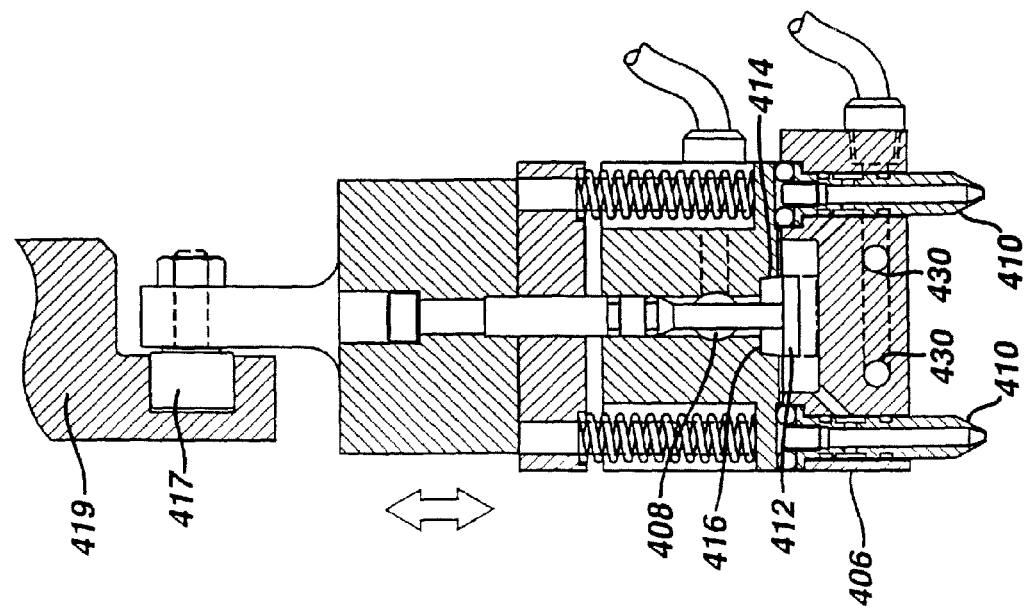
FIG. 83 is a front view of a thermal setting molding module according to the invention.

FIGS. 82-85 depict a preferred embodiment of the thermal setting molding module 400. FIG. 82 is a side view, while FIGS. 83, 84 and 85A-D are front views. The thermal setting molding module 400 generally includes a main rotor 402 as shown in FIGS. 3 and 82, on which are mounted a plurality of injection nozzle assemblies 404. Each injection nozzle assembly 404 includes a housing 406, which is shown in FIGS. 82-84, comprising a flow path 408 through which the starting material may flow. Mounted to each housing 406 are a plurality of nozzles 410. Although any number of nozzles may be employed in each injection nozzle assembly 404, preferably four are present. Mounted below each injection nozzle assembly 404 is a thermal mold assembly 420 comprising a plurality of molding chambers 422 that correspond to the nozzles 410 in each injection nozzle assembly 404.

A control valve 412, as shown in FIG. 83, is disposed within the housing 406 for controlling the flow of starting material to each nozzle 410. Disposed above the valve 412 may be a valve seat 414 and a gasket 416 for sealing the valve 412 when it is in the closed position. Each flow path 408 is connected to a reservoir 418 of starting material. Preferably, reservoir 418 is pressurized and heated with a suitable type of heater (such an electronic resistance or induction type heat) to a temperature whereby the starting material will flow. In a preferred embodiment where the starting material comprises a polymer such as polyethylene glycol, the temperature of the starting material is maintained between about 50 and 80° C. in the reservoir.

Mounted below the nozzles is a plate 428 as shown in FIGS. 82 and 85A-D. The plate 428 moves with nozzles 410 as shown in FIGS. 85A-D and as described below. Disposed within the plate 428 are cooling channels 424 for coolant fluid to flow around the plate 428. The nozzles are preferably heated, for example by a heat transfer fluid delivered through channels 430 in housing 406. Coolant is provided to the mold assembly 420 and the plates 428. As described below, coolant flows through channels 424 in order to cool and thereby harden the injected starting material. Plates 428 are coupled to the housing 406 by any suitable means and in the preferred embodiment mechanical fasteners can be used.

As shown in FIG. 82, shafts 442 are preferably slidably mounted within linear bearings 440. Preferably two shafts are present. Disposed beneath the housing 406 and around a portion of the shafts 442 that extend from the housing are springs 444. Shafts 442 extend beneath the springs 444 as shown in FIGS. 85A-D into a block 446. As shown in FIGS. 82 and 85A-D, and as described in more detail below, block 446 is moveable in response to a cam follower 448, thereby moving closer to housing 406 by compressing springs 444.

As shown in FIG. 85A-D, block 446 is mounted about two shafts 450 and moves up and down with the shafts 450. Shafts 450, as is shown in FIGS. 85A-D, are mounted within a bearing 452 that is coupled to cam follower 448, which rides in a cam track of the type known in the art. As cam follower 448 travels around the thermal setting molding module 400 due to rotation of the rotor 402, cam follower 448 rides up and down in the cam track. As cam follower 448 moves up and down, housing 406, plate 428 and nozzles 410 also move. For instance, in FIG. 85A, cam follower 448 is at a high point. As rotor 402 rotates, cam follower 448 rides down in the cam track and moves the mechanically linked bearing 452 and block 446 in the downward direction to the position shown in FIG. 85B. Housing 406 and plate 428 also move. In this position, plate 428 is disposed proximate to molding chambers 422, but nozzles 410 are still disposed below the molding chambers 422.

Figure 85D:
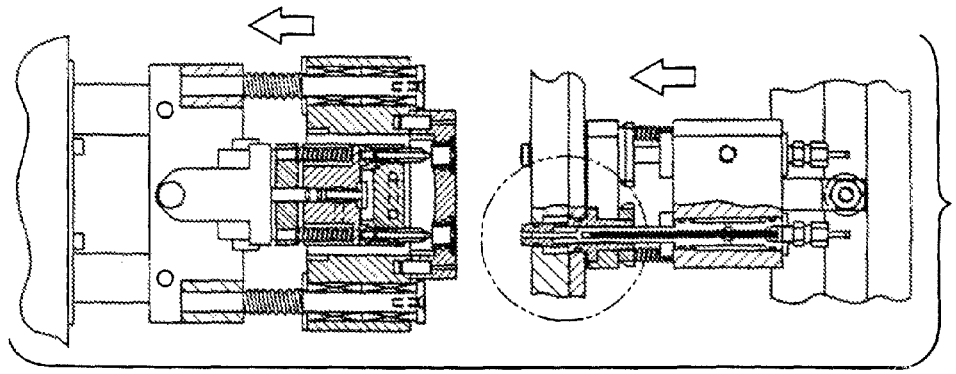
FIGS. 85A-D illustrate operation of the thermal setting molding module.
Figure 85C:
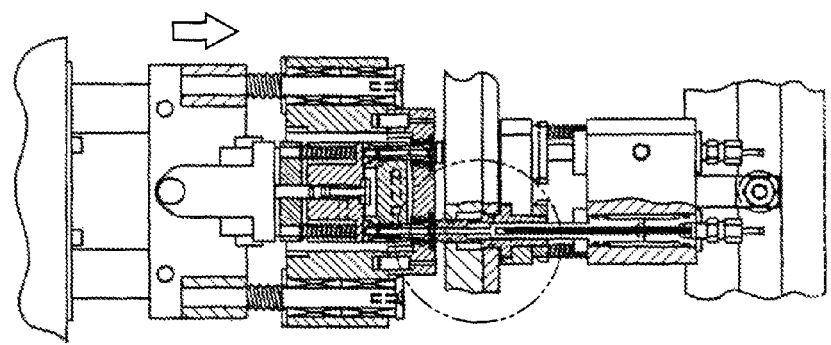
Figure 85B:
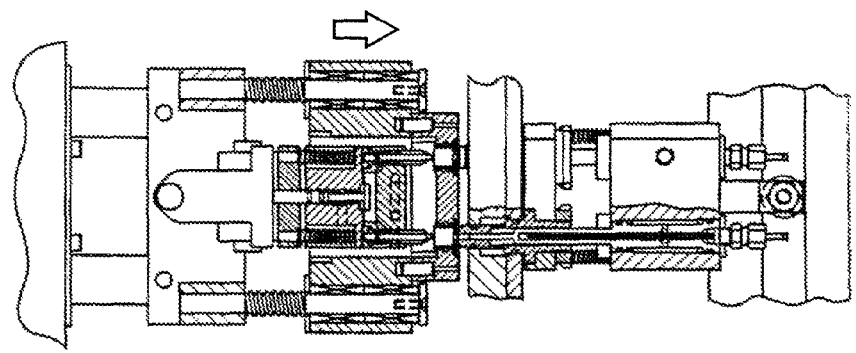
Figure 85A:
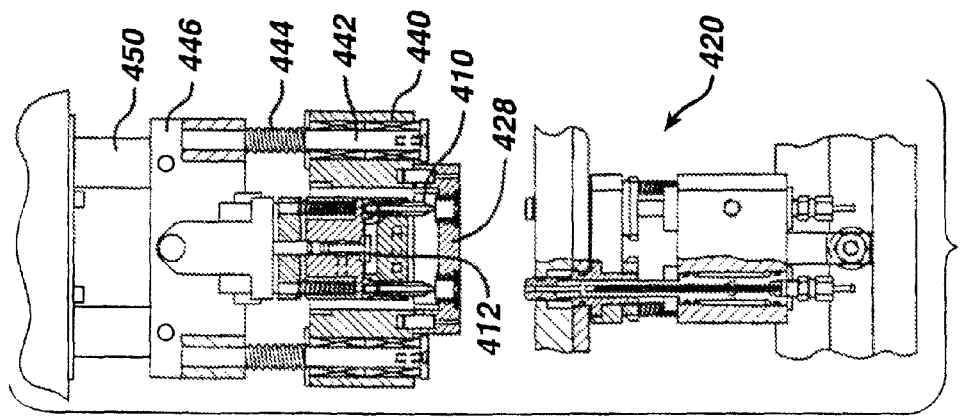

Referring to FIG. 85C, continued rotation of rotor 402 moves cam follower 448 downward within the cam track. Plate 428, which is coupled to housing 406, cannot move downward because it is disposed against the thermal setting mold assembly 420. Consequently, block 446 exerts a force on springs 444, compressing them. Block 446 pushes housing 406 down into plate 428 and proximate the molding chambers 422. In this position, the starting material can be injected through the nozzles 410 and into the molding chambers 422.

When housing 406 moves down as shown in FIG. 85C, control valve 412 opens due to action of valve cam follower 417 in valve cam track 419. Starting material is ported through control valve 412 and nozzles 410 to fill mold chambers 422. Similarly, when cam follower 417 moves down from the position of FIG. 85C to the position of FIG. 85D, control valve 412 closes to stop the flow of starting material. In a preferred embodiment of the invention, valve 412 is designed to provide a "suck back" action upon closing. As shown in FIGS. 83 and 84, the valve seat 414 preferably has the geometry of a gradually tapering hole extending from edge 414A to bottoming point 414B. As gasket 416, which is preferably made of an elastomeric material, moves to a closed position it enters the tapered valve seat 414 and creates a seal against the wall of the valve seat 414. As gasket 416 continues to move it acts like a piston forcing fluid in front of it and behind it to move upward as shown in FIG. 83. This in turn sucks back fluid from the tips of the nozzles 410, which assures that no starting material drools from or accumulates on the tips of the nozzles. The volume of starting material sucked back by movement of gasket 416 can be controlled and adjusted by the depth to which the gasket penetrates into the valve seat.

As shown in FIG. 82, the thermal setting mold assemblies 420 are mounted to the rotor 402 by any suitable means. In a preferred embodiment, mechanical fasteners are used. When used in conjunction with other operating modules, rotor 402 may be attached to a common drive system with the other modules, so that they rotate in synchronicity, preferably by driven motor 50 as shown in FIG. 3.

Figure 86:
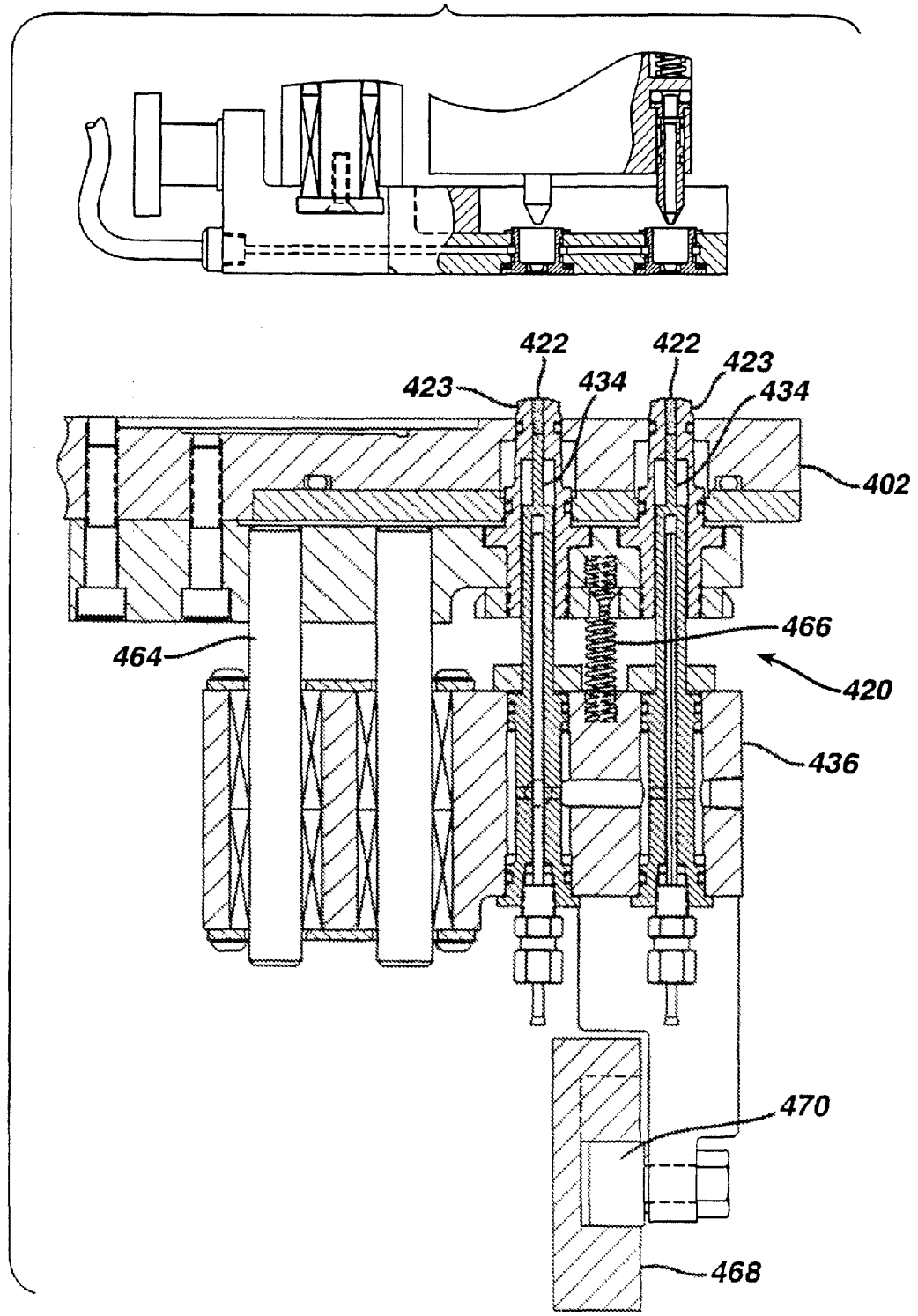
FIG. 86 is a cross-sectional view of a preferred thermal setting molding module according to the invention.

A preferred embodiment of a thermal setting mold assembly 420 is shown in FIG. 86, which is a cross-section. Although one thermal setting mold assembly 420 is depicted, each of the thermal setting mold assemblies 420 are preferably the same. Each thermal setting mold assembly 420 preferably comprises a plurality of molding chambers 422, which are empty volumetric spaces within the thermal setting mold inserts 423. Preferably, one thermal setting mold insert 423 corresponds with each nozzle 410. In a preferred embodiment, there are four thermal setting mold inserts 423 aligned with each of four nozzles 410, as best understood with reference to FIGS. 82 and 85. Although the molding chambers 422 may be any shape and size suitable for molding, they are preferably generally cylindrically shaped.

Disposed within each thermal setting mold insert 423 is a piston 434. It will be appreciated from FIG. 86 that placement of piston 434 within the each thermal setting mold insert 423 defines the volume of the mold cavity 422. By specifically sizing each mold cavity 422 and adjusting the position of piston 434, a desired volume and therefore proper dosage of the starting material is obtained.

Preferably, the pistons 434 are adjustably controlled by the position of cam follower 470 and associated cam track 468. Pistons 434 are attached to piston attachment block 436 by suitable mechanical means so that pistons 434 move with piston attachment block 436. Piston attachment block 436 slides along the shafts 464 up and down. Preferably, there are two shafts 464 as shown in FIG. 86. Mounted to piston attachment block 436 is cam follower 470. One or more springs 466 bias piston attachment block 436 and therefore pistons 434 into the inject position as viewed in FIG. 85C. As thermal setting mold assembly 420 travels with rotor 402, cam follower 468 riding in its cam track actuates pistons 434 into the eject position, which empties the molding chamber in preparation for the next cycle (FIG. 85D).

Figure 88:
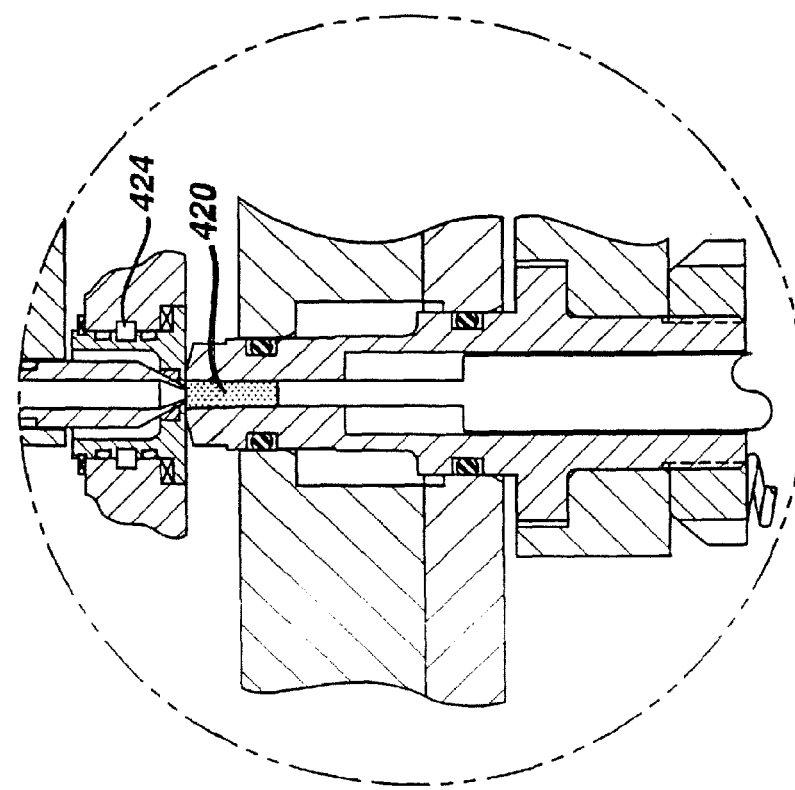
FIGS. 87 and 88 illustrate ejection of an insert from a thermal setting molding module.
Figure 87:
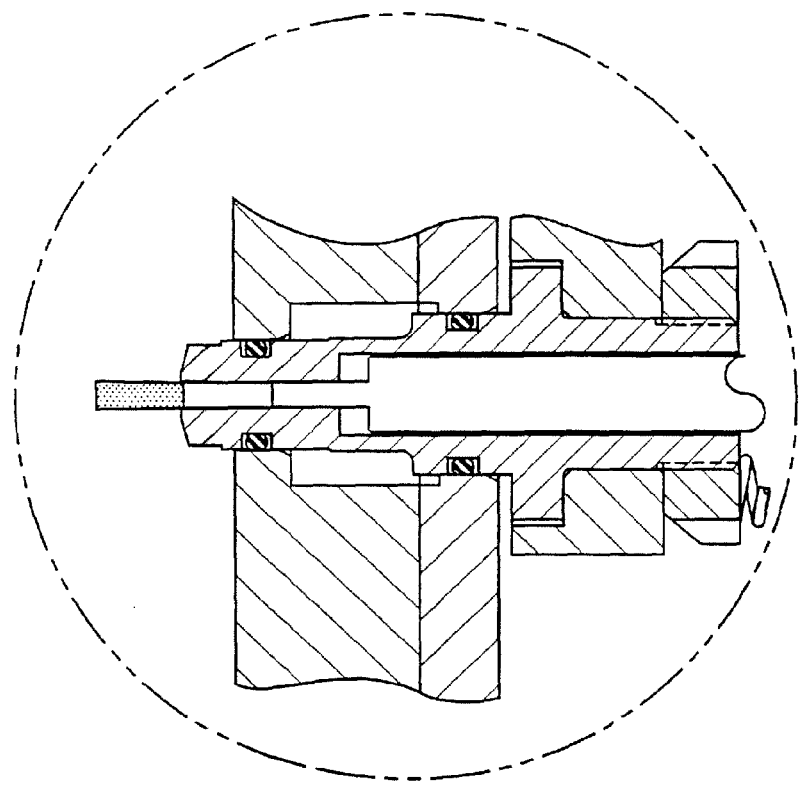

Accordingly, during operation of the thermal setting molding module 400, nozzles 410 move up during rotation of the thermal setting molding module 400 and inject a starting material into molding chambers 422. Next, starting material is hardened within the molding chambers 422 into shaped pellets. Nozzles 410 are then retracted from the molding chambers. All of this occurs as the molding chambers 422 and nozzles 410 are rotating. After the starting material has hardened into shaped pellets, it is ejected from the molding chambers. See FIGS. 87 and 88.

When used with a transfer device 700 according to the invention, the transfer device 700 rotates between the molding chambers 422 and plate 428. The retainers 330 of the transfer device 700 receive the shaped pellets and transfers them to the another operating module, for example a compression module 100. In the case of coupling a thermal setting molding module 400 with a compression module 100 via a transfer device 700, transfer device 700 inserts a shaped pellet into each die cavity 132 after the fill zone 102 but before the compression zone 106 of the compression module. It will be appreciated that a linked thermal setting molding module 400, transfer device 700 and compression module 100 are synchronized so that a shaped pellet is placed into each die cavity 132. The process is a continuous one of forming shaped pellets, transferring the shaped pellets, and inserting the shaped pellets.

The thermal setting molding module has several unique features. One is the ability to mass produce shaped pellets relatively rapidly, in particular molded dosage forms comprising polymers that are typically solids or solid-like between about 0 and about 35° C. The thermal setting molding module accomplishes this is by heating the starting material prior to injecting it into the molding chambers and then cooling the starting material after injection.

Another unique feature of the thermal setting molding module is the adjustable volume of the molding chambers. Adjustability and tuning of volume and therefore weight is especially advantageous for the production of shaped pellets comprising high potency or highly concentrated drugs, which are dosed in small amounts. Another advantage of the thermal setting molding module is that it can employ liquids. Unlike a particulate solid, such as powders typically used to make dosage forms, the volume of a liquid is relatively invariable at constant temperature. Density variations, which are troublesome in powder compression, are therefore avoided with liquids. Very accurate weights, especially at very low weights (i.e. with starting materials comprising high potency medicants) are achievable. Moreover, blend uniformity is also less assured with solid powders. Powder beds tend to segregate based on differences in particle size, shape, and density.

Another advantage of the thermal setting molding module is that it molds starting material while continuously rotating. This permits its integration with other continuously operating rotary devices, resulting in a continuous process. Conventional molding operations are typically stationary and have one nozzle feeding multiple mold cavities. Runners are often formed using in conventional equipment. By providing a nozzle for each molding chamber, runners are eliminated. Preferably, one control valve controls multiple nozzles. This simplifies the design of the thermal setting molding module, reducing cost. The thermal setting molding module may, of course be designed to operate without rotation of the rotor, for example on an indexing basis whereby a stationary group of nozzles engages molding chambers on a indexing rotary turn table or a linear recalculating indexing belt or platen system. However, by using a rotary system higher output rates can be achieved since products are continuously produced.

Specific embodiments of the present invention are illustrated by way of the following examples. This invention is not confined to the specific limitations set forth in these examples, but rather to the scope of the appended claims. Unless otherwise stated, the percentages and ratios given below are by weight.

Figure 89:
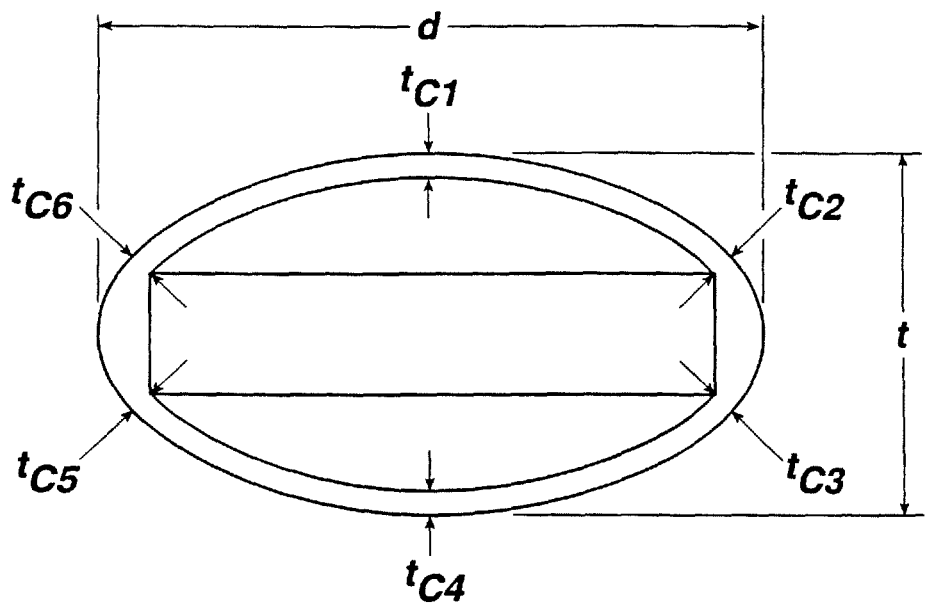
FIG. 89 is a cross-section of a dosage.

In the examples, measurements were made as follows.
Coating thickness is measured using an environmental scanning electron microscope, model XL 30 ESEM LaB6, Philips Electronic Instruments Company, Mahwah, Wis. Six tablets from each sample are measured at 6 different locations on each tablet, as shown in FIG. 89.

Location 1: center of first major face, $t_{c1}$

Locations 2 and 3: edges (near punch land) of intersection between first major face and side, $t_{c2}$ and $t_{c3}$ Location 4: center of second major face, $t_{c4}$ Locations 5 and 6: edges (near punch land) of intersection between second major face and side, $t_{c5}$ and $t_{c6}$ Overall dosage form thickness and diameter are measured for 20 dosage forms using a calibrated electronic digital caliper. For thickness, the caliper is positioned across t as shown in FIG. 89. For diameter, the caliper is positioned at the midsections of the widest point of the dosage form sides shown in FIG. 89 as d.

Example 1

A series of tablets having a molded gelatin coating thereon were made according to the invention as follows.
Part A: Compressed Tablets
The following ingredients were mixed well in a plastic bag: 89.4 parts acetaminophen USP (590 mg/tablet) and 8.0 parts of synthetic wax X-2068 T20 (53 mg/tablet). Next, 2.1 parts of sodium starch glycolate (EXPLOTAB) (13.9 mg/tablet) and 0.09 parts of silicon dioxide (0.6 mg/tablet) were added to the bag, and mixed well. Then 0.36 parts of magnesium stearate NF (2.4 mg/tablet) were added to the bag, and the ingredients were again mixed. The resulting dry blend was compressed into tablets on a compression module according to the invention using 7/16 inch extra deep concave tablet tooling.

The resulting tablets had an average weight of 660 mg, thickness of 0.306 inches, and hardness of 3.2 kp.

The tablets from Part A were conveyed to a thermal cycle molding module according to the invention via a transfer device also according to the present invention. The tablets were coated with red gelatin on one half thereof, and yellow gelatin on the other half thereof.

The red gelatin coating was made as follows. Purified water (450 g), Opatint Red DD-1761 (4.4 g), and Opatint Yellow DD-2125 (1.8 g) were mixed at room temperature till uniform. 275 Bloom Pork Skin Gelatin (150 g) and 250 Bloom Bone Gelatin (150 g) were added together in a separate container. The dry gelatin granules were manually stirred to mix. The purified water/Opatint solution was added to the gelatin granules, and mixed for about 1 minute to completely wet the gelatin granules. The gelatin slurry was placed in a water bath and heated to 55 C to melt and dissolve the gelatin. The gelatin solution was held at 55 C for approximately 3 hours (holding times at this temperature can generally range between about 2 and about 16 hours). The solution was then mixed until uniform (about 5 to 15 minutes), and transferred to a jacketed feed tank equipped with a propeller-type electric mixer. The gelatin solution was maintained at 55 C with continuous mixing during its use in the thermal cycling molding module.

The yellow gelatin coating was made as follows. Purified water (450 g), and Opatint Yellow DD-2125 (6.2 g) were mixed at room temperature till uniform. 275 Bloom Pork Skin Gelatin (150 g) and 250 Bloom Bone Gelatin (150 g) were added together in a separate container. The dry gelatin granules were stirred manually to mix. The purified water/Opatint solution was added to the gelatin granules, and mixed for about 1 minute to completely wet the gelatin granules. The gelatin slurry was placed in a water bath and heated to 55 C to melt and dissolve the gelatin. The gelatin solution was held at 55 C for approximately 3 hours (holding times at this temperature can generally range between about 2 and about 16 hours). The solution was then mixed until uniform (about 5 to 15 minutes), and transferred to a jacketed feed tank equipped with a propeller-type electric mixer. The gelatin solution was maintained at 55 C with continuous mixing during its use in the thermal cycling molding module.

Example 2

Coating thickness was measured for samples of the following tablets:
A. Extra Strength Tylenol GelTabs
B. Excedrine Migrane Geltabs
C. Tablets of produced according to Example 1.
The results are shown in Table 1 below.

TABLE 1

|  | A | B | C |
|---|---|---|---|
| average coating thickness at major faces (locations 1, 4) for 6 tablets | 145.17 microns | 220.40 microns | 195.37 microns |
| variability in coating thickness at major faces (locations 1, 4) for 6 tablets | 10.12% | 5.01% | 8.79% |
| average coating thickness (locations 1-6 for 6 tablets) | 85 microns | 244.83 microns | 209.62 microns |

TABLE 1-continued

|  | A | B | C |
|---|---|---|---|
| coating thickness variability (rsd for locations 1-6 for 6 tablets) | 52.71% | 12.64% | 18.49% |
| average coating thickness at edges | 54.92 microns | 257.05 microns | 216.74 microns |
| coating thickness variability at edges (rsd for locations 2, 3, 5, 6 for 6 tablets) | 19.80 | 11.88 | 20.56 |
| average difference in coating thickness between major face and edge (location 1-location 2, location 4-location 5) | 63.25% | 16.99% | 15.93% |
| maximum difference in coating thickness between major face and edge (location 1-location 2, location 4-location 5) | 72% | 33.4% | 40.6% |
| minimum difference in coating thickness between major face and edge (location 1-location 2, location 4-location 5) | 54% | 7.1% | 4.1% |

Thicknesses and diameters of 20 coated tablets from each of the three samples were also measured. The results are summarized in Table 2 below:

TABLE 2

|  | A | B | C |
|---|---|---|---|
| average coated tablet thickness at major faces (across locations 1, 4) for 20 tablets | 7.67 mm | 6.55 mm | 7.99 mm |
| variability in coated tablet thickness at major faces (locations 1, 4) for 20 tablets | 0.407% | 1.44% | 0.292% |
| average coated tablet diameter (across locations 7, 8 for 20 tablets) | 11.46 mm | 12.58 mm | 11.74 mm |
| variability in coated tablet diameter (rsd across locations 7, 8 for 20 tablets) | 0.183% | 0.476% | 0.275% |

Example 3

Compressed tablets were prepared according the method described in Example 1. Press settings were held constant for a period of 7 hours, 47 minutes. Tablets were sampled every 15 minutes. The resulting tablets had the following properties:

| Weight (mg) (average): | 603.5 |
|---|---|
| Weight (mg) (minimum): | 582.2 |
| Weight (mg) (maximum): | 615.2 |
| Weight (relative standard deviation (%)) | 1.619 |
| Thickness (inches) (average): | 0.293 |
| Thickness (inches) (minimum): | 0.29 |
| Thickness (inches) (maximum): | 0.30 |
| Thickness (relative standard deviation (%)) | 1.499 |
| Hardness (kp) (average): | 1.713 |
| Hardness (kp) (minimum): | 1.12 |
| Hardness (kp) (maximum): | 3.16 |
| Hardness (relative standard deviation (%)) | 21.8 |

Example 4

A flowable material suitable for coating a compressed dosage form was made as follows. The flowable material may be applied using a thermal cycle molding module according to the invention.

| Material | % w/w |
|---|---|
| PEG 1450 (part 1) | 30.0 |
| PEG 1450 (part 2) | 30-50% |
| Polyethylene Oxide 300,000 | 15.0-25% |
| Glycerin | 0-10% |
| Red color solution* (3% w/w) | 5 |

*Red color solution
Propylene Glycol (4.85)
Red #40 dye (0.15)

Polyethylene glycol (PEG) 1450 (part 1) and polyethylene oxide (PEO) 300,000 were shaken in a plastic bag until powders were mixed evenly. The (5 qt) bowl of a planetary mixer (Hobart Corp., Dayton, Ohio) was heated to 80 C by circulating hot water. PEG 1450 (part 2) was poured into the bowl and melted to form a liquid. The color solution, and optionally, the glycerin were added while mixing at low speed. The PEG/PEO powder mixture was added and the mixture mixed for 15 minutes. The resulting mixture was allowed to stand in the Hobart bowl for 2 hours while maintaining the temperature at 80 C. Cast films (approximately 0.8 mm thick) were prepared using a stainless steel mold (2"×5"×0.8 mm). The solution was transferred to a jacketed beaker (80 C) and de-aerated by vacuum for 6 hours. A second film was prepared using the same mold.

Increasing PEO from 15 to 25% (with corresponding decrease in PEG from 85 to 75%) increased yield stress (maximum force per unit area which can be applied before the film will deform permanently), and increased strain (% film elongation at break point).

Decreasing glycerin from 10% to 2% increased Tensile Strength (force per unit area required to break the film). Deaerating the glycerin-containing films prior to casting generally decreased tensile strength.

Example 5

Another flowable material suitable for coating a compressed dosage form was made as follows. The flowable material may be applied using a thermal cycle molding module according to the invention.

| Material | % w/w |
| --- | --- |
| PEG 1450 granular | 70-75% |
| Polyethylene Oxide 600,000 | 15% |
| White beeswax | 5-10% |
| Red color solution* (3% w/w) | 5 |

*Red color solution
Propylene Glycol (4.85)
Red #40 dye (0.15)

The (5 qt) bowl of a planetary mixer (Hobart Corp., Dayton, Ohio) was heated to 80 C by circulating hot water. PEG 3350 granular was poured into the bowl and melted to form a liquid. The white beeswax, color solution, and polyethylene oxide were added while mixing at low speed. The resulting mixture was mixed for a total of 12 minutes, then allowed to stand in the Hobart bowl for 2 hours while maintaining the temperature at 80 C. Cast films were prepared using a glass slide. The solution was transferred to a jacketed beaker (80 C) and de-aerated by vacuum for 6 hours. A second film was prepared using the same mold.

The white beeswax formula had increased tensile strength compared to the glycerin formulas.

Examples 4 and 5 illustrate suitable formulations for the flowable material. Advantageously, these formulations are solvent (including water) free. This eliminates the need to evaporate solvent from coatings made from such formulations, shortening and simplifying drying. Accordingly, in one embodiment of the invention, the flowable material is substantially solvent-free, that is contains less than about 1 weight percent, preferably no, solvent.

What is claimed is:

1. A method of preparing two or more compressed dosage forms comprising the steps of:
   (i) placing a supply of powder in flow communication with two or more dies, said two or more dies each comprising a die cavity therein;
   (ii) applying suction using a suction source to said two or more die cavities so as to cause powder to flow into said two or more die cavities; and
   (iii) compressing said powder in said two or more die cavities so as to form a compressed dosage form,
   wherein said method is performed while said two or more die cavities travel along a circular path.

2. The method of according to claim 1, wherein said compressed dosage forms each comprise a first medicant.

3. The method according to claim 1, wherein each of said compressed dosage forms comprises an insert embedded therein.

4. The method according to claim 3, wherein said insert comprises a thermal-setting material.

5. The method of claim 3, wherein said insert comprises a second medicant.

6. The method of claim 1, wherein said suction source comprises a vacuum pump and a vacuum manifold.

* * * * *